US010954228B2

(12) United States Patent
Maloney et al.

(10) Patent No.: US 10,954,228 B2
(45) Date of Patent: *Mar. 23, 2021

(54) 1 H-PYRAZOL-1-YL-THIAZOLES AS INHIBITORS OF LACTATE DEHYDROGENASE AND METHODS OF USE THEREOF

(71) Applicants: NATIONAL INSTITUTES OF HEALTH, UNITED STATES DEPARTMENT OF HEALTH AND HUMAN SERVICES, Bethesda, MD (US); Vanderbilt University, Nashville, TN (US); The UAB Research Foundation, Birmingham, AL (US); The Trustees of the University of Pennsylvania, Philadelphia, PA (US)

(72) Inventors: David J. Maloney, Points of Rocks, MD (US); Alex Gregory Waterson, Nashville, TN (US); Ganesha Rai Bantukallu, Arlington, VA (US); Kyle Ryan Brimacombe, Brook Park, OH (US); Plamen Christov, Mount Juliet, TN (US); Chi V. Dang, Penn Valley, PA (US); Victor M. Darley-Usmar, Birmingham, AL (US); Matthew Hall, Darnestown, MD (US); Xin Hu, Frederick, MD (US); Ajit Jadhav, Chantilly, VA (US); Somnath Jana, Nashville, TN (US); Kwangho Kim, Nashville, TN (US); William J. Moore, Hagerstown, MD (US); Bryan T. Mott, College Park, MD (US); Leonard M. Neckers, Bethesda, MD (US); Anton Simeonov, Bethesda, MD (US); Gary Allen Sulikowski, Brentwood, TN (US); Daniel Jason Urban, Poolesville, MD (US); Shyh Ming Yang, Doylestown, PA (US)

(73) Assignees: THE TRUSTEES OF THE UNIVERSITY OF PENNSYLVANIA, Philadelphia, PA (US); THE UAB RESEARCH FOUNDATION, Birmingham, AL (US); VANDERBILT UNIVERSITY, Nashville, TN (US); NATIONAL INSTITUTES OF HEALTH, UNITED STATES DEPT. OF HEALTH AND HUMAN SERVICES, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/313,727

(22) PCT Filed: Jun. 29, 2017

(86) PCT No.: PCT/US2017/040021
§ 371 (c)(1),
(2) Date: Dec. 27, 2018

(87) PCT Pub. No.: WO2018/005807
PCT Pub. Date: Jan. 4, 2018

(65) Prior Publication Data
US 2019/0276448 A1 Sep. 12, 2019

Related U.S. Application Data

(60) Provisional application No. 62/356,065, filed on Jun. 29, 2016.

(51) Int. Cl.
C07D 417/04 (2006.01)
C07D 417/14 (2006.01)
(Continued)

(52) U.S. Cl.
CPC ............ *C07D 417/14* (2013.01); *A61P 11/00* (2018.01); *A61P 35/00* (2018.01); *C07D 417/04* (2013.01)

(58) Field of Classification Search
CPC .......................... C07D 417/04; C07D 417/14
See application file for complete search history.

(56) References Cited

U.S. PATENT DOCUMENTS 10,351,532 B2 * 7/2019 Maloney
2010/0029690 A1 2/2010 Atobe et al.

FOREIGN PATENT DOCUMENTS

WO 2010002465 A2 1/2010
WO 2011054525 A1 5/2011
(Continued)

OTHER PUBLICATIONS

PubChem CID 121461851, National Center for Biotechnology Information. PubChem Database. CID=121461851, https://pubchem.ncbi.nlm.nih.gov/compound/121461851 (accessed on Aug. 26, 2019), create date Aug. 6, 2016. (Year: 2016).*

(Continued)

*Primary Examiner* — Laura L Stockton
(74) *Attorney, Agent, or Firm* — Cantor Colburn LLP

(57) ABSTRACT

The disclosure provides a compound of the formula (II) and pharmaceutically acceptable salts thereof. The variables, e.g. n, R, $R^3$, $R^{10}$, X, Y, and Z are defined herein. These compounds act as lactate dehydrogenase inhibitors and are useful for treating cancer and fibrosis. The compounds may be particularly useful for treating forms of cancer in which a metabolic switch from oxidative phosphorylation to glycolysis has occurred. The disclosure also provides pharmaceutical compositions containing a compound of this formula and method for treating patients having cancer, fibrosis, or other conditions in which a metabolic switch from oxidative phosphorylation to glycolysis has occurred.

(Continued)

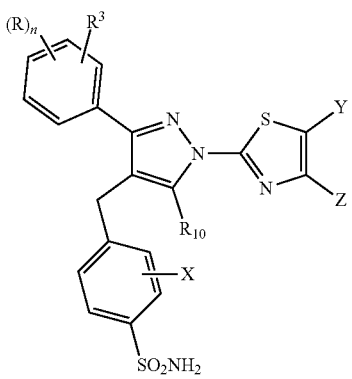

18 Claims, No Drawings

(51) Int. Cl.
*A61P 11/00* (2006.01)
*A61P 35/00* (2006.01)

(56) References Cited

FOREIGN PATENT DOCUMENTS

| WO | 2012061557 A2 | 5/2012 |
|---|---|---|
| WO | 2013092753 A1 | 6/2013 |
| WO | 2013096151 A1 | 6/2013 |
| WO | 2013096153 A1 | 6/2013 |
| WO | 2015054283 A1 | 4/2015 |
| WO | 2015140133 A1 | 9/2015 |
| WO | 2016109559 A2 | 7/2016 |

OTHER PUBLICATIONS

PubChem CID 121461914, National Center for Biotechnology Information. PubChem Database. CID=121461914, https://pubchem.ncbi.nlm.nih.gov/compound/121461914 (accessed on Aug. 26, 2019), create date Aug. 6, 2016. (Year: 2016).*
PubChem CID 121461606, National Center for Biotechnology Information. PubChem Database. CID=121461606, https://pubchem.ncbi.nlm.nih.gov/compound/121461606 (accessed on Aug. 26, 2019), create date Aug. 6, 2016. (Year: 2016).*
Chemical Abstracts Registry No. 1964517-04-1, indexed in the Registry file Aug. 1, 2016. (Year: 2016).*
International Search Report; International Application No. PCT/US2017/040021; International Filing Date—Jun. 29, 2017; dated—Aug. 11, 2017; 6 pages.
Written Opinion; International Application No. PCT/US2017/040021; International Filing Date—Jun. 29, 2017; dated—Aug. 11, 2017; 7 pages.
Kawamori, et al., "Chemopreventive Effects of ONO-8711, a Selective Prostaglandin E Receptor EP1, Antagonist, on Breast Cancer Development," Carcinogenesis, vol. 22, No. 12, (2001), pp. 2001-2004.
Kawamori, et al., "Evaluation of a Selective Prostaglandin E Receptor EP1 Antagonist for Potential Properties in Colon Carcinogenesis," Anticancer Research No. 21, (2001), pp. 3865-3869.
Matsuo, et al., "Inhibition of Human Glioma Cell Growth by a PHS-2 Inhibitor, NS398, and a Prostaglandin E Receptor Subtype EP1-Selective Antagonist, SC51089," Journal of Neuro-Oncology, No. 66, (2004), pp. 285-292.
Niho, et al., "Suppression of Azoxymethane-Induced Colon Cancer Development in Rats by a Prostaglandin E Receptor EP1 -Selective Antagonist," Cancer Science, vol. 96, No. 5, (2005), pp. 260-264.
Tober, et al., "Importance of the EP1 Receptor in Cutaneous UVB-Induced Inflammation and Tumor Development," The Society of Investigative Dermatology, (2006), pp. 205-211.

* cited by examiner

1 H-PYRAZOL-1-YL-THIAZOLES AS INHIBITORS OF LACTATE DEHYDROGENASE AND METHODS OF USE THEREOF

CROSS REFERENCE TO RELATED APPLICATIONS

This application is a National Stage application of PCT/US2017/040021, filed Jun. 29, 2017, which claims priority to U.S. Provisional Application No. 62/356,065 filed Jun. 29, 2016; and all the benefits accruing therefrom under 35 U.S.C. § 119, the content of which is incorporated by reference in its entirety.

BACKGROUND

Agents that target enzymes involved in cancer cell metabolism offer an attractive therapeutic route in view of the potential to preferentially target cancer tissue over normal tissue. While normal tissue typically uses glycolysis only when the oxygen supply is low, cancer tissue relies heavily on aerobic glycolysis regardless of the oxygen supply level. This property is known as the Warburg effect (Vander Heiden et al., *Science*, 2009, 324(5930): 1029-1033). Lactate dehydrogenase (LDH) is involved in the final step of glycolysis, in which pyruvate is converted to lactate. The decrease in the rate of pyruvate entering the TCA (tricarboxylic acid) cycle and the concurrent increase in lactate production is vital for the growth and survival of tumors. There are two different subunits of LDH, LDHA and LDHB, but both subunits have the same active site and catalyze the conversion of pyruvate to lactate. In cancer patients, serum total lactate dehydrogenase (LDH5, a tetramer of LDHA sub-units; the major LDH isoenzyme involved in glycolysis) levels are often increased, and the gene for LDHA, is up-regulated. Tumor cells can then metabolize lactate as an energy source. Inhibition of LDH results in the stimulation of mitochondrial respiration as a compensatory mechanism. LDH inhibition is expected to reduce the ability of the cell to effectively metabolize glucose and reduce tumor cell proliferation and tumor growth. Thus, compounds that inhibit LDH activity have potential for the development of anti-cancer therapeutics.

LDHA inhibitors have been known previously. For example, gossypol is a nonselective inhibitor of LDH that blocks the binding of NADH, with a $K_i$ for LDHA and lactate dehydrogenase B (LDHB) of 1.9 and 1.4 µM, respectively (Doherty et al., *J. Clin. Invest.*, 2013, 123(9): 3685-3692). Billiard et al. (*Cancer and Metabolism*, 2013, 1(19): 1-17) reports that certain derivatives of 3-((3-carbamoyl-7-(3,5-dimethylisoxazol-4-yl)-6-methoxyquinolin-4-yl) amino) benzoic acid are potent inhibitors of LDH and were 10- to 80-fold more selective for LDHA inhibition than LDHB inhibition. However, the in vivo bioavailability of the inhibitors was found to be poor.

In view of the foregoing, there remains a need to provide novel LDH inhibitors with improved potency, selectivity, and/or bioavailability for the treatment of cancer.

SUMMARY

A compound of formula (II):

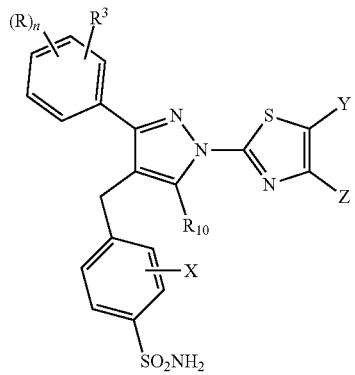

or a pharmaceutically acceptable salt thereof wherein:
X is hydrogen or a halogen;
Y is hydrogen or $C_1$-$C_2$alkyl;
Z is —$CO_2H$, —$CONH_2$, —CONH(CN), —$CONHSO_2CH_3$, —CONH(OH), —$COCF_3$, $CH(OH)CF_3$, —$CH_2OH$, or —$B(OH)_2$;
n is 0, 1, 2, or 3;
R is independently chosen at each occurrence from halogen, hydroxyl, $C_1$-$C_4$alkyl, $C_1$-$C_4$alkoxy;
$R^3$ is a —$C(O)CH_3$, substituted or unsubstituted phenyl group, a substituted or unsubstituted indanyl group, a substituted or unsubstituted tetrahydronaphthyl group, a substituted or unsubstituted cyclohexenyl group, a substituted or unsubstituted indenyl group, substituted or unsubstituted 2,6-diazaspiro[3.3]heptanyl group, a substituted or unsubstituted imidazolyl group, a substituted or unsubstituted dihydrofuranyl group, a substituted or unsubstituted pyrrolidinyl group, a substituted or unsubstituted pyridyl group, a substituted or unsubstituted pyrimidinyl group, a substituted or unsubstituted thiazolyl group, a substituted or unsubstituted spiro[2.5]oct-5-enyl, a substituted or unsubstituted benzimidazolyl group, or -L-Q, wherein L is an acetylenylene group, an ethylenylene group, a cyclopropylene group, or a cyclobutylene group, and wherein Q is hydrogen, a $C_1$-$C_5$alkyl group, a substituted or unsubstituted five-membered heterocycle having 1 to 3 heteroatoms selected from N, O, and S, —$NR^5C(O)R^4$, —$C(O)NR^5R^6$, wherein $R^4$ is hydrogen, $C_1$-$C_5$alkyl, or substituted or unsubstituted phenyl, $R^5$ and $R^6$ are each independently hydrogen or $C_1$-$C_5$alkyl, wherein $R^5$ and $R^6$ optionally form a ring, and wherein $R^4$ and $R^5$ optionally form a ring; and
$R^{10}$ is (cyclopropyl)$C_0$-$C_4$alkyl, which cyclopropyl is optionally substituted with methyl or cyclopropyl or fused to a cyclopropyl group in spiro orientation.

It has been discovered that a compound defined by formula (II) is effective in inhibiting lactate dehydrogenase A (LDHA) and/or lactate dehydrogenase B (LDHB) activity, thereby making the compound effective in treating cancer. It has also been discovered that inhibitors of LDHA and/or LDHB are useful for treating fibrosis, including idiopathic pulmonary fibrosis. LDH inhibitors are indicated for pathologies which involve a metabolic switch from oxidative phosphorylation to glycolysis. Thus the disclosure provides a method for treating a pathology which involves a metabolic switch to glycolysis comprising administering a compound of the disclosure to a patient suffering from such a disclosure. Metabolic switching to glycolysis occurs often occurs in cancer cells. It is envisioned that a compound of formula (II) is desirable for treating cancer because the compound tends to be selective for LDHA and/or LDHB relative to other dehydrogenases (e.g., GAPDH and PHGDH) and/or have a desired solubility, permeability, and/or pharmacokinetics profile (e.g., ADME) for an anti-cancer agent.

Thus, the disclosure further provides a method of treating cancer in a patient comprising administering to the patient an effective amount of the compound of formula (II) or a prodrug or a pharmaceutically acceptable salt thereof.

In another embodiment the disclosure provides a method of treating fibrosis, including idiopathic pulmonary fibrosis, in a patient comprising administering to the patient an effective amount of the compound of formula (II) or a prodrug or a pharmaceutically acceptable salt thereof.

Also provided is a method of treating a patient with cancer cells resistant to an anti-cancer agent, comprising administering to the patient an effective amount of the compound of formula (II) or a prodrug or a pharmaceutically acceptable salt thereof, and the anti-cancer agent, whereby the compound, prodrug, or pharmaceutically acceptable salt thereof re-sensitizes the cancer cells to the anti-cancer agent.

The invention provides a method of inhibiting lactate dehydrogenase A (LDHA) and/or lactate dehydrogenase B activity (LDHB) in a cell comprising administering a compound of formula (II) or a prodrug or a pharmaceutically acceptable salt thereof to a cell.

DETAILED DESCRIPTION

The present invention provides a compound of formula (I)

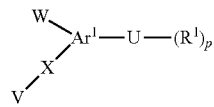

Or a pharmaceutically acceptable salt or prodrug thereof. The following conditions are met for formula (I).

$Ar^1$ is an optionally substituted moiety comprising at least one 5- or 6-membered monocyclic heteroaryl that contains one, two, or three heteroatoms selected from nitrogen, oxygen, and sulfur.

U is aryl, —C(O)aryl, Het, or —C(O)Het, each of which is optionally substituted, wherein Het is a monocyclic or bicyclic moiety comprising a heterocycloalkyl that contains at least two double bonds and one, two, or three heteroatoms selected from nitrogen, oxygen, and sulfur.

$R^1$ is independently chosen from halo, —$CO_2R^4$, —C(O)$NR^5R^6$, —($C_1$-$C_8$hydrocarbyl), —C(O)NHOH, —($C_0$-$C_4$hydrocarbyl)((mono- or bicyclic heterocycle having 1 to 4 heteroatoms independently chosen from N, O, and S), —C(O)O—($C_0$-$C_4$hydrocarbyl)(mono- or bicyclic heterocycle having 1 to 4 heteroatoms independently chosen from N, O, and S), —P(O)(OH)$_2$, —SO$_2$(OH), —B(OR$^{13}$)(OR$^{14}$), —C(O)NHS(O)$_2$Me and —SO$_2$NR$^5R^6$, each of which $R^1$ except halo is substituted or unsubstituted.

$R^2$ is independently chosen from hydroxyl, halo, —CN, —NO$_2$, $C_1$-$C_5$hydrocarbyl, —O($C_1$-$C_5$hydrocarbyl), —($C_0$-$C_4$hydrocarbyl)$C_3$-$C_8$cycloalkyl, —O($C_0$-$C_4$hydrocarbyl)$C_3$-$C_8$ cycloalkyl, —($C_0$-$C_4$hydrocarbyl)$C_3$-$C_8$cycloalkenyl, —O($C_0$-$C_4$hydrocarbyl)$C_3$-$C_8$cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S), —P(O)(OH)$_2$, —B(OR$^{13}$)(OR$^{14}$), —SO$_2$(OH), —C(O)NHS(O)$_2$Me and —SO$_2$NR$^5R^6$, each of which $R^1$ except halo is substituted or unsubstituted.

V is aryl, heteroaryl, or heterocycloalkyl, each of which is substituted with —($R^2$)$_n$, wherein the heteroaryl or heterocycloalkyl is a 5- or 6-membered monocyclic moiety that contains one, two, or three heteroatoms selected from nitrogen, oxygen, and sulfur.

W is —($R^3$)$_m$ or

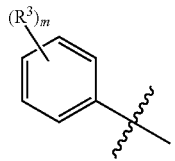

$R^2$ is independently chosen from hydroxyl, halo, —CN, —NO$_2$, $C_1$-$C_5$hydrocarbyl, —O($C_1$-$C_5$hydrocarbyl), —($C_0$-$C_4$hydrocarbyl)$C_3$-$C_8$cycloalkyl, —O($C_0$-$C_4$hydrocarbyl)$C_3$-$C_8$ cycloalkyl, —($C_0$-$C_4$hydrocarbyl)$C_3$-$C_8$cycloalkenyl, —O($C_0$-$C_4$hydrocarbyl)$C_3$-$C_8$cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S), —C(O)R$^4$, —CO$_2R^4$, —C(O)NR$^5R^6$, —NR$^5$C(O)R$^4$, —(CH$_2$)$_q$NR$^5$(SO$_2$)R$^4$, —(CH$_2$)$_q$NR$^5$C(O)R$^4$, —(CH$_2$)$_q$NR$^7$C(O)NR$^5R^6$, —(CH$_2$)$_q$NR$^5R^6$, —(CH$_2$)$_q$SO$_2$NR$^5R^6$, —(CH$_2$)$_q$SO$_2R^4$, each of which $C_1$-$C_8$hydrocarbyl, —O($C_1$-$C_5$hydrocarbyl), —($C_0$-$C_4$hydrocarbyl)$C_3$-$C_8$ cycloalkyl, —O($C_0$-$C_4$hydrocarbyl)$C_3$-$C_8$ cycloalkyl, —($C_0$-$C_4$hydrocarbyl)$C_3$-$C_8$ cycloalkenyl, —O($C_0$-$C_4$hydrocarbyl)$C_3$-$C_8$ cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S) is substituted or unsubstituted.

$R^3$ is independently chosen from hydroxyl, halo, —CN, —NO$_2$, —SF$_5$, $C_1$-$C_5$hydrocarbyl, —O($C_1$-$C_5$hydrocarbyl), —($C_0$-$C_4$hydrocarbyl)$C_3$-$C_8$ cycloalkyl, —O($C_0$-$C_4$hydrocarbyl)$C_3$-$C_8$ cycloalkyl, —($C_0$-$C_4$hydrocarbyl)$C_3$-$C_8$ cycloalkenyl, —O($C_0$-$C_4$hydrocarbyl)$C_3$-$C_8$ cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S), —C(O)R$^4$, —CO$_2R^4$, —C(O)NR$^5R^6$, —NR$^5$C(O)R$^4$, —(CH$_2$)$_q$NR$^5$(SO$_2$)R$^4$, —(CH$_2$)$_q$NR$^5$C(O)R$^4$, —(CH$_2$)$_q$NR$^7$C(O)NR$^5R^6$, —(CH$_2$)$_q$NR$^5R^6$, —(CH$_2$)$_q$SO$_2$NR$^5R^6$, —(CH$_2$)$_q$SO$_2R^4$, each of which $C_1$-$C_8$hydrocarbyl, —O($C_1$-$C_5$hydrocarbyl), —($C_0$-$C_4$hydrocarbyl)$C_3$-$C_8$ cycloalkyl, —O($C_0$-$C_4$hydrocarbyl)$C_3$-$C_8$ cycloalkyl, —($C_0$-$C_4$hydrocarbyl)$C_3$-$C_8$ cycloalkenyl, —O($C_0$-$C_4$hydrocarbyl)$C_3$-$C_8$ cycloalkenyl, —O($C_0$-$C_4$hydrocarbyl)$C_6$-$C_{12}$aryl, —($C_0$-

$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S) is substituted or unsubstituted; or when W is phenyl, then two $R^3$ moieties and the phenyl group to which they are attached form a naphthyl group that is optionally substituted with at least one additional $R^3$ moiety.

Each $R^4$, $R^5$, $R^6$, $R^7$, $R^8$, and $R^9$ is the same or different and each is hydrogen, $C_1$-$C_8$ alkyl, $C_2$-$C_8$ alkenyl, $C_3$-$C_6$ cycloalkyl, $C_6$-$C_{12}$aryl, heteroaryl, or heterocycloalkyl.

Each $R^{13}$ and $R^{14}$ is the same or different and each is hydrogen, $C_1$-$C_8$ alkyl, $C_2$-$C_8$ alkenyl, $C_3$-$C_6$ cycloalkyl, $C_6$-$C_{12}$ aryl, wherein $R^{13}$ and $R^{14}$ are optionally connected to each other to form a ring.

X is a bond, —$CR^8R^9$—, —$NR^5$—, —$CR^8NR^5$—, —$NR^5CR^8$—, —$NR^5C(O)$, —O—, —SO—, —$SO_2$—, or —S—.

m, n, and q are the same or different and each is 0 or an integer from 1-5; and p is 0, 1, or 2.

Provided that when $Ar^1$ is quinolinyl, then U is not pyrimidinyl; and when $Ar^1$—U is 2-(1H-indol-1-yl)thiazolyl, then X at the 3-position on the indolyl group is not a bond or —$CH_2$—, or W at the 3-position on the indolyl group is not phenyl, or $R^3$ at the 3-position on the indolyl group is not benzyl; and when $Ar^1$—U is 2-(1H-pyrazol-1-yl)thiazolyl, then W at the 3-position on the pyrazolyl group is not 4-trifluoromethylphenyl or 4-nitrophenyl, or X at the 4-position on the pyrazolyl group is not a bond.

The disclosure includes a compound or pharmaceutically acceptable salt of formula (II):

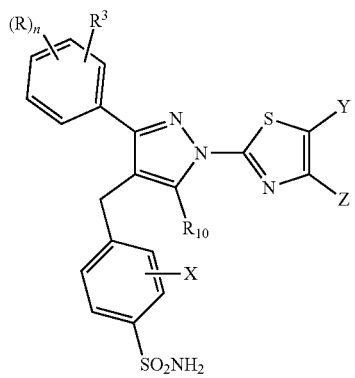

in which
  X is hydrogen or a halogen;
  Y is hydrogen or $C_1$-$C_2$alkyl;
  Z is —$CO_2H$, —$CONH_2$, —CONH(CN), —$CONHSO_2CH_3$, —CONH(OH), —$COCF_3$, $CH(OH)CF_3$, —$CH_2OH$, or —$B(OH)_2$;
  n is 0, 1, 2, or 3;
  R is independently chosen at each occurrence from halogen, hydroxyl, $C_1$-$C_4$alkyl, $C_1$-$C_4$ alkoxy;
  $R^3$ is a —$C(O)CH_3$, substituted or unsubstituted phenyl group, a substituted or unsubstituted indanyl group, a substituted or unsubstituted tetrahydronaphthyl group, a substituted or unsubstituted cyclohexenyl group, a substituted or unsubstituted indenyl group, substituted or unsubstituted 2,6-diazaspiro[3.3]heptanyl group, a substituted or unsubstituted imidazolyl group, a substituted or unsubstituted dihydrofuranyl group, a substituted or unsubstituted pyrrolidinyl group, a substituted or unsubstituted pyridyl group, a substituted or unsubstituted pyrimidinyl group, a substituted or unsubstituted thiazolyl group, a substituted or unsubstituted spiro[2.5]oct-5-enyl; substituted or unsubstituted benzimidazolyl group, or -L-Q, wherein L is an acetylenylene group, an ethylenylene group, a cyclopropylene group, or a cyclobutylene group, and wherein Q is hydrogen, $C_1$-$C_5$alkyl group, a substituted or unsubstituted five-membered heterocycle having 1 to 3 heteroatoms selected from N, O, and S, —$NR^5C(O)R^4$, —$C(O)NR^5R^6$, wherein $R^4$ is hydrogen, $C_1$-$C_5$alkyl, or substituted or unsubstituted phenyl, $R^5$ and $R^6$ are each independently hydrogen or $C_1$-$C_5$alkyl, wherein $R^5$ and $R^6$ optionally form a ring, and wherein $R^4$ and $R^5$ optionally form a ring;

$R^{10}$ is (cyclopropyl)$C_1$-$C_4$alkyl, which cyclopropyl is optionally substituted with methyl or cyclopropyl or fused to a cyclopropyl group in spiro orientation, or $R^{10}$ is (cyclopropyl)$C_1$-$C_4$alkyl in which the $C_1$-$C_4$alkyl is substituted with cyclopropyl.

In formula (II), X may be fluorine, -chlorine, alkyl, or cycloalkyl, and may be in the ortho or meta position (with respect to the point of attachment of the phenyl). The disclosure includes compounds and salts of formula (II) in which X is fluorine and is in the meta position with respect to the point of attachment of the phenyl.

Groups that may substitute $R^3$ include halogen, CHO, $C_1$-$C_6$alkyl, $C_1$-$C_6$alkoxy, cyclopropyl, cyclobutyl, mono- and di ($C_1$-$C_4$alkylamine)$C_0$-$C_2$alkyl, $C_1$-$C_2$haloalkyl, and $C_1$-$C_2$haloalkoxy.

In formula (II), $R^3$ may be a substituted phenyl group, substituted with fluorine, chlorine, a $C_1$-$C_5$alkyl group, —$CF_3$, —$CHF_2$, $CH_3CO$—, $CH_3CO$—, —CN, —$N(CH_3)_2$, or a combination thereof.

In formula (II), $R^3$ may be a -L-Q and Q is furanyl, thiophenyl, oxazolyl, thiazolyl, or 2,3-dihydrofuranyl group, each of which $R^3$ may be unsubstituted or substituted with one or more substituents independently selected at each occurrence from halogen, $C_1$-$C_4$alkyl, $C_1$-$C_4$alkoxy, trifluoromethyl, difluoromethyl, cyclopropyl, and cyclobutyl.

In formula (II), $R^3$ may be a 1-cyclohexene group substituted with a $C_1$-$C_5$alkyl group, —$CF_3$, or $CH_3O$—.

In formula (II), $R^3$ may be a spiro[2.5]oct-5-enyl group.

In formula (II), $R^3$ is a cis-ethylenylene group or a trans-ethylenylene group.

In formula (II), $R^3$ may be a five-membered heterocycle substituted with fluorine, chlorine, $C_1$-$C_5$alkyl, —$CHF_2$, —$CF_3$, or a combination thereof.

In formula (II), $R^3$ may be a 2,6-diazaspiro[3.3]heptanyl group of the formula

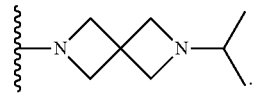 [SMILES: *N1CC2(C1)CN(C(C)C)C2]

In formula (II), $R^{10}$ may be (cyclopropyl)$CH_2$—.

In formula (II) $R^3$ may be -L-Q, where L is an ethynyl group and Q is a five-membered heteroaryl group, which is unsubstituted or substituted with one or more substituents independently chosen from halogen, $C_1$-$C_5$alkyl, $C_1$-$C_5$alkoxy, —$CHF_2$, —$CF_3$, cyclopropyl, and cyclobutyl.

In formula (II) Q may be a five-membered heteroaryl group chosen from thienyl, thiazolyl, oxazolyl, and furanyl, each of which is unsubstituted or substituted with one or more substituents independently chosen from halogen, $C_1$-$C_5$alkyl, $C_1$-$C_5$alkoxy, —$CHF_2$, —$CF_3$, cyclopropyl, and cyclobutyl.

In formula (II) $R^{10}$ may be (cyclopropyl)$CH_2$— or (cyclopropyl)$CH_2CH_2$—.

In formula (II) Y may be is hydrogen.

In formula (II) Z may be —COOH, —$CH_2OH$, or —$CONH_2$.

Any of the foregoing definitions of variables for compounds of formula (II) may be combined so long as a stable compound results and all such combinations are within the scope of the disclosure.

The disclosure includes compounds and pharmaceutically acceptable salts of Formula (II) in which
n is 0; X is florine in the meta position; Y is hydrogen; Z is —COOH, —$CH_2OH$, or —$CONH_2$;
$R^3$ is -L-Q, where L is an ethynyl group and Q is a five-membered heteroaryl group, chosen from thienyl, thiazolyl, oxazolyl, and furanyl, each of which is unsubstituted or substituted with one or more substituents independently chosen from halogen, $C_1$-$C_5$alkyl, $C_1$-$C_5$alkoxy, —$CHF_2$, —$CF_3$, cyclopropyl, and cyclobutyl; and
$R^{10}$ is (cyclopropyl)$C_0$-$C_4$alkyl.

Formula (II) may include the following compounds of Table 7, below, or their pharmaceutically acceptable salts:

Compounds of formula (I), including compounds of formulas (Ia) and (II), are set forth below in Table 7 as representative examples. Prodrugs and pharmaceutically acceptable salts of the exemplified compounds are also included in the disclosure.

Terminology

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or language denoting examples (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The term "substituted", as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes a heteroaromatic moiety, the resulting molecule can sometimes adopt tautomeric forms. For example a pyridyl group substituted by oxo at the 2- or 4-position can sometimes be written as a pyridine or hydroxypyridine. Combinations of substituents and/or variables are permissible only if such combinations result in stable compounds or useful synthetic intermediates. A stable compound or stable structure is meant to imply a compound that is sufficiently robust to survive isolation from a reaction mixture and subsequent formulation into an effective therapeutic agent. Unless otherwise specified, substituents are named into the core structure. For example, it is to be understood that aminoalkyl means the point of attachment of this substituent to the core structure is in the alkyl portion and alkylamino means the point of attachment is a bond to the nitrogen of the amino group.

Suitable groups that may be present on a "substituted" or "optionally substituted" position include, but are not limited to, halogen (fluorine, chlorine, bromine, and iodine); cyano; —OH; —$CH_2F$, —$CHF_2$, —$CF_3$, nitro; linear, branched, or cyclic alkyl groups (including cycloalkyl and (cycloalkyl) alkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms, alkanoyl groups having 2 to about 8 carbon atoms. For example, suitable groups that may be present on a "substituted" or "optionally substituted" position include hydroxyl, halogen, —$CH_2F$, —$CHF_2$, —$CF_3$, cyano, alkyl groups, and alkoxy groups. Two geminal alkyl substituents (i.e., two substituents attached to the same carbon atom) may optionally form a ring. Non-limiting examples of such substituted groups are spiro[2.5]octanyl and spiro[2.5]octenyl groups.

In any of the embodiments above, the term "alkyl" implies a straight-chain or branched alkyl substituent containing from, for example, from about 1 to about 8 carbon atoms, e.g., from about 1 to about 6 carbon atoms. Examples of alkyl group include methyl, ethyl, n-propyl, isopropyl, n-butyl, sec-butyl, isobutyl, tert-butyl, n-pentyl, isopentyl, n-hexyl, and the like. This definition also applies wherever "alkyl" occurs as part of a group, such as, e.g., in $C_3$-$C_6$ cycloalkylalkyl, hydroxyalkyl, haloalkyl (e.g., monohaloalkyl, dihaloalkyl, and trihaloalkyl), cyanoalkyl, aminoalkyl, alkylamino, dialkylamino, arylalkyl, etc. The alkyl can be substituted or unsubstituted, as described herein. Even in instances in which the alkyl is an alkylene chain (e.g., —($CH_2$)$_n$—), the alkyl group can be substituted or unsubstituted. An example of a substituted alkylene chain includes —$CF_2$-cyclopropyl.

In any of the embodiments above, the term "hydroxy" refers to the group —OH.

In any of the embodiments above, the term "alkoxy" includes linear or branched alkyl groups, that are attached to a divalent oxygen. The alkyl groups are the same as described herein.

In any of the embodiments above, the term "halo" refers to a halogen selected from fluorine, chlorine, bromine, and iodine.

In any of the embodiments described herein, a compound of the present invention can also be provided as a prodrug, which is a drug derivative or drug precursor compound that typically is inactive or less than fully active until it is converted in the body through a normal metabolic process such as, for example, hydrolysis of an ester or amide form of the drug, to the active drug. A prodrug may be selected and used instead of the parent drug because, for example, in its prodrug form it is less toxic, and/or may have better absorption, distribution, metabolism and excretion (ADME) characteristics, and the like, than the parent drug. A prodrug might also be used to improve how selectively the drug interacts with cells or processes that are not its intended target. This approach may be employed particularly, for example, to prevent or decrease adverse effects, especially in cancer treatments, which may be especially prone to having severe unintended and undesirable side effects.

The term "prodrug" denotes a derivative of a compound, which derivative, when administered to warm-blooded animals, e.g., humans, is converted into the compound (drug). For example, the enzymatic and/or chemical hydrolytic cleavage of a derivative compound of the present invention occurs in such a manner that the proven drug form is released, and the moiety or moieties split off remain nontoxic or are metabolized so that nontoxic metabolites are produced. For example, a carboxylic acid group can be esterified, e.g., with a methyl group or ethyl group to yield an ester. When an ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound.

The prodrug can be prepared in situ during the isolation and purification of the compound of formula (I), including a compound of formula (Ia), or by separately reacting the purified compound with a suitable derivatizing agent. For example, hydroxy groups can be converted into esters via treatment with a carboxylic acid in the presence of a catalyst. Examples of cleavable alcohol prodrug moieties include substituted or unsubstituted, branched or unbranched alkyl ester moieties, e.g., ethyl esters, alkenyl esters, di-alkylamino alkyl esters, e.g., dimethylaminoethyl ester, acylamino alkyl esters, acyloxy alkyl esters (e.g., pivaloyloxymethyl ester), aryl esters, e.g., phenyl ester, aryl-alkyl esters, e.g., benzyl ester, optionally substituted, e.g., with methyl, halo, or methoxy substituents aryl and aryl-alkyl esters, amides, alkyl amides, di-alkyl amides, and hydroxy amides.

Knowing the disclosures herein, it will be appreciated also that a compound of the present invention can be in the form of a prodrug, and that such prodrugs can be prepared using reagents and synthetic transformations that are well-known to those having ordinary skill in the art. The effectiveness of a particular prodrug can be determined using one or more analytical methods (e.g. pharmacokinetics, bioassays, in vivo efficacy studies, and the like) that are well-known to those of ordinary skill in the art.

More specifically, a prodrug of a compound of formula (I), including a compound of formula (Ia), may be prepared using routine chemical procedures. For example, a hydroxyl substituent on a compound of formula (I) can be substituted with —CO-alkyl, —CO$_2$alkyl, —CONH-alkyl, —CO-alkenyl, —CO$_2$-alkenyl, —CONH-alkenyl, —CO-aryl, —CO$_2$-aryl, —CONH-aryl, —CO-heterocycle, —CO$_2$-heterocycle, —CONH-heterocycle, or —PO$_3$H$_2$. Specific modifying groups of hydroxyl include, for example, acetyl, propionyl, isobutyryl, pivaloyl, palmitoyl, benzoyl, 4-methylbenzoyl, dimethylcarbamoyl, dimethylaminomethylcarbonyl, sulfo, alanyl, and fumaryl group.

An amino group can be substituted with —CO-alkyl, —CO$_2$-alkyl, —CO-alkenyl, —CO$_2$— alkenyl, —CO$_2$-aryl, —CO-aryl, —CO-heterocycle, —CO$_2$-heterocycle, or —PO$_3$H$_2$. The alkyl, alkenyl, aryl, and heterocycle moieties are optionally substituted by halogen, alkyl, hydroxyl, alkoxy, carboxy, amino, an amino acid residue, —PO$_3$H$_2$, —SO$_3$H, —OPO$_3$H$_2$, and —OSO$_3$H. Specific modifying groups of amino include, for example, tert-butyl, docosanoyl, pivaloylmethyloxy, alanyl, hexylcarbamoyl, pentylcarbamoyl, 3-methylthio-1-(acetylamino)propylcarbonyl, 1-sulfo-1-(3-ethoxy-4-hydroxyphenyl)methyl, (5-methyl-2-oxo-1,3-dioxol-4-yl)methyl, (5-methyl-2-oxo-1,3-dioxol-4-yl)methoxycarbonyl, tetrahydrofuranyl, and pyrrolidylmethyl.

Suitable modifying groups of carboxyl include, for example, methyl, ethyl, propyl, isopropyl, butyl, isobutyl, tert-butyl, pivaloyloxymethyl, carboxymethyl, dimethylaminomethyl, 1-(acetyloxy)ethyl, 1-(ethoxycarbonyloxy)ethyl, 1-(isopropyloxycarbonyloxy)ethyl, 1-(cyclohexyloxycarbonyloxy)ethyl, carboxylmethyl, (5-methyl-2-oxo-1,3-dioxol-4-yl)methyl, benzyl, phenyl, o-tolyl, morpholinoethyl, N,N-diethylcarbamoylmethyl, and phthalidyl.

In any of the embodiments above, the phrase "salt" or "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. For example, an inorganic acid (e.g., hydrochloric acid, sulfuric acid, phosphoric acid, or hydrobromic acid), an organic acid (e.g., oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, or benzylsulfonic acid), an inorganic base (e.g., sodium hydroxide, potassium hydroxide, calcium hydroxide, magnesium hydroxide, or ammonium hydroxide), an organic base (e.g., methylamine, diethylamine, triethylamine, triethanolamine, ethylenediamine, tris(hydroxymethyl)methylamine, guanidine, choline, or cinchonine), or an amino acid (e.g., lysine, arginine, or alanine) can be used. Generally, non-aqueous media such as ether, ethyl acetate, ethanol, isopropanol, or acetonitrile are typical. Lists of suitable salts are found in *Remington's Pharmaceutical Sciences*, 18th ed., Mack Publishing Company, Easton, Pa., 1990, p. 1445, and *Journal of Pharmaceutical Science*, 66, 2-19 (1977). For example, they can be a salt of an alkali metal (e.g., sodium or potassium), alkaline earth metal (e.g., calcium), or ammonium of salt.

The methods described herein comprise administering a compound of formula (I) or a prodrug or a pharmaceutically acceptable salt thereof in the form of a pharmaceutical composition. In particular, a pharmaceutical composition will comprise at least one compound of formula (I) or a prodrug or a pharmaceutically acceptable salt thereof and a pharmaceutically acceptable carrier. The pharmaceutically acceptable excipients described herein, for example, vehicles, adjuvants, carriers or diluents, are well-known to those who are skilled in the art and are readily available to the public. Typically, the pharmaceutically acceptable carrier is one that is chemically inert to the active compounds and one that has no detrimental side effects or toxicity under the conditions of use.

The pharmaceutical compositions can be administered as oral, sublingual, transdermal, subcutaneous, topical, absorption through epithelial or mucocutaneous linings, intravenous, intranasal, intraarterial, intramuscular, intratumoral, peritumoral, interperitoneal, intrathecal, rectal, vaginal, or aerosol formulations. In some aspects, the pharmaceutical composition is administered orally or intravenously.

In accordance with any of the embodiments, the compound of formula (I) or a prodrug or a pharmaceutically acceptable salt thereof can be administered orally to a subject in need thereof. Formulations suitable for oral administration can consist of (a) liquid solutions, such as an effective amount of the compound dissolved in diluents, such as water, saline, or orange juice and include an additive, such as cyclodextrin (e.g., α-, β-, or γ-cyclodextrin, hydroxypropyl cyclodextrin) or polyethylene glycol (e.g., PEG400); (b) capsules, sachets, tablets, lozenges, and troches, each containing a predetermined amount of the active ingredient, as solids or granules; (c) powders; (d) suspensions in an appropriate liquid; and (e) suitable emulsions and gels. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound of formula (I) or a salt thereof can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the inhibitors in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The inhibitors may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Topically applied compositions are generally in the form of liquids (e.g., mouthwash), creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution, such as a mouthwash. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

The compound of formula (I) or a prodrug or a pharmaceutically acceptable salt thereof, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

The dose administered to the mammal, particularly human and other mammals, in accordance with the present invention should be sufficient to affect the desired response. One skilled in the art will recognize that dosage will depend upon a variety of factors, including the age, condition or disease state, predisposition to disease, genetic defect or defects, and body weight of the mammal. The size of the dose will also be determined by the route, timing and frequency of administration as well as the existence, nature, and extent of any adverse side-effects that might accompany the administration of a particular inhibitor and the desired effect. It will be appreciated by one of skill in the art that various conditions or disease states may require prolonged treatment involving multiple administrations.

The inventive methods comprise administering an effective amount of a compound of formula (I) or a prodrug or a pharmaceutically acceptable salt thereof. An "effective amount" means an amount sufficient to show a meaningful benefit in an individual, e.g., promoting at least one aspect of tumor cell cytotoxicity (e.g., inhibition of growth, inhibiting survival of a cancer cell, reducing proliferation, reducing size and/or mass of a tumor (e.g., solid tumor)), or treatment, healing, prevention, delay of onset, halting, or amelioration of other relevant medical condition(s) associated with a particular cancer. The meaningful benefit observed in the patient can be to any suitable degree (10, 20, 30, 40, 50, 60, 70, 80, 90% or more). In some aspects, one or more symptoms of the cancer are prevented, reduced, halted, or eliminated subsequent to administration of a compound of formula (I), including a compound of formula (Ia), or a prodrug or a pharmaceutically acceptable salt thereof, thereby effectively treating the cancer to at least some degree.

Effective amounts may vary depending upon the biological effect desired in the individual, condition to be treated, and/or the specific characteristics of the compound of formula (I)), including a compound of formula (Ia), or a prodrug or a pharmaceutically acceptable salt thereof, and the individual. In this respect, any suitable dose of the compound of formula (I) or a prodrug or a pharmaceutically acceptable salt thereof can be administered to the patient (e.g., human), according to the type of cancer to be treated. Various general considerations taken into account in determining the "effective amount" are known to those of skill in the art and are described, e.g., in Gilman et al., eds., Goodman And Gilman's: *The Pharmacological Bases of Therapeutics,* 8th ed., Pergamon Press, 1990; and Remington's Pharmaceutical Sciences, 17th Ed., Mack Publishing Co., Easton, Pa., 1990, each of which is herein incorporated by reference. The dose of the compound of formula (I), including a compound of formula (Ia), or a prodrug or a pharmaceutically acceptable salt thereof desirably comprises about 0.1 mg per kilogram (kg) of the body weight of the mammal (mg/kg) to about 400 mg/kg (e.g., about 0.75 mg/kg, about 5 mg/kg, about 30 mg/kg, about 75 mg/kg, about 100 mg/kg, about 200 mg/kg, or about 300 mg/kg). In another embodiment, the dose of the compound of formula (I), including a compound of formula (Ia), comprises about 0.5 mg/kg to about 300 mg/kg (e.g., about 0.75 mg/kg, about 5 mg/kg, about 50 mg/kg, about 100 mg/kg, or about 200 mg/kg), about 10 mg/kg to about 200 mg/kg (e.g., about 25 mg/kg, about 75 mg/kg, or about 150 mg/kg), or about 50 mg/kg to about 100 mg/kg (e.g., about 60 mg/kg, about 70 mg/kg, or about 90 mg/kg).

In an aspect, a compound formula (I) inhibits LDHA and/or LDHB. In an embodiment, a compound of formula (I) is selective for LDHA and/or LDHB relative to other dehydrogenases (e.g., GAPDH and PHGDH). For example, the compound can be at least 2 times (e.g., at least 5 times, at least 10 times, at least 20 times, at least 50 times, or at least 100 times) more selective for LDHA and/or LDHB compared to one or more other dehydrogenases.

While elevated levels of LDHA are a marker for many types of cancer, the majority of which are glycolytic and/or hypoxic, LDHB can be overexpressed in some cancers (e.g., lung adenocarcinoma, prostate cancer). See, e.g., McCleland et al., *Clin Cancer Res,* 2013; 19(4): 773-784 and Leiblich et al., *Oncogene,* 2006; 25(20): 2953-2960. Thus, in some aspects of the invention, it is envisioned to provide a compound that can selectively inhibit LDHB or inhibit both LDHA and LDHA. In an embodiment, a compound of formula (I) can effectively inhibit LDHB. In such embodiments, the compound may or may not have selectivity for LDHA, such that the inhibition is more selective for LDHA compared to LDHB or the inhibition of LDHA is about equal to the inhibition of LDHB or the inhibition is more selective for LDHB relative to LDHA.

Inhibition of LDHA and/or LDHB has been described in the art as a viable treatment of cancer. See, e.g., Billiard et al. (*Cancer and Metabolism,* 2013, 1(19): 1-17). Thus, certain invention compounds of formula (I), which includes compounds of formulas (Ia), or a prodrug or pharmaceutically acceptable salt thereof, can be administered to a patient in need thereof to treat cancer. While not wishing to be bound by any particular theory, it is believed that inhibition of LDH stimulates mitochondrial respiration and reduces cellular proliferative and tumorigenic potential. Anti-cancer activity can be measured by any suitable method, including the assays described herein. In general, activity will be measured as a function of lactate output, % ECAR (extracellular acidification rate), which quantifies glycolysis, and/ or % OCR (oxygen consumption rate), which is a measure of mitochondrial respiration.

The type of cancer is not particularly limited, but in certain aspects, the cancer is characterized as hypoxic and/or highly glycolytic relative to normal tissue of the same type. "Hypoxic" cells as used herein relates to one or more cells that are exposed, transiently or permanently, to an oxygen partial pressure (pO2) that is lower than the typical pO2 in cells in tissue that is considered as normal or healthy. Hypoxic cells can include, for example, cells with reduced or no access to vasculature, such as in a solid tumor.

Examples of cancer treatable with the inventive method include cancers of the head and neck, eye, skin, mouth, throat, esophagus, chest, bone, lung, colon, sigmoid, rectum, stomach, prostate, breast, ovaries, kidney, liver, pancreas, brain, intestine, heart, or adrenals. More particularly, cancers include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-borne tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acutenonlymphocyctic leukemia, acute undifferentiated leukemia, chronic myelocytic leukemia, chronic lymphocytic leukemia, hairy cell leukemia, or multiple myeloma. See, e.g., *Harrison's Principles of Internal Medicine*, Eugene Braunwald et al., eds., pp. 491 762 (15th ed. 2001). In some aspects, the cancer is a solid tumor. In accordance with an embodiment, the cancer is selected from leukemia, melanoma, liver cancer, pancreatic cancer, lung cancer, colon cancer, brain cancer, ovarian cancer, breast cancer, prostate cancer, and renal cancer. In another embodiment, the cancer is liver cancer, pancreatic cancer, non-small cell lung cancer, breast cancer, or renal cancer.

The invention provides a method of treating a patient with cancer cells resistant to an anti-cancer agent, comprising administering to the patient an effective amount of the compound of formula (I), including a compound of formula (Ia), or a prodrug or a pharmaceutically acceptable salt thereof, and the anti-cancer agent, whereby the compound, prodrug, or pharmaceutically acceptable salt thereof re-sensitizes the cancer cells to the anti-cancer agent. The cancer cell is the same as described herein. In accordance with an embodiment, the cancer cells are selected from leukemia, melanoma, liver cancer, pancreatic cancer, lung cancer, colon cancer, brain cancer, ovarian cancer, breast cancer, prostate cancer, and renal cancer. In another embodiment, the cancer cells are liver cancer, pancreatic cancer, non-small cell lung cancer, breast cancer, or renal cancer.

In certain embodiments of this method, the compound of formula (I), including a compound of formula (Ia), or a prodrug or a pharmaceutically acceptable salt thereof can be co-administered with an anti-cancer agent (e.g., a chemotherapeutic agent) and/or radiation therapy. In an aspect, the method comprises administering an amount of a compound, prodrug, or salt that is effective to sensitize the cancer cells to one or more therapeutic regimens (e.g., chemotherapy or radiation therapy). The terms "co-administered" or "co-administration" refer to simultaneous or sequential administration. A compound may be administered before, concurrently with, or after administration of another compound.

One or more than one, e.g., two, three, or more anti-cancer agents can be administered. In this regard, the present invention is directed a pharmaceutical composition comprising a pharmaceutically acceptable carrier and a combination of the compound of formula (I), including a compound of formula (Ia), or a prodrug or a pharmaceutically acceptable salt thereof and at least one anti-cancer agent (e.g., chemotherapeutic agent).

Examples of anti-cancer agents include platinum compounds (e.g., cisplatin, carboplatin, oxaliplatin), alkylating agents (e.g., cyclophosphamide, ifosfamide, chlorambucil, nitrogen mustard, thiotepa, melphalan, busulfan, procarbazine, streptozocin, temozolomide, dacarbazine, bendamustine), antitumor antibiotics (e.g., daunorubicin, doxorubicin, idarubicin, epirubicin, mitoxantrone, bleomycin, mytomycin C, plicamycin, dactinomycin), taxanes (e.g., paclitaxel and docetaxel), antimetabolites (e.g., 5-fluorouracil, cytarabine, premetrexed, thioguanine, floxuridine, capecitabine, and methotrexate), nucleoside analogues (e.g., fludarabine, clofarabine, cladribine, pentostatin, nelarabine), topoisomerase inhibitors (e.g., topotecan and irinotecan), hypomethylating agents (e.g., azacitidine and decitabine), proteosome inhibitors (e.g., bortezomib), epipodophyllotoxins (e.g., etoposide and teniposide), DNA synthesis inhibitors (e.g., hydroxyurea), vinca alkaloids (e.g., vicristine, vindesine, vinorelbine, and vinblastine), tyrosine kinase inhibitors (e.g., imatinib, dasatinib, nilotinib, sorafenib, sunitinib), monoclonal antibodies (e.g., rituximab, cetuximab, panetumumab, tositumomab, trastuzumab, alemtuzumab, gemtuzumab ozogamicin, bevacizumab), nitrosoureas (e.g., carmustine, fotemustine, and lomustine), enzymes (e.g., L-Asparaginase), biological agents (e.g., interferons and interleukins), hexamethylmelamine, mitotane, angiogenesis inhibitors (e.g., thalidomide, lenalidomide), steroids (e.g., prednisone, dexamethasone, and prednisolone), hormonal agents (e.g., tamoxifen, raloxifene, leuprolide, bicaluatmide, granisetron, flutamide), aromatase inhibitors (e.g., letrozole and anastrozole), arsenic trioxide, tretinoin, nonselective cyclooxygenase inhibitors (e.g., nonsteroidal anti-inflammatory agents, salicylates, aspirin, piroxicam, ibuprofen, indomethacin, naprosyn, diclofenac, tolmetin, ketoprofen, nabumetone, oxaprozin), selective cyclooxygenase-2 (COX-2) inhibitors, or any combination thereof.

For purposes of the present invention, the term "patient" typically is directed to a mammal. For example, the subject can be any patient with a disease that requires chemotherapy and/or radiation therapy. Mammals include, but are not limited to, the order Rodentia, such as mice, and the order Logomorpha, such as rabbits. In some aspects, the mammals are from the order Carnivora, including Felines (cats) and Canines (dogs), Artiodactyla, including Bovines (cows) and Swines (pigs) or of the order Perssodactyla, including Equines (horses). In some aspects, the mammals are of the order Primates, Ceboids, or Simioids (monkeys) or of the order Anthropoids (humans and apes). In embodiments of the invention, the patient is a human.

The invention is further directed to a method of inhibiting lactate dehydrogenase A (LDHA) and/or lactate dehydrogenase b (LDHB) activity in a cell comprising administering a compound of formula (I), including a compound of formula (Ia), or a prodrug or a pharmaceutically acceptable salt thereof to a cell, whereby activity of LDHA and/or LDHB is inhibited. LDHA and LDHB activity can be measured by any method known in the art for measuring enzyme inhibitions, including by the assays described herein. Typically, inhibition of LDHA and LDHB activity will be demonstrated by a decrease in lactate accumulation and/or an increase in pyruvate relative to a control sample.

The following examples are provided for further illustration, and should not be construed as limiting in any way.

EXAMPLES

Example 1

This example describes a human LDHA primary biochemical assay employed in the characterization of a compound of formula (I) in an embodiment of the invention.

Test compounds were placed in a Greiner Bio-One (Monroe, N.C.) 1536-well black solid bottom assay plate. 200 millimolar (mM) Tris HCl, pH 7.4, 100 micromolar (μM) EDTA and 0.01% TWEEN-20™, final concentration, was used as the assay buffer. The LDHA reagent was 2 nanomolar (nM) Human LDHA (Meridian Life Science, Inc., Memphis, Tenn.), final concentration, in assay buffer. The substrate reagent was 0.06 mM NADH and 0.2 mM sodium pyruvate, final concentration, in assay buffer. The resazurin/diaphorase coupling reagent was 0.037 mM resazurin and 0.133 milligrams per milliliter (mg/mL) diaphorase, final concentration, in assay buffer. The sequence of steps, amount and types of reagents, and time required for each step are set forth in Table 1. The inhibition of LDHA activity was measured by fluorescence emission.

TABLE 1

| Sequence | Parameter | Value | Notes |
| --- | --- | --- | --- |
| 1 | Reagent | 3 μL | LDHA reagent |
| 2 | Compound | 23 nL | Compound of formula (I) |
| 3 | Time | 15 min | RT incubation |
| 4 | Reagent | 1 μL | Substrate reagent |
| 5 | Time | 7 min | RT incubation |
| 6 | Reagent | 1 μL | Resazurin/diaphorase coupling reagent |
| 7 | Detector | Fluorescence (ex 525 nm/em 598 nm) | VIEWLUX ™ in endpoint mode: 2 sec exp., 5000 excitation energy |

Example 2

This example describes a human LDHB counterscreen biochemical assay employed in the characterization of a compound of formula (I) in an embodiment of the invention.

Test compounds were placed in a Greiner Bio-One (Monroe, N.C.) 1536-well black solid bottom assay plate. 200 mM Tris HCl, pH 7.4, 100 μM EDTA and 0.01% TWEEN-20™, final concentration, was used as the assay buffer. The LDHB reagent was 2 nM Human LDHB (Meridian Life Science, Inc., Memphis, Tenn.), final concentration, in assay buffer. The substrate reagent was 0.13 mM NADH and 0.16 mM sodium pyruvate, final concentration, in assay buffer. The resazurin/diaphorase coupling reagent was 0.037 mM resazurin and 0.133 mg/mL diaphorase, final concentration, in assay buffer. The sequence of steps, amount and types of reagents, and time required for each step are set forth in Table 2. The inhibition of LDHB activity was measured by fluorescence emission.

TABLE 2

| Sequence | Parameter | Value | Notes |
| --- | --- | --- | --- |
| 1 | Reagent | 3 μL | LDHB reagent |
| 2 | Compound | 23 nL | Compound of formula (I) |
| 3 | Time | 15 min | RT incubation |
| 4 | Reagent | 1 μL | Substrate reagent |
| 5 | Time | 7 min | RT incubation |
| 6 | Reagent | 1 μL | Resazurin/diaphorase coupling reagent |
| 7 | Detector | Fluorescence (ex 525 nm/em 598 nm) | VIEWLUX ™ in endpoint mode: 2 sec exp., 5000 excitation energy |

Example 3

This example describes a human PHGDH counterscreen biochemical assay employed in the characterization of a compound of formula (I) in an embodiment of the invention.

Test compounds were placed in a Greiner Bio-One (Monroe, N.C.) 1536-well black solid bottom assay plate. 50 mM TEA, pH 8.0, 10 mM $MgCl_2$, 0.05% BSA, and 0.01% TWEEN-20™, final concentration, was used as the assay buffer. The substrate reagent was 10 μM EDTA, 0.625 mM glutamate, 500 nM human PSAT1, 500 nM human PSPH, 0.05 mM 3-phosphoglycerate, 0.1 mM resazurin, and 0.1 mg/mL diaphorase, final concentration, in assay buffer. The PHGDH reagent was 0.15 mM $NAD^+$ and 10 nM human PHGDH, final concentration, in assay buffer. The sequence of steps, amount and types of reagents, and time required for each step are set forth in Table 3. The inhibition of PHGDH activity was measured by fluorescence emission.

TABLE 3

| Sequence | Parameter | Value | Notes |
| --- | --- | --- | --- |
| 1 | Reagent | 3 μL | Substrate reagent |
| 2 | Compound | 23 nL | Compound of formula (I) |
| 3 | Reagent | 1 μL | PHGDH reagent |
| 4 | Detector | Fluorescence (ex 525 nm/em 598 nm) | VIEWLUX ™ in endpoint mode: 2 sec exp., 5000 excitation energy, use Δ between 0 and 30 min |

Example 4

This example describes a human GAPDH counterscreen biochemical assay employed in the characterization of a compound of formula (I) in an embodiment of the invention.

Test compounds were placed in a Greiner Bio-One (Monroe, N.C.) 1536-well black solid bottom assay plate. 105 mM Tris HCl, pH 7.4, 10 μM EDTA, 1.27 mM $KH_2PO_4$, 0.875 mM $MgCl_2$, 0.0875% BSA, 0.01 mM DTT, and 0.01% TWEEN-20™, final concentration, was used as the assay buffer. The substrate reagent was 0.48 mM glyceraldehyde 3-phosphate, 0.06 mM resazurin, and 0.21 mg/mL diaphorase, final concentration, in assay buffer. The GAPDH reagent was 0.007 mM $NAD^+$ and 2.5 nM human GAPDH, final concentration, in assay buffer. The sequence of steps, amount and types of reagents, and time required for each step are set forth in Table 4. The inhibition of GAPDH activity was measured by fluorescence emission.

TABLE 4

| Sequence | Parameter | Value | Notes |
| --- | --- | --- | --- |
| 1 | Reagent | 3 μL | Substrate reagent |
| 2 | Compound | 23 nL | Compound of formula (I) |
| 3 | Reagent | 1 μL | GAPDH reagent |

TABLE 4-continued

| Sequence | Parameter | Value | Notes |
|---|---|---|---|
| 4 | Detector | Fluorescence (ex 525 nm/em 598 nm) | VIEWLUX ™ in kinetic mode: 1 sec exp., 5000 excitation energy, use Δ between 0 and 20 min |

Example 5

This example describes cell-based metabolite assay by mass spectrometry (MS) employed in the characterization of a compound of formula (I) in an embodiment of the invention.

The sequence of steps, amount and types of reagents, and time required for each step are set forth in Table 5.

TABLE 5

| Sequence | Parameter | Value | Notes |
|---|---|---|---|
| 1 | Reagent | Snu398 cells | 100k/well in 100 µL RPMI 10% FBS - phenol red |
| 2 | Time | 24 h | 37° C., 5% $CO_2$ incubation |
| 3 | Reagent | Wash | Aspirate media and replace with fresh |
| 4 | Reagent | Compound | Dose LDHA inhibitors/controls in media |
| 5 | Time | 48 h | 37° C., 5% $CO_2$ incubation |
| 6 | Reagent | Media | Aspirate 75 µL of media and collect in separate plate. Snap freeze and store at −80° C. Pyruvate/lactate/NADH ion counts collected by Quintara Discovery, Inc. using MS-MS. |

Example 6

This example describes a cell-based metabolite assay by colorimetric/fluorometric detection employed in the characterization of a compound of formula (I) in an embodiment of the invention.

Cell-based HT Lactate assay is a miniaturized Biovision Lactate Colorimetric/Fluorometric Assay Kit (Cat #K607-100). The assay is roughly a 3.5 hour assay run in a 1536 plate format. Cell number optimization should be run for each cell line to achieve an optimal number in which lactate production equals roughly 90% of the standard curve range. Cell number per well optimization has been performed with the following cell lines: MiaPaCa2—500 cells/well, SNU398—500 cells/well, and P493—500 cells/well. The sequence of steps, amount and types of reagents, and time required for each step are set forth in Table 6.

TABLE 6

| Sequence | Parameter | Value | Notes |
|---|---|---|---|
| 1 | Reagent | MiaPaCa2 cells | 500/well in 4 µL in DMEM 4.5 g/L Glucose, - Glutamate, - FBS, - Phenol Red |
| 2 | Reagent | Compound | Dose LDHA inhibitors with pin tool |
| 3 | Time | 2.5 hr | 37° C., 5% CO2 incubation |
| 4 | Reagent | Compound | 2 µL/well |
| 5 | Time | 48 h | RT |
| 6 | Read | Media | Absorbance (570 nm) and Fluorescence (Ex/Em = 535/590 nm) |

Examples 7-33 describe general methodology to prepare the instantly claimed compounds.

Example 7

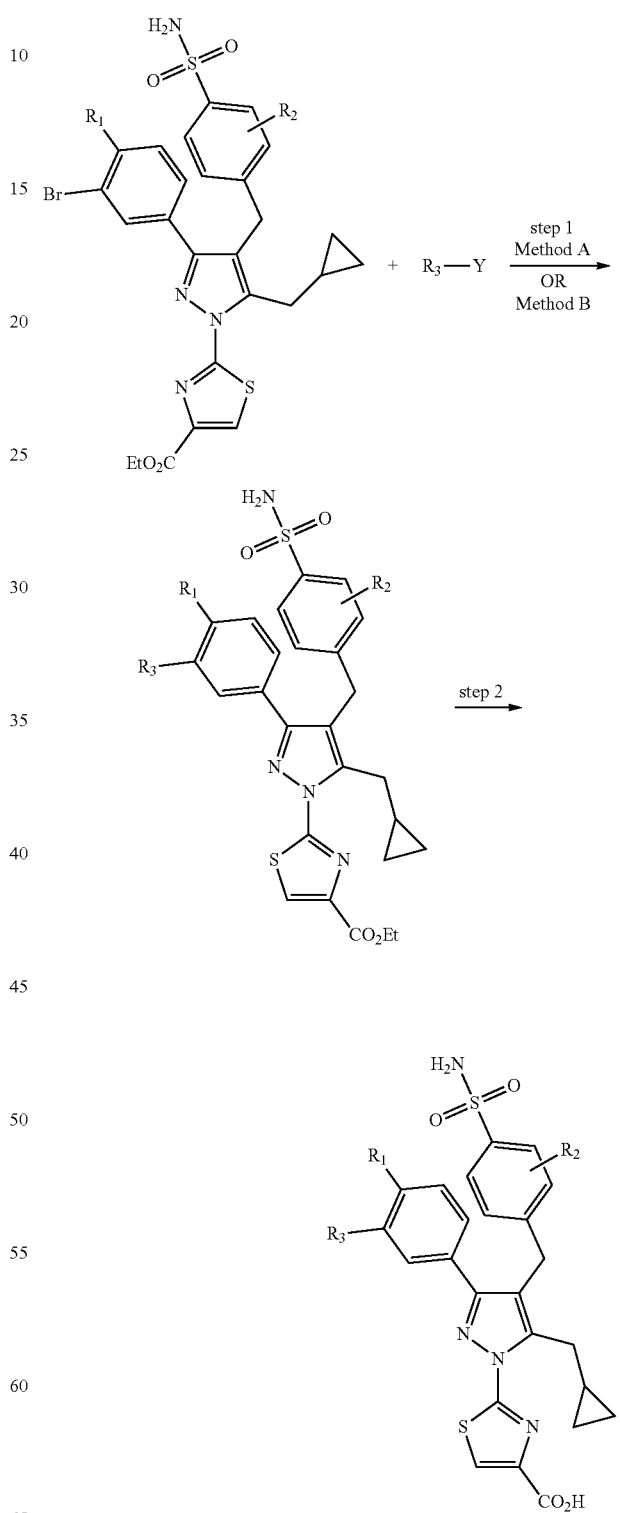

-continued $R_1$ = H or F
$R_2$ = 2-F, 3-F, 2-Cl
$R_3$ = Aryl, heteroaryl, alkynyl, alkenyl Y = -H, -B(OH)$_2$, -BF$_3^-$K$^+$, 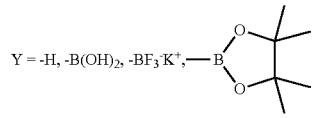

Step 1: General Synthesis of ethyl 2-(3-(3-substituted-4-substitutedphenyl)-5-(cyclopropylmethyl)-4-(3-substituted-4-sulfamoylbenzyl)-1H-pyrazol-1-yl)thiazole-4-carboxylate Method A—Dioxane (2 mL) and water (0.5 mL) were added to a mixture of ethyl 2-(3-(3-bromo-4-substitutedphenyl)-5-(cyclopropylmethyl)-4-(3-substituted-4-sulfamoylbenzyl)-1H-pyrazol-1-yl)thiazole-4-carbox-ylate (0.2 mmol, 1 eq), potassium phosphate (0.4 mmol, 2 eq), S-PHOS (5 mol %), SPhos Palladacycle G3 (2.5 mol %) and appropriate boronic acid/ester or potassium trifluoroborate in a sealed microwave vial. The reaction mixture was bubbled with argon for few minutes then stirred at 100° C. in a preheated heating block for 1-6 h. Upon completion of the reaction as detected by LCMS, the reaction mixture was cooled and stirred with a metal scavenger for 1 h. The reaction mixture was then diluted with ethyl acetate and filtered through a pad of celite. The filtrate was concentrated and purified directly on silica using gradient elution (20-40% ethyl acetate in hexanes).

Method B—A mixture of ethyl 2-(3-(3-bromo-4-substituted phenyl)-5-(substituted)-4-(3/4-fluoro-4-sulfamoylbenzyl)-1H-pyrazol-1-yl)thiazole-4-carboxylate (1 mmol), tri(tert-butylphosphonium)tetrafluoroborate (10 mol %), allylpalladium chloride dimer (5 mol %) and DABCO (2 mmol, 2 eq) in dioxane (0.5 molar concentration) was bubbled with argon for 5 minutes. The appropriate alkyne (1.5 mmol, 1.5 eq) was added and the reaction mixture was stirred at room temperature overnight. After completion of the reaction, silica bound palladium scavenger was added and the slurry was stirred at room temperature for 1 hr, subsequently diluted with ethyl acetate and filtered through a pad of celite. The filtrate was concentrated and the residue was purified directly on silica using gradient elution (20-40% ethyl acetate in hexanes) yielding the desired compound which was taken to the next step.

Step 2: 2-(3-(3-substituted-4-substitutedphenyl)-5-(cyclopropylmethyl)-4-(3-substituted-4-sulfamoylbenzyl)-1H-pyrazol-1-yl)thiazole-4-carboxylic Acid A 1.5 molar solution of LiOH in water was added to a solution of ethyl 2-(3-(3-substituted-4-substitutedphenyl)-5-(cyclopropylmethyl)-4-(3-substituted-4-sulfamoylbenzyl)-1H-pyrazol-1-yl)thiazole-4-carboxylate (1 eq) in THF/MeOH (3 mL/1.5 mL) and stirred at room temperature for 0.5-1 h. After completion of the reaction, the solvent was evaporated under reduced pressure, and the residue was taken up in DMSO. Finally the title compound was purified on preparative HPLC.

Example 8

This example describes the synthesis of 2-(5-(alkyl)-3-phenyl-4-(4-sulfamoylbenzyl)-1H-pyrazol-1-yl)thiazole-4-carboxylic acids and 2-(3-(alkyl)-5-phenyl-4-(4-sulfamoylbenzyl)-1H-pyrazol-1-yl)thiazole-4-carboxylic acids in an embodiment of the invention. See Scheme 1.

SCHEME 1

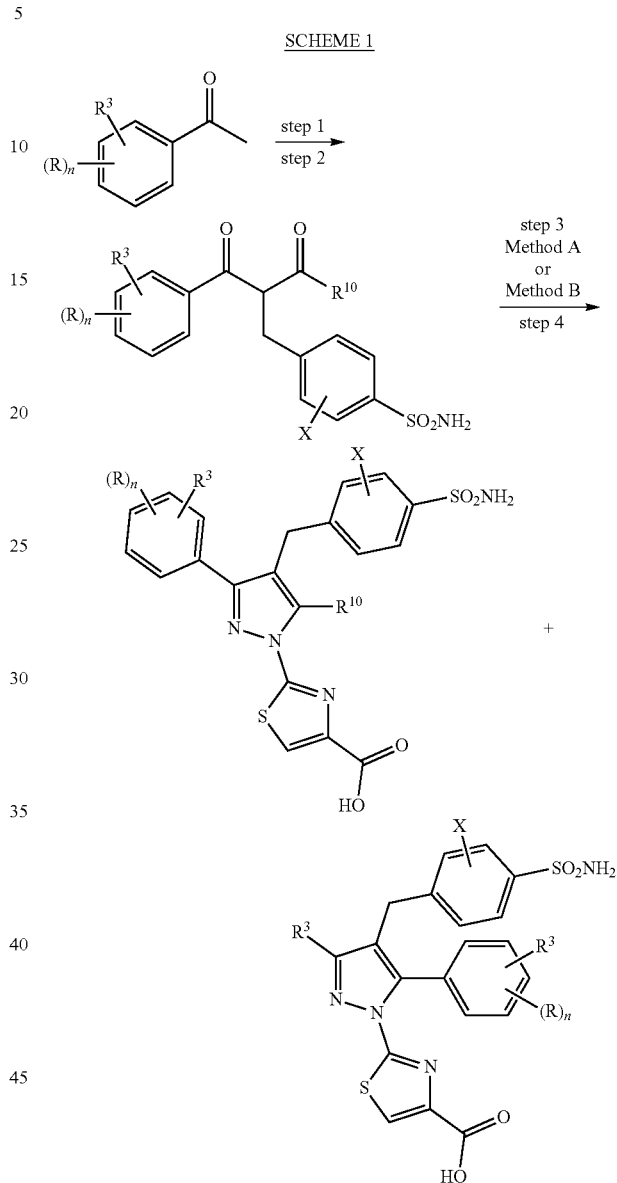

Step 1: Synthesis of 1-phenyl-3-alkyl-1,3-diones

To a stirring solution of 1-(1H-benzo[d][1,2,3]triazol-1-yl)-2-alkyl ketone (200 mmol) and magnesium bromide diethyl etherate (413 mmol) in CH$_2$Cl$_2$ was added 1-phenylethanone derivatives (165 mmol). Diisopropyl ethyl amine (500 mmol) was added dropwise over several minutes and the reaction mixture was stirred at rt for 2 h. Upon completion as detected by LCMS, the reaction was slowly quenched with 1.0 M HCl and washed with 1.0 M HCl and brine. The residue was dried over Na$_2$SO$_4$, filtered, and concentrated under reduced pressure. The residue was purified directly on silica using gradient elution (0-30% ethyl acetate in hexanes over 20 CV). The resulting oils were used in the next step without further purification or characterization.

Step 2: Synthesis of 4-(2-benzoyl-3-oxo)-3-alkyl-benzenesulfonamides 1-phenyl-3-alkyl-1,3-diones (150 mmol) and cesium carbonate ($Cs_2CO_3$, 226 mmol) were dissolved in DMSO (50 ml). The reaction mixture was stirred at rt for 10 minutes at which time potassium iodide were added (KI, 150 mmol) and 4-(bromomethyl)-benzenesulfonamides (165 mmol). The resulting mixture was stirred at rt for 1 h. Upon completion as detected by LCMS, the reaction mixture was diluted with a large excess of ethyl acetate and filtered through celite. The filtrate was washed with 1 M HCl, sat aq $NH_4Cl$ and brine, dried over $Na_2SO_4$, filtered, and concentrated under reduced pressure. The residue was purified directly on silica using gradient elution (20-40% ethyl acetate in hexanes over 16 CV).

Step 3: ethyl 2-(5-(alkyl)-3-phenyl)-4-(4-sulfamoyl-benzyl)-1H-pyrazol-1-yl)thiazole-4-carboxylates Method A—A solution of 4-(2-benzoyl-3-oxo)-3-alkyl-benzenesulfonamide (6.7 mmol), ethyl 2-hydrazinylthiazole-4-carboxylate, 2 HBr (7.3 mmol) and p-toluene sulfonic acid (pTsOH, 20 mmol) in dioxane was heated in a sealed vessel in the microwave for 15 min at 160° C.

Upon completion as detected by LCMS, the reaction mixture was diluted with ethyl acetate and filtered through celite. The solvent was removed under reduced pressure and the crude product was purified directly on silica using gradient elution (0-100% ethyl acetate in hexanes over 15 CV).

Method B—A solution of 4-(2-(benzoyl)-3-oxo-3-alkyl-benzenesulfonamide (113 mmol), p-toluene sulfonic acid (pTsOH, 57 mmol) and pyrrolidine (57 mmol) in ethanol was stirred at 100° C. for 1 h, after which time ethyl 2-hydrazinylthiazole-4-carboxylate, 2 HBr (136 mmol) was added. The resulting reaction mixture was refluxed overnight. Upon completion as detected by LCMS, the solvent was removed under reduced pressure and the residue was purified without work-up directly on silica using gradient elution (20-40% ethyl acetate in hexanes over 20 CV). A mixture of regioisomers was collected as a single peak. After removing the solvent, the regioisomers were separated via reverse phase preparative column using gradient elution (50-100% acetonitrile modified with 0.1% TFA in water modified with 0.1% TFA over 25 CV). The second elution peak was pooled and concentrated, and the resulting solid was stirred with a clear solution of $NaHCO_3$. The precipitate was collected by filtration, washed with water and sequentially dried, first under air overnight then by high vacuum under $P_2O_5$, resulting in a colorless powder.

Step 4: Synthesis of 2-(5-(alkyl)-3-phenyl)-4-(4-sulfamoylbenzyl)-1H-pyrazol-1-yl)thiazole-4-carboxylic Acids To a solution of ethyl 2-(5-(alkyl)-3-phenyl)-4-(4-sulfamoylbenzyl)-1H-pyrazol-1-yl)thiazole-4-carboxylate (0.07 mmol) in THF/MeOH was added 1.5 M LiOH (0.27 mmol). The reaction mixture was stirred at rt for 1 h. Upon completion as detected by LCMS, the solvent was removed by forced air. The residue was taken into DMSO and purified directly via preparative reverse phase using gradient elution (4-100% acetonitrile modified with 0.1% TFA in water modified with 0.1% TFA). The product fractions were directly frozen and lyophilized overnight, yielding an off-white powder.

Example 9

This example describes the preparation of tert-butyl 2-bromothiazole-4-carboxylate 1 in an embodiment of the invention. See Scheme 2.

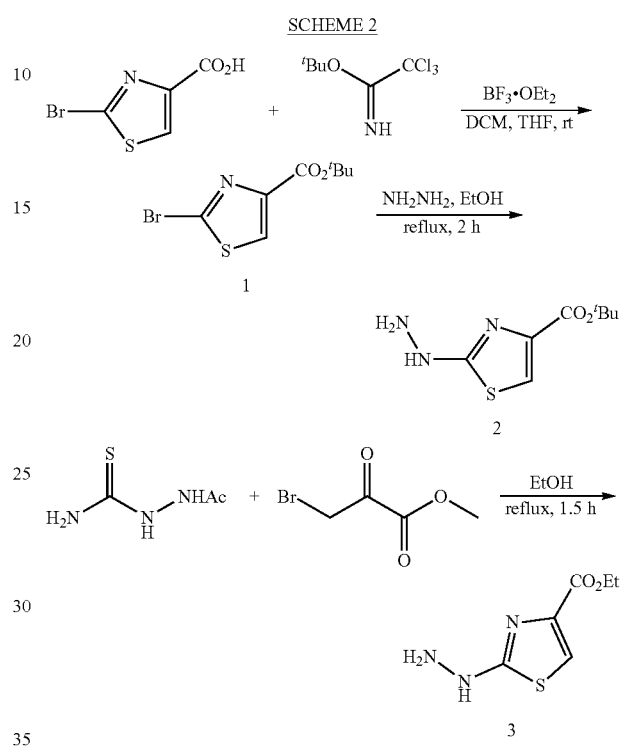

SCHEME 2

Tert-butyl 2,2,2-trichloroacetimidate (17.20 ml, 96 mmol, 2 eq) was added to a stirred suspension of 2-bromothiazole-4-carboxylic acid (10 g, 48.1 mmol, 1 eq) in dichloromethane (DCM) (100 mL) and tetrahydrofuran (THF) (50 mL), followed by dropwise addition of $BF_3.OEt_2$ (0.938 ml, 7.40 mmol, 10 mol %). The mixture was stirred at room temperature for 16 h, concentrated, quenched slowly with a saturated bicarbonate solution, and extracted with ethyl acetate. The organic layer was washed with saturated bicarbonate and brine, then dried, and the crude product was purified in a Biotage (Charlotte, N.C.) flash system eluting with 5-30% ethyl acetate in hexanes over 12 column volumes. The product fraction was concentrated to provide tert-butyl 2-bromothiazole-4-carboxylate 1 as a white solid (10.4 g, 82%).

Example 10

This example describes the preparation of tert-butyl 2-hydrazinylthiazole-4-carboxylate 2 in an embodiment of the invention. See Scheme 2.

A solution of tert-butyl 2-bromothiazole-4-carboxylate 1 (10.96 g, 41.5 mmol, 1 eq) from Example 1 and hydrazine hydrate (13 ml, 415 mmol, 10 eq) in EtOH (80 mL) was refluxed for 2 hr. After completion of the reaction, the solvent was removed and ice water was added. The precipitate formed was collected by filtration, washed with cold water, and dried under air. The crude product (tert-butyl 2-hydrazinylthiazole-4-carboxylate 2) was pure enough to be used for the following reaction.

Example 11

This example describes the preparation of ethyl 2-hydrazinylthiazole-4-carboxylate 3 in an embodiment of the invention. See Scheme 2.

Ethyl bromopyruvate (15.71 ml, 113 mmol) was added to a suspension of 2-acetylhydrazinecarbothioamide (15 g, 113 mmol) in ethanol (200 mL) and stirred at room temperature for 30 minutes until the solution became clear, then refluxed for 1.5 h. The solution was then concentrated and agitated with 20 mL of MeOH and 300 mL of ether. The yellow precipitate was collected by filtration, washed with ether, and dried to obtain a yellow solid (ethyl 2-hydrazinylthiazole-4-carboxylate 3) as HBr salt.

Example 12

This example describes a general procedure for the synthesis of substituted benzoyl acetonitriles 4 in an embodiment of the invention. See Scheme 3.

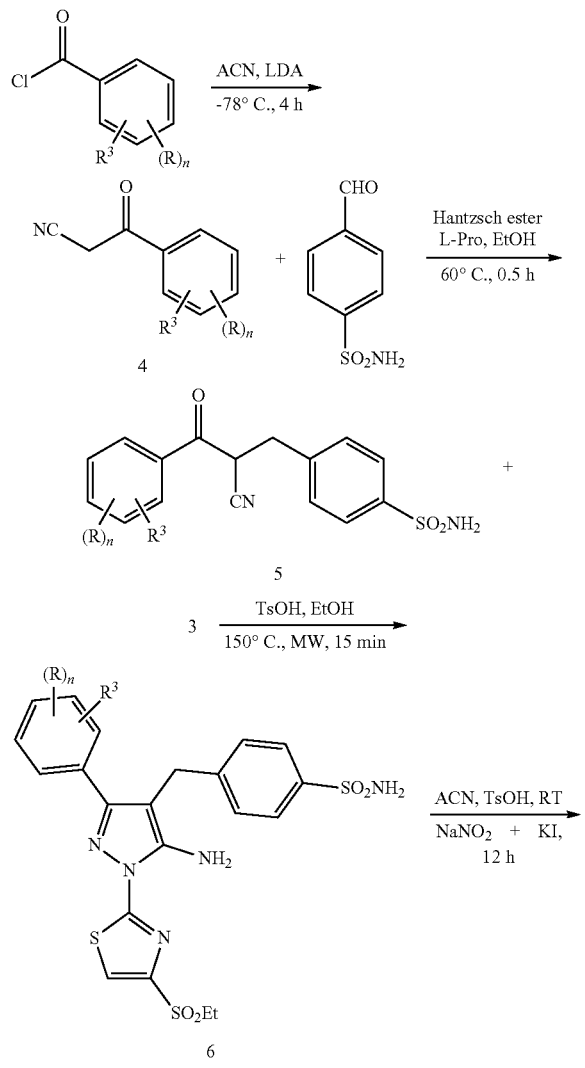

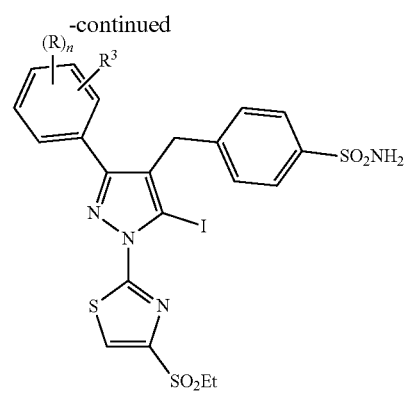

Acetonitrile (ACN) (5.33 ml, 102 mmol, 2 eq) was added dropwise to a cooled solution of 1 molar lithium diisopropylamide (LDA) (102 ml, 102 mmol, 2 eq) in THF (40 mL) at −78° C. The reaction mixture was stirred for 30 minutes, and then a solution of an acid chloride (51.0 mmol, 1 eq) in 20 mL of THF was added dropwise over 15 minutes. The reaction was allowed to come to room temperature over 4 h and then quenched with 1 M (molar) HCl. The product was extracted ethyl acetate. The organic layer was subsequently washed with water and brine and dried over $MgSO_4$. The crude product was purified on Biotage (Charlotte, N.C.) flash system eluting with 5-75% ethyl acetate in hexanes over 12 column volumes to obtain a substituted benzoyl acetonitrile 4 as a yellow solid.

Example 13

This example describes a general procedure for the synthesis of 4-(2-cyano-3-oxo-3-arylpropyl)benzenesulfonamide 5 in an embodiment of the invention. See Scheme 3.

2,6-Dimethyl-1,4-dihydro-pyridine-3,5-dicarboxylic acid diethyl ester (Hantzsch ester) (12.21 g, 48.2 mmol, 1.4 eq) and L-proline (0.793 g, 6.89 mmol, 20 mol %) were added to a solution of 3-oxo-3-phenyl-propanenitrile 4 (34.4 mmol, 1 eq) and 4-formylbenzenesulfonamide (7.02 g, 37.9 mmol, 1.1 eq) in ethanol (150 mL). The mixture was stirred at 60° C. for 30 minutes. The mixture was then cooled, mixed with silica gel, concentrated, and purified on a Biotage (Charlotte, N.C.) flash system with 20-100% ethyl acetate in hexanes over 6 column volumes then with 100% ethyl acetate over 8 column volumes to obtain 4-(2-cyano-3-oxo-3-arylpropyl)benzenesulfonamide 5 as a white solid.

Example 14

This example describes a general procedure for the synthesis of 2-(5-amino-3-aryl-4-(4-sulfamoylbenzyl)-1H-pyrazol-1-yl)thiazole-4-carboxylate 6 in an embodiment of the invention. See Scheme 3.

A mixture of ethyl 2-hydrazinylthiazole-4-carboxylate hydrogen bromide salt (3, 1.5 g, 5.59 mmol, 1 eq), 4-(2-cyano-3-oxo-3-arylpropyl)benzenesulfonamide (5.59 mmol, 1 eq) and tosic acid (2.128 g, 11.19 mmol, 2 eq) in ethanol (15 mL) was heated in a microwave for 15 minutes. The precipitate formed was collected by filtration and washed with cold ethanol to obtain pure product (ethyl 2-(5-amino-3-aryl-4-(4-sulfamoylbenzyl)-1H-pyrazol-1-yl)thiazole-4-carboxylate 6) as a yellow solid.

Example 15

This example describes a general procedure for the synthesis of ethyl 2-(5-iodo-3-aryl-4-(4-sulfamoylbenzyl)-1H-pyrazol-1-yl)thiazole-4-carboxylate 7 in an embodiment of the invention. See Scheme 3.

Tosic acid (5.37 g, 28.2 mmol, 3.5 eq) was added to a suspension of ethyl 2-(5-amino-3-aryl-4-(4-sulfamoylbenzyl)-1H-pyrazol-1-yl)thiazole-4-carboxylate 6 (8.07 mmol, 1 eq) in ACN (100 mL) and stirred for 10 minutes. During this period, the solution became clear, then a premixed solution of NaNO$_2$ (1.113 g, 16.13 mmol, 2 eq) and KI (4.02 g, 24.20 mmol, 3 eq) in 10 mL water was added dropwise over a period of 10-15 minutes at room temperature. The reaction mixture was allowed to stir at room temperature overnight. After completion of the reaction, the excess solvent was removed under reduce pressure, and the crude product was extracted with ethyl acetate. The organic layer was subsequently washed with saturated sodium thiosulfate solution, water, and brine. The crude product was purified on a Biotage (Charlotte, N.C.) flash system using a high performance column eluting with either 1-15% acetone in dichloromethane or 1-100% ethyl acetate in hexanes over 20 column volumes to obtain pure products.

Example 16

This example describes a general procedure for the trifluoromethylation of ethyl 2-(5-iodo-3-aryl-4-(4-sulfamoylbenzyl)-1H-pyrazol-1-yl)thiazole-4-carboxylates 7 in an embodiment of the invention.

A mixture of ethyl 2-(5-iodo-3-aryl-4-(4-sulfamoylbenzyl)-1H-pyrazol-1-yl)thiazole-4-carboxylate 7 (0.4 g, 0.673 mmol) 7 and 1,10-phenanthroline)(trifluoromethyl)copper (I) 8 (0.316 g, 1.009 mmol, 1.5 eq) was degassed with argon, then DMF (2 mL) was added and stirred at 55° C. for 1 h. The reaction mixture was diluted with ethyl acetate and washed with 1 molar HCl, water, and brine. The organic layer was dried with MgSO$_4$, concentrated, and purified on a Biotage (Charlotte, N.C.) flash system eluting with 20-100% ethyl acetate in hexanes over 12 column volumes to obtain an ethyl 2-(5-trifluoromethyl-3-aryl-4-(4-sulfamoylbenzyl)-1H-pyrazol-1-yl)thiazole-4-carboxylate 9 as a white solid.

Example 17

This example describes a general procedure for the Suzuki coupling of ethyl 2-(5-iodo-3-aryl-4-(4-sulfamoylbenzyl)-1H-pyrazol-1-yl)thiazole-4-carboxylates 7 in an embodiment of the invention. See Scheme 4.

In a sealed microwave vial, 2 molar Na$_2$CO$_3$ (0.17 mL, 0.336 mmol, 2 eq) was added to a mixture of ethyl 2-(5-iodo-3-aryl-4-(4-sulfamoylbenzyl)-1H-pyrazol-1-yl)thiazole-4-carboxylate 7 (0.168 mmol, 1 eq), SILIACAT™ DPP-Pd (0.1 g), boronic acid (0.336 mmol, 2 eq) in dimethyl ether (DME) (2 mL), then heated in a microwave for 30 minutes at 130° C. The reaction mixture was concentrated by blowing forced air. The residue was taken up in DMF (2 mL) and stirred with a silica-bound DMT, followed by filtering

SCHEME 4

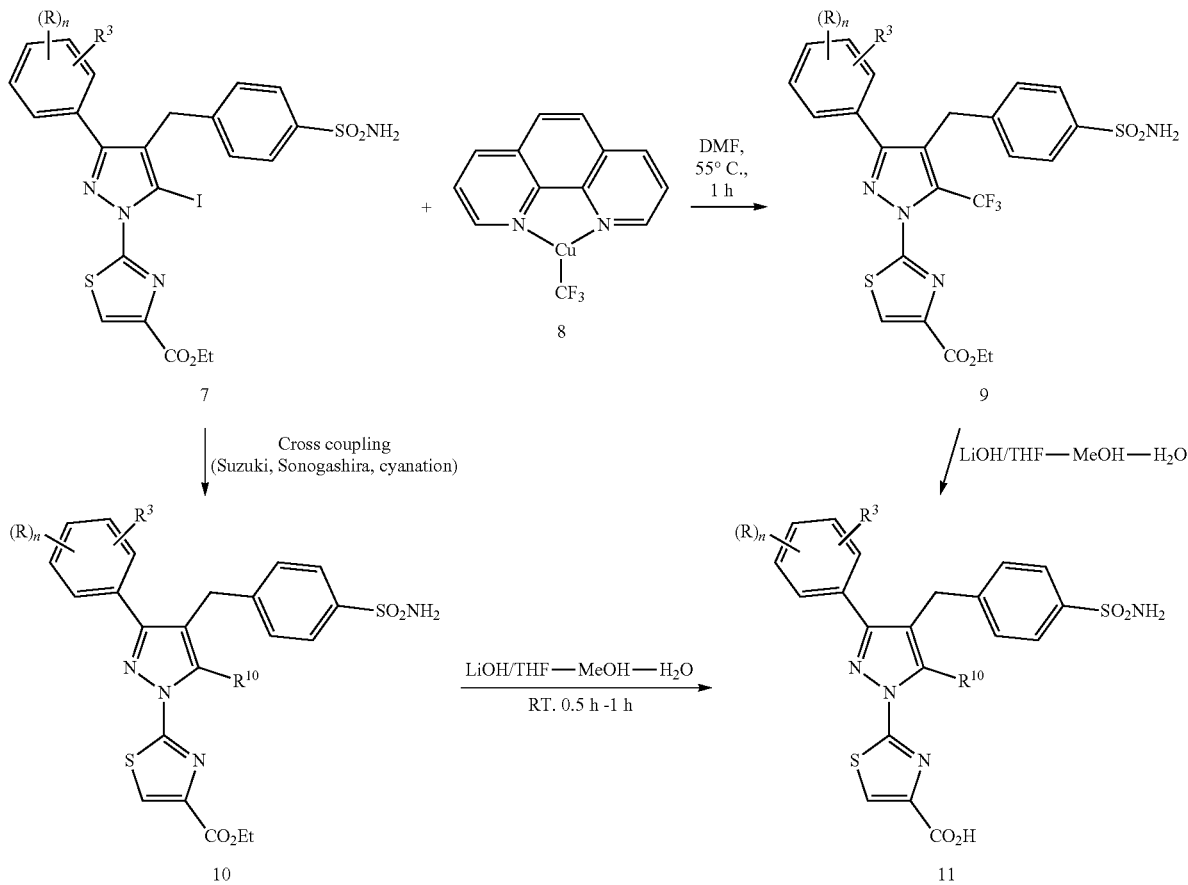

through a thiol resin cartridge to remove any leached palladium. Finally the compounds were purified on a preparative HPLC to obtain pure coupling products 10.

Example 18

This example describes a general procedure for the Sonogashira coupling of ethyl 2-(5-iodo-3-aryl-4-(4-sulfamoylbenzyl)-1H-pyrazol-1-yl)thiazole-4-carboxylates (7) in an embodiment of the invention. See Scheme 4.

A mixture of ethyl 2-(5-iodo-3-aryl-4-(4-sulfamoylbenzyl)-1H-pyrazol-1-yl)thiazole-4-carboxylate 7 (0.202 mmol, 1 eq), bis(triphenylphosphine)palladium(II) chloride (0.014 g, 0.020 mmol, 10 mol %), and CuI (3.84 mg, 0.020 mmol, 10 mol %) in THF (1 mL) was added triethylamine (TEA) (0.169 ml, 1.211 mmol, 6 eq) followed by the alkyne (0.404 mmol, 2 eq) under a nitrogen atmosphere. The vial was sealed and stirred at 80° C. for 4 h. After completion of the reaction, the product was extracted with ethyl acetate and the organic layer was washed with 1 molar HCl and brine. The crude product was purified on a Biotage (Charlotte, N.C.) flash system eluting with 20-100% ethyl acetate or in preparative HPLC to obtain pure coupling products 10.

Example 19

This example describes a general procedure for the cyanation of ethyl 2-(5-iodo-3-aryl-4-(4-sulfamoylbenzyl)-1H-pyrazol-1-yl)thiazole-4-carboxylates 7 in an embodiment of the invention. See Scheme 4.

A mixture of ethyl 2-(5-iodo-3-aryl-4-(4-sulfamoylbenzyl)-1H-pyrazol-1-yl)thiazole-4-carboxylate 7 (0.168 mmol, 1 eq) and CuCN (0.023 g, 0.252 mmol, 1.5 eq) in dimethylsulfoxide (DMSO) (0.5 ml) was heated in a microwave for 0.5 h at 160° C. The product was extracted with ethyl acetate. The organic layer was washed with a saturated bicarbonate solution, water, and brine. The crude product was purified on a Biotage (Charlotte, N.C.) flash system eluting with 30-100% ethyl acetate in hexanes over 15 column volumes to obtain pure products 10.

Example 20

This example describes a general procedure for the hydrolysis of the ethyl and methyl esters 10 in an embodiment of the invention. See Scheme 4.

A 1.5 molar solution of LiOH in water was added to a solution of ethyl 2-(3-aryl-4-(4-sulfamoylbenzyl)-1H-pyrazol-1-yl)thiazole-4-carboxylate 10 (0.252 mmol, 1 eq) in THF/MeOH (3 mL/1.5 mL) and stirred at room temperature for 0.5-1 h. After completion of the reaction, the solvent was evaporated under reduced pressure, and the residue was taken up in DMSO. Finally the compounds 11 were purified on preparative HPLC.

Example 21

This example describes the synthesis of 2-(5-(cyclopropylmethyl)-4-(3-fluoro-4-sulfamoylbenzyl)-3-(3-(2-(5-methylthiophen-2-yl)cyclopropyl)phenyl)-1H-pyrazol-1-yl) thiazole-4-carboxylic acid 130 in an embodiment of the invention. See Scheme 5.

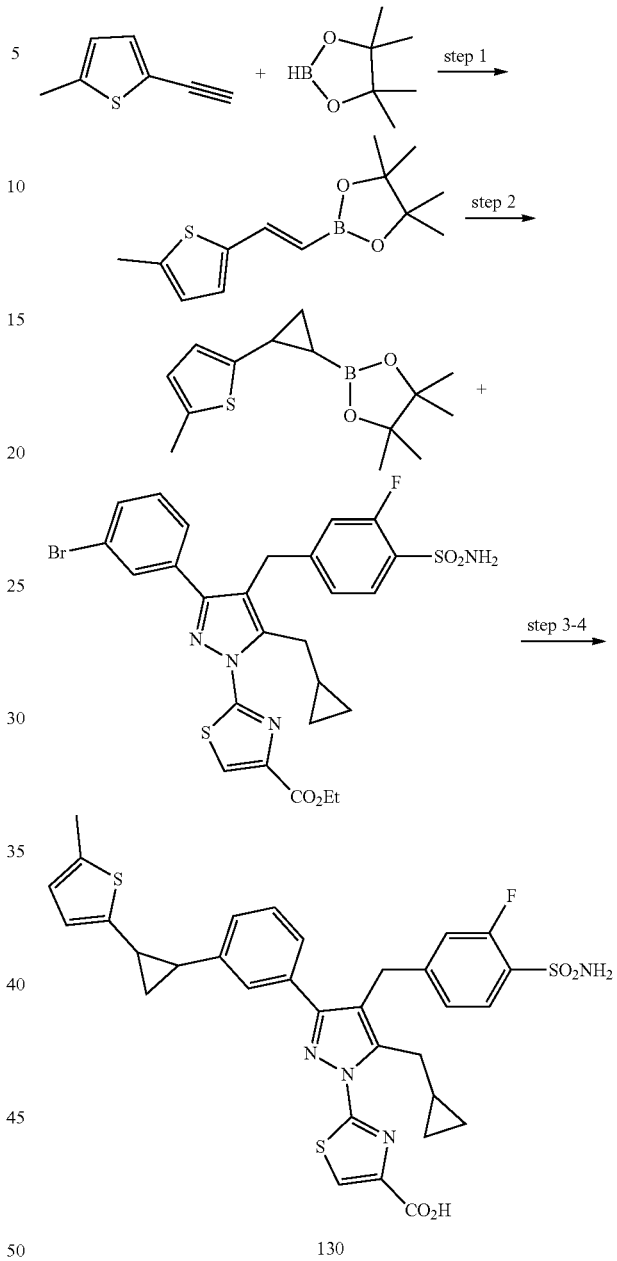

Step 1: Synthesis of (E)-4,4,5,5-tetramethyl-2-(2-(5-methylthiophen-2-yl) vinyl)-1,3,2-dioxaborolane 2-ethynyl-5-methylthiophene (1.5 g, 12.28 mmol), 4,4,5,5-tetramethyl-1,3,2-dioxaborolane (3.56 ml, 24.55 mmol) in DCM was added bis(cyclopentadienyl)zirconium(IV) chloride hydride (0.317 g, 1.228 mmol) and TEA (0.171 ml, 1.228 mmol) under argon bubbling then vial was capped and stirred at 60° C. for 2 h. The reaction mixture was diluted with DCM, washed with water and brine. The crude product was purified on a 80 g silica column on a flash system eluting with 0-40% ethyl acetate in hexanes over 20 column volumes. Yellow solid (2.9 g with 94% yield).

Step 2: 4,4,5,5-tetramethyl-2-((1R,2R)-2-(5-methyl-thiophen-2-yl)cyclopropyl)-1,3,2-dioxa-borolane To a solution of diiodomethane (3.22 ml, 40.0 mmol) in DCM (40 mL) was added diethylzinc (19.99 ml, 19.99 mmol) (1 molar solution in hexanes) upon cooling in an ice bath. The reaction was stirred for 2 h at this temperature, then a solution of (E)-4,4,5,5-tetramethyl-2-(2-(5-methylthiophen-2-yl)vinyl)-1,3,2-dioxaborolane (2 g, 7.99 mmol) in DCM (20 mL) was added at 0° C., and then the reaction was stirred at room temperature (RT) for another 3 days at RT. The reaction mixture was quenched with water/HCl and extracted with DCM. The organic layer was with water and brine. The crude product was purified on a 120 g silica column on a flash system eluting with 0-100% ethyl acetate in hexanes over 25 CV column volumes. Yellow oil (1.56 g with 73% yield).

Steps 3-4: 2-(5-(cyclopropylmethyl)-4-(3-fluoro-4-sulfamoylbenzyl)-3-(3-(2-(5-methylthiophen-2-yl)cyclopropyl)phenyl)-1H-pyrazol-1-yl)thiazole-4-carboxylic acid, TFA Ethyl 2-(3-(3-bromophenyl)-5-(cyclopropylmethyl)-4-(3-fluoro-4-sulfamoylbenzyl)-1H-pyrazol-1-yl)thiazole-4-carboxylate (0.1 g, 0.161 mmol), 4,4,5,5-tetramethyl-2-((1R, 2R)-2-(5-methylthiophen-2-yl)cyclopropyl)-1,3,2-dioxaborolane (0.064 g, 0.242 mmol), potassium phosphate (0.069 g, 0.323 mmol) and dichloro[1,1'-bis(di-t-butylphosphino)ferrocene]palladium(II) (6.45 mg, 0.016 mmol) in dioxane/water was bubbled with argon then capped and stirred at 110° C. for 6 h. The reaction was diluted with ethyl acetate, and filtered through celite then stirred with Pd scavenger, filtered again to get crude solid which was purified on a 12 g silica column on a flash system eluting with 20-40% ethyl acetate in hexanes over 20 column volumes.

The product ethyl 2-(5-(cyclopropylmethyl)-4-(3-fluoro-4-sulfamoylbenzyl)-3-(3-(2-(5-methylthiophen-2-yl)cyclopropyl)phenyl)-1H-pyrazol-1-yl)thiazole-4-carboxylate (0.11 g, 0.163 mmol) was hydrolyzed with 1.5 molar LiOH (5 eq) in water, in THF/MeOH, acidified with 1 molar HCl and extracted with ethyl acetate. After evaporating the solvent the crude material was taken in DMSO and purified on a preparative HPLC.

Example 22

This example describes the synthesis of cis-2-(5-(cyclopropylmethyl)-4-(3-fluoro-4-sulfamoylbenzyl)-3-(3-(-3-(5-methylthiophen-2-yl)cyclobutyl)phenyl)-1H-pyrazol-1-yl)thiazole-4-carboxylic acid 132 and trans-2-(5-(cyclopropylmethyl)-4-(3-fluoro-4-sulfamoylbenzyl)-3-(3-(-3-(5-methylthiophen-2-yl)cyclobutyl)phenyl)-1H-pyrazol-1-yl)thiazole-4-carboxylic acid 133 in an embodiment of the invention. See Scheme 6.

SCHEME 6

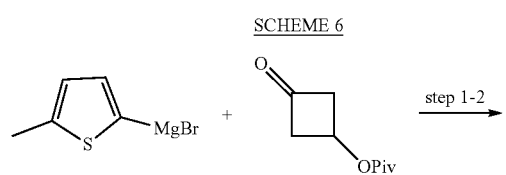

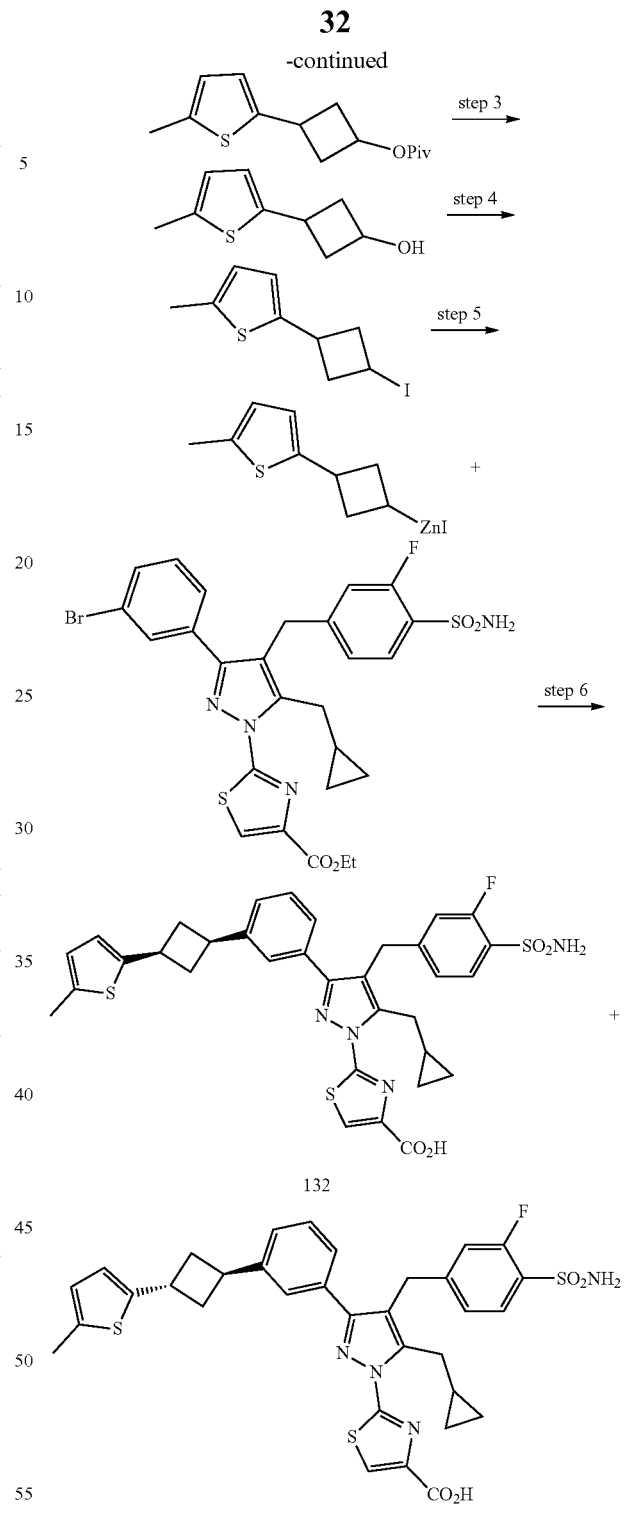

Steps 1-2: Synthesis of 3-(5-methylthiophen-2-yl)cyclobutyl Pivaloate 3-oxocyclobutyl pivaloate (5 g, 29.4 mmol) in ether was added (5-methylthiophen-2-yl)magnesium bromide (64.6 ml, 32.3 mmol) drop wise upon cooling in an ice/acetone bath then allowed to stir at room temperature overnight. The reaction was quenched with ammonium chloride and extracted with ethyl acetate. The organic layer was washed with brine. The crude product was purified on a 220 g gold silica column on a flash system eluting with 0-30% ethyl acetate in hexanes over 16 column volumes. Yellow oil (3.8 g with 48% yield).

The above 3-hydroxy-3-(5-methylthiophen-2-yl)cyclobutyl pivaloate (3.3 g, 12.30 mmol, 1 eq) and triethylsilane (2.357 ml, 14.76 mmol, 1.2 eq) in DCM (50 mL) was added trifluoroacetic acid (1.895 ml, 24.59 mmol, 2 eq) upon cooling to 0° C. The reaction was stirred at RT for 2 h then quenched with bicarbonate solution. The organic layer was further washed with bicarbonate and brine, dried over magnesium sulfate and concentrated to get oil which was used as such in the next step.

Step 3: Synthesis of 3-(5-methylthiophen-2-yl)cyclobutan-1-ol

The crude yellow oil from the step 2 was dissolved in THF-MeOH and treated with 1.5 molar LiOH in water (5 eq) to hydrolyze the ester. After stirring at RT for 4 h, the reaction mixture was concentrated and extracted with ethyl acetate twice. The crude product was purified on a 120 g gold silica column on a flash system eluting with 0-50% ethyl acetate in hexanes over 25 CV column volumes. Yellow oil (1.1 g with 53% yield).

Step 4: 2-(3-iodocyclobutyl)-5-methylthiophene 3-(5-methylthiophen-2-yl)cyclobutanol (0.5 g, 2.97 mmol, 1 eq), triphenylphosphine (1.013 g, 3.86 mmol, 1.3 eq) and imidazole (0.303 g, 4.46 mmol, 1.5 eq) in DCM was added iodine (0.905 g, 3.57 mmol, 1.2 eq) upon cooling in an ice bath. The reaction mixture was refluxed overnight. Excess DCM was removed and the residue was suspended in ether and filtered through celite. The filtrate was concentrated and purified on a 40 g gold silica column on a flash system eluting with hexanes over 15 CV column volumes. Yellow oil (0.38 g with 46% yield).

Step 5: Synthesis of cis and trans 2-(5-(cyclopropylmethyl)-4-(3-fluoro-4-sulfamoylbenzyl)-3-(3-(3-(5-methylthiophen-2-yl)cyclobutyl)phenyl) 1H-pyrazol-1-yl)thiazole-4-carboxylic acid Zinc (nano zinc dust from Strem Cat #30-1500) (0.132 g, 2.018 mmol) in a microwave vial was degassed with argon then heated using a torch under argon. Upon cooling added 0.5 mL of dry THF then 1,2-dibromoethane (0.017 ml, 0.202 mmol) and heated with a torch until it bubbles cooled and the process repeated twice. The mixture was cooled to RT again and added TMS-Cl (0.026 ml, 0.202 mmol) then heated with a torch until it bubbles cooled and the process repeated twice. The reaction was cooled to RT and added 2-(3-iodocyclobutyl)-5-methylthiophene (0.224 g, 0.807 mmol) warmed with heat gun gently and stirred at RT vigorously for 0.5 h.

In another vial was taken ethyl 2-(3-(3-bromophenyl)-5-(cyclopropylmethyl)-4-(3-fluoro-4-sulfamoylbenzyl)-1H-pyrazol-1-yl)thiazole-4-carboxylate (0.125 g, 0.202 mmol), CPhos (4.40 mg, 10.09 µmol) and CPhos Pd G3 (sigma cat #763004) (4.07 mg, 5.04 µmol) under argon in 0.5 mL THF. The first solution was syringed out (use a filter between the needle and syringe to remove solid particles) and added to the THF suspension of the starting materials and catalysts at RT then stirred at 65° C. for 1 h. The reaction mixture was quenched with 1 molar HCl then extracted with ethyl acetate. The organic layer was washed with water and brine then purified on a 12 g silica column on a flash system eluting with hexanes over 20 column volumes.

Ethyl 2-(5-(cyclopropylmethyl)-4-(3-fluoro-4-sulfamoylbenzyl)-3-(3-(3-(5-methylthiophen-2-yl)cyclobutyl)phenyl)-1H-pyrazol-1-yl)thiazole-4-carboxylate (0.12 g, 0.174 mmol) was hydrolyzed with 1.5 molar LiOH in water, in THF/MeOH. The reaction mixture was acidified with 1 molar HCl and extracted with ethyl acetate. The crude material obtained after evaporating ethyl acetate was taken in DMSO and purified on a preparative HPLC to separate the isomers. There 2 peaks in the final gradient elute very closely. The first peak is assumed to be cis-isomer 132 and the second one—trans-isomer 133.

Example 23

Synthesis of (2-(5-(cyclopropylmethyl)-4-(3-fluoro-4-sulfamoylbenzyl)-3-(3-((5-methylthiophen-2-yl)ethynyl)phenyl)-1H-pyrazol-1-yl)thiazol-4-yl)boronic acid 135 in an embodiment of the invention. See Scheme 7.

SCHEME 7

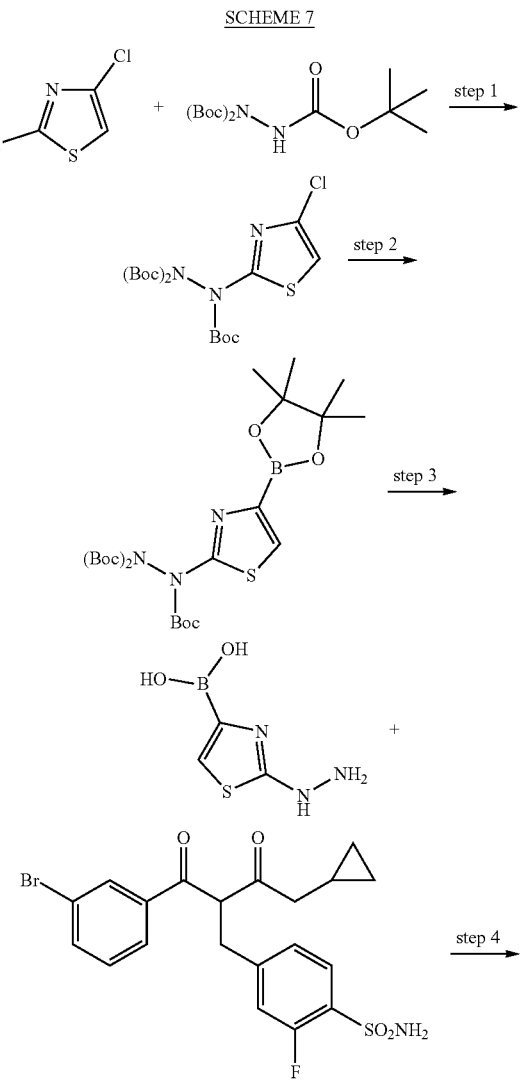

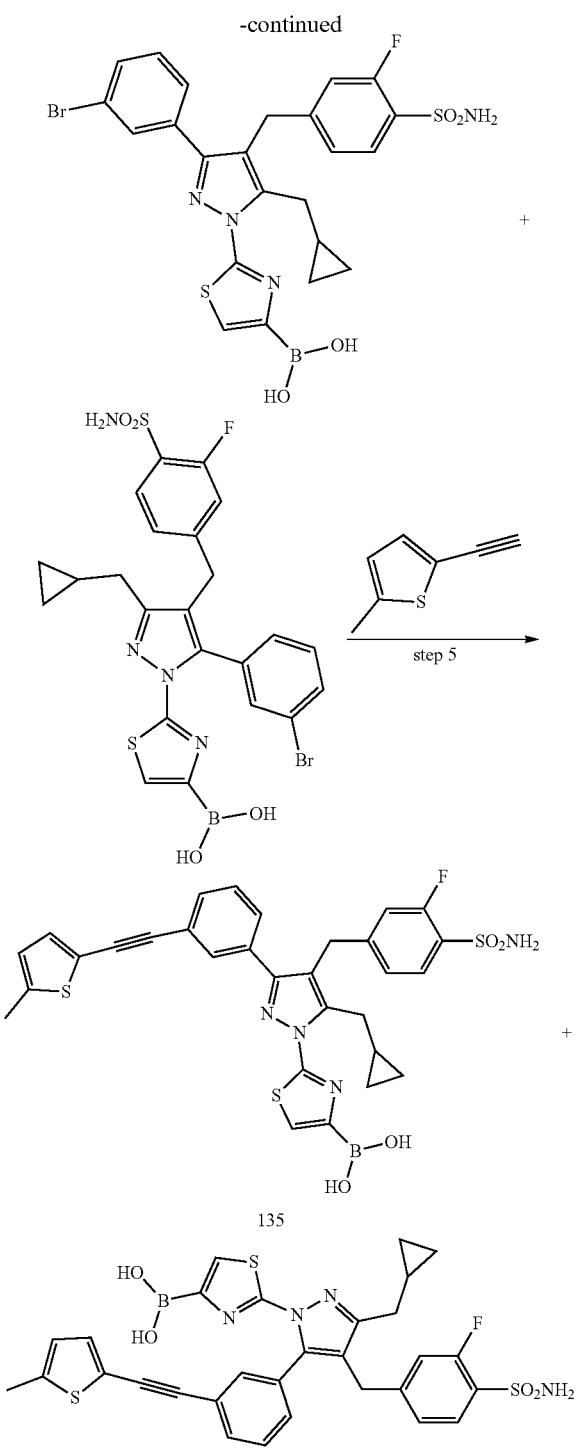

Step 1: Synthesis of tri-tert-butyl 2-(4-chlorothiazol-2-yl)hydrazine-1,1,2-tricarboxylate 2,4-dichlorothiazole (9 g, 58.4 mmol), tri-tert-butyl hydrazine-1,1,2-tricarboxylate (24.28 g, 73.0 mmol), $Cs_2CO_3$ (28.6 g, 88 mmol) and [tBuXPhos Pd(allyl)]OTf (http://jmcct.com/products-services/productp_582.html Cat #Pd-174) (1.691 g, 2.92 mmol) in t-butanol (100 ml) was bubbled with argon for 5 minutes then stirred at 80° C. for overnight. The reaction was stirred with silia-DMT to remove any residual palladium then diluted with ethyl acetate, and filtered through a pad of celite. The filtrate was concentrated to get a dark residue which was purified on a 220 g gold silica column on a flash system eluting with 0-30% ethyl acetate in hexanes over 25 column volumes. Yellow solid (9.3 g with 36% yield).

Step 2: Synthesis of tri-tert-butyl 2-(4-(4,4,5,5-tetramethyl-1,3,2-dioxaborolan-2-yl)thiazol-2-yl)hydrazine-1,1,2-tricarboxylate A mixture of tri-tert-butyl 2-(4-chlorothiazol-2-yl)hydrazine-1,1,2-tricarboxylate (0.73 g, 1.622 mmol), bis(pinacolato)diboron (0.824 g, 3.24 mmol), XPhosPd(crotyl)Cl (http://jmcct.com/products-services/product_p578.html) (cat #Pd-170) (0.055 g, 0.081 mmol) and potassium acetate (0.478 g, 4.87 mmol) in dioxane (Volume: 5 ml) was bubbled with argon then stirred at 110° C. for 6 h. The reaction was stirred with silia-DMT to remove any residual palladium then diluted with ethyl acetate, and filtered through a pad of celite. The filtrate was concentrated and purified on a 40 g gold silica column on a flash system eluting with 5-40% ethyl acetate in hexanes over 25 CV column volumes. Yellow solid (0.73 g with 83% yield).

Step 3: (2-hydrazinylthiazol-4-yl)boronic acid, 2HCl

Tri-tert-butyl 2-(4-(4,4,5,5-tetramethyl-1,3,2-dioxaborolan-2-yl)thiazol-2-yl)hydrazine-1,1,2-tricarboxylate (4.43 g, 8.18 mmol) in dioxane (15 mL) was added 4 molar HCl (100 mL) in dioxane then stirred at RT for 4 h. The reaction mixture was concentrated and the residue was suspended in 200 mL diethyl ether to get a white precipitate which was collected by filtration and dried under high vacuum under $P_2O_5$ desiccator to get white solid. (1.25 g with 66% yield).

Step 4: Synthesis of (2-(3-(3-bromophenyl)-5-(cyclopropylmethyl)-4-(3-fluoro-4-sulfamoylbenzyl)-1H-pyrazol-1-yl)thiazol-4-yl)boronic acid and (2-(5-(3-bromophenyl)-3-(cyclopropylmethyl)-4-(3-fluoro-4-sulfamoylbenzyl)-1H-pyrazol-1-yl)thiazol-4-yl) boronic Acid 4-(2-(3-bromobenzoyl)-4-cyclopropyl-3-oxobutyl)-2-fluorobenzenesulfonamide (2.455 g, 5.24 mmol) in ethanol was added pyrrolidine (0.217 ml, 2.62 mmol) and tosic acid (0.499 g, 2.62 mmol) then refluxed for 6 h. The reaction mixture was cooled and added (2-hydrazinylthiazol-4-yl)boronic acid (1.25 g, 7.86 mmol) stirred overnight at 70° C. The LCMS after 2 h shows the 2 products with same mass as regioisomers which were separated in reverse phase flash system using a 120 g gold C188 column eluting with 40-100% acetonitrile (0.1% TFA) in water (0.1% TFA).

Step 5: Synthesis of (2-(3-(3-bromophenyl)-5-(cyclopropylmethyl)-4-(3-fluoro-4-sulfamoylbenzyl)-1H-pyrazol-1-yl)thiazol-4-yl)boronic acid or (2-(3-(cyclopropylmethyl)-4-(3-fluoro-4-sulfamoylbenzyl)-5-(3-((5-methylthiophen-2-yl)ethynyl)phenyl)-1H-pyrazol-1-yl)thiazol-4-yl) boronic Acid (2-(3-(3-bromophenyl)-5-(cyclopropylmethyl)-4-(3-fluoro-4-sulfamoylbenzyl)-1H-pyrazol-1-yl)thiazol-4-yl) boronic acid or (2-(5-(3-bromophenyl)-3-(cyclopropylmethyl)-4-(3-fluoro-4-sulfamoylbenzyl)-1H-pyrazol-1-yl)

thiazol-4-yl)boronic acid (0.1 g, 0.169 mmol), 2-ethynyl-5-methylthiophene (0.026 g, 0.211 mmol), [P(tBu)3]Pd(crotyl)Cl (http://jmcct.com/products-services/product_p429.html) (cat #Pd-162) (1.688 mg, 4.23 μmol) and DABCO (0.038 g, 0.338 mmol) in DMF (1 mL) was stirred at room temperature for 4 h. After completion of the reaction, the reaction mixture was stirred with palladium scavenger (silia-DMT) for 1 h then filtered through a syringe and purified on a preparative HPLC to obtain (2-(5-(cyclopropylmethyl)-4-(3-fluoro-4-sulfamoylbenzyl)-3-(3-((5-methylthiophen-2-yl)ethynyl)-phenyl)-1H-pyrazol-1-yl)thiazol-4-yl)boronic acid 135 or (2-(3-(cyclopropylmethyl)-4-(3-fluoro-4-sulfamoylbenzyl)-5-(3-((5-methylthiophen-2-yl)ethynyl)phenyl)-1H-pyrazol-1-yl)thiazol-4-yl)boronic acid.

Example 24

This example describes the synthesis of 2-(3-(3-(tert-butylcarbamoyl)-4-fluorophenyl)-5-(cyclopropylmethyl)-4-(3-fluoro-4-sulfamoylbenzyl)-1H-pyrazol-1-yl) thiazole-4-carboxylic acid 147 in an embodiment of the invention. See Scheme 8.

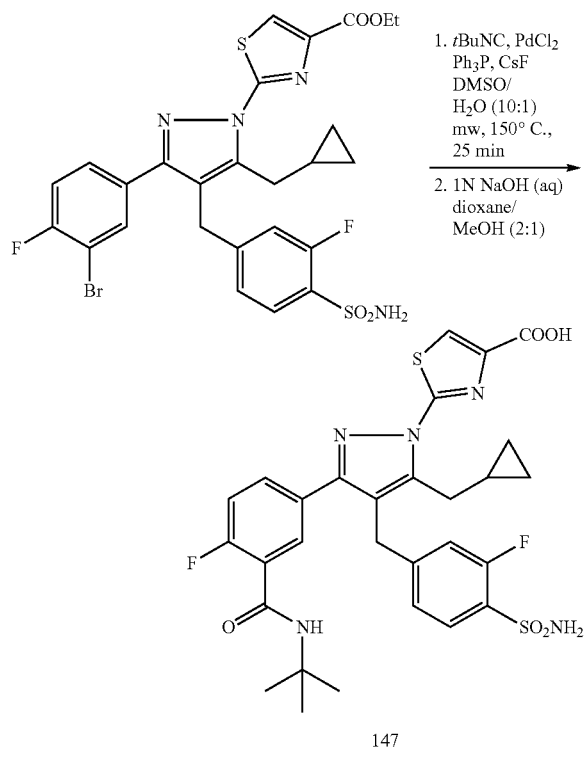

147

Step 1: Synthesis of ethyl 2-(3-(3-(tert-butylcarbamoyl)-4-fluorophenyl)-5-(cyclopropylmethyl)-4-(3-fluoro-4-sulfamoylbenzyl)-1H-pyrazol-1-yl)thiazole-4-carboxylate To a mixture of ethyl 2-(3-(3-bromo-4-fluorophenyl)-5-(cyclopropylmethyl)-4-(3-fluoro-4-sulfamoylbenzyl)-1H-pyrazol-1-yl)thiazole-4-carboxylate (100.0 mg, 0.156 mmol), PdCl₂ (1.38 mg, 0.0078 mmol) and PPh₃ (4.0 mg, 0.0156 mmol) in DMSO (1.8 mL) was added CsF (26.0 mg, 0.171 mmol) and water (0.2 mL) successively. The reaction mixture was allowed to stir for 5 min at rt, and tert-butyl isocyanide (26.4 μL, 0.234 mmol) was added. The reaction mixture was irradiated at 150° C. for 25 min in a microwave reactor. The reaction mixture was poured into water and extracted with ethyl acetate (3×15 mL). The organic layers were washed with brine (1×20 mL) and dried with anhydrous magnesium sulfate. The combined organic layer was concentrated in rotary evaporator and the crude (43.0 mg) was used in the next step.

Step 2. Synthesis of 2-(3-(3-(tert-butylcarbamoyl)-4-fluorophenyl)-5-(cyclopropylmethyl)-4-(3-fluoro-4-sulfamoylbenzyl)-1H-pyrazol-1-yl) thiazole-4-carboxylic Acid Ethyl 2-(3-(3-(tert-butylcarbamoyl)-4-fluorophenyl)-5-(cyclopropylmethyl)-4-(3-fluoro-4-sulfamoylbenzyl)-1H-pyrazol-1-yl)thiazole-4-carboxylate from Step 1 (43.0 mg, 0.065 mmol) was dissolved in a mixture of dioxane and MeOH (1.0 mL/0.5 mL) and 1.0 mL of 1 N aqueous NaOH was added. The reaction mixture was stirred at room temperature for 2 h. The reaction mixture was neutralized by the addition of 1.0 M aqueous hydrochloric acid, diluted with ethyl acetate (15 mL), washed with water (10 mL), and dried with anhydrous magnesium sulfate. The organic layer was concentrated using a rotary evaporator and the residue was dissolved in DMSO and purified by HPLC (Phenomenex Gemini C18, H₂O/CH₃CN gradient from 40% to 100% CH₃CN for 4 min, 0.1% TFA) to give the title compound 147 (11.0 mg, 26%). 2-(3-(3-(tert-butylcarbamoyl)-4-fluorophenyl)-5-(cyclopropylmethyl)-4-(3-fluoro-4-sulfamoylbenzyl)-1H-pyrazol-1-yl) thiazole-4-carboxylic acid: $^1$H-NMR (MeOD) δ: 8.21 (s, 1H), 7.79-7.69 (m, 3H), 7.19 (dd, J=8.6, 10.0 Hz, 1H), 7.11-7.05 (m, 2H), 4.21 (s, 2H), 3.28 (d, J=6.8 Hz, 2H), 1.44 (s, 9H), 1.18-1.10 (m, 1H), 0.43-0.39 (m, 2H), 0.28-0.24 (m, 2H); MS (ES) 630.1 [M+H]⁺, LCMS RT=1.048 min.

Example 25

Synthesis of 2-(5-(cyclopropylmethyl)-3-(4-fluoro-3-(6-isopropyl-2,6-diazaspiro[3.3]heptan-2-yl)phenyl)-4-(3-fluoro-4-sulfamoylbenzyl)-1H-pyrazol-1-yl)thiazole-4-carboxylic acid 158 in an embodiment of the invention. See Scheme 9.

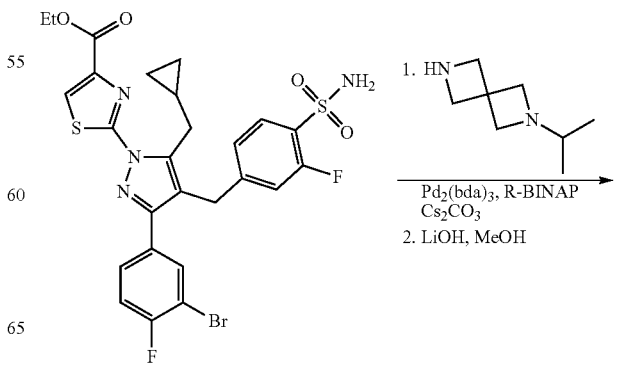

HO-continued

158

A mixture of ethyl 2-(3-(3-bromo-4-fluorophenyl)-5-(cyclopropylmethyl)-4-(3-fluoro-4-sulfamoylbenzyl)-1H-pyrazol-1-yl)thiazole-4-carboxylate (50 mg 0.078 mmol, 1 eq), 2-isopropyl-2,6-diazaspiro[3.3]heptane (12 mg, 0.086 mmol, 1.1 eq), and toluene (2.5 mL) were added to a vial under argon. Pd$_2$(dba)$_3$ (3.5 mg, 0.004 mmol, 0.05 eq), R-BINAP (7.3 mg, 0.012 mmol, 0.15 eq), Cs$_2$CO$_3$ (77 mg, 0.235 mmol, 3.0 eq), and 2 drops of Et$_3$N were added and the reaction mixture was heated to 110° C., with stirring, for 16 hours. After cooling to room temperature, the precipitate was removed by filtration and washed with EtOAc and MeOH. The filtrate was concentrated in vacuo, then redissolved in MeOH and treated with 1M aqueous LiOH (2 mL), and stirred at room temperature for 2 hours. The reaction was quenched with 2 M HCl and then extracted with CH$_2$Cl$_2$ (×3). The combined organic layers were concentrated in vacuo and the resulting organic residue was purified by HPLC to afford 6.0 mg (11.4%) of the desired compound 158. $^1$H NMR (MeOD) δ: 8.19 (s, 1H), 7.79 (t, J=8.1 Hz, 1H), 7.10 (s, 1H), 7.08 (d, J=4.8 Hz, 1H), 7.00 (d, J=8.9 Hz, 2H), 6.28 (d, J=8.5 Hz, 1H), 4.35 (d, J=11.7 Hz, 2H), 4.28 (d, J=11.6 Hz, 2H), 3.70 (s, 2H), 3.45 (p, J=6.5, 12.8 Hz, 1H), 3.28 (d, J=6.9 Hz, 2H), 2.66 (s, 2H), 1.24 (d, J=6.48 Hz, 6H), 1.17-1.12 (m, 1H), 0.34-0.32 (m, 2H), 0.22-0.21 (m, 2H); MS (ES) m/z 669.0 [M+H]$^+$; LCMS RT=0.970 min.

Example 26

Synthesis of 2-(5-(cyclopropylmethyl)-4-(3-fluoro-3-((5-methylthiophen-2-yl)ethynyl)phenyl)-4-(3-fluoro-4-sulfamoylbenzyl)-1H-pyrazol-1-yl)thiazole-4-carboxamide 162 in an embodiment of the invention. See Scheme 10.

SCHEME 10

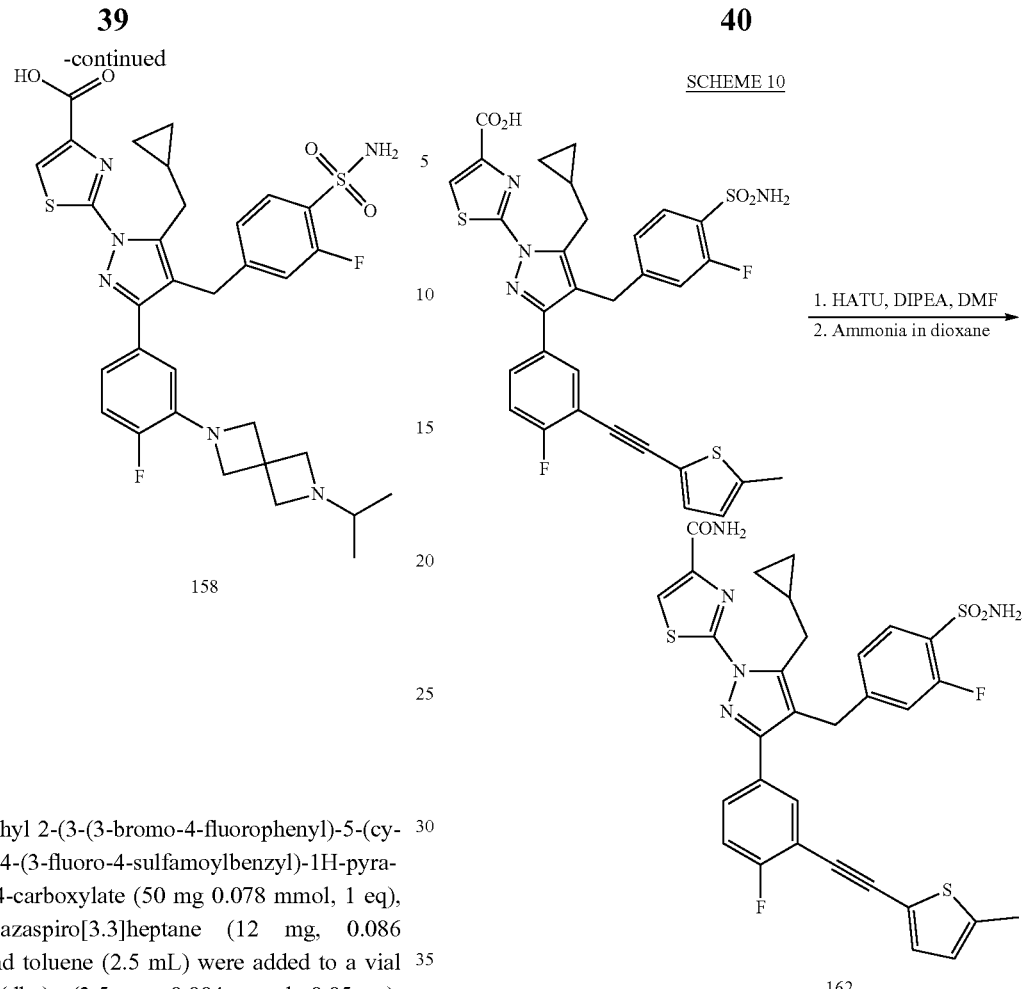

A flamed dried round bottom flask was charged with the 2-(5-(cyclopropylmethyl)-3-(4-fluoro-3-((5-methylthiophen-2-yl)ethynyl)phenyl)-4-(3-fluoro-4-sulfamoylbenzyl)-1H-pyrazol-1-yl)thiazole-4-carboxylic acid (20 mg, 0.032 mmol). DMF (750 mL) was added and the solution was cooled to 0° C. HATU (13.2 mg, 0.035 mmol) and DIPEA (8.4 uL, 0.048 mmol) were added and the reaction mixture was stirred for 30 min at 0° C. Ammonia (10 μL, 0.5 M in 1,4-dioxane) was added and the reaction mixture was stirred at room temperature for 15 min. The reaction mixture was purified by HPLC (Phenomenex Gemini C18, H$_2$O/CH$_3$CN gradient from 50% to 95% CH$_3$CN for 5 min, 0.1% TFA) to give the title compound 162 (11 mg, 36%). $^1$H-NMR (d$^6$-DMSO) δ 8.12 (s, 1H), 7.72-7.44 (m, 5H), 7.62 (s, 2H), 7.24 (d, 1H, J=4 Hz), 7.16 (d, 1H, J=12 Hz), 7.06 (d, 1H, J=8 Hz), 6.83 (d, 1H, J=2 Hz), 4.18 (s, 2H), 3.16 (m, 2H), 2.5 (s, 3H), 1.08 (m, 1H), 0.34 (m, 2H), 0.17 (m, 2H); MS (ES) m/z 632.2 [M+H]$^+$; LCMS RT=0.77 min.

Example 27

This example describes the synthesis of 2-(5-(cyclopropylmethyl)-4-(3-fluoro-4-sulfamoylbenzyl)-3-(3',4',6-trifluoro-[1,1'-biphenyl]-3-yl)-1H-pyrazol-1-yl)thiazole-4-carboxylic acid 136 in an embodiment of the invention according to the following general scheme. See Scheme 11.

SCHEME 11

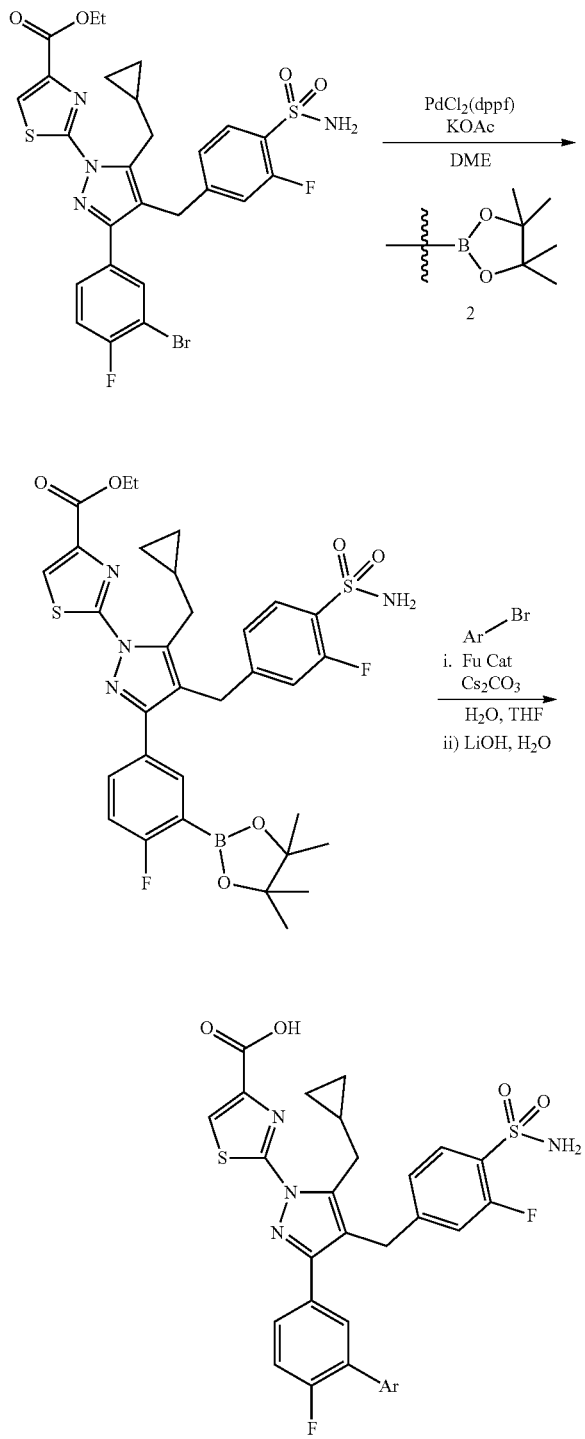

Step 1: Synthesis of ethyl 2-(5-(cyclopropylmethyl)-3-(4-fluoro-3-(4,4,5,5-tetramethyl-1,3,2-dioxaborolan-2-yl)phenyl)-4-(3-fluoro-4-sulfamoylbenzyl)-1H-pyrazol-1-yl)thiazole-4-carboxylate To a mixture of ethyl 2-(3-(3-bromo-4-fluorophenyl)-5-(cyclopropylmethyl)-4-(3-fluoro-4-sulfamoylbenzyl)-1H-pyrazol-1-yl)thiazole-4-carboxylate (500.0 mg, 0.78 mmol), bis(pinacolato)diboron (400 mg, 1.56 mmol), and PdCl$_2$(dppf) (58.0 mg, 0.078 mmol) was added KOAc (300 mg, 3.13 mmol) with DME (8.0 mL). The reaction mixture was irradiated at 150° C. for 20 min in a microwave reactor. The reaction mixture was cooled to rt, diluted with EtOAc, and filtered over a silica plug. The plug was then washed with EtOAc. The crude product was absorbed onto celite and purified on a silica gel column with 0-50% hexane:EtOAc to afford ethyl 2-(5-(cyclopropylmethyl)-3-(4-fluoro-3-(4,4,5,5-tetramethyl-1,3,2-dioxaborolan-2-yl)phenyl)-4-(3-fluoro-4-sulfamoylbenzyl)-1H-pyrazol-1-yl)thiazole-4-carboxylate (399 mg, 74%) %): $^1$H NMR (MeOD) δ 8.19 (s, 1H), 7.82-7.80 (m, 1H), 7.77-7.72 (m, 2H), 7.08-7.04 (m, 3H), 4.38 (q, 7.27, 14.29 Hz, 2H), 4.16 (s, 2H), 3.25 (d, J=6.78 Hz, 2H), 1.40 (t, 7.27 Hz, 3H), 1.32 (s, 12H), 1.14-1.12 (m, 1H), 0.42-0.38 (m, 2H), 0.29-0.25 (m, 2H); MS (ES) m/z 685.0 [M+H]$^+$; LCMS RT=1.217 min.

Step 2: Synthesis of 2-(5-(cyclopropylmethyl)-4-(3-fluoro-4-sulfamoylbenzyl)-3-(3',4',6-trifluoro-[1,1'-biphenyl]-3-yl)-1H-pyrazol-1-yl)thiazole-4-carboxylic Acid Ethyl 2-(5-(cyclopropylmethyl)-3-(4-fluoro-3-(4,4,5,5-tetramethyl-1,3,2-dioxaborolan-2-yl)phenyl)-4-(3-fluoro-4-sulfamoylbenzyl)-1H-pyrazol-1-yl)thiazole-4-carboxylate (50 mg, 0.075 mmol, 1.0 eq), 4-bromo-1-chloro-2-methylbenzene (45 mg, 0.22 mmol, 3.0 eq), PdCl$_2$(dppf) (5.3 mg, 0.0073 mmol, 0.1 eq), THF (2.0 mL), and 1 M aqueous Cs$_2$CO$_3$ (0.9 mL, 0.9 mmol, 12.0 eq) were combined in a vial and then heated in a microwave reactor at 120° C. for 45 min. After cooling to room temperature, the reaction mixture was diluted with H$_2$O then extracted with EtOAc (×3). The combined organic layers were washed with saturated aqueous NaCl, dried over Na$_2$SO$_4$, then filtered and concentrated in vacuo. The organic residue was purified by flash chromatography on silica (gradient of 0-100% EtOAc in Hexanes). The purified ethyl ester was dissolved in MeOH (3.0 mL) and treated with 1 M aqueous LiOH (2 mL). The reaction was stirred at room temperature for 16 hours, then quenched with 1 M HCl and extracted with EtOAc (×3). The combined organic layers were concentrated in vacuo and the resulting organic residue was then purified by HPLC to give 2-(5-(cyclopropylmethyl)-4-(3-fluoro-4-sulfamoylbenzyl)-3-(3',4',6-trifluoro-[1,1'-biphenyl]-3-yl)-1H-pyrazol-1-yl)thiazole-4-carboxylic acid (11.1 mg, 23%): $^1$H NMR (MeOD) δ: 8.19 (s, 1H), 7.75 (t, J=7.9 Hz, 1H), 7.65-7.61 (m, 1H), 7.54 (dd, J=2.19, 7.37 Hz, 1H), 7.34 (bs, 1H), 7.22 (dd, J=8.63, 10.59 Hz, 1H), 7.18 (d, =9.55 Hz, 1H), 7.10 (bs, 1H), 7.08 (d, J=4.03 Hz, 1H), 4.19 (s, 2H), 3.27 (d, J=6.85 Hz, 2H), 2.41 (s, 3H), 1.16-1.10 (m, 1H), 0.42-0.37 (m, 2H), 0.26-0.23 (m, 2H); MS (ES) m/z 665.0 [M+H]$^+$, LCMS RT=1.307 min.

Example 28

This example describes the synthesis of 2-(5-(cyclopropylmethyl)-4-(3-fluoro-4-sulfamoylbenzyl)-3-(3',4',6-trifluoro-[1,1'-biphenyl]-3-yl)-1H-pyrazol-1-yl)thiazole-4-carboxylic acid 136 in an embodiment of the invention. See Scheme 12.

SCHEME 12

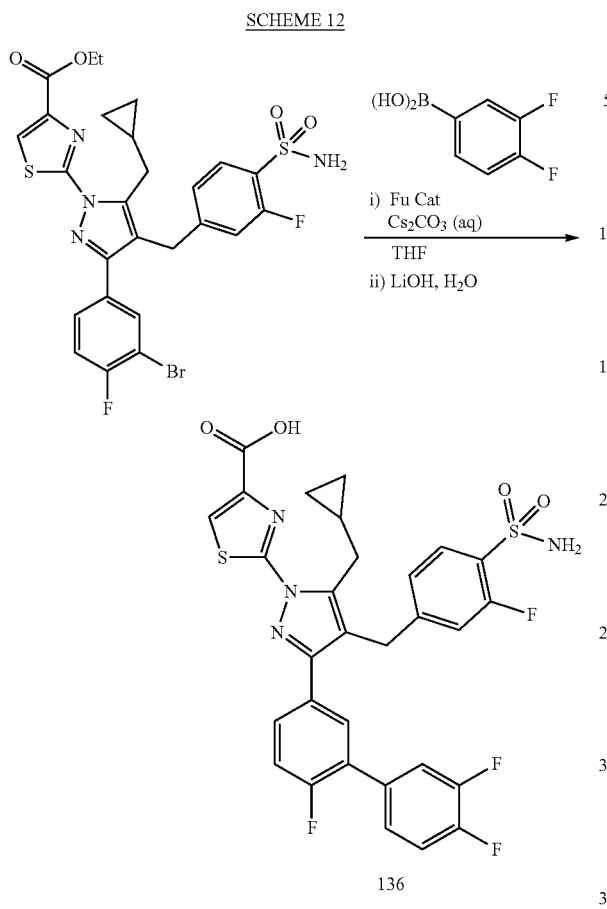

Synthesis of 2-(5-(cyclopropylmethyl)-4-(3-fluoro-4-sulfamoylbenzyl)-3-(3',4',6-trifluoro-[1,1'-biphenyl]-3-yl)-1H-pyrazol-1-yl)thiazole-4-carboxylic acid To a mixture of ethyl 2-(3-(3-bromo-4-fluorophenyl)-5-(cyclopropylmethyl)-4-(3-fluoro-4-sulfamoylbenzyl)-1H-pyrazol-1-yl)thiazole-4-carboxylate (50.0 mg, 0.078 mmol), bis(tri-tert-butylphosphine) palladium (8.0 mg, 0.016 mmol) and (3,4-difluorophenyl)boronic acid (24.7 mg, 0.16 mmol) in THF (4.0 mL) was added a 1.0 M solution of cesium carbonate (2.0 mL). The reaction mixture was irradiated at 120° C. for 30 min in a microwave reactor. The reaction mixture was cooled to rt. To this reaction mixture was then added 1.0M LiOH (aq) (3.0 mL) and allowed to stir at rt for 16 h. At this time the reaction was acidified with aqueous HCl and extracted with ethyl acetate (3×15 mL). The organic layers were dried with anhydrous magnesium sulfate. The organic layer was concentrated using a rotary evaporator, and the residue was dissolved in DMSO and purified by HPLC (Phenomenex Gemini C18, $H_2O/CH_3CN$ gradient from 40% to 100% $CH_3CN$ for 4 min, 0.1% TFA) to give the title compound (10.0 mg, 24%). $^1$H NMR (MeOD) δ 8.19 (s, 1H), 7.75 (t, 8.01 Hz, 1H), 7.65-7.61 (m, 1H), 7.54 (dd, J=2.11, 7.59 Hz, 1H), 7.42-7.37 (m, 1H), 7.35-7.30 (m, 1H), 7.23 (dd, J=8.43, 10.54 Hz, 1H), 7.12-7.06 (m, 3H), 4.18 (s, 2H), 3.27 (d, J=6.89 Hz, 2H), 1.18-1.08 (m, 1H), 0.42-0.38 (m, 1H), 0.27-0.23 (m, 1H); MS (ES) m/z 642.9 [M+H]$^+$; LCMS RT=1.256 min.

Example 29

This example describes the synthesis of 2-(3-(3-acetyl-4-fluorophenyl)-5-(cyclopropylmethyl)-4-(3-fluoro-4-sulfamoylbenzyl)-1H-pyrazol-1-yl)thiazole-4-carboxylic acid 140 in an embodiment of the invention. Scheme 13.

SCHEME 13

Synthesis of 2-(3-(3-acetyl-4-fluorophenyl)-5-(cyclopropylmethyl)-4-(3-fluoro-4-sulfamoylbenzyl)-1H-pyrazol-1-yl)thiazole-4-carboxylic Acid 140

A dry microwave vial was charged with Ethyl 2-(3-(3-bromo-4-fluorophenyl)-5-(cyclopropylmethyl)-4-(3-fluoro-4-sulfamoylbenzyl)-1H-pyrazol-1-yl)thiazole-4-carboxylate (150 mg, 0.235 mmol), 1-4 dioxane (5 mL), Pd(PPh$_3$)$_4$(5.5 mg, 0.0047 mmol) and tributyl (1-ethoxyvinyl) stannane (238 µL, 0.705 mmol). The vial was capped and heated in a microwave reactor at 120° C. for 30 min. The reaction mixture was cooled down and concentrated by rotary evaporator. The residue was purified by flash chromatography (Combi-flash Rf, hexane:ethylacetate, 0-50% gradient) to give ethyl 2-(3-(3-acetyl-4-fluorophenyl)-5-(cyclopropylmethyl)-4-(3-fluoro-4-sulfamoylbenzyl)-1H-pyrazol-1-yl)thiazole-4-carboxylate (100 mg, 71%). The ester (100 mg, 0.166 mmol) was dissolved in THF/MeOH (1 mL:1 mL) and LiOH (5 M, 500 µL) was added. The reaction mixture was stirred at room temperature overnight. The reaction mixture was neutralized by addition of hydrochloric acid (1.2 M), diluted with ethyl acetate (15 mL), washed with water (10 mL), and dried with anhydrous magnesium sulfate. The organic layer was concentrated using a rotary evaporator, dissolved in a mixture of DMSO and MeOH, and purified by HPLC (Phenomenex Gemini C18, H₂O/CH₃CN gradient from 40% to 100% CH₃CN for 4 min, 0.1% TFA) to give the title compound 140 (40 mg, 42%). MS (ES) nm/z 573.0 [M+H]⁺; LCMS RT=1.07 min.

Example 31

This example describes the synthesis of 2-(5-(cyclopropylmethyl)-3-(4-fluoro-3-(pyrrolidine-1-carbonyl)phenyl)-4-(3-fluoro-4-sulfamoylbenzyl)-1H-pyrazol-1-yl)thiazole-4-carboxylic acid 154 in an embodiment of the invention. See Scheme 14.

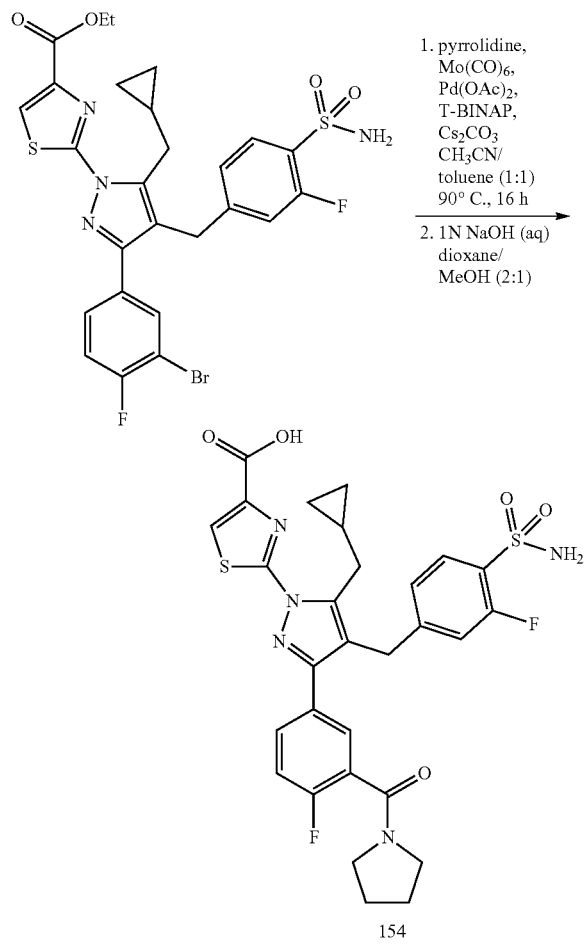

154

Synthesis of 2-(5-(cyclopropylmethyl)-3-(4-fluoro-3-(pyrrolidine-1-carbonyl)phenyl)-4-(3-fluoro-4-sulfamoylbenzyl)-1H-pyrazol-1-yl)thiazole-4-carboxylic Acid

Step 1

To a solution of ethyl 2-(3-(3-bromo-4-fluorophenyl)-5-(cyclopropylmethyl)-4-(3-fluoro-4-sulfamoylbenzyl)-1H-pyrazol-1-yl)thiazole-4-carboxylate (100.0 mg, 0.156 mmol) in CH₃CN (1.0 mL) and toluene (1.0 mL) were added Mo(CO)₆ (61.7 mg, 0.234 mmol), Pd(OAc)₂ (3.5 mg, 0.0156 mmol), T-BINAP (10.5 mg, 0.0156 mmol), Cs₂CO₃ (76.2 mg, 0.234 mmol) and pyrrolidine (20.0 μL, 0.234 mmol). The reaction mixture was heated at 90° C. for 16 h. The reaction mixture was poured into water and extracted with ethyl acetate (3×15 mL). The organic layers were washed with brine (1×20 mL) and dried with anhydrous magnesium sulfate. The combined organic layer was concentrated in rotary evaporator and the crude product (31.0 mg) was used for the next step.

Step 2

Ethyl 2-(5-(cyclopropylmethyl)-3-(4-fluoro-3-(pyrrolidine-1-carbonyl)phenyl)-4-(3-fluoro-4-sulfamoylbenzyl)-1H-pyrazol-1-yl)thiazole-4-carboxylate (31.0 mg, 0.047 mmol) was dissolved in dioxane/MeOH (1.0 mL/0.5 mL) and NaOH (1.0 mL, 1N aqueous) was added. The reaction mixture was stirred at room temperature 2 h. The reaction mixture was neutralized by addition of hydrochloric acid (1.0 M aqueous), diluted with ethyl acetate (15 mL), washed with water (10 mL), and dried with anhydrous magnesium sulfate. The organic layer was concentrated using a rotary evaporator, dissolved in DMSO and purified by HPLC (Phenomenex Gemini C, 18, H₂O/CH₃CN gradient from 40% to 100% CH₃CN for 4 min, 0.1% TFA) to give the title compound 154 (10.0 mg, 24%): ¹H NMR (MeOD) δ 8.22 (s, 1H), 7.75-7.71 (m, 2H), 7.54 (dd, J=2.2, 6.4 Hz, 1H), 7.24 (t, J=8.8 Hz, 1H), 7.07 (t, J=7.4 Hz, 2H), 4.20 (s, 2H), 3.59 (t, J=7.1 Hz, 2H), 3.30 (d, J=6.9 Hz, 2H), 3.19 (t, J=2H), 2.03-1.91 (m, 4H), 0.95-0.86 (m, 1H), 0.45-0.40 (m, 2H), 0.29-0.25 (m, 2H); MS (ES) m/z 628.0 [M+H]⁺; LCMS RT=0.968 min.

Example 32

This example describes the synthesis of 2-(5-(cyclopropylmethyl)-3-(4-fluoro-3-(2-oxopyrrolidin-1-yl)phenyl)-4-(3-fluoro-4-sulfamoylbenzyl)-1H-pyrazol-1-yl)thiazole-4-carboxylic acid 202 in an embodiment of the invention. See Scheme 15.

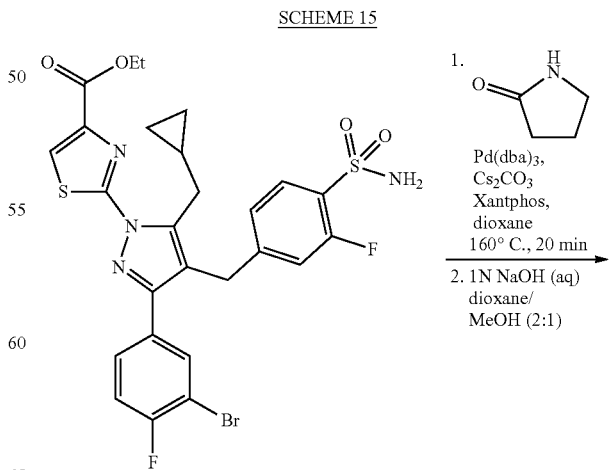

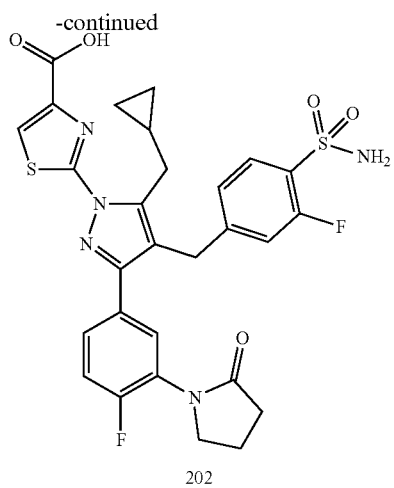

202

Synthesis of 2-(5-(cyclopropylmethyl)-3-(4-fluoro-3-(2-oxopyrrolidin-1-yl)phenyl)-4-(3-fluoro-4-sulfamoylbenzyl)-1H-pyrazol-1-yl)thiazole-4-carboxylic Acid

Step 1

To the mixture of ethyl 2-(3-(3-bromo-4-fluorophenyl)-5-(cyclopropylmethyl)-4-(3-fluoro-4-sulfamoylbenzyl)-1H-pyrazol-1-yl)thiazole-4-carboxylate (100.0 mg, 0.156 mmol), $Pd_2(dba)_3$ (7.1 mg, 0.0078 mmol) and Xantphos (13.5 mg, 0.0234 mmol) in 1,4-dioxane (2.5 mL), $Cs_2CO_3$ (71.1 mg, 0.218 mmol) was added. The reaction mixture stirred for 5 min at rt and benzamide (24.5 mg, 0.202 mmol) was added. The reaction mixture was heated at 160° C. for 20 min in a microwave reactor. The reaction mixture was filtered through Celite, washed with $CH_2Cl_2$, and concentrated in vacuo. The crude product (50.0 mg) was used for the next step.

Step 2

Ethyl 2-(5-(cyclopropylmethyl)-3-(4-fluoro-3-(2-oxopyrrolidin-1-yl)phenyl)-4-(3-fluoro-4-sulfamoylbenzyl)-1H-pyrazol-1-yl)thiazole-4-carboxylate (50.0 mg) was dissolved in dioxane/MeOH (1.0 mL/0.5 mL) and NaOH (1.0 mL, 1N aqueous) was added. The reaction mixture was stirred at room temperature for 2 h. The reaction mixture was neutralized by addition of hydrochloric acid (1.0 M aqueous), diluted with ethyl acetate (15 mL), washed with water (10 mL), and dried with anhydrous magnesium sulfate. The organic layer was concentrated using a rotary evaporator, dissolved in DMSO and purified by HPLC (Phenomenex Gemini C18, $H_2O/CH_3CN$ gradient from 40% to 100% $CH_3CN$ for 4 min, 0.1% TFA) to give the title compound 202 (11.0 mg, 11%): MS (ES) m/z 614.0 [M+H]$^+$; LCMS RT=1.005 min.

Example 33

SCHEME 16

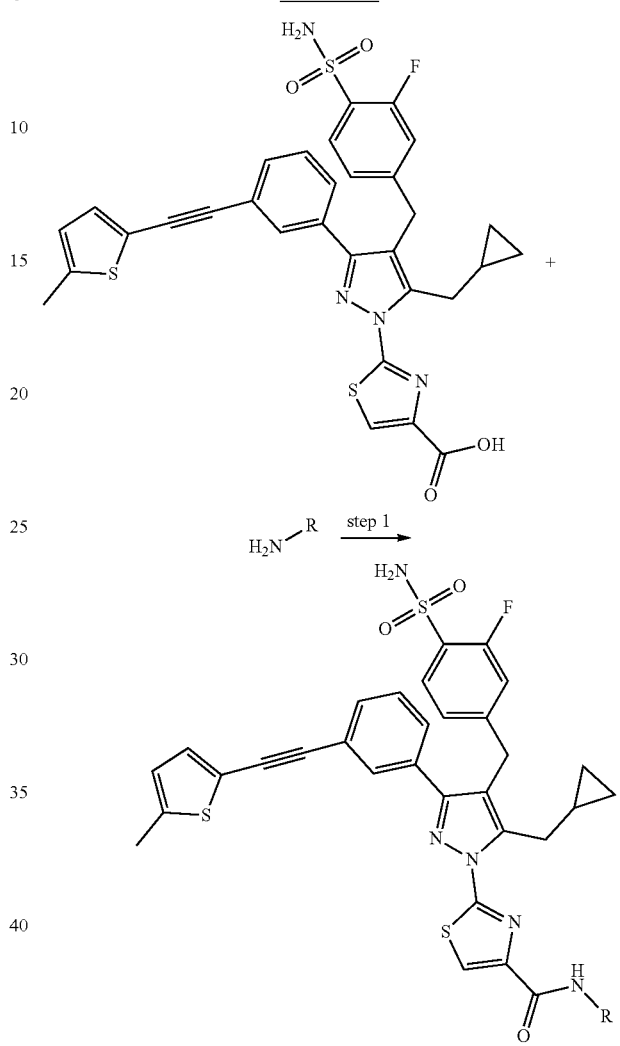

Step 1: Synthesis of 2-(5-(cyclopropylmethyl)-4-(3-fluoro-4-sulfamoylbenzyl)-3-(3-((5-methylthiophen-2-yl)ethynyl)phenyl)-1H-pyrazol-1-yl)-N-substituted thiazole-4-carboxamide. See Scheme 16

A mixture of 2-(5-(cyclopropylmethyl)-4-(3-fluoro-4-sulfamoylbenzyl)-3-(3-((5-methylthio-phen-2-yl)ethynyl)phenyl)-1H-pyrazol-1-yl)thiazole-4-carboxylic acid (0.1 g, 0.158 mmol) and CDI (0.051 g, 0.316 mmol) in ACN was stirred at 60° C. for 0.5 h then added appropriate amine (2 eq) and DBU (0.048 ml, 0.316 mmol) again stirred at 60° C. for 12 h. The reaction mixture was filtered and the solvent was removed using forced air. The crude material was taken in DMSO and purified on a preparative HPLC.

Example 34

This example describes the biochemical LDHA inhibitory activity, as measured by the assay set forth in Example 1, of exemplified compounds of formula (I) as embodiments. See Table 7. The compounds are assigned and activity level based on IC$_{50}$ as follows: +++<100 nM; ++100 nM-1000 nM; +>1000 nM-57000 nM; and −>57000 nM.

TABLE 7

| Cmpd ID | Structure | Compound name and physical data | Inhibitory activity IC$_{50}$ (μM) | Example Method |
|---|---|---|---|---|
| 101 | 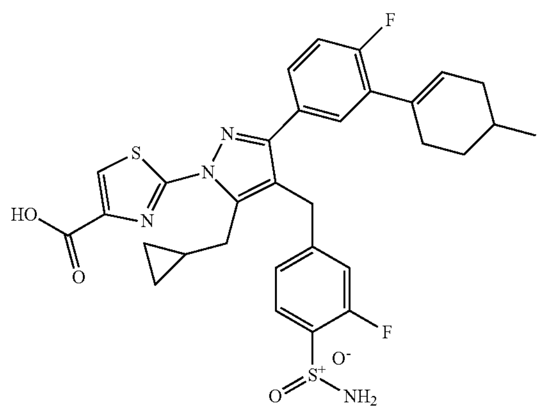 | 2-(5-(cyclopropylmethyl)-3-(6-fluoro-4'-methyl-2',3',4',5'-tetrahydro-[1,1'-biphenyl]-3-yl)-4-(3-fluoro-4-sulfamoylbenzyl)-1H-pyrazol-1-yl)thiazole-4-carboxylic acid, 1H NMR (400 MHz, DMSO-d6) δ 13.16 (s, 1H), 8.27 (s, 1H), 7.67 (t, J = 7.9 Hz, 1H), 7.57 (s, 2H), 7.48 (ddd, J = 8.5, 4.8, 2.3 Hz, 1H), 7.29 (dd, J = 7.5, 2.3 Hz, 1H), 7.22 (s, 1H), 7.21-7.13 (m, 2H), 7.05 (dd, J = 8.1, 1.6 Hz, 1H), 4.13 (s, 2H), 3.18 (d, J = 6.7 Hz, 3H), 2.32-2.07 (m, 3H), 1.83-1.57 (m, 2H), 1.37-1.21 (m, 1H), 1.20-1.09 (m, 1H), 0.97 (d, J = 6.4 Hz, 3H), 0.38-0.31 (m, 2H), 0.26-0.19 (m, 2H); MS (M + H)+ = 625 | +++ | 7 |
| 102 | 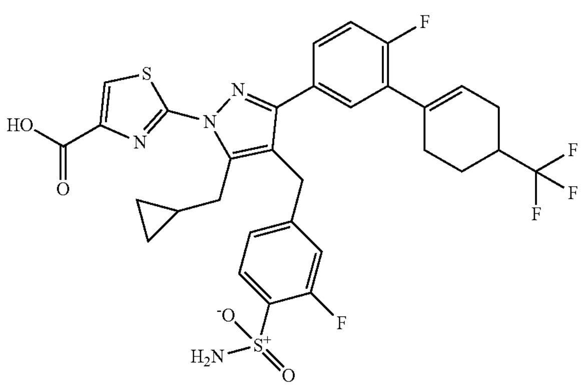 | 2-(5-(cyclopropylmethyl)-3-(6-fluoro-4'-(trifluoromethyl)-2',3',4',5'-tetrahydro-[1,1'-biphenyl]-3-yl)-4-(3-fluoro-4-sulfamoylbenzyl)-1H-pyrazol-1-yl)thiazole-4-carboxylic acid, 1H NMR (400 MHz, DMSO-d6) δ 13.15 (s, 1H), 8.29 (s, 1H), 7.66 (t, J = 7.9 Hz, 1H), 7.58 (s, 2H), 7.51 (ddd, J = 8.5, 4.8, 2.3 Hz, 1H), 7.31 (dd, J = 7.5, 2.3 Hz, 1H), 7.27-7.14 (m, 2H), 7.04 (dd, J = 8.1, 1.6 Hz, 1H), 5.83 (dd, J = 5.0, 2.5 Hz, 1H), 4.14 (s, 2H), 3.19 (d, J = 6.9 Hz, 2H), 2.47-2.13 (m, 3H), 2.08-1.97 (m, 1H), 1.63-1.47 (m, 1H), 1.22-1.08 (m, 1H), 0.39-0.31 (m, 2H), 0.28-0.19 (m, 2H); MS (M + H)+ = 679 | +++ | 7 |
| 103 | 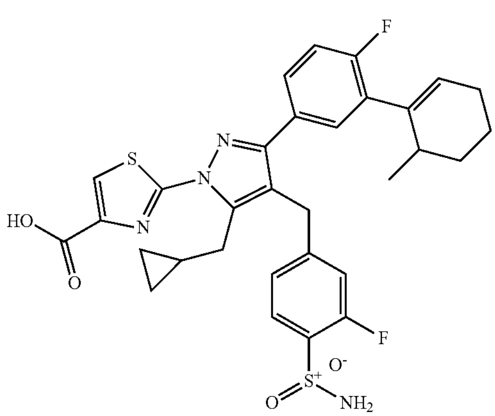 | 2-(5-(cyclopropylmethyl)-3-(6-fluoro-2'-methyl-2',3',4',5'-tetrahydro-[1,1'-biphenyl]-3-yl)-4-(3-fluoro-4-sulfamoylbenzyl)-1H-pyrazol-1-yl)thiazole-4-carboxylic acid, 1H NMR (400 MHz, DMSO-d6) δ 13.14 (s, 1H), 7.67 (t, J = 7.9 Hz, 1H), 7.57 (s, 2H), 7.48 (ddd, J = 8.5, 4.8, 2.3 Hz, 1H), 7.32-7.13 (m, 3H), 7.05 (dd, J = 8.1, 1.6 Hz, 1H), 5.80 (d, J = 3.1 Hz, 1H), 4.13 (s, 2H), 3.18 (d, J = 6.9 Hz, 2H), 2.24 (dd, J = 13.4, 4.8 Hz, 2H), 2.14 (d, J = 17.0 Hz, 1H), 1.79-1.63 (m, 4H), 1.27 (dtd, J = 12.4, 10.3, 5.1 Hz, 1H), 1.22-1.05 (m, 1H), 0.97 (d, J = 6.4 Hz, 3H), 0.40-0.30 (m, 2H), 0.33-0.19 (m, 2H); MS (M + H)+ = 625 | +++ | 7 |

TABLE 7-continued

| Cmpd ID | Structure | Compound name and physical data | Inhibitory activity IC$_{50}$ (μM) | Example Method |
|---|---|---|---|---|
| 104 | 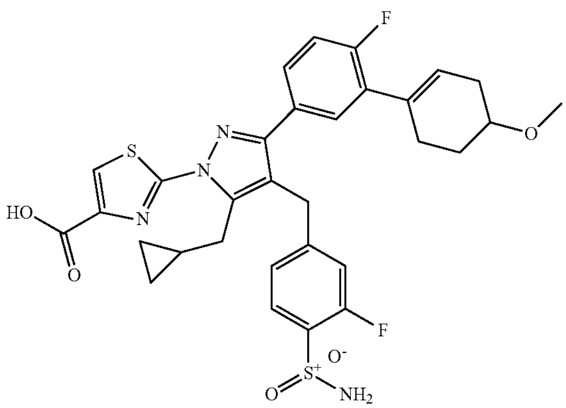 | 2-(5-(cyclopropylmethyl)-3-(6-fluoro-4'-methoxy-2',3',4',5'-tetrahydro-[1,1'-biphenyl]-3-yl)-4-(3-fluoro-4-sulfamoylbenzyl)-1H-pyrazol-1-yl)thiazole-4-carboxylic acid, 1H NMR (400 MHz, DMSO-d6) δ 13.14 (s, 1H), 8.29 (s, 1H), 7.67 (t, J = 7.9 Hz, 1H), 7.58 (s, 2H), 7.49 (ddd, J = 8.5, 4.8, 2.3 Hz, 1H), 7.29 (dd, J = 7.5, 2.3 Hz, 1H), 7.24-7.14 (m, 2H), 7.05 (dd, J = 8.1, 1.6 Hz, 1H), 5.73 (dd, J = 8.3, 4.3 Hz, 1H), 4.13 (s, 2H), 3.47 (dddd, J = 8.0, 6.7, 5.1, 2.9 Hz, 1H), 3.28 (s, 3H), 3.18 (d, J = 6.9 Hz, 2H), 2.45 (d, J = 5.5 Hz, 1H), 2.36-2.13 (m, 2H), 2.14-2.00 (m, 1H), 2.00-1.82 (m, 1H), 1.71-1.51 (m, 1H), 1.23-1.04 (m, 1H), 0.37-0.28 (m, 2H), 0.27-0.17 (m, 2H); MS (M + H)+ = 641 | +++ | 7 |
| 105 | 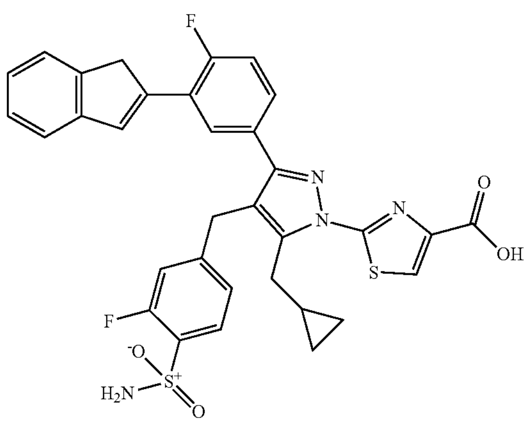 | 2-(5-(cyclopropylmethyl)-3-(4-fluoro-3-(1H-inden-2-yl)phenyl)-4-(3-fluoro-4-sulfamoylbenzyl)-1H-pyrazol-1-yl)thiazole-4-carboxylic acid, 1H NMR (400 MHz, DMSO-d6) δ 13.16 (s, 1H), 8.31 (s, 1H), 7.73 (t, J = 7.9 Hz, 1H), 7.61 (s, 2H), 7.67-7.54 (m, 2H), 7.56-7.44 (m, 2H), 7.41-7.16 (m, 5H), 7.13 (dd, J = 8.1, 1.6 Hz, 1H), 4.21 (s, 2H), 3.59 (d, J = 1.6 Hz, 2H), 3.20 (d, J = 6.9 Hz, 2H), 1.26-1.10 (m, 1H), 0.41-0.31 (m, 2H), 0.29-0.20 (m, 2H); MS (M + H)+ = 645 | +++ | 7 |
| 106 | 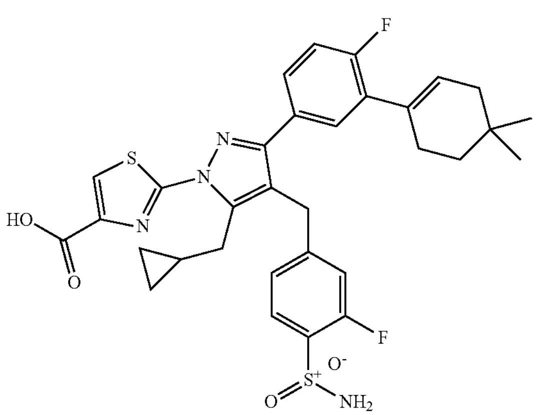 | 2-(5-(cyclopropylmethyl)-3-(6-fluoro-4',4'-dimethyl-2',3',4',5'-tetrahydro-[1,1'-biphenyl]-3-yl)-4-(3-fluoro-4-sulfamoylbenzyl)-1H-pyrazol-1-yl)thiazole-4-carboxylic acid, 1H NMR (400 MHz, DMSO-d6) δ 13.11 (s, 1H), 8.27 (d, J = 1.0 Hz, 1H), 7.64 (t, J = 7.9 Hz, 1H), 7.55 (s, 2H), 7.51-7.44 (m, 1H), 7.29-7.16 (m, 2H), 7.16 (t, J = 10.0 Hz, 2H), 7.02 (d, J = 8.1 Hz, 1H), 5.72 (dt, J = 4.9, 2.5 Hz, 1H), 4.11 (s, 2H), 3.15 (d, J = 6.8 Hz, 2H), 2.12 (d, J = 6.8 Hz, 2H), 1.90 (d, J = 3.3 Hz, 2H), 1.39 (t, J = 6.4 Hz, 2H), 1.12 (p, J = 6.6 Hz, 1H), 0.90 (s, 6H), 0.32 (d, J = 7.9 Hz, 2H), 0.21 (d, J = 4.9 Hz, 2H); MS (M + H)+ = 639 | +++ | 7 |

TABLE 7-continued

| Cmpd ID | Structure | Compound name and physical data | Inhibitory activity IC$_{50}$ (μM) | Example Method |
|---|---|---|---|---|
| 107 | 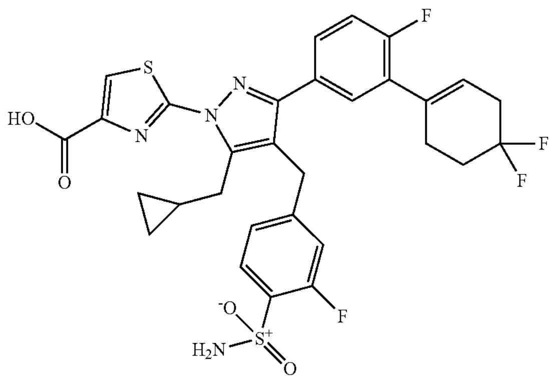 | 2-(5-(cyclopropylmethyl)-4-(3-fluoro-4-sulfamoylbenzyl)-3-(4',4',6-trifluoro-2',3',4',5'-tetrahydro-[1,1'-biphenyl]-3-yl)-1H-pyrazol-1-yl)thiazole-4-carboxylic acid, 1H NMR (400 MHz, DMSO-d6) δ 13.14 (s, 1H), 8.30 (s, 1H), 7.67 (t, J = 7.9 Hz, 1H), 7.59 (s, 2H), 7.53 (ddd, J = 8.5, 4.8, 2.3 Hz, 1H), 7.33 (dd, J = 7.5, 2.3 Hz, 1H), 7.25 (dd, J = 11.0, 8.6 Hz, 1H), 7.17 (dd, J = 11.3, 1.6 Hz, 1H), 7.05 (dd, J = 8.1, 1.6 Hz, 1H), 5.73 (d, J = 17.8 Hz, 1H), 4.14 (s, 2H), 3.24-3.13 (m, 3H), 2.78-2.63 (m, 2H), 2.48 (d, J = 11.3 Hz, 4H), 2.12 (tt, J = 14.0, 6.7 Hz, 2H), 1.23-1.08 (m, 1H), 0.39-0.31 (m, 2H), 0.27-0.19 (m, 2H); MS (M + H)+ = 647 | +++ | 7 |
| 108 | 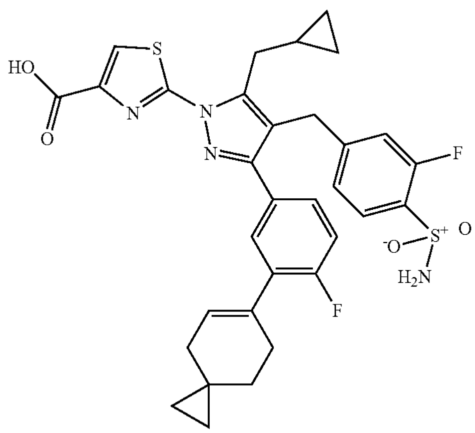 | 2-(5-(cyclopropylmethyl)-3-(4-fluoro-3-(spiro[2.5]oct-5-en-6-yl)phenyl)-4-(3-fluoro-4-sulfamoylbenzyl)-1H-pyrazol-1-yl)thiazole-4-carboxylic acid, 1H NMR (400 MHz, DMSO-d6) δ 13.13 (s, 1H), 8.30 (s, 1H), 7.67 (t, J = 7.9 Hz, 1H), 7.58 (s, 2H), 7.51 (ddd, J = 8.5, 4.8, 2.3 Hz, 1H), 7.29 (dd, J = 7.5, 2.3 Hz, 1H), 7.27-7.15 (m, 2H), 7.06 (dd, J = 8.1, 1.6 Hz, 1H), 5.86 (td, J = 3.6, 2.1 Hz, 1H), 4.14 (s, 2H), 3.18 (d, J = 6.9 Hz, 2H), 2.22 (q, J = 4.7, 4.2 Hz, 2H), 2.04 (dd, J = 3.9, 2.3 Hz, 2H), 1.44 (t, J = 6.1 Hz, 2H), 1.22-1.09 (m, 1H), 0.40-0.28 (m, 6H), 0.27-0.19 (m, 2H); MS (M + H)+ = 637 | +++ | 7 |
| 109 | 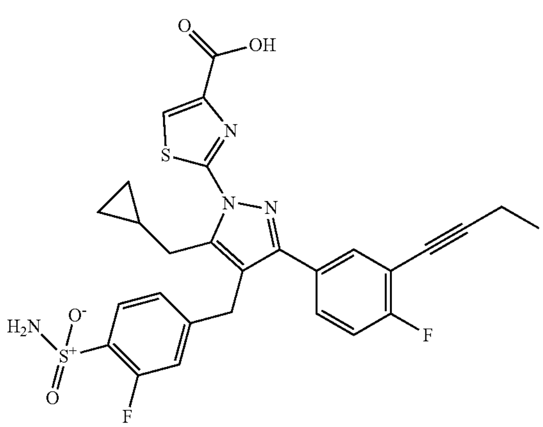 [SMILES: CCC#Cc1cc(-c2nn(-c3nc(C(=O)O)cs3)c(CC3CC3)c2Cc2ccc([S+](N)(=O)[O-])c(F)c2)ccc1F] | 2-(3-(3-(but-1-yn-1-yl)-4-fluorophenyl)-5-(cyclopropylmethyl)-4-(3-fluoro-4-sulfamoylbenzyl)-1H-pyrazol-1-yl)thiazole-4-carboxylic acid, 1H NMR (400 MHz, DMSO-d6) δ 8.00 (s, 1H), 7.66 (t, J = 7.9 Hz, 1H), 7.60-7.51 (m, 2H), 7.29 (dd, J = 9.4, 8.6 Hz, 1H), 7.15 (dd, J = 11.4, 1.6 Hz, 1H), 7.04 (dd, J = 8.1, 1.6 Hz, 1H), 4.14 (s, 2H), 3.17 (d, J = 6.9 Hz, 3H), 2.45 (t, J = 7.5 Hz, 2H), 1.17 (t, J = 7.5 Hz, 3H), 1.13-1.04 (m, 1H), 0.39-0.28 (m, 2H), 0.24-0.15 (m, 2H); MS (M + H)+ = 583 | +++ | 7 |

TABLE 7-continued

| Cmpd ID | Structure | Compound name and physical data | Inhibitory activity IC$_{50}$ (μM) | Example Method |
|---|---|---|---|---|
| 110 | 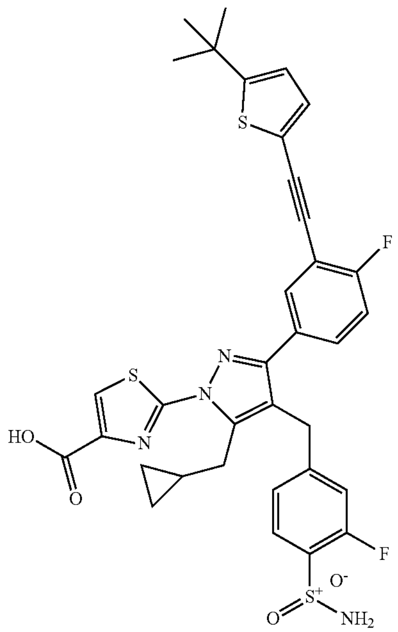 | 2-(3-(3-((5-(tert-butyl)thiophen-2-yl)ethynyl)-4-fluorophenyl)-5-(cyclopropylmethyl)-4-(3-fluoro-4-sulfamoylbenzyl)-1H-pyrazol-1-yl)thiazole-4-carboxylic acid, 1H NMR (400 MHz, DMSO-d6) δ 13.15 (s, 1H), 8.32 (s, 1H), 7.76-7.56 (m, 3H), 7.57 (s, 2H), 7.42-7.33 (m, 1H), 7.29 (d, J = 3.8 Hz, 1H), 7.16 (dd, J = 11.3, 1.6 Hz, 1H), 7.06 (dd, J = 8.2, 1.6 Hz, 1H), 6.92 (d, J = 3.7 Hz, 1H), 4.17 (s, 2H), 3.18 (d, J = 6.9 Hz, 2H), 1.36 (s, 9H), 1.26-1.07 (m, 1H), 0.40-0.30 (m, 2H), 0.27-0.19 (m, 2H); MS (M + H)+ = 693 | ++ | 7 |
| 111 | 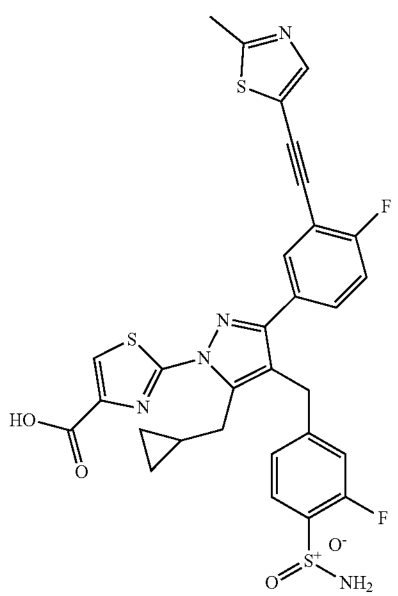 | 2-(5-(cyclopropylmethyl)-3-(4-fluoro-3-((2-methylthiazol-5-yl)ethynyl)phenyl)-4-(3-fluoro-4-sulfamoylbenzyl)-1H-pyrazol-1-yl)thiazole-4-carboxylic acid, 1H NMR (400 MHz, DMSO-d6) δ 13.13 (s, 1H), 8.29 (s, 1H), 7.99 (s, 1H), 7.75 (dd, J = 6.8, 2.3 Hz, 1H), 7.68-7.59 (m, 2H), 7.54 (s, 2H), 7.42-7.33 (m, 1H), 7.14 (dd, J = 11.3, 1.5 Hz, 1H), 7.03 (dd, J = 8.1, 1.6 Hz, 1H), 4.15 (s, 2H), 3.16 (d, J = 6.8 Hz, 2H), 2.68 (s, 3H), 1.26-1.00 (m, 1H), 0.37-0.26 (m, 2H), 0.27-0.16 (m, 2H); MS (M + H)+ = 652 | +++ | 7 |

TABLE 7-continued

| Cmpd ID | Structure | Compound name and physical data | Inhibitory activity IC$_{50}$ (μM) | Example Method |
|---|---|---|---|---|
| 112 | 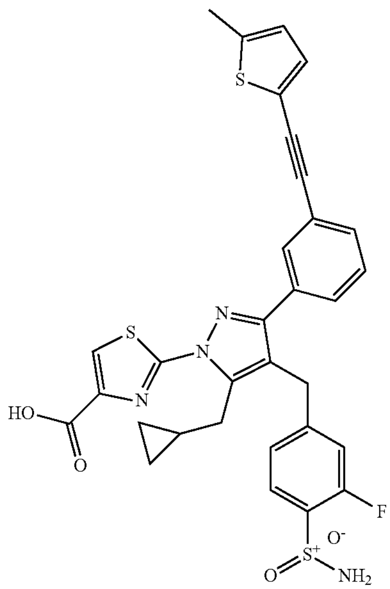 | 2-(5-(cyclopropylmethyl)-4-(3-fluoro-4-sulfamoylbenzyl)-3-(3-((5-methylthiophen-2-yl)ethynyl)phenyl)-1H-pyrazol-1-yl)thiazole-4-carboxylic acid, $^1$H NMR (400 MHz, DMSO-d6) δ 13.15 (s, 1H), 8.29 (s, 1H), 7.69-7.60 (m, 2H), 7.59-7.47 (m, 4H), 7.42 (t, J = 7.7 Hz, 1H), 7.22 (d, J = 3.6 Hz, 1H), 7.14 (dd, J = 11.3, 1.5 Hz, 1H), 7.04 (dd, J = 8.1, 1.5 Hz, 1H), 6.81 (dd, J = 3.6, 1.3 Hz, 1H), 4.16 (s, 2H), 3.16 (d, J = 7.1 Hz, 2H), 2.47-2.44 (m, 3H), 1.13 (dqd, J = 14.8, 7.2, 5.0 Hz, 1H), 0.38-0.28 (m, 2H), 0.26-0.15 (m, 2H); (M + H)+ = 633 | +++ | 7 |
| 113 | 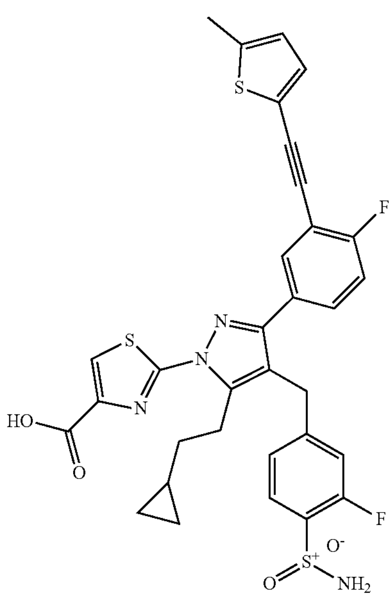 | 2-(5-(2-cyclopropylethyl)-3-(4-fluoro-3-((5-methylthiophen-2-yl)ethynyl)phenyl)-4-(3-fluoro-4-sulfamoylbenzyl)-1H-pyrazol-1-yl)thiazole-4-carboxylic acid, 1H NMR (400 MHz, DMSO-d6) δ 13.09 (s, 1H), 8.27 (s, 1H), 7.74-7.54 (m, 3H), 7.56 (s, 2H), 7.37 (dd, J = 9.4, 8.7 Hz, 1H), 7.26 (dd, J = 3.6, 0.5 Hz, 1H), 7.16 (dd, J = 11.3, 1.6 Hz, 1H), 7.04 (dd, J = 8.1, 1.6 Hz, 1H), 6.83 (dt, J = 3.5, 1.1 Hz, 1H), 4.14 (s, 2H), 3.27-3.18 (m, 2H), 2.46 (d, J = 1.0 Hz, 3H), 1.41 (q, J = 7.3 Hz, 2H), 0.87-0.61 (m, 1H), 0.34-0.25 (m, 2H), 0.14-0.05 (m, 2H); MS (M + H)+ = 665 | +++ | 7, 8 |

TABLE 7-continued

| Cmpd ID | Structure | Compound name and physical data | Inhibitory activity IC$_{50}$ (μM) | Example Method |
|---|---|---|---|---|
| 114 | 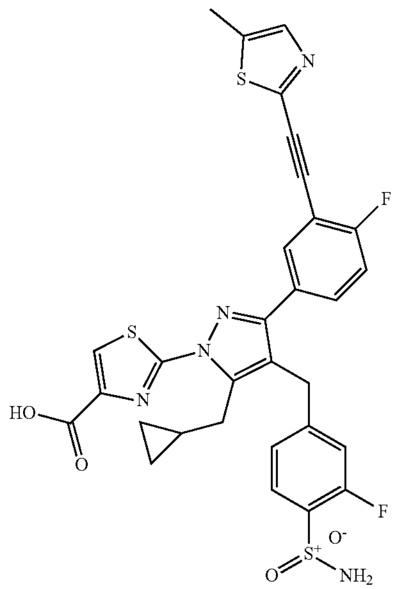 | 2-(5-(cyclopropylmethyl)-3-(4-fluoro-3-((5-methylthiazol-2-yl)ethynyl)phenyl)-4-(3-fluoro-4-sulfamoylbenzyl)-1H-pyrazol-1-yl)thiazole-4-carboxylic acid, 1H NMR (400 MHz, DMSO-d6) δ 13.13 (s, 1H), 8.27 (s, 1H), 7.85 (dd, J = 6.8, 2.3 Hz, 1H), 7.72-7.59 (m, 3H), 7.54 (s, 2H), 7.41 (t, J = 9.1 Hz, 1H), 7.13 (d, J = 10.9 Hz, 1H), 7.03 (dd, J = 8.1, 1.6 Hz, 1H), 4.17 (s, 2H), 3.15 (dd, J = 6.0, 4.6 Hz, 3H), 2.50 (d, J = 1.2 Hz, 3H), 1.24-0.99 (m, 1H), 0.38-0.28 (m, 2H), 0.24-0.16 (m, 2H); MS (M + H)+ = 652 | +++ | 7 |
| 115 | 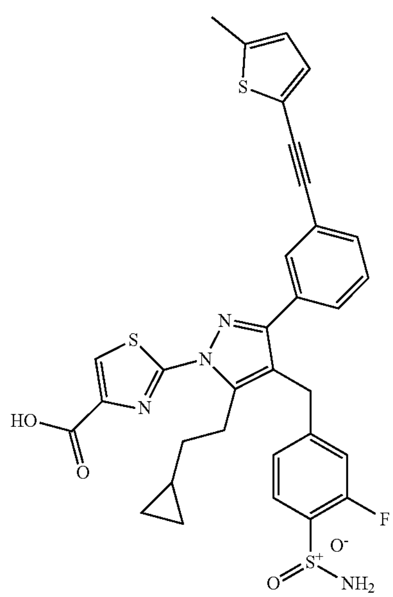 | 2-(5-(2-cyclopropylethyl)-4-(3-fluoro-4-sulfamoylbenzyl)-3-(3-((5-methylthiophen-2-yl)ethynyl)phenyl)-1H-pyrazol-1-yl)thiazole-4-carboxylic acid, 1H NMR (400 MHz, DMSO-d6) δ 13.09 (s, 1H), 8.26 (s, 1H), 7.70-7.62 (m, 2H), 7.57-7.53 (m, 3H), 7.51 (dt, J = 7.7, 1.4 Hz, 1H), 7.44 (td, J = 7.7, 0.6 Hz, 1H), 7.22 (dd, J = 3.6, 0.5 Hz, 1H), 7.16 (dd, J = 11.3, 1.6 Hz, 1H), 7.05 (dd, J = 8.1, 1.6 Hz, 1H), 6.81 (dt, J = 3.4, 1.1 Hz, 1H), 4.15 (s, 2H), 3.27-3.18 (m, 2H), 2.45 (d, J = 1.0 Hz, 3H), 1.41 (q, J = 7.3 Hz, 2H), 0.85-0.59 (m, 1H), 0.33-0.15 (m, 2H), 0.18--0.03 (m, 2H); MS (M + H)+ = 647 | +++ | 7, 8 |

TABLE 7-continued

| Cmpd ID | Structure | Compound name and physical data | Inhibitory activity IC$_{50}$ (μM) | Example Method |
|---|---|---|---|---|
| 116 | 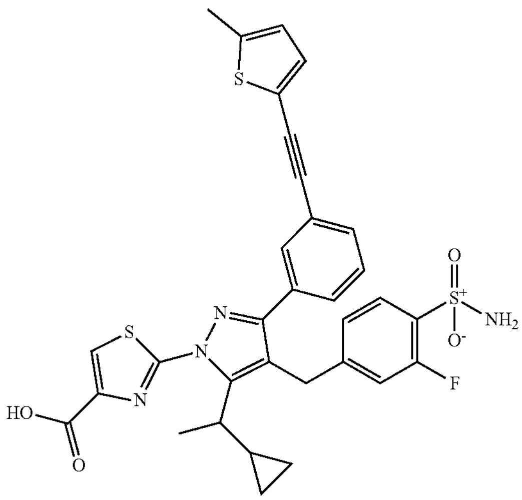 [SMILES: Cc1ccc(C#Cc2cccc(-c3nn(-c4nc(C(=O)O)cs4)c(C(C)C4CC4)c3Cc3ccc([S+](N)(=O)[O-])c(F)c3)c2)s1] | 2-(5-(1-cyclopropylethyl)-4-(3-fluoro-4-sulfamoylbenzyl)-3-(3-((5-methylthiophen-2-yl)ethynyl)phenyl)-1H-pyrazol-1-yl)thiazole-4-carboxylic acid, 1H NMR (400 MHz, DMSO-d6) δ 13.11 (s, 1H), 8.30 (s, 1H), 7.70-7.60 (m, 2H), 7.57-7.38 (m, 5H), 7.23-7.11 (m, 2H), 7.04 (dd, J = 8.1, 1.6 Hz 1H) 6.80 (dt J = 3.5, 1.1 Hz 1H) 4.25-4.19 (m, 2H), 2.45 (d, J = 1.0 Hz, 3H), 1.35 (d, J = 7.2 Hz, 3H), 0.47 (td, J = 8.9, 8.1, 4.0 Hz, 1H), 0.26-0.09 (m, 2H); MS (M + H)+ = 647 | ++ | 7, 8 |
| 117 | 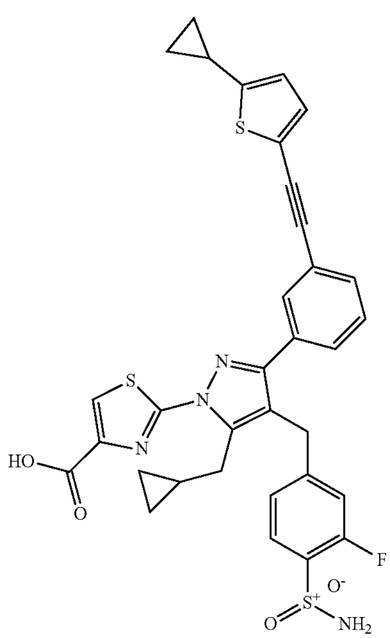 | 2-(5-(cyclopropylmethyl)-3-(3-((5-cyclopropylthiophen-2-yl)ethynyl)phenyl)-4-(3-fluoro-4-sulfamoylbenzyl)-1H-pyrazol-1-yl)thiazole-4-carboxylic acid, 1H NMR (400 MHz, DMSO-d6) δ 13.12 (s, 1H), 8.29 (s, 1H), 7.68-7.60 (m, 2H), 7.58-7.52 (m, 3H), 7.48 (dt, J = 7.7, 1.5 Hz, 1H), 7.42 (td, J = 7.7, 0.6 Hz, 1H), 7.19 (d, J = 3.7 Hz, 1H), 7.13 (dd, J = 11.4, 1.6 Hz, 1H), 7.04 (dd, J = 8.1, 1.6 Hz, 1H), 6.79 (dd, J = 3.7, 0.7 Hz, 1H), 4.15 (s, 2H), 3.16 (d, J = 6.9 Hz, 2H), 2.15 (ttd, J = 8.3, 5.0, 0.7 Hz, 1H), 1.12 (dddd, J = 13.4, 8.1, 5.0, 1.9 Hz, 1H), 1.06-0.98 (m, 2H), 0.74-0.67 (m, 2H), 0.37-0.28 (m, 2H), 0.24-0.16 (m, 2H); MS (M + H)+ = 659 | ++ | 7 |

TABLE 7-continued

| Cmpd ID | Structure | Compound name and physical data | Inhibitory activity IC$_{50}$ (μM) | Example Method |
|---|---|---|---|---|
| 118 | 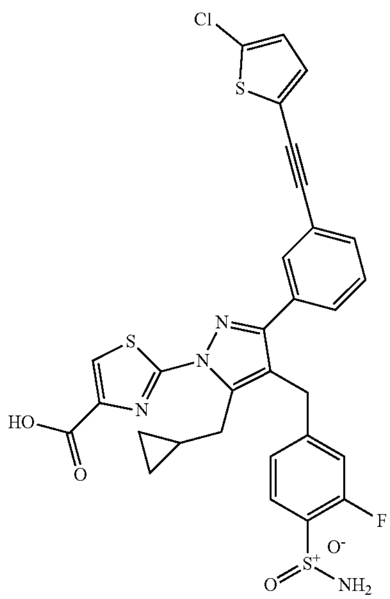 | 2-(3-(3-((5-chlorothiophen-2-yl)ethynyl)phenyl)-5-(cyclopropylmethyl)-4-(3-fluoro-4-sulfamoylbenzyl)-1H-pyrazol-1-yl)thiazole-4-carboxylic acid, 1H NMR (400 MHz, DMSO-d6) δ 13.13 (s, 1H), 8.29 (s, 1H), 7.68 (td, J = 1.7, 0.6 Hz, 1H), 7.66-7.57 (m, 2H), 7.56-7.49 (m, 3H), 7.44 (td, J = 7.8, 0.6 Hz, 1H), 7.31 (d, J = 3.9 Hz, 1H), 7.18-7.11 (m, 2H), 7.04 (dd, J = 8.1, 1.6 Hz, 1H), 4.16 (s, 2H), 3.24-3.12 (m, 2H), 1.23-1.03 (m, 1H), 0.41-0.26 (m, 2H), 0.24-0.16 (m, 2H); MS (M + H)+ = 654 | +++ | 7 |
| 119 | 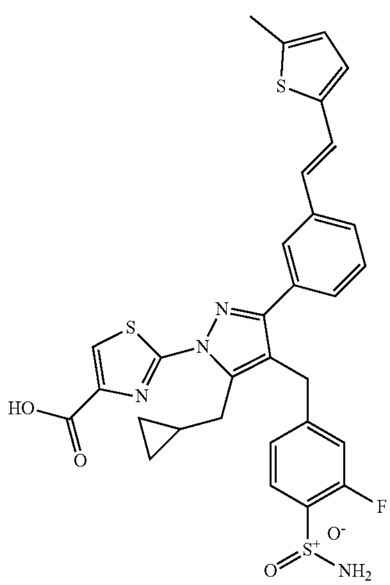 | (E)-2-(5-(cyclopropylmethyl)-4-(3-fluoro-4-sulfamoylbenzyl)-3-(3-(2-(5-methylthiophen-2-yl)vinyl)phenyl)-1H-pyrazol-1-yl)thiazole-4-carboxylic acid, 1H NMR (400 MHz, DMSO-d6) δ 13.11 (s, 1H), 7.68-7.59 (m, 2H), 7.56-7.48 (m, 3H), 7.44-7.31 (m, 2H), 7.20 (dd, J = 16.2, 0.6 Hz, 1H), 7.15 (dd, J = 11.4, 1.5 Hz, 1H), 7.05 (dd, J = 8.1, 1.6 Hz, 1H), 6.97 (d, J = 3.5 Hz, 1H), 6.81-6.70 (m, 2H), 4.16 (s, 2H), 3.16 (d, J = 6.9 Hz, 2H), 2.43 (d, J = 1.1 Hz, 3H), 1.29-0.96 (m, 1H), 0.38-0.27 (m, 2H), 0.25-0.17 (m, 2H); MS (M + H)+ = 635 | +++ | 7, 21 |

TABLE 7-continued

| Cmpd ID | Structure | Compound name and physical data | Inhibitory activity IC$_{50}$ (μM) | Example Method |
|---|---|---|---|---|
| 120 | 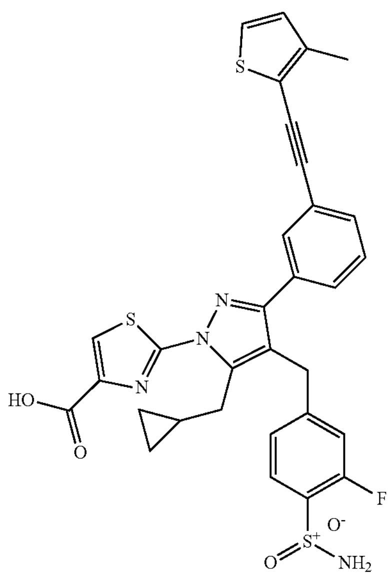 | 2-(5-(cyclopropylmethyl)-4-(3-fluoro-4-sulfamoylbenzyl)-3-(3-((3-methylthiophen-2-yl)ethynyl)phenyl)-1H-pyrazol-1-yl)thiazole-4-carboxylic acid, 1H NMR (400 MHz, DMSO-d6) δ 13.13 (s, 1H), 8.29 (s, 1H), 7.68-7.39 (m, 6H), 7.54 (s, 2H), 7.15 (dd, J = 11.4, 1.6 Hz, 1H), 7.09-6.96 (m, 2H), 4.17 (s, 2H), 3.15 (d, J = 6.9 Hz, 2H), 2.29 (s, 3H), 1.23-0.95 (m, 1H), 0.37-0.28 (m, 2H), 0.25-0.16 (m, 2H); MS (M + H)+ = 633 | +++ | 7 |
| 121 | 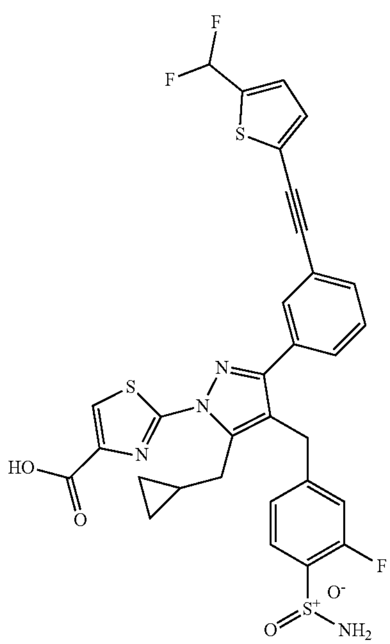 | 2-(5-(cyclopropylmethyl)-3-(3-((5-(difluoromethyl)thiophen-2-yl)ethynyl)phenyl)-4-(3-fluoro-4-sulfamoylbenzyl)-1H-pyrazol-1-yl)thiazole-4-carboxylic acid, 1H NMR (400 MHz, DMSO-d6) δ 13.13 (s, 1H), 8.28 (s, 1H), 7.72 (td, J = 1.7, 0.6 Hz, 1H), 7.67-7.52 (m, 3H), 7.54 (s, 2H), 7.50-7.40 (m, 3H), 7.19-7.10 (m, 1H), 7.04 (dd, J = 8.1, 1.6 Hz, 1H), 4.17 (s, 2H), 3.16 (d, J = 6.9 Hz, 2H), 1.32-0.93 (m, 1H), 0.38-0.17 (m, 4H); MS (M + H)+ = 669 | +++ | 7 |

TABLE 7-continued

| Cmpd ID | Structure | Compound name and physical data | Inhibitory activity IC$_{50}$ (μM) | Example Method |
|---|---|---|---|---|
| 122 | 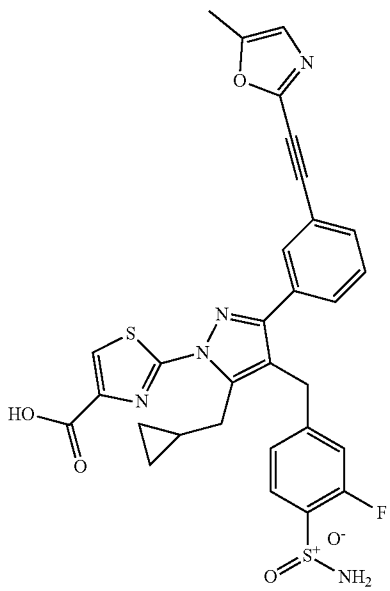 | 2-(5-(cyclopropylmethyl)-4-(3-fluoro-4-sulfamoylbenzyl)-3-(3-((5-methyloxazol-2-yl)ethynyl)phenyl)-1H-pyrazol-1-yl)thiazole-4-carboxylic acid, MS (M + H)+ = 618 | +++ | 7 |
| 123 | 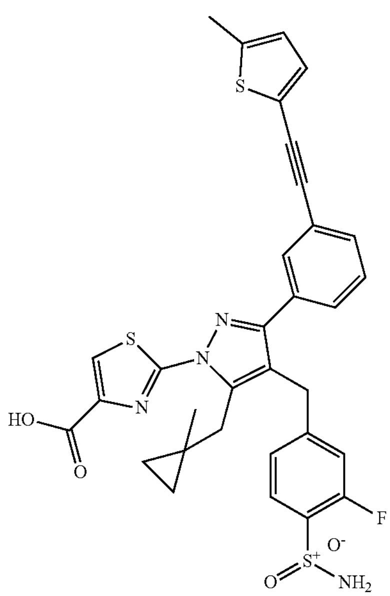 | 2-(4-(3-fluoro-4-sulfamoylbenzyl)-5-((1-methylcyclopropyl)methyl)-3-(3-((5-methylthiophen-2-yl)ethynyl)phenyl)-1H-pyrazol-1-yl)thiazole-4-carboxylic acid, 1H NMR (400 MHz, DMSO-d6) δ 13.13 (s, 1H), 7.67 (td, J = 1.7, 0.6 Hz, 1H), 7.61 (t, J = 7.9 Hz, 1H), 7.58-7.51 (m, 3H), 7.48 (dt, J = 7.7, 1.4 Hz, 1H), 7.40 (td, J = 7.7, 0.6 Hz, 1H), 7.21 (dd, J = 3.6, 0.5 Hz, 1H), 7.14-6.97 (m, 2H), 6.81 (dt, J = 3.6, 1.1 Hz, 1H), 4.19 (s, 2H), 3.42 (s, 2H), 2.45 (d, J = 1.0 Hz, 3H), 0.98 (s, 3H), 0.37-0.26 (m, 2H), 0.16-0.05 (m, 2H); MS (M + H)+ = 647 | +++ | 7, 8 |

TABLE 7-continued

| Cmpd ID | Structure | Compound name and physical data | Inhibitory activity IC$_{50}$ (μM) | Example Method |
|---|---|---|---|---|
| 124 | 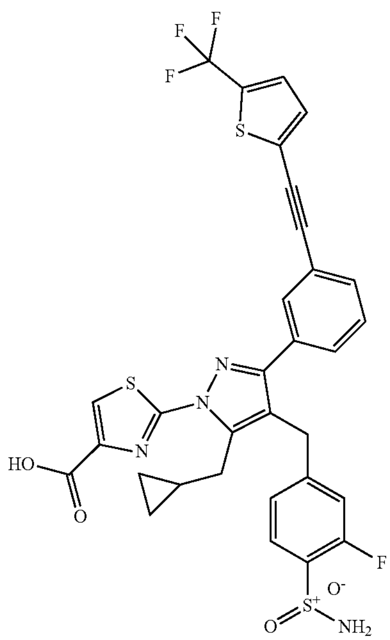 | 2-(5-(cyclopropylmethyl)-4-(3-fluoro-4-sulfamoylbenzyl)-3-(3-((5-(trifluoromethyl)thiophen-2-yl)ethynyl)phenyl)-1H-pyrazol-1-yl)thiazole-4-carboxylic acid, 1H NMR (400 MHz, DMSO-d6) δ 13.14 (s, 1H), 8.29 (s, 1H), 7.76-7.70 (m, 2H), 7.68-7.59 (m, 2H), 7.64-7.50 (m, 2H), 7.54 (s, 2H), 7.54-7.42 (m, 2H), 7.14 (dd, J = 11.4, 1.6 Hz, 1H), 7.04 (dd, J = 8.1, 1.6 Hz, 1H), 4.17 (s, 2H), 3.17 (d, J = 6.9 Hz, 2H), 1.34-1.00 (m, 1H), 0.38-0.17 (m, 4H); MS (M + H)+ = 687 | ++ | 7 |
| 125 | 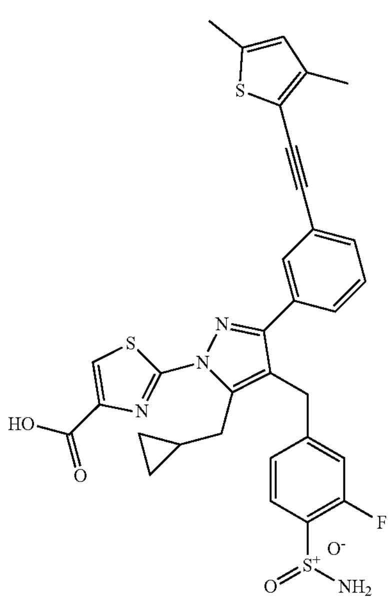 | 2-(5-(cyclopropylmethyl)-3-(3-((3,5-dimethylthiophen-2-yl)ethynyl)phenyl)-4-(3-fluoro-4-sulfamoylbenzyl)-1H-pyrazol-1-yl)thiazole-4-carboxylic acid, 1H NMR (400 MHz, DMSO-d6) δ 13.12 (s, 1H), 8.29 (s, 1H), 7.68-7.59 (m, 2H), 7.64-7.47 (m, 2H), 7.54 (s, 2H), 7.52-7.38 (m, 2H), 7.14 (dd, J = 11.4, 1.6 Hz, 1H), 7.05 (dd, J = 8.1, 1.6 Hz, 1H), 6.69 (dt, J = 1.4, 0.7 Hz, 1H), 4.16 (s, 2H), 3.15 (d, J = 6.9 Hz, 2H), 2.39 (d, J = 1.1 Hz, 3H), 2.21 (s, 3H), 1.26-0.96 (m, 1H), 0.37-0.27 (m, 2H), 0.25-0.16 (m, 2H); MS (M + H)+ = 647 | +++ | 7 |

TABLE 7-continued

| Cmpd ID | Structure | Compound name and physical data | Inhibitory activity IC$_{50}$ (μM) | Example Method |
|---|---|---|---|---|
| 126 | 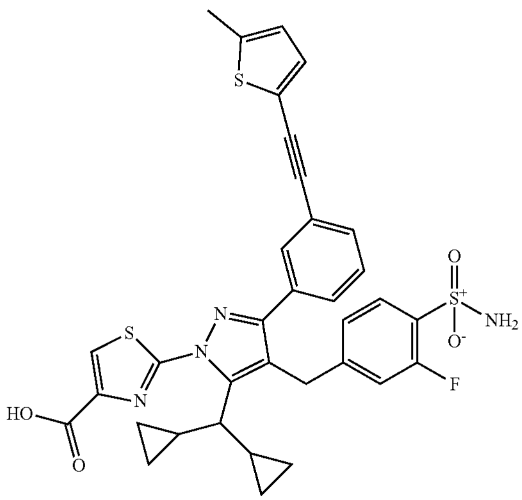 [SMILES: Cc1ccc(C#Cc2cccc(-c3nn(-c4nc(C(=O)O)cs4)c(C(C4CC4)C4CC4)c3Cc3ccc([S+](N)(=O)[O-])c(F)c3)c2)s1] | 2-(5-(dicyclopropylmethyl)-4-(3-fluoro-4-sulfamoylbenzyl)-3-(3-((5-methylthiophen-2-yl)ethynyl)phenyl)-1H-pyrazol-1-yl)thiazole-4-carboxylic acid, 1H NMR (400 MHz, DMSO-d6) δ 13.09 (s, 1H), 8.30 (s, 1H), 7.70-7.65 (m, 1H), 7.63 (d, J = 7.9 Hz, 1H), 7.59-7.51 (m, 3H), 7.49 (dt, J = 7.7, 1.4 Hz, 1H), 7.41 (td, J = 7.7, 0.6 Hz, 1H), 7.20 (dd, J = 3.6, 0.5 Hz, 1H), 7.16-6.98 (m, 2H), 6.80 (dt, J = 3.4, 1.1 Hz, 1H), 4.23 (d, J = 11.1 Hz, 2H), 2.45 (d, J = 1.0 Hz, 3H), 1.79-1.21 (m, 2H), 0.63-0.46 (m, 2H), 0.31 (dq, J = 9.4, 4.7 Hz, 2H), 0.15 (tt, J = 9.1, 4.3 Hz, 2H), −0.03 (s, 2H); MS (M + H)+ = 673 | + | 7, 8 |
| 127 | 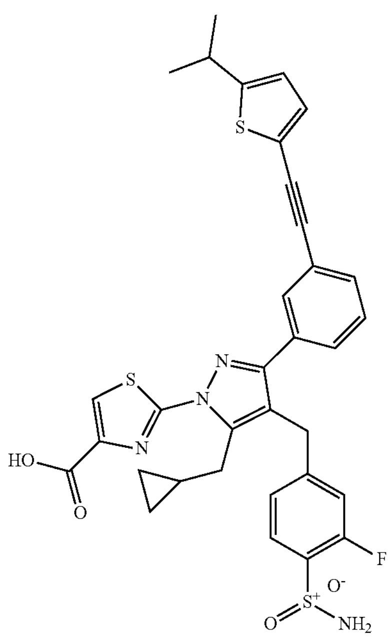 | 2-(5-(cyclopropylmethyl)-4-(3-fluoro-4-sulfamoylbenzyl)-3-(3-((5-isopropylthiophen-2-yl)ethynyl)phenyl)-1H-pyrazol-1-yl)thiazole-4-carboxylic acid, 1H NMR (400 MHz, DMSO-d6) δ 13.13 (s, 1H), 8.29 (s, 1H), 7.70-7.60 (m, 2H), 7.58-7.51 (m, 3H), 7.51 (s, 1H), 7.42 (td, J = 7.7, 0.6 Hz, 1H), 7.23 (d, J = 3.6 Hz, 1H), 7.18-6.99 (m, 2H), 6.86 (dd, J = 3.7, 1.0 Hz, 1H), 4.16 (s, 2H), 3.20-3.10 (m, 3H), 1.28 (s, 3H), 1.26 (s, 3H), 1.23-1.03 (m, 1H), 0.37-0.28 (m, 2H), 0.24-0.15 (m, 2H); MS (M + H)+ = 661 | ++ | 7 |

TABLE 7-continued

| Cmpd ID | Structure | Compound name and physical data | Inhibitory activity IC$_{50}$ (μM) | Example Method |
|---|---|---|---|---|
| 128 | 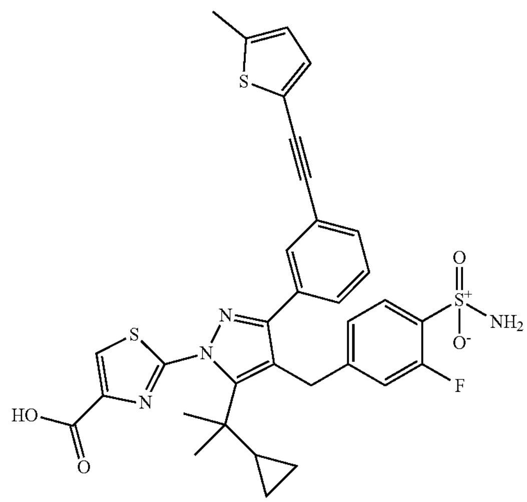 [SMILES: Cc1ccc(C#Cc2cccc(-c3nn(-c4nc(C(=O)O)cs4)c(C(C)(C)C4CC4)c3Cc3ccc([S+](N)(=O)[O-])c(F)c3)c2)s1] | 2-(5-(2-cyclopropylpropan-2-yl)-4-(3-fluoro-4-sulfamoylbenzyl)-3-(3-((5-methylthiophen-2-yl)ethynyl)phenyl)-1H-pyrazol-1-yl)thiazole-4-carboxylic acid, 1H NMR (400 MHz, DMSO-d6) δ 13.24 (s, 1H), 8.55 (s, 1H), 7.72 (t, J = 7.9 Hz, 1H), 7.57 (s, 2H), 7.53 (td, J = 1.6, 0.7 Hz, 1H), 7.49 (dt, J = 7.1, 1.8 Hz, 1H), 7.44-7.35 (m, 2H), 7.20-7.16 (m, 1H), 7.16-7.04 (m, 2H), 6.79 (dt, J = 3.4, 1.1 Hz, 1H), 4.28 (s, 2H), 2.44 (dd, J = 1.1, 0.4 Hz, 3H), 1.26 (tt, J = 8.3, 5.7 Hz, 1H), 1.17 (s, 6H), 0.27-0.12 (m, 4H); MS (M + H)+ = 661 | ++ | 7, 8 |
| 129 | 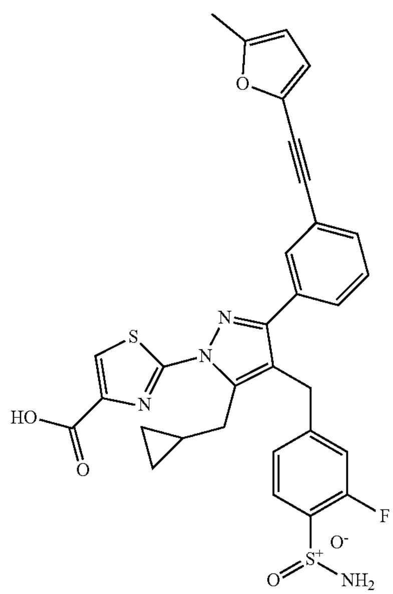 | 2-(5-(cyclopropylmethyl)-4-(3-fluoro-4-sulfamoylbenzyl)-3-(3-((5-methylfuran-2-yl)ethynyl)phenyl)-1H-pyrazol-1-yl)thiazole-4-carboxylic acid, 1H NMR (400 MHz, DMSO-d6) δ 13.13 (s, 1H), 8.28 (s, 1H), 7.68 (td, J = 1.7, 0.6 Hz, 1H), 7.63 (t, J = 7.9 Hz, 1H), 7.59-7.48 (m, 4H), 7.43 (td, J = 7.7, 0.6 Hz, 1H), 7.18-7.01 (m, 2H), 6.78 (dd, J = 3.3, 0.6 Hz, 1H), 6.20 (dq, J = 3.1, 1.0 Hz, 1H), 4.16 (s, 2H), 3.15 (d, J = 6.9 Hz, 2H), 2.29 (t, J = 0.7 Hz, 3H), 1.22-1.02 (m, 1H), 0.40-0.27 (m, 2H), 0.28-0.15 (m, 2H); MS (M + H)+ = 617 | +++ | 7 |
| 130 | 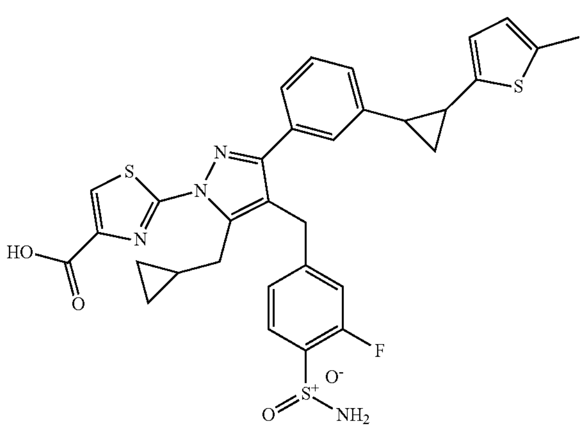 | 2-(5-(cyclopropylmethyl)-4-(3-fluoro-4-sulfamoylbenzyl)-3-(3-(2-(5-methylthiophen-2-yl)cyclopropyl)phenyl)-1H-pyrazol-1-yl)thiazole-4-carboxylic acid, 1H NMR (400 MHz, DMSO-d6) δ 13.13 (s, 1H), 8.28 (s, 1H), 7.65 (t, J = 7.9 Hz, 1H), 7.56 (s, 2H), 7.42-7.26 (m, 3H), 7.21-7.10 (m, 2H), 7.06 (dd, J = 8.1, 1.6 Hz, 1H), 6.66 (dd, J = 3.4, 0.7 Hz, 1H), 6.60 (dq, J = 3.4, 1.1 Hz, 1H), 4.15 (s, 2H), 3.17 (d, J = 7.0 Hz, 2H), 2.37 (d, J = 1.1 Hz, 3H), 2.26 (td, J = 7.2, 4.5 Hz, 1H), 2.20-2.09 (m, 1H), 1.37-1.28 (m, 2H), 1.21-1.04 (m, 1H), 0.45-0.29 (m, 2H), 0.27-0.15 (m, 2H); MS (M + H)+ = 649 | +++ | 21 |

TABLE 7-continued

| Cmpd ID | Structure | Compound name and physical data | Inhibitory activity IC$_{50}$ (μM) | Example Method |
|---|---|---|---|---|
| 131 | 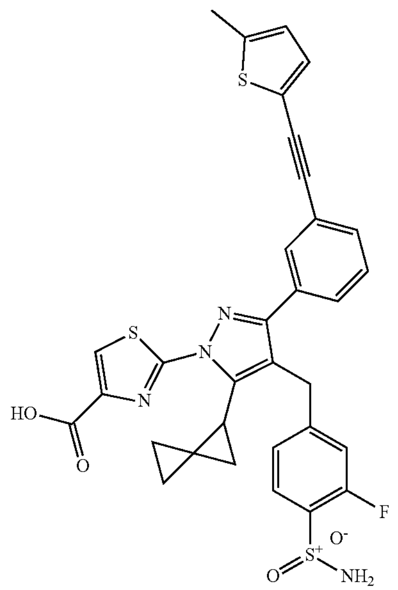 | 2-(4-(3-fluoro-4-sulfamoylbenzyl)-3-(3-((5-methylthiophen-2-yl)ethynyl)phenyl)-5-(spiro[2.2]pentan-1-yl)-1H-pyrazol-1-yl)thiazole-4-carboxylic acid, 1H NMR (400 MHz, DMSO-d6) δ 13.16 (s, 1H), 8.30 (d, J = 4.1 Hz, 1H), 7.71-7.59 (m, 2H), 7.59-7.37 (m, 5H), 7.21 (ddd, J = 3.6, 2.7, 0.5 Hz, 1H), 7.13 (ddd, J = 11.4, 8.2, 1.6 Hz, 1H), 7.03 (ddd, J = 8.1, 3.1, 1.6 Hz, 1H), 6.81 (dq, J = 3.3, 1.1 Hz, 1H), 4.21 (t, J = 8.9 Hz, 2H), 3.73 (s, 1H), 3.57 (s, 1H), 2.70-2.59 (m, 1H), 2.45 (p, J = 0.5 Hz, 3H), 1.50 (ddd, J = 8.8, 5.4, 3.4 Hz, 1H), 1.39 (dd, J = 7.8, 4.5 Hz, 1H), 1.18 (t, J = 4.9 Hz, 1H), 0.67 (ddd, J = 8.7, 5.2, 3.5 Hz, 1H), 0.52 (dt, J = 9.0, 4.4 Hz, 1H), 0.48-0.41 (m, 1H), 0.18 (dt, J = 9.2, 4.5 Hz, 1H); MS (M + H)+ = 645 | +++ | 7,8 |
| 132 | 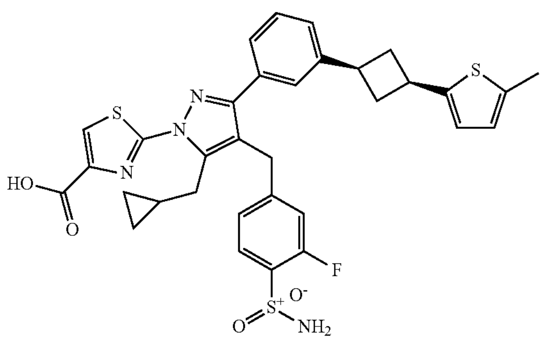 | 2-(5-(cyclopropylmethyl)-4-(3-fluoro-4-sulfamoylbenzyl)-3-(3-((cis)-3-(5-methylthiophen-2-yl)cyclobutyl)phenyl)-1H-pyrazol-1-yl)thiazole-4-carboxylic acid, 1H NMR (400 MHz, Methanol-d4) δ 13.14 (s, 1H), 8.29 (s, 1H), 7.65 (t, J = 7.9 Hz, 1H), 7.56 (s, 2H), 7.45-7.31 (m, 3H), 7.27 (dtd, J = 7.1, 1.7, 0.6 Hz, 1H), 7.13 (dd, J = 11.3, 1.6 Hz, 1H), 7.06 (dd, J = 8.1, 1.6 Hz, 1H), 6.69-6.54 (m, 2H), 4.15 (s, 2H), 3.65-3.51 (m, 1H), 3.42 (tt, J = 10.1, 7.8 Hz, 1H), 3.16 (d, J = 6.9 Hz, 2H), 2.80-2.64 (m, 2H), 2.39 (d, J = 1.1 Hz, 3H), 2.05 (tdd, J = 10.2, 8.3, 2.7 Hz, 2H), 1.25-1.03 (m, 1H), 0.39-0.30 (m, 2H), 0.26-0.19 (m, 2H); MS (M + H)+ = 663 | +++ | 22 |
| 133 | 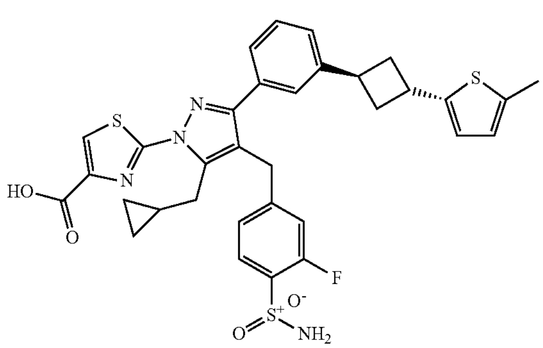 | 2-(5-(cyclopropylmethyl)-4-(3-fluoro-4-sulfamoylbenzyl)-3-(3-(3-(5-methylthiophen-2-yl)cyclobutyl)phenyl)-1H-pyrazol-1-yl)thiazole-4-carboxylic acid, 1H NMR (400 MHz, Methanol-d4) δ 13.14 (s, 1H), 8.28 (s, 1H), 7.66 (t, J = 7.9 Hz, 1H), 7.57 (s, 2H), 7.46-7.38 (m, 2H), 7.39-7.29 (m, 2H), 7.16 (dd, J = 11.4, 1.6 Hz, 1H), 7.07 (dd, J = 8.2, 1.6 Hz, 1H), 6.76 (dd, J = 3.3, 1.1 Hz, 1H), 6.64 (dq, J = 3.4, 1.1 Hz, 1H), 4.16 (s, 2H), 3.64 (qt, J = 13.7, 7.2 Hz, 2H), 3.18 (d, J = 6.9 Hz, 2H), 2.49-2.30 (m, 6H), 1.26-1.08 (m, 1H), 0.42-0.30 (m, 2H), 0.29-0.19 (m, 2H); MS (M + H)+ = 663 | +++ | 22 |

TABLE 7-continued

| Cmpd ID | Structure | Compound name and physical data | Inhibitory activity IC$_{50}$ (μM) | Example Method |
|---|---|---|---|---|
| 134 | 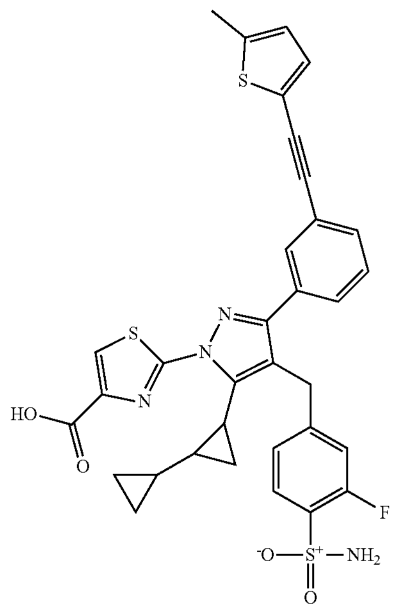 | 2-(5-([1,1'-bi(cyclopropan)]-2-yl)-4-(3-fluoro-4-sulfamoylbenzyl)-3-(3-((5-methylthiophen-2-yl)ethynyl)phenyl)-1H-pyrazol-1-yl)thiazole-4-carboxylic acid, 1H NMR (400 MHz, DMSO-d6) δ 13.10 (s, 1H), 8.28 (s, 1H), 7.70-7.61 (m, 2H), 7.60-7.48 (m, 4H), 7.44 (td, J = 7.7, 0.6 Hz, 1H), 7.22 (dd, J = 3.6, 0.5 Hz, 1H), 7.17 (dd, J = 11.3, 1.6 Hz, 1H), 7.06 (dd, J = 8.2, 1.6 Hz, 1H), 6.81 (dt, J = 3.5, 1.1 Hz, 1H), 4.12 (s, 2H), 3.19 (q, J = 8.6, 7.9 Hz, 2H), 2.75-2.61 (m, 1H), 2.45 (d, J = 1.1 Hz, 3H), 1.77 (ddq, J = 75.7, 14.6, 7.6 Hz, 2H), 0.75 (ddt, J = 13.1, 8.2, 4.2 Hz, 1H), 0.44 (dq, J = 12.3, 4.3, 3.7 Hz, 1H), 0.36-0.20 (m, 2H), 0.03--0.06 (m, 1H). MS (M + H)+ = 649 | ++ | 7, 8 |
| 135 | 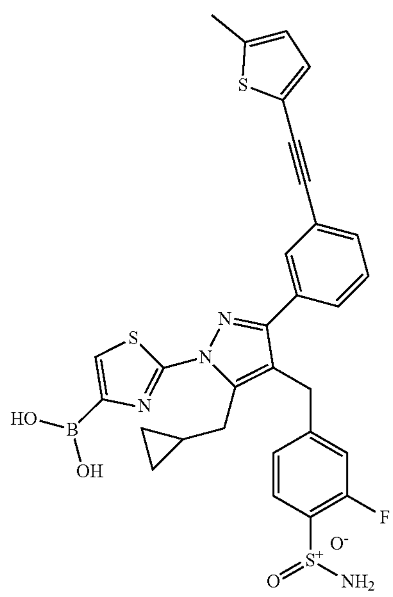 | (2-(5-(cyclopropylmethyl)-4-(3-fluoro-4-sulfamoylbenzyl)-3-(3-((5-methylthiophen-2-yl)ethynyl)phenyl)-1H-pyrazol-1-yl)thiazol-4-yl)boronic acid, MS (M + H)+ = 633 | + | 23 |
| 136 | 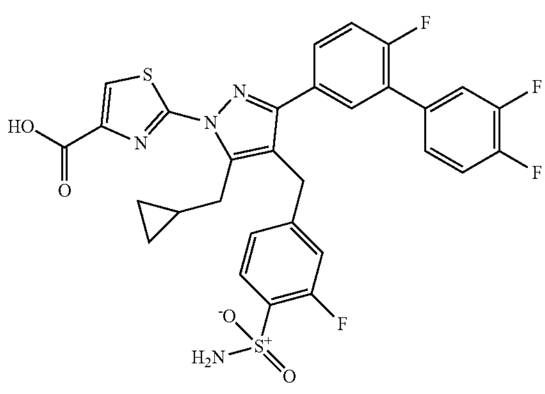 | 2-(5-(cyclopropylmethyl)-4-(3-fluoro-4-sulfamoylbenzyl)-3-(3',4',6-trifluoro-[1,1'-biphenyl]-3-yl)-1H-pyrazol-1-yl)thiazole-4-carboxylic acid. $^1$H NMR (MeOD) δ 8.19 (s, 1H), 7.75 (t, 8.01 Hz, 1H), 7.65-7.61 (m, 1H), 7.54 (dd, J = 2.11, 7.59 Hz, 1H), 7.42-7.37 (m, 1H), 7.35-7.30 (m, 1H), 7.23 (dd, J = 8.43, 10.54 Hz, 1H), 7.12-7.06 (m, 3H), 4.18 (s, 2H), 3.27 (d, J = 6.89 Hz, 2H), 1.18-1.08 (m, 1H), 0.42-0.38 (m, 1H), 0.27-0.23 (m, 1H); MS (ES) m/z 642.9 [M + H]$^+$; LCMS RT = 1.256 min. | +++ | 28 |

TABLE 7-continued

| Cmpd ID | Structure | Compound name and physical data | Inhibitory activity IC$_{50}$ (μM) | Example Method |
|---|---|---|---|---|
| 137 | 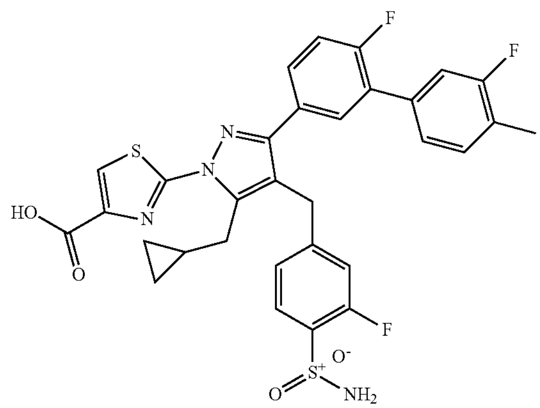 | 2-(5-(cyclopropylmethyl)-3-(3',6-difluoro-4'-methyl-[1,1'-biphenyl]-3-yl)-4-(3-fluoro-4-sulfamoylbenzyl)-1H-pyrazol-1-yl)thiazole-4-carboxylic acid $^1$H NMR (MeOD) δ 8.18 (s, 1H), 7.77-7.73 (m, 1H), 7.61-7.57 (m, 1H), 7.54 (dd, J = 2.15, 7.45 Hz, 1H), 7.28 (t, J = 8.11, 1H), 7.22-7.17 (m, 1H), 7.14 (d, J = 10.91 Hz, 1H), 7.10-7.06 (m, 2H), 7.02 (d, J = 7.83 Hz, 1H), 4.17 (s, 2H), 3.26 (d, J = 6.72 Hz, 2H), 2.30 (d, J = 0.83 Hz, 3H), 1.14-1.09 (m, 1H), 0.41-0.37 (m, 2H), 0.26-0.26 (m, 2H); MS (ES) m/z 639.0 [M + H]$^+$; LCMS RT = 1.287 min. | +++ | 28 |
| 138 | 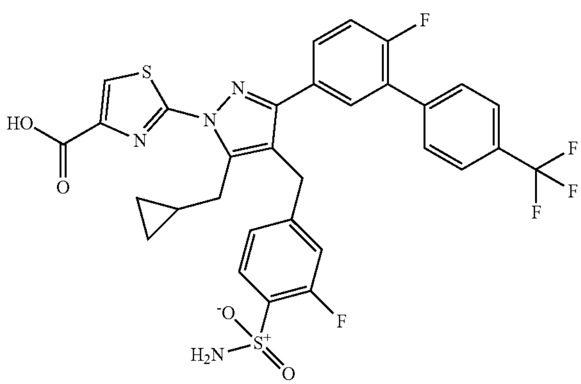 | 2-(5-(cyclopropylmethyl)-3-(6-fluoro-4'-(trifluoromethyl)-[1,1'-biphenyl]-3-yl)-4-(3-fluoro-4-sulfamoylbenzyl)-1H-pyrazol-1-yl)thiazole-4-carboxylic acid. $^1$H NMR (MeOD) δ 8.19 (s, 1H), 7.77-7.73 (m, 3H), 7.69-7.65 (m, 2H), 7.59-7.55 (m, 3H), 7.22 (dd, J = 8.66, 10.43 Hz, 1H), 7.09 (s, 1H), 7.07 (d, 2.75 Hz, 1H), 4.18 (s, 2H), 3.27 (d, J = 6.29 Hz, 2H), 1.19-1.09 (m, 1H), 0.42-0.37 (m, 2H), 0.27-0.23 (m, 2H); MS (ES) m/z 674.9 [M + H]$^+$; LCMS RT = 1.316 min. | +++ | 28 |
| 139 | 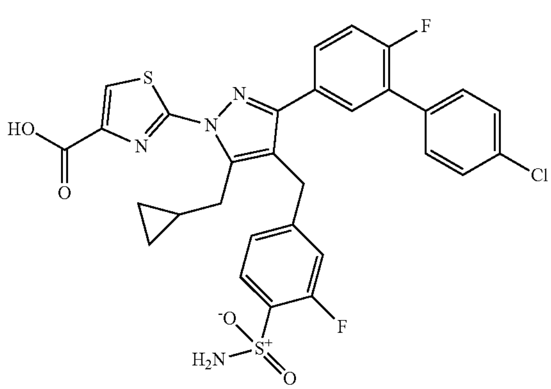 | 2-(3-(4'-chloro-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid. MS (ES) m/z 640.9 [M + H]$^+$; LCMS RT = 1.299 min. | +++ | 28 |

TABLE 7-continued

| Cmpd ID | Structure | Compound name and physical data | Inhibitory activity IC$_{50}$ (μM) | Example Method |
|---|---|---|---|---|
| 140 | 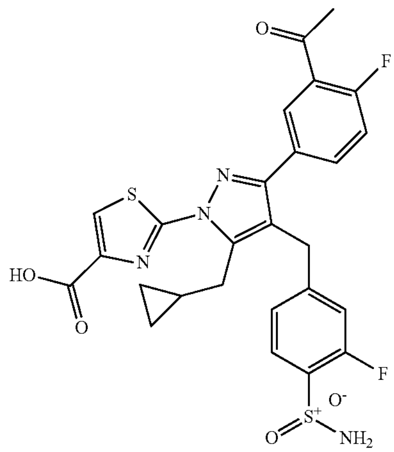 | 2-(3-(3-acetyl-4-fluorophenyl)-5-(cyclopropylmethyl)-4-(3-fluoro-4-sulfamoylbenzyl)-1H-pyrazol-1-yl)thiazole-4-carboxylic acid. MS (ES) m/z 573.0 [M + H]$^+$; LCMS RT = 1.07 min. | +++ | 29 |
| 141 | 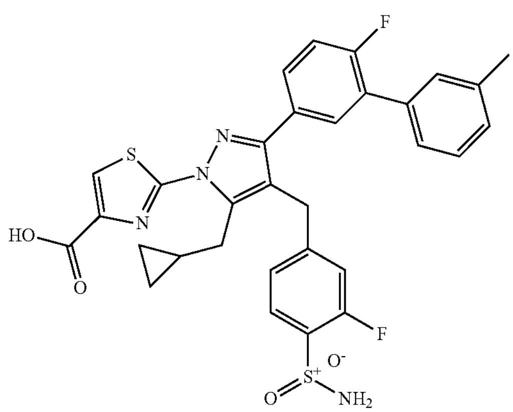 | 2-(5-(cyclopropylmethyl)-3-(6-fluoro-3'-methyl-[1,1'-biphenyl]-3-yl)-4-(3-fluoro-4-sulfamoylbenzyl)-1H-(MeOD) δ 8.17 (s, 1H), 7.77 (t, J = 15.8 Hz, 1H), 7.59-7.63 (m, 1H), 7.54-7.56 (m, 1H) 7.31 (t, J = 16 Hz, 1H), 7.08-7.23 (m, 7H), 4.19 (s, 2H), 3.32 (d, J = 4 Hz, 2H), 2.35 (s, 3H), 1.11-1.14 (m, 1H), 0.39-0.41 (m, 2H), 0.24-0.25 (m, 2H); MS (ES) m/z 621 [M + H]$^+$; LCMS RT = 1.38 min. | +++ | 28 |
| 142 | 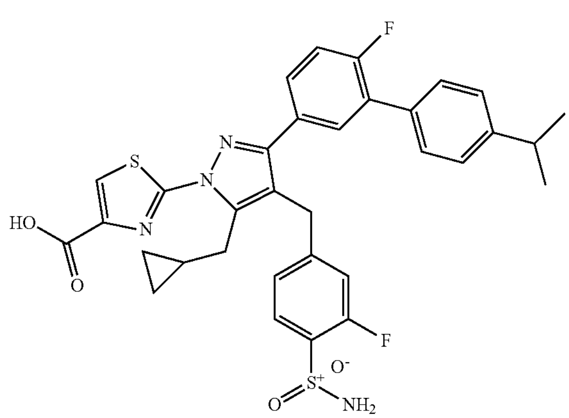 | 2-(5-(cyclopropylmethyl)-3-(6-fluoro-4'-isopropyl-[1,1'-biphenyl]-3-yl)-4-(3-fluoro-4-sulfamoylbenzyl)-1H-pyrazol-1-yl)thiazole-4-carboxylic acid. $^1$H NMR (CDCl$_3$) δ 8.12 (s, 1H), 7.81 (t, J = 16 Hz, 1H), 7.54-7.5 (m, 1H), 7.42-7.46 (m, 1H), 7.38 (d, J = 8 Hz, 2H), 7.31 (d, J = 8 Hz, 2H) 7.13-7.18 (m, 1H), 7.08 (d, J = 8 Hz, 1H), 7.00 (d, J = 8 Hz, 1H), 5.14 (s, 2H), 4.10 (s, 2H), 3.21 (d, J = 8 Hz, 2H), 2.94-3.01 (m, 1H), 1.31 (d, J = 8 Hz, 6H), 1.15-1.18 (m, 1H), 0.46-0.48 (m, 2H), 0.25-0.26 (m, 2H); MS (ES) m/z 649 [M + H]$^+$; LCMS RT = 1.48 min. | ++ | 28 |

TABLE 7-continued

| Cmpd ID | Structure | Compound name and physical data | Inhibitory activity IC$_{50}$ (μM) | Example Method |
|---|---|---|---|---|
| 143 | 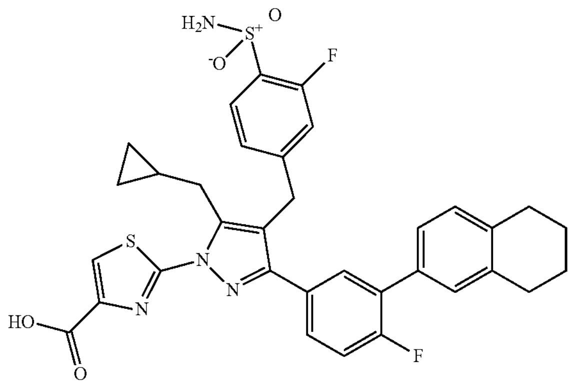 | 2-(5-(cyclopropylmethyl)-3-(4-fluoro-3-(5,6,7,8-tetrahydronaphthalen-2-yl)phenyl)-4-(3-fluoro-4-sulfamoylbenzyl)-1H-pyrazol-1-yl)thiazole-4-carboxylic acid. $^1$H NMR (d$^6$-DMSO) δ 8.29 (s, 1H), 7.81 (t, 1H, J = 4 Hz), 7.62 (s, 2H), 7.51 (d, 1H, J = 2 Hz), 7.35 (t, 1H, J = 8 Hz), 7.21 (d, 1H, J = 12 Hz), 7.13-7.07 (m, 5H), 4.18 (s, 2H), 3.16 (m, 2H), 2.74 (m, 4H), 1.76 (m, 4H), 1.42 (m, 1H), 0.35 (m, 2H), 0.22 (m, 2H); MS (ES) m/z 661 [M + H]$^+$; LCMS RT = 1.39 min. | +++ | 28 |
| 144 | 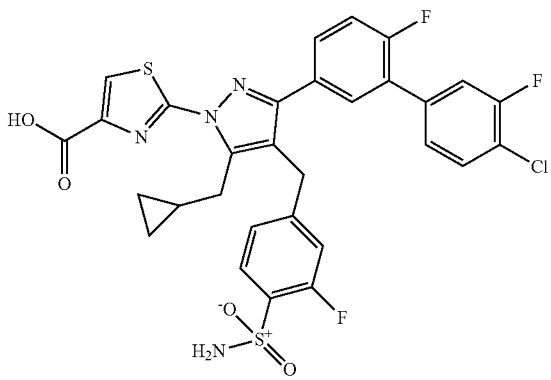 | 2-(3-(4'-chloro-3',6-difluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid. $^1$H NMR (CDCl$_3$) δ: 7.99 (s, 1H), 7.74 (t, J = 8.0 Hz, 1H), 7.50 (dd, J = 2.0, 7.6 Hz, 1H), 7.45-7.38 (m, 2H), 7.20 (d, J = 10.0 Hz, 1H), 7.13-7.09 (m, 2H), 7.00 (d, J = 8.1 Hz, 1H), 6.93 (d, J = 11.0 Hz, 1H), 4.03 (s, 2H), 3.15 (d, J = 6.8 Hz, 2H), 1.06-1.03 (m, 1H), 0.39-0.34 (m, 2H), 0.19-0.15 (m, 2H); MS (ES) m/z 659.0 [M + H]$^+$; LCMS RT = 1.298 min. | +++ | 28 |
| 145 | 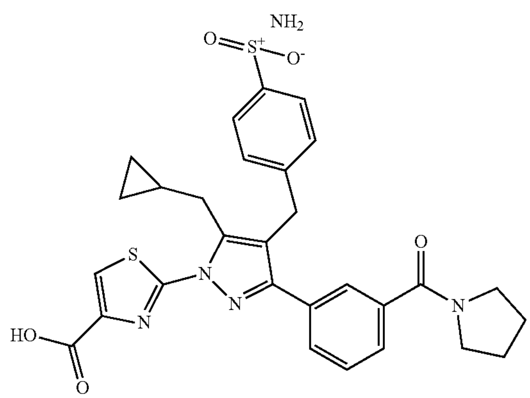 | 2-(5-(cyclopropylmethyl)-3-(3-(pyrrolidine-1-carbonyl)phenyl)-4-(4-sulfamoylbenzyl)-1H-pyrazol-1-yl)thiazole-4-carboxylic acid MS (ES) 628.0 (M + H)+, LCMS RT = 0.968 min. | +++ | 31 |
| 146 | 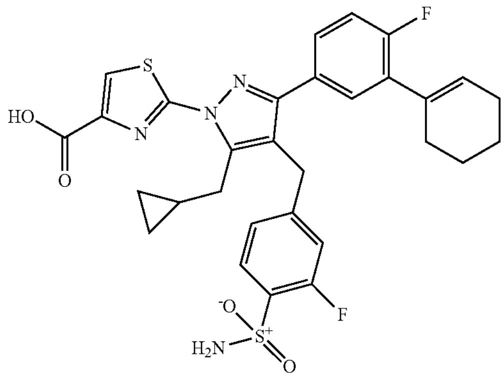 | 2-(5-(cyclopropylmethyl)-3-(6-fluoro-2',3',4',5'-tetrahydro-[1,1'-biphenyl]-3-yl)-4-(3-fluoro-4-sulfamoylbenzyl)-1H-pyrazol-1-yl)thiazole-4-carboxylic acid. $^1$H NMR (d$^6$-DMSO) δ 8.28 (s, 1H), 7.68 (tr, 1H, J = 8 Hz), 7.65 (s, 2H), 7.48-7.46 (m, 1H), 7.29-7.27 (m, 1H), 7.23-7.16 (m, 2H, J = 8 Hz), 5.82 (m, 1H), 4.13 (s, 2H), 3.18-3.16 (m, 2H), 2.16-2.14 (m, 4H), 1.67-1.65 (m, 2H), 1.60-1.57 (m, 2H), 1.17-1.15 (m, 1H), 0.37-0.33 (m, 2H), 0.25-0.23 (m, 2H); MS (ES) m/z 611.0 [M + H]$^+$; LCMS RT = 1.30 min. | +++ | 28 |

TABLE 7-continued

| Cmpd ID | Structure | Compound name and physical data | Inhibitory activity IC$_{50}$ (μM) | Example Method |
|---|---|---|---|---|
| 147 | 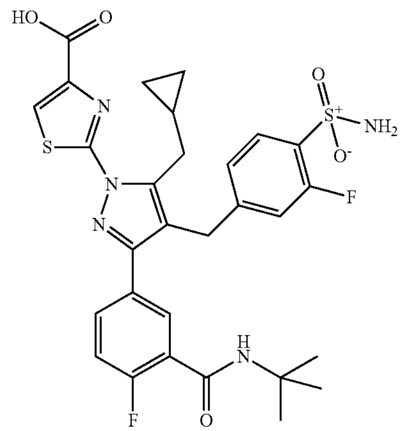 [SMILES: CC(C)(C)NC(=O)c1cc(-c2nn(-c3nc(C(=O)O)cs3)c(CC3CC3)c2Cc2ccc([S+](N)(=O)[O-])c(F)c2)ccc1F] | 2-(3-(3-(tert-butylcarbamoyl)-4-fluorophenyl)-5-(cyclopropylmethyl)-4-(3-fluoro-4-sulfamoylbenzyl)-1H-pyrazol-1-yl) thiazole-4-carboxylic acid: $^1$H-NMR (MeOD) δ: 8.21 (s, 1H), 7.79-7.69 (m, 3H), 7.19 (dd, J = 8.6, 10.0 Hz, 1H), 7.11-7.05 (m, 2H), 4.21 (s, 2H), 3.28 (d, J = 6.8 Hz, 2H), 1.44 (s, 9H), 1.18-1.10 (m, 1H), 0.43-0.39 (m, 2H), 0.28-0.24 (m, 2H); MS (ES) 630.1 [M + H]$^+$, LCMS RT = 1.048 min. | +++ | 24 |
| 148 | 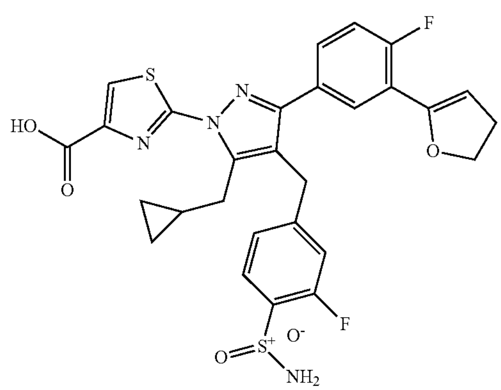 | 2-(5-(cyclopropylmethyl)-3-(3-(4,5-dihydrofuran-2-yl)-4-fluorophenyl)-4-(3-fluoro-4-sulfamoylbenzyl)-1H-pyrazol-1-yl)thiazole-4-carboxylic acid | +++ | 7 |
| 149 | 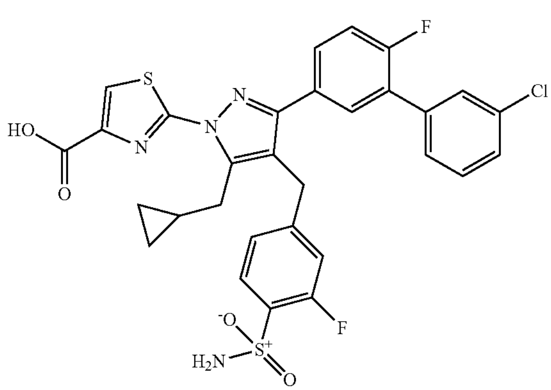 | 2-(3-(3'-chloro-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid. $^1$H NMR (CDCl$_3$) δ: 7.97 (s, 1H), 7.63 (t, J = 7.6 Hz, 1H), 7.37-7.31 (m, 2H), 7.20-7.12 (m, 4H), 6.99 (dd, J = 9.2, 10.0 Hz, 1H,), 6.90 (d, J = 8.0 Hz, 1H), 6.81 (d, J = 10.8 Hz, 1H), 3.92 (s, 2H), 3.29 (s, 3H), 3.04 (d, J = 6.7 Hz, 2H), 0.95-0.92 (m, 1H), 0.28-0.23 (m, 2H), 0.07-0.04 (m, 2H). MS (ES) m/z 641.0 [M + H]$^+$; LCMS RT = 1.293 min. | +++ | 28 |

TABLE 7-continued

| Cmpd ID | Structure | Compound name and physical data | Inhibitory activity IC$_{50}$ (μM) | Example Method |
|---|---|---|---|---|
| 150 | 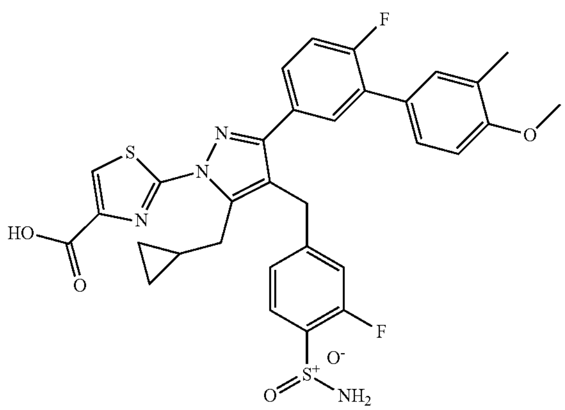 | 2-(5-(cyclopropylmethyl)-3-(6-fluoro-4'-methoxy-3'-methyl-[1,1'-biphenyl]-3-yl)-4-(3-fluoro-4-sulfamoylbenzyl)-1H-pyrazol-1-yl)thiazole-4-carboxylic acid. $^1$H NMR (CDCl$_3$) δ: 8.09 (s, 1H), 7.78 (t, J = 7.6 Hz, 1H), 7.48 (d, J = 7.3 Hz, 1H), 7.26 (bs, 1H), 7.25 (d, J = 6.6 Hz, 2H), 7.17 (d, J = 8.3 Hz, 1H), 7.12 (t, J = 9.4 Hz, 1H), 7.05 (d, J = 8.0 Hz, 1H), 6.98 (d, J = 11.0 Hz, 1H), 6.87 (d, J = 8.4 Hz, 1H), 4.07 (s, 2H), 3.86 (s, 3H), 3.17 (d, J = 6.4 Hz, 2H), 2.24 (s, 3H), 1.13 (bs, 1H), 0.45-0.43 (m, 2H), 0.23-0.22 (m, 2H); MS (ES) m/z 651.0 [M + H]$^+$; LCMS RT = 1.277 min. | +++ | 28 |
| 151 | 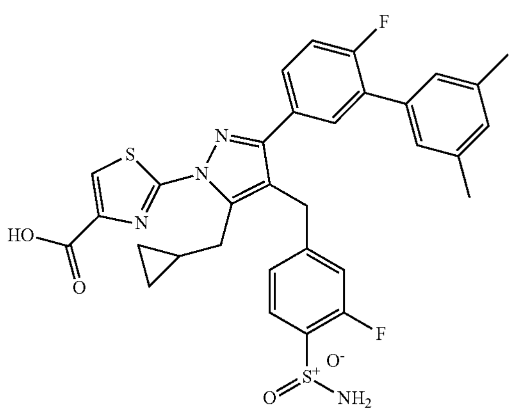 | 2-(5-(cyclopropylmethyl)-3-(6-fluoro-3',5'-dimethyl-[1,1'-biphenyl]-3-yl)-4-(3-fluoro-4-sulfamoylbenzyl)-1H-pyrazol-1-yl)thiazole-4-carboxylic acid. MS (ES) m/z 634.0 [M + H]$^+$; LCMS RT = 1.313 min. | ++ | 28 |
| 152 | 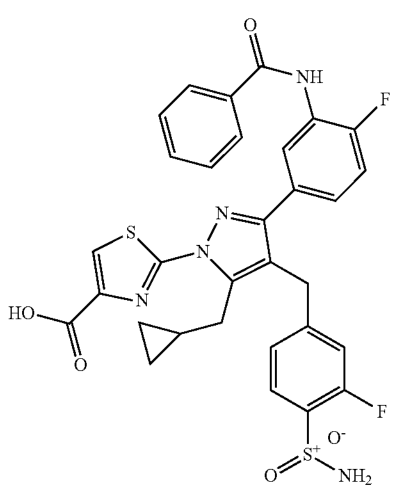 | 2-(3-(3-benzamido-4-fluorophenyl)-5-(cyclopropylmethyl)-4-(3-fluoro-4-sulfamoylbenzyl)-1H-pyrazol-1-yl)thiazole-4-carboxylic acid. MS (ES) m/z 650.0 [M + H]$^+$; LCMS RT = 1.100 min. | +++ | 32 |

TABLE 7-continued

| Cmpd ID | Structure | Compound name and physical data | Inhibitory activity IC$_{50}$ (μM) | Example Method |
|---|---|---|---|---|
| 153 | 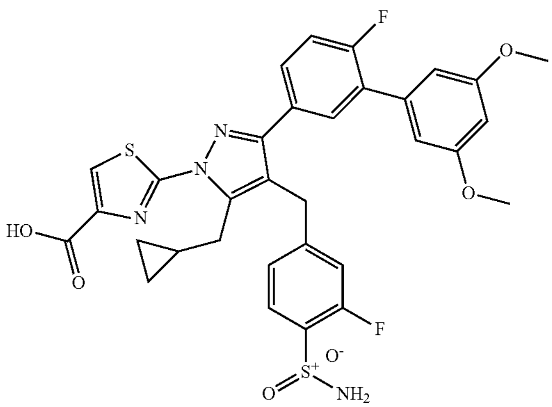 | 2-(5-(cyclopropylmethyl)-3-(6-fluoro-3',5'-dimethoxy-[1,1'-biphenyl]-3-yl)-4-(3-fluoro-4-sulfamoylbenzyl)-1H-pyrazol-1-yl)thiazole-4-carboxylic acid. MS (ES) m/z 666.0 [M + H]$^+$; LCMS RT = 1.223 min. | +++ | 28 |
| 154 | 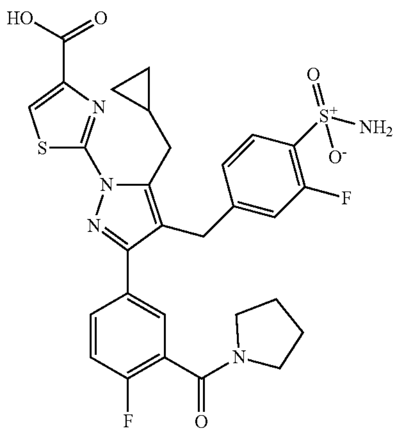 [SMILES: N[S+](=O)([O-])c1ccc(Cc2c(-c3ccc(F)c(C(=O)N4CCCC4)c3)nn(-c3nc(C(=O)O)cs3)c2CC2CC2)cc1F] | 2-(5-(cyclopropylmethyl)-3-(4-fluoro-3-(2-oxopyrrolidin-1-yl)phenyl)-4-(3-fluoro-4-sulfamoylbenzyl)-1H-pyrazol-1-yl)thiazole-4-carboxylic acid. $^1$H NMR (MeOD) δ 8.22 (s, 1H), 7.75-7.71 (m, 2H), 7.54 (dd, J = 2.2, 6.4 Hz, 1H), 7.24 (t, J = 8.8 Hz, 1H), 7.07 (t, J = 7.4 Hz, 2H), 4.20 (s, 2H), 3.59 (t, J = 7.1 Hz, 2H), 3.30 (d, J = 6.9 Hz, 2H), 3.19 (t, J = 2H), 2.03-1.91 (m, 4H), 0.95-0.86 (m, 1H), 0.45-0.40 (m, 2H), 0.29-0.25 (m, 2H); MS (ES) m/z 628.0 [M + H]$^+$; LCMS RT = 0.968 min. | +++ | 31 |
| 155 | 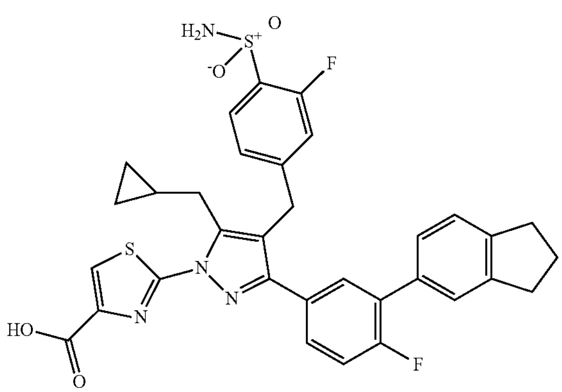 | 2-(5-(cyclopropylmethyl)-3-(3-(2,3-dihydro-1H-inden-5-yl)-4-fluorophenyl)-4-(3-fluoro-4-sulfamoylbenzyl)-1H-pyrazol-1-yl)thiazole-4-carboxylic acid. MS (ES) m/z 647.0 [M + H]$^+$; LCMS RT = 1.34 min. | +++ | 28 |

TABLE 7-continued

| Cmpd ID | Structure | Compound name and physical data | Inhibitory activity IC$_{50}$ (μM) | Example Method |
|---|---|---|---|---|
| 156 | 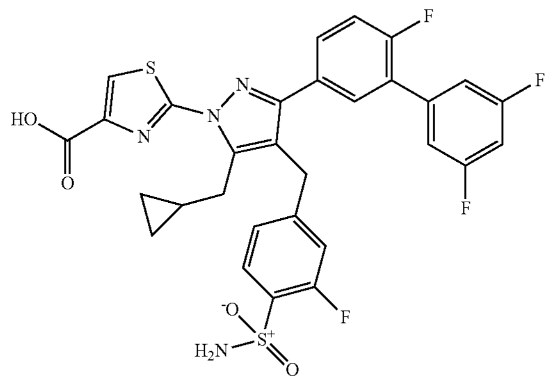 | 2-(5-(cyclopropylmethyl)-4-(3-fluoro-4-sulfamoylbenzyl)-3-(3',5',6-trifluoro-[1,1'-biphenyl]-3-yl)-1H-pyrazol-1-yl)thiazole-4-carboxylic acid. MS (ES) m/z 642.0 [M + H]$^+$; LCMS RT = 1.260 min. | +++ | 28 |
| 157 | 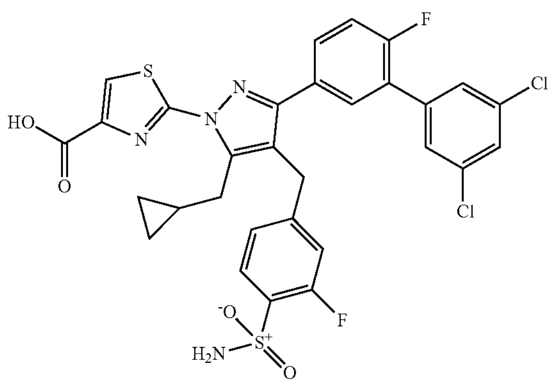 | 2-(5-(cyclopropylmethyl)-3-(3',5'-dichloro-6-fluoro-[1,1'-biphenyl]-3-yl)-4-(3-fluoro-4-sulfamoylbenzyl)-1H-pyrazol-1-yl)thiazole-4-carboxylic acid. MS (ES) m/z 674.0 [M + H]$^+$; LCMS RT = 1.365 min. | ++ | 28 |
| 158 | 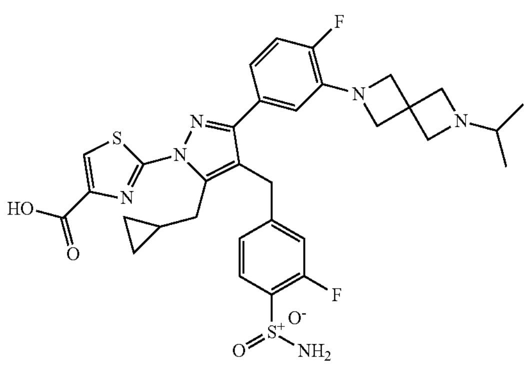 | 2-(5-(cyclopropylmethyl)-3-(4-fluoro-3-(6-isopropyl-2,6-diazaspiro[3.3]heptan-2-yl)phenyl)-4-(3-fluoro-4-sulfamoylbenzyl)-1H-pyrazol-1-yl)thiazole-4-carboxylic acid; $^1$H-NMR (MeOD) δ acid,: 8.19 (s, 1H), 7.79 (t, J = 8.1 Hz, 1H), 7.10 (s, 1H), 7.08 (d, J = 4.8 Hz, 1H), 7.00 (d, J = 8.9 Hz, 2H), 6.28 (d, J = 8.5 Hz, 1H), 4.35 (d, J = 11.7 Hz, 2H), 4.28 (d, J = 11.6 Hz, 2H), 3.70 (s, 2H), 3.45 (p, J = 6.5, 12.8 Hz, 1H), 3.28 (d, J = 6.9 Hz, 2H), 2.66 (s, 2H), 1.24 (d, J = 6.48 Hz, 6H), 1.17-1.12 (m, 1H), 0.34-0.32 (m, 2H), 0.22-0.21 (m, 2H). MS (ES) 669.0 [M + H]$^+$, LCMS RT = 0.970 min. | +++ | 25 |
| 159 | 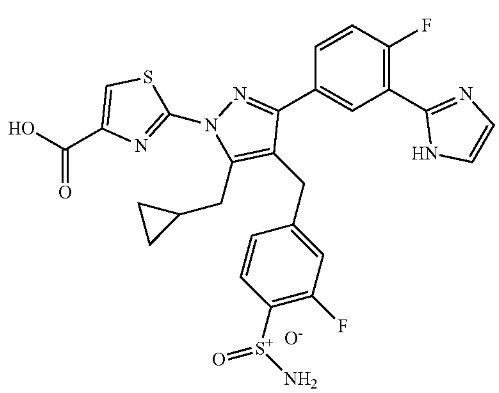 | 2-(5-(cyclopropylmethyl)-3-(4-fluoro-3-(1H-imidazol-2-yl)phenyl)-4-(3-fluoro-4-sulfamoylbenzyl)-1H-pyrazol-1-yl)thiazole-4-carboxylic acid. MS (ES) m/z 597.1 [M + H]$^+$; LCMS RT = 0.863 min. | +++ | 27 |

TABLE 7-continued

| Cmpd ID | Structure | Compound name and physical data | Inhibitory activity IC$_{50}$ (μM) | Example Method |
|---|---|---|---|---|
| 160 | 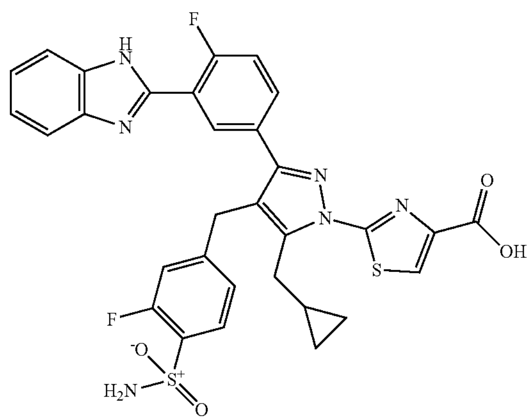 | 2-(3-(3-(1H-benzo[d]imidazol-2-yl)-4-fluorophenyl)-5-(cyclopropylmethyl)-4-(3-fluoro-4-sulfamoylbenzyl)-1H-pyrazol-1-yl)thiazole-4-carboxylic acid. MS (ES) m/z 647.1.0 [M + H]$^+$; LCMS RT = 0.987 min. | +++ | 27 |
| 161 | 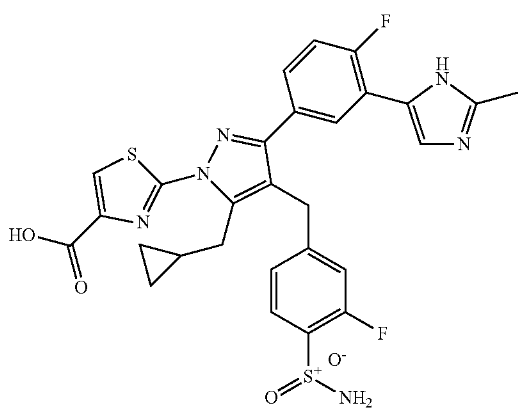 | 2-(5-(cyclopropylmethyl)-3-(4-fluoro-3-(2-methyl-1H-imidazol-5-yl)phenyl)-4-(3-fluoro-4-sulfamoylbenzyl)-1H-pyrazol-1-yl)thiazole-4-carboxylic acid. $^1$H NMR (MeOD) δ: 8.19 (s, 1H), 7.84 (t, J = 6.0 Hz, 1H), 7.68 (t, J = 7.6 Hz, 1H), 7.64 (s, 1H), 7.59 (bs, 1H), 7.31 (t, J = 10.4 Hz, 1H), 7.02 (t, J = 9.6 Hz, 2H), 4.17 (s, 2H), 2.70 (s, 3H), 1.14 (bs, 1H), 0.43-0.41 (m, 2H), 0.27-0.25 (m, 2H). MS (ES) m/z 611.0 [M + H]$^+$; LCMS RT = 0.912 min. | +++ | 28 |
| 162 | 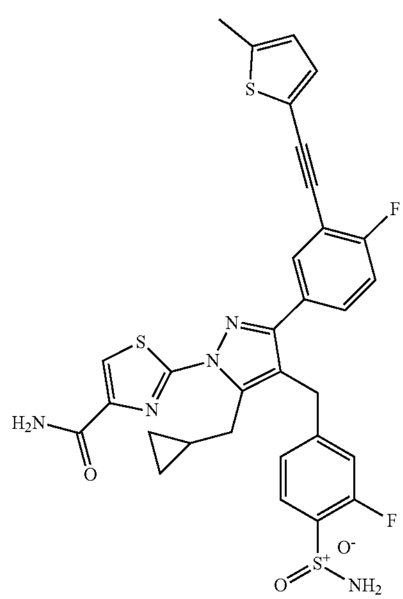 | 2-(5-(cyclopropylmethyl)-3-(4-fluoro-3-((5-methylthiophen-2-yl)ethynyl)phenyl)-4-(3-fluoro-4-sulfamoylbenzyl)-1H-pyrazol-1-yl)thiazole-4-carboxamide; $^1$H-NMR (d$_6$-DMSO) δ 8.13 (s, 1H), 7.75-7.54 (m, 3H), 7.62 (s, 2H), 7.38 (tr, 1H, J = 16 Hz), 7.36 (d, 1H, J = 4 Hz), 7.15 (d, 1H, J = 12 Hz), 7.06 (d, 1H, J = 8 Hz), 6.85 (d, 1H, J = 4 Hz), 4.18 (s, 2H), 3.18-315 (m, 2H), 2.5 (s, 3H), 1.18-1.15 (m, 1H), 0.34-0.32 (m, 2H), 0.19-0.17 (m, 2H); MS (ES) 651.1 [M + H]$^+$, LCMS RT = 0.78 min. | +++ | 26 |

TABLE 7-continued

| Cmpd ID | Structure | Compound name and physical data | Inhibitory activity IC$_{50}$ (μM) | Example Method |
|---|---|---|---|---|
| 163 | 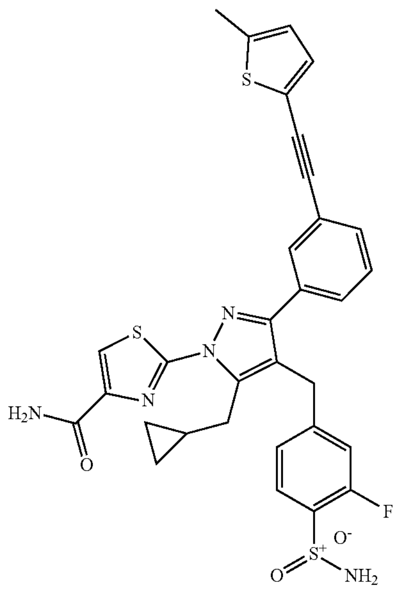 | 2-(5-(cyclopropylmethyl)-4-(3-fluoro-4-sulfamoylbenzyl)-3-(3-((5-methylthiophen-2-yl)ethynyl)phenyl)-1H-pyrazol-1-yl)thiazole-4-carboxamide. $^1$H NMR (d$^6$-DMSO) δ 8.12 (s, 1H), 7.72-7.44 (m, 5H), 7.62 (s, 2H), 7.24 (d, 1H, J = 4 Hz), 7.16 (d, 1H, J = 12 Hz), 7.06 (d, 1H, J = 8 Hz), 6.83 (d, 1H, J = 2 Hz), 4.18 (s, 2H), 3.16 (m, 2H), 2.5 (s, 3H), 1.08 (m, 1H), 0.34 (m, 2H), 0.17 (m, 2H); MS (ES) m/z 632.2 [M + H]$^+$; LCMS RT = 0.77 min. | + | 26 |
| 164 | 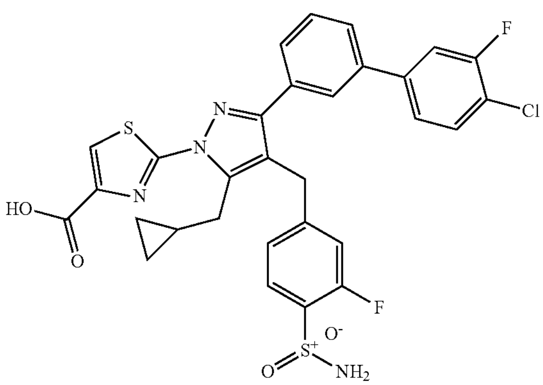 | 2-(3-(4'-chloro-3'-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid. $^1$H NMR (MeOD) δ 8.20 (s, 1H), 7.76 (t, J = 7.76 Hz, 1H), 7.70 (t, J = 1.63 Hz, 1H), 7.62 (dd, J = 1.63, 7.76 Hz, 2H), 7.52 (t, J = 8.17 Hz, 1H), 7.48 (t, J = 7.84 Hz, 1H), 7.43 (dd, J = 2.05, 10.59 Hz, 1H), 7.21 (dd, J = 1.71, 8.41 Hz, 1H), 7.12-7.07 (m, 2H), 4.20 (s, 2H), 3.28 (d, J = 6.39 Hz, 2H), 1.19-1.09 (m, 1H), 0.43-0.38 (m, 2H), 0.27-0.23 (m, 2H); MS (ES) m/z 640.9 [M + H]$^+$, LCMS RT = 1.432 min. | +++ | 28 |
| 165 | 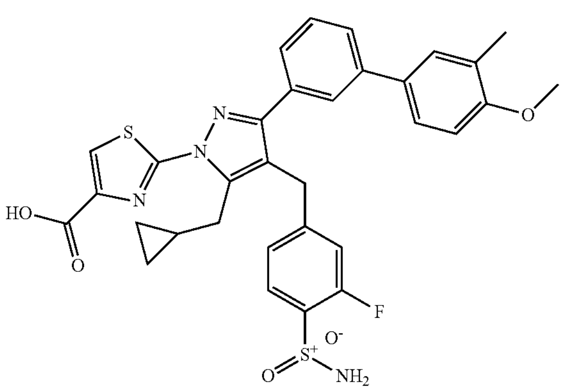 | 2-(5-(cyclopropylmethyl)-4-(3-fluoro-4-sulfamoylbenzyl)-3-(4'-methoxy-3'-methyl-[1,1'-biphenyl]-3-yl)-1H-pyrazol-1-yl)thiazole-4-carboxylic acid. $^1$H NMR (MeOD) δ 8.19 (s, 1H), 7.79-7.76 (m, 1H), 7.58-7.51 (m, 3H), 7.40 (t, J = 7.69 Hz, 1H), 7.25 (d, J = 1.81 Hz, 1H), 7.14-7.09 (m, 3H), 6.93 (d, J = 8.50 Hz, 1H), 4.17 (s, 2H), 3.85 (s, 3H), 3.26 (d, J = 6.65 Hz, 2H), 2.22 (s, 3H), 1.18-1.08 (m, 1H), 0.42-0.37 (m, 2H), 0.26-0.22 (m, 2H); MS (ES) m/z 633.0 [M + H]$^+$, LCMS RT = 1.412 min. | +++ | 28 |

TABLE 7-continued

| Cmpd ID | Structure | Compound name and physical data | Inhibitory activity IC$_{50}$ (μM) | Example Method |
|---|---|---|---|---|
| 166 | 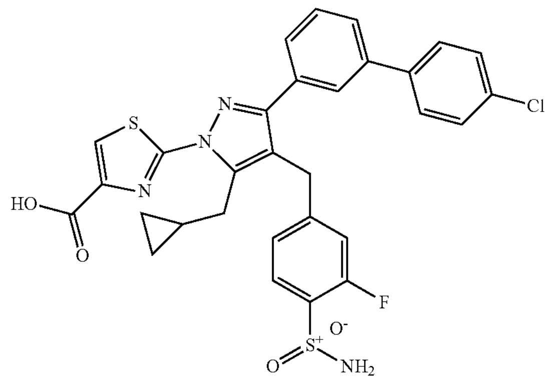 | 2-(3-(4'-chloro-[1,1'-biphenyl]-3-yl)-5-(cyclopropylmethyl)-4-(3-fluoro-4-sulfamoylbenzyl)-1H-pyrazol-1-yl)thiazole-4-carboxylic acid. $^1$H NMR (MeOD) δ 8.20 (s, 1H), 7.77 (t, J = 8.02 Hz, 1H), 7.63 (dd, J = 1.50, 12.98 Hz, 2H), 7.59 (d, J = 1.43 Hz, 1H), 7.46 (t, J = 7.72 Hz, 1H), 7.41 (s, 4H), 7.11-7.08 (m, 2H), 4.19 (s, 2H), 3.27 (d, J = 6.85 Hz, 2H), 1.19-1.09 (m, 1H), 0.42-0.38 (m, 2H), 0.27-0.23 (m, 2H); MS (ES) m/z 622.9 [M + H]$^+$, LCMS RT = 1.261 min. | +++ | 28 |
| 167 | 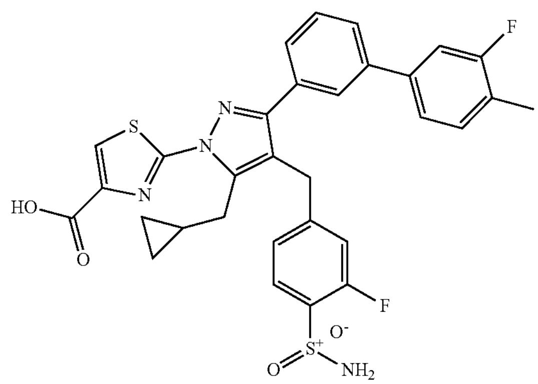 | 2-(5-(cyclopropylmethyl)-3-(3'-fluoro-4'-methyl-[1,1'-biphenyl]-3-yl)-4-(3-fluoro-4-sulfamoylbenzyl)-1H-pyrazol-1-yl)thiazole-4-carboxylic acid. $^1$H NMR (MeOD) δ 8.19 (s, 1H), 7.78-7.74 (m, 1H), 7.67 (t, J = 1.52, 1H), 7.60-7.56 (m, 2H), 7.44 (t, J = 7.82 Hz, 1H), 7.27 (t, J = 8.04 Hz, 1H), 7.19 (dd, J = 1.70, 11.21 Hz, 1H), 7.12-7.08 (m, 3H), 4.19 (s, 2H), 3.27 (d, J = 6.83 Hz, 2H), 2.28 (d, J = 1.42 Hz, 3H), 1.18-1.08 (m, 1H), 0.42-0.37 (m, 2H), 0.27-0.23 (m, 2H); MS (ES) m/z 621.0 [M + H]$^+$, LCMS RT = 1.256 min | +++ | 28 |
| 168 | 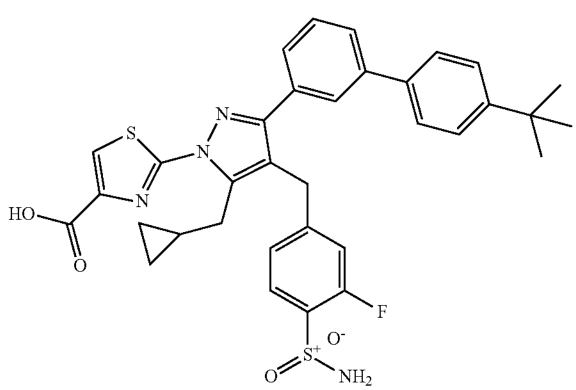 | 2-(3-(4'-(tert-butyl)-[1,1'-biphenyl]-3-yl)-5-(cyclopropylmethyl)-4-(3-fluoro-4-sulfamoylbenzyl)-1H-pyrazol-1-yl)thiazole-4-carboxylic acid. $^1$H NMR (MeOD) δ 8.17 (s, 1H), 7.79-7.75 (m, 1H), 7.63-7.62 (m, 1H), 7.59 (d, J = 7.82 Hz, 1H), 7.53 (d, J = 7.82 Hz, 1H), 7.45-7.39 (m, 3H), 7.32 (d, J = 8.50 Hz, 2H), 7.10 (s, 1H), 7.08 (d, J = 3.84 Hz, 1H), 4.15 (s, 2H), 3.25 (d, J = 6.72 Hz, 2H), 1.34 (s, 9H), 1.18-1.08 (m, 1H), 0.41-0.36 (m, 2H), 0.26-0.22 (m, 2H); MS (ES) m/z 645.0 [M + H]$^+$; LCMS RT = 1.348 min. | ++ | 28 |

TABLE 7-continued

| Cmpd ID | Structure | Compound name and physical data | Inhibitory activity IC$_{50}$ (μM) | Example Method |
|---|---|---|---|---|
| 169 | 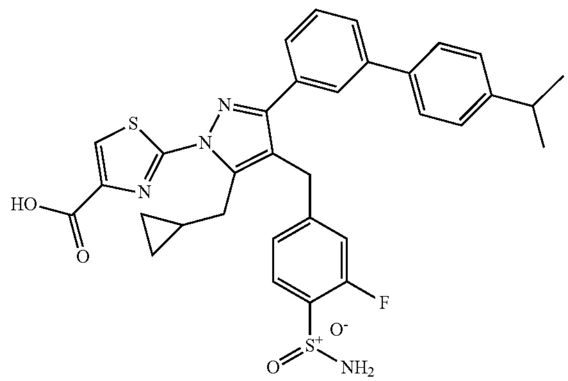 | 2-(5-(cyclopropylmethyl)-4-(3-fluoro-4-sulfamoylbenzyl)-3-(4'-isopropyl-[1,1'-biphenyl]-3-yl)-1H-pyrazol-1-yl)thiazole-4-carboxylic acid. $^1$H NMR (MeOD) δ 8.18 (s, 1H), 7.79-7.75 (m, 1H), 7.64 (t, J = 1.49 Hz, 1H), 7.57 (dd, J = 7.75, 19.38 Hz, 2H), 7.42 (t, J = 7.75 Hz, 1H), 7.33 (d, J = 8.35 Hz, 2H), 7.28 (d, J = 8.35 Hz, 2H), 7.11-7.08 (m, 2H), 4.17 (s, 2H), 3.21 (d, J = 6.71 Hz, 2H), 2.97-2.87 (m, 1H), 1.27 (d, J = 6.86 Hz, 6H), 1.18-1.08 (m, 1H), 0.41-0.37 (m, 2H), 0.26-0.22 (m, 2H); MS (ES) m/z 631.0 [M + H]$^+$; LCMS RT = 1.313 min. | +++ | 28 |
| 170 | 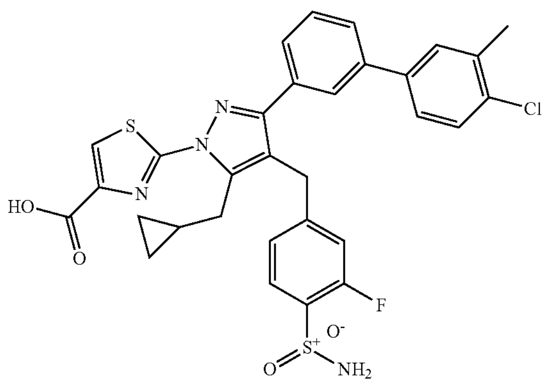 | 2-(3-(4'-chloro-3'-methyl-[1,1'-biphenyl]-3-yl)-5-(cyclopropylmethyl)-4-(3-fluoro-4-sulfamoylbenzyl)-1H-pyrazol-1-yl)thiazole-4-carboxylic acid. $^1$H NMR (MeOD) δ: 8.15 (s, 1H), 7.67 (t, J = 7.8 Hz, 1H), 7.13 (d, J = 8.6 Hz, 1H), 7.08 (d, J = 7.9 Hz, 1H), 7.04-6.95 (m, 4H), 6.88 (t, J = 8.2 Hz, 2H), 6.77 (dd, J = 2.0, 7.9 Hz, 1H), 4.08 (s, 2H), 3.15 (d, J = 6.7 Hz, 2H), 2.22 (s, 3H), 0.97-0.94 (m, 1H), 0.26-0.21 (m, 2H), 0.09-0.08 (m, 2H). | + | 27 |
| 171 | 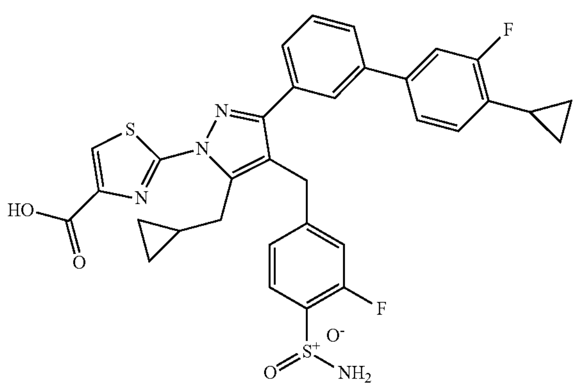 | 2-(3-(4'-cyclopropyl-3'-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid. $^1$H NMR (MeOD) δ: 8.15 (s, 1H), 7.67 (t, J = 7.72 Hz, 1H), 7.10 (t, J = 7.8 Hz, 1H), 7.05-7.02 (m, 2H), 6.97 (d, J = 11.9 Hz, 1H), 6.87 (d, J = 7.6 Hz, 1H), 6.82-6.74 (m, 4H), 4.08 (s, 2H), 3.15 (d, J = 6.48 Hz, 2H), 1.95-1.90 (m, 1H), 0.97-0.87 (m 3H), 0.62-0.58 (m, 2H), 0.26-0.22 (m, 2H), 0.99-0.76 (m, 2H). | + | 27 |
| 172 | 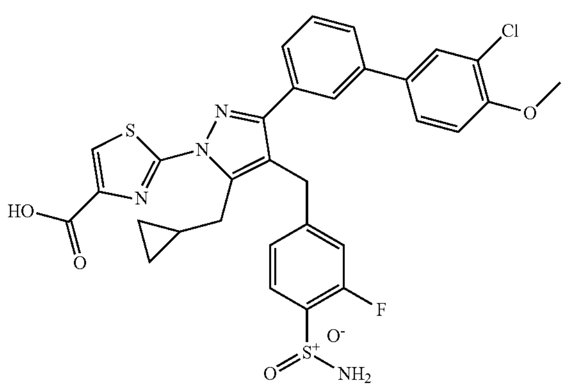 | 2-(3-(3'-chloro-4'-methoxy-[1,1'-biphenyl]-3-yl)-5-(cyclopropylmethyl)-4-(3-fluoro-4-sulfamoylbenzyl)-1H-pyrazol-1-yl)thiazole-4-carboxylic acid. $^1$H NMR (MeOD) δ: 8.14 (s, 1H), 7.60 (t, J = 7.72 Hz, 1H), 7.12 (t, J = 8.4 Hz, 2H), 7.03-6.79 (m, 6H), 6.77 (d, J = 1.9 Hz, 1H), 4.09 (s, 2H), 3.78 (s, 3H), 3.15 (d, J = 6.1 Hz, 2H), 0.99 (bs, 1H), 0.28-0.25 (m, 2H), 0.10-0.09 (m, 2H). | ++ | 27 |

TABLE 7-continued

| Cmpd ID | Structure | Compound name and physical data | Inhibitory activity IC$_{50}$ (μM) | Example Method |
|---|---|---|---|---|
| 173 | 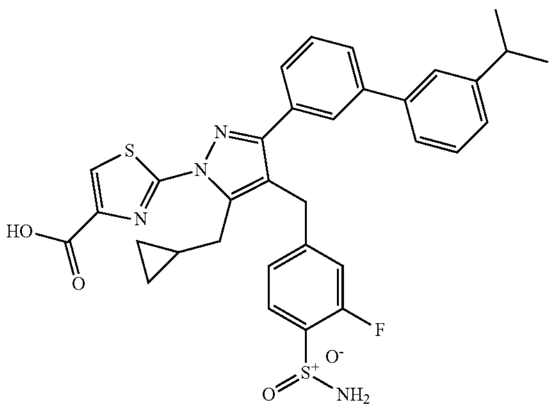 | 2-(5-(cyclopropylmethyl)-4-(3-fluoro-4-sulfamoylbenzyl)-3-(3'-isopropyl-[1,1'-biphenyl]-3-yl)-1H-pyrazol-1-yl)thiazole-4-carboxylic acid. $^1$H NMR (CDCl$_3$) δ 8.11 (s, 1H), 7.80 (t, J = 7.71 Hz, 1H), 7.67 (s, 1H), 7.61 (d, J = 6.72 Hz, 1H), 7.48-7.42 (m, 1H), 7.37-7.34 (m, 2H), 7.28-7.22 (m, 2H), 7.08 (d, J = 7.96 Hz, 1H), 7.00 (d, J = 10.95 Hz, 1H), 4.11 (s, 2H), 3.17 (d, J = 6.47 Hz, 2H), 3.00-2.90 (m, 1H), 1.29 (d, J = 6.97 Hz, 6H), 1.22-1.12 (m, 1H), 0.50-0.46 (m, 2H), 0.25-0.22 (m, 2H); MS (ES) m/z 631.0 [M + H]$^+$; LCMS RT = 1.359 min. | +++ | 28 |
| 174 | 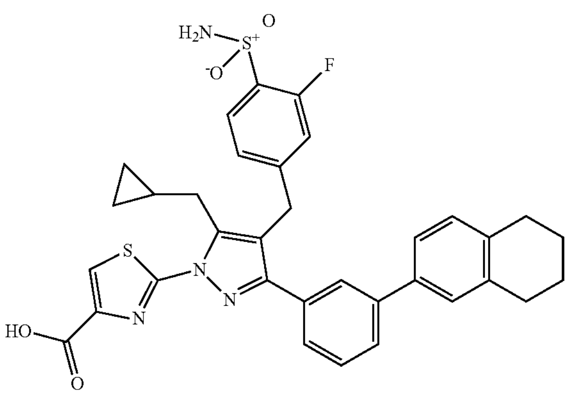 | 2-(5-(cyclopropylmethyl)-4-(3-fluoro-4-sulfamoylbenzyl)-3-(3-(5,6,7,8-tetrahydronaphthalen-2-yl)phenyl)-1H-pyrazol-1-yl)thiazole-4-carboxylic acid. $^1$H NMR (CDCl$_3$) δ 8.10 (s, 1H), 7.79 (t, J = 7.85 Hz, 1H), 7.61 (s, 1H), 7.58 (d, J = 6.90 Hz, 1H), 7.46-7.40 (m, 2H), 7.18 (s, 2H), 7.13-7.11 (m, 1H), 7.07 (d, J = 8.08 Hz, 1H), 6.98 (d, J = 10.94 Hz, 1H), 4.10 (s, 2H), 3.17 (d, J = 6.56 Hz, 2H), 2.80 (s, 4H), 1.83 (s, 4H), 1.23-1.13 (m, 1H), 0.51-0.46 (m, 2H), 0.25-0.21 (m, 2H); MS (ES) m/z 643.0 [M + H]$^+$; LCMS RT = 1.377 min. | ++ | 28 |
| 175 | 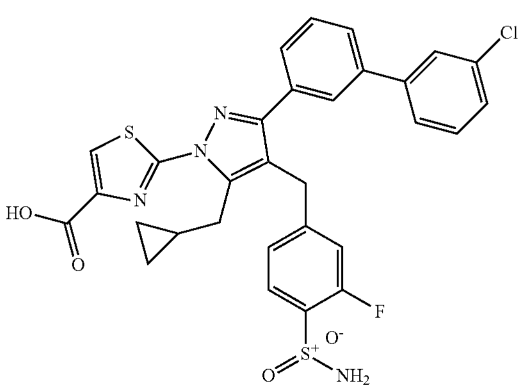 | 2-(3-(3'-chloro-[1,1'-biphenyl]-3-yl)-5-(cyclopropylmethyl)-4-(3-fluoro-4-sulfamoylbenzyl)-1H-pyrazol-1-yl)thiazole-4-carboxylic acid. $^1$H NMR (MeOD) δ 8.21 (s, 1H), 7.77 (t, J = 7.84 Hz, 1H), 7.69 (t, J = 1.63 Hz, 1H), 7.65-7.59 (m, 3H), 7.53 (t, J = 1.81, 1H), 7.48 (t, J = 7.72 Hz, 1H), 7.45-7.39 (m, 2H), 7.37-7.34 (m, 2H), 7.34-7.32 (m, 1H), 7.14-7.08 (m, 2H), 4.22 (s, 2H), 3.28 (d, J = 6.85 Hz, 2H), 1.19-1.09 (m, 1H), 0.43-0.38 (m, 2H), 0.27-0.24 (m, 2H); MS (ES) m/z 623.0 [M + H]$^+$; LCMS RT = 1.364 min. | +++ | 28 |

TABLE 7-continued

| Cmpd ID | Structure | Compound name and physical data | Inhibitory activity IC$_{50}$ (μM) | Example Method |
|---|---|---|---|---|
| 176 | 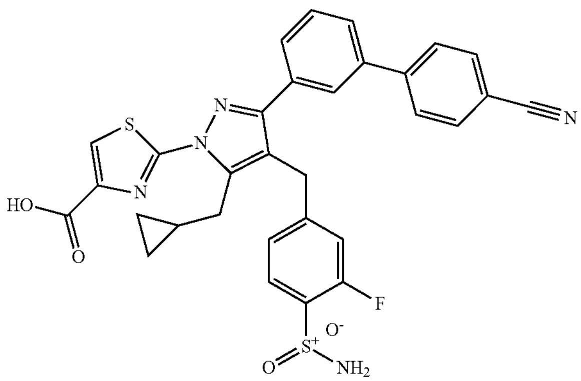 | 2-(3-(4'-cyano-[1,1'-biphenyl]-3-yl)-5-(cyclopropylmethyl)-4-(3-fluoro-4-sulfamoylbenzyl)-1H-pyrazol-1-yl)thiazole-4-carboxylic acid. $^1$H NMR (CDCl$_3$) δ 8.11 (s, 1H), 7.82 (t, J = 7.60 Hz, 1H), 7.74-7.72 (m, 3H), 7.61-7.60 (m, 1H), 7.57 (d, J = 8.54 Hz, 2H), 7.53-7.50 (m,. 1H), 7.49 (d, J = 7.46 Hz, 1H), 7.07 (d, J = 8.21 Hz, 1H), 7.01 (d, 11.07 Hz, 1H), 4.11 (s, 2H), 3.18 (d, J = 6.87, 2H), 1.22-1.12 (m, 1H), 0.51-0.47 (m, 2H), 0.25-0.21 (m, 2H); MS (ES) m/z 631.0 [M + H]$^+$: LCMS RT = 1.167 min. | +++ | 28 |
| 177 | 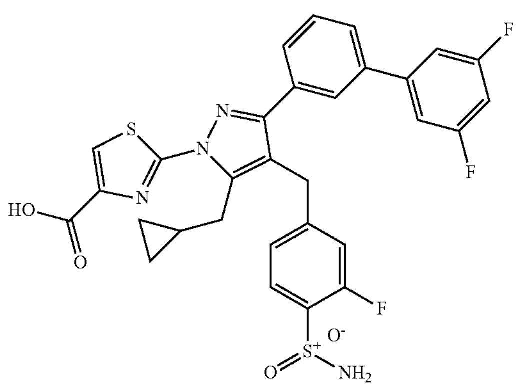 | 2-(5-(cyclopropylmethyl)-3-(3',5'-difluoro-[1,1'-biphenyl]-3-yl)-4-(3-fluoro-4-sulfamoylbenzyl)-1H-pyrazol-1-yl)thiazole-4-carboxylic acid. $^1$H NMR (CDCl$_3$) δ 8.20 (s, 1H), 7.77-7.73 (m, 2H), 7.64-7.61 (m, 2H), 7.48 (t, J = 7.74 Hz, 1H), 7.16-7.12 (m, 2H), 7.11-7.06 (m, 2H), 6.93 (tt, J = 2.26, 9.05 Hz, 1H), 4.22 (s, 2H), 3.27 (d, J = 6.79 Hz, 2H), 1.18-1.08 (m, 1H), 0.42-0.38 (m, 2H), 0.27-0.23 (m, 2H); MS (ES) m/z 614.2 [M + H]$^+$; LCMS RT = 0.954 min. | +++ | 28 |
| 178 | 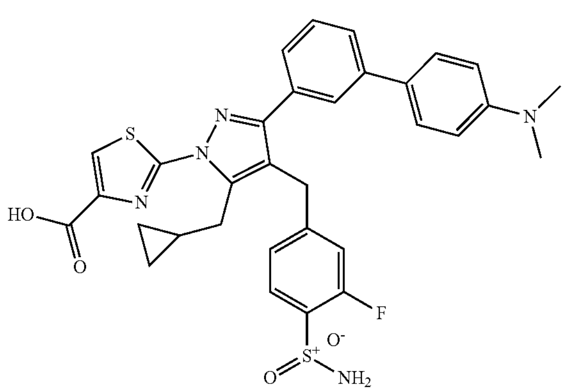 | 2-(5-(cyclopropylmethyl)-3-(4'-(dimethylamino)-[1,1'-biphenyl]-3-yl)-4-(3-fluoro-4-sulfamoylbenzyl)-1H-pyrazol-1-yl)thiazole-4-carboxylic acid. $^1$H NMR (MeOD) δ: 8.21 (s, 1H), 7.79 (t, J = 7.5 Hz, 1H), 7.59 (t, J = 9.0 Hz, 2H), 7.49-7.44 (m, 2H), 7.17-7.15 (m, 2H), 7.12 (d, J = 2.42 Hz, 1H), 4.18 (s, 2H), 3.13 (s, 6H), 1.19-1.12 (m, 1H), 0.44-0.40 (m, 2H), 0.28-0.25 (m, 2H); MS (ES) m/z 632.0 [M + H]$^+$; LCMS RT 0.943 min. | +++ | 28 |

TABLE 7-continued

| Cmpd ID | Structure | Compound name and physical data | Inhibitory activity IC$_{50}$ (μM) | Example Method |
|---|---|---|---|---|
| 179 | 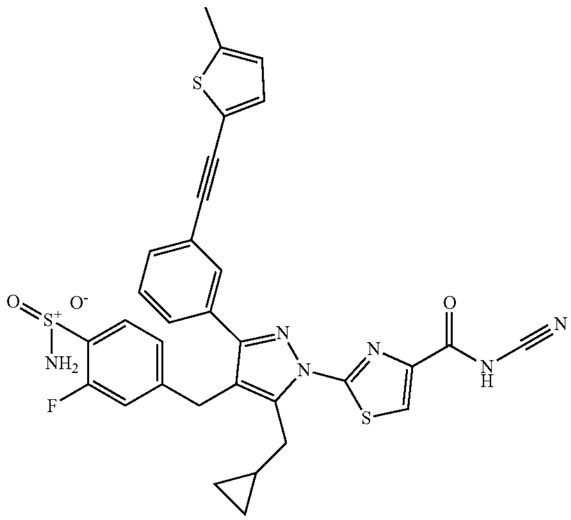 | N-cyano-2-(5-(cyclopropylmethyl)-4-(3-fluoro-4-sulfamoylbenzyl)-3-(3-((5-methylthiophen-2-yl)ethynyl)phenyl)-1H-pyrazol-1-yl)thiazole-4-carboxamide | + | 33 |
| 180 | 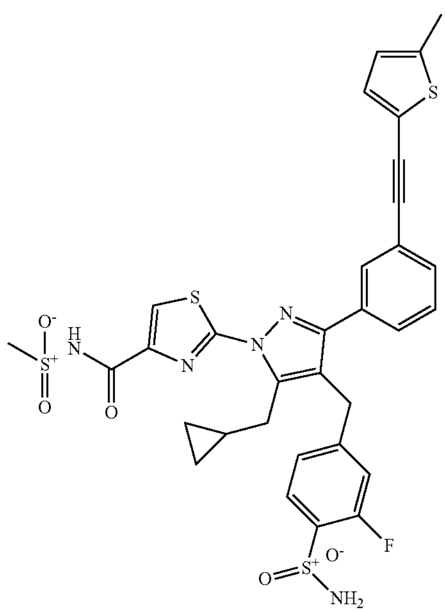 | 2-(5-(cyclopropylmethyl)-4-(3-fluoro-4-sulfamoylbenzyl)-3-(3-((5-methylthiophen-2-yl)ethynyl)phenyl)-1H-pyrazol-1-yl)-N-(methylsulfonyl)thiazole-4-carboxamide | + | 33 |

TABLE 7-continued

| Cmpd ID | Structure | Compound name and physical data | Inhibitory activity IC$_{50}$ (μM) | Example Method |
|---|---|---|---|---|
| 181 | 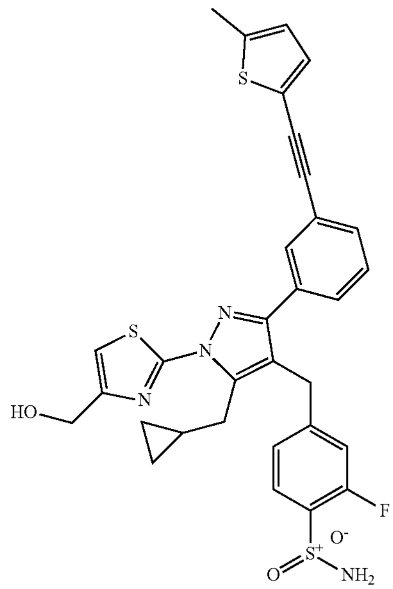 | 4-((5-(cyclopropylmethyl)-1-(4-(hydroxymethyl)thiazol-2-yl)-3-(3-((5-methylthiophen-2-yl)ethynyl)phenyl)-1H-pyrazol-4-yl)methyl)-2-fluorobenzenesulfonamide | – | 33 |
| 182 | 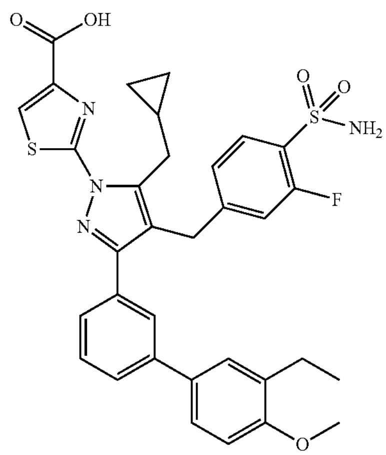 [SMILES: CCc1cc(-c2cccc(-c3nn(-c4nc(C(=O)O)cs4)c(CC4CC4)c3Cc3ccc(S(N)(=O)=O)c(F)c3)c2)ccc1OC] | 2-(5-(cyclopropylmethyl)-3-(3'-ethyl-4'-methoxy-[1,1'-biphenyl]-3-yl)-4-(3-fluoro-4-sulfamoylbenzyl)-1H-pyrazol-1-yl)thiazole-4-carboxylic acid: $^1$H NMR (MeOD) δ: 8.18 (s, 1H), 7.78 (t, J = 7.9 Hz, 1H), 7.62 (s, 1H), 7.59-7.52 (m, 2H), 7.43 (t, J = 7.7 Hz, 1H), 7.28 (d, J = 2.4 Hz, 2H), 7.16-7.10 (m, 3H), 6.96-(d, J = 8.55 Hz, 1H), 4.20 (s, 2H), 3.86 (s, 3H), 2.65 (q, J = 7.55, 15.09 Hz, 2H), 1.19 (t, J = 7.55 Hz), 1.15-1.10 (m, 1H), 0.42-0.38 (m, 2H), 0.26-0.23 (m, 2H); MS (ES) m/z 647.0 [M + H]$^+$; LCMS RT = 1.296 min. | ++ | 27 |
| 183 | 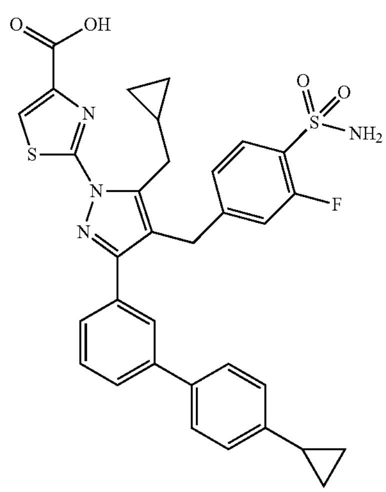 [SMILES: NS(=O)(=O)c1ccc(Cc2c(-c3cccc(-c4ccc(C5CC5)cc4)c3)nn(-c3nc(C(=O)O)cs3)c2CC2CC2)cc1F] | 2-(3-(4'-cyclopropyl-[1,1'-biphenyl]-3-yl)-5-(cyclopropylmethyl)-4-(3-fluoro-4-sulfamoylbenzyl)-1H-pyrazol-1-yl)thiazole-4-carboxylic acid: $^1$H NMR (MeOD) δ: 8.19 (s, 1H), 7.77 (t, J = 7.6 Hz, 1H), 7.61 (t, J = 1.6 Hz, 1H), 7.59-7.53 (m, 2H), 7.42 (t, J = 7.71 Hz, 1H), 7.29-7.27 (m, 2H), 7.12-7.08 (m, 4H), 4.17 (s, 2H), 3.26 (d, J = 6.73 Hz, 2H), 1.95-1.88 (m, 1H), 1.16-1.11 (m, 1H), 1.00-0.95 (m, 2H), 0.74-0.70 (m, 2H), 0.42-0.38 (m, 2H), 0.27-0.23 (m, 2H); MS (ES) m/z 629.0 [M + H]$^+$; LCMS RT = 1.301 min. | +++ | 27 |

TABLE 7-continued

| Cmpd ID | Structure | Compound name and physical data | Inhibitory activity IC$_{50}$ (μM) | Example Method |
|---|---|---|---|---|
| 184 | 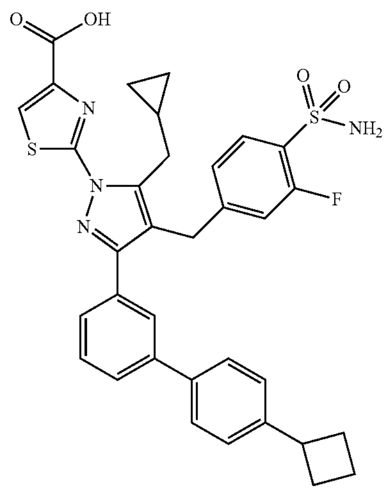 [SMILES: NS(=O)(=O)c1ccc(Cc2c(-c3cccc(-c4ccc(C5CCC5)cc4)c3)nn(-c3nc(C(=O)O)cs3)c2CC2CC2)cc1F] | 2-(3-(4'-cyclobutyl-[1,1'-biphenyl]-3-yl)-5-(cyclopropylmethyl)-4-(3-fluoro-4-sulfamoylbenzyl)-1H-pyrazol-1-yl)thiazole-4-carboxylic acid: $^1$H NMR (MeOD) δ: 8.19 (s, 1H), 7.78 (t, J = 7.8 Hz, 1H), 7.65 (s, 1H), 7.61-7.55 (m, 2H), 7.44 (t, J = 7.7, 1H), 7.35 (d, J = 8.1 Hz, 2H), 7.29-7.27 (m, 2H), 7.13-7.09 (m, 2H), 4.20 (s, 2H), 3.60-3.54 (m, 1H), 3.28 (d, J = 7.32 Hz, 2H), 2.40-2.33 (m, 2H), 2.21-2.14 (m, 2H), 2.09-2.02 (m, 1H), 1.93-1.88 (m, 1H), 1.16-1.11 (m, 1H), 0.41-0.38 (m, 2H), 0.27-0.23 (m, 2H); MS (ES) m/z 643.0 [M + H]$^+$; LCMS RT = 1.380 min. | ++ | 27 |
| 185 | 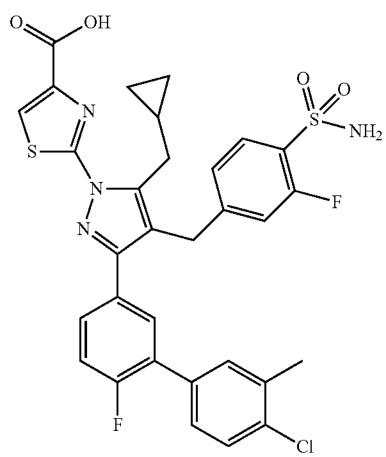 | 2-(3-(4'-chloro-6-fluoro-3'-methyl-[1,1'-biphenyl]-3-yl)-5-(cyclopropylmethyl)-4-(3-fluoro-4-sulfamoylbenzyl)-1H-pyrazol-1-yl)thiazole-4-carboxylic acid: - $^1$H NMR (MeOD) δ: 8.19 (s, 1H), 7.75 (t, J = 7.9 Hz, 1H), 7.65-7.61 (m, 1H), 7.54 (dd, J = 2.19, 7.37 Hz, 1H), 7.34 (bs, 1H), 7.22 (dd, J = 8.63, 10.59 Hz, 1H), 7.18 (d, = 9.55 Hz, 1H), 7.10 (bs, 1H), 7.08 (d, J = 4.03 Hz, 1H), 4.19 (s, 2H), 3.27 (d, J = 6.85 Hz, 2H), 2.41 (s, 3H), 1.16-1.10 (m, 1H), 0.42-0.37 (m, 2H), 0.26-0.23 (m, 2H); MS (ES) m/z 665.0 [M + H]$^+$; LCMS RT = 1.307 min. | ++ | 27 |
| 186 | 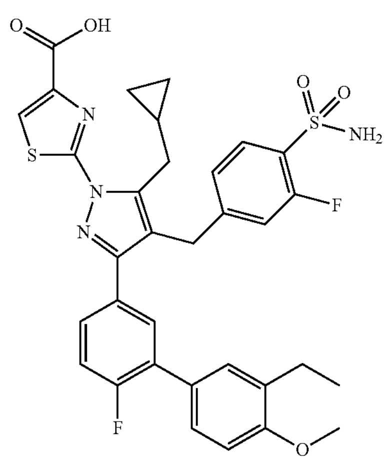 | 2-(5-(cyclopropylmethyl)-3-(3'-ethyl-6-fluoro-4'-methoxy-[1,1'-biphenyl]-3-yl)-4-(3-fluoro-4-sulfamoylbenzyl)-1H-pyrazol-1-yl)thiazole-4-carboxylic acid: MS (ES) m/z 654.9 [M + H]$^+$; LCMS RT = 1.322 min. | ++ | 27 |

TABLE 7-continued

| Cmpd ID | Structure | Compound name and physical data | Inhibitory activity IC$_{50}$ (μM) | Example Method |
|---|---|---|---|---|
| 187 | 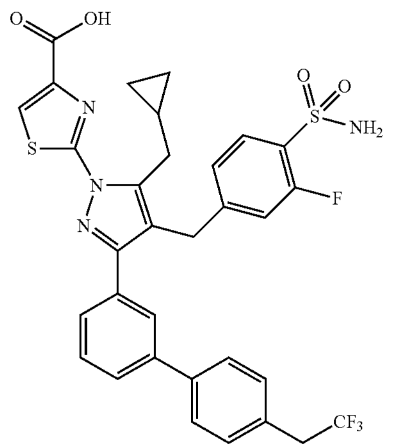 [SMILES: NS(=O)(=O)c1ccc(Cc2c(-c3cccc(-c4ccc(CC(F)(F)F)cc4)c3)nn(-c3nc(C(=O)O)cs3)c2CC2CC2)cc1F] | 2-(5-(cyclopropylmethyl)-4-(3-fluoro-4-sulfamoylbenzyl)-3-(4'-(2,2,2-trifluoroethyl)-[1,1'-biphenyl]-3-yl)-1H-pyrazol-1-yl)thiazole-4-carboxylic acid: $^1$H NMR (MeOD) δ: 8.20 (s, 1H), 7.77 (t, J = 8.0 Hz, 1H), 7.69 (bs, 1H), 7.64-7.59 (m, 2H), 7.46 (dd, J = 8.4, 10.5 Hz, 1H), 7.43 (bs, 1H), 7.40-7.39 (m, 2H), 7.13-7.09 (m, 2H), 4.20 (s, 2H), 3.51 (1, J = 11.1, 22.2 Hz, 2H) 3.28 (d, J = 7.0 Hz, 2H), 1.17-1.11 (m, 1H), 0.43-0.38 (m, 2H), 0.27-0.24 (m, 2H); MS (ES) m/z 671.0 [M + H]$^+$; LCMS RT = 1.252 min. | ++ | 27 |
| 188 | 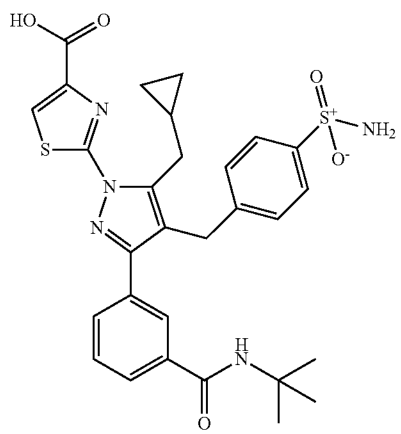 [SMILES: CC(C)(C)NC(=O)c1cccc(-c2nn(-c3nc(C(=O)O)cs3)c(CC3CC3)c2Cc2ccc([S+](N)(=O)[O-])cc2)c1] | 2-(3-(3-(tert-butylcarbamoyl)phenyl)-5-(cyclopropylmethyl)-4-(4-sulfamoylbenzyl)-1H-pyrazol-1-yl)thiazole-4-carboxylic acid: MS (ES) 594.0 [M + H]$^+$, LCMS RT = 1.062 min. | +++ | 24 |
| 189 | 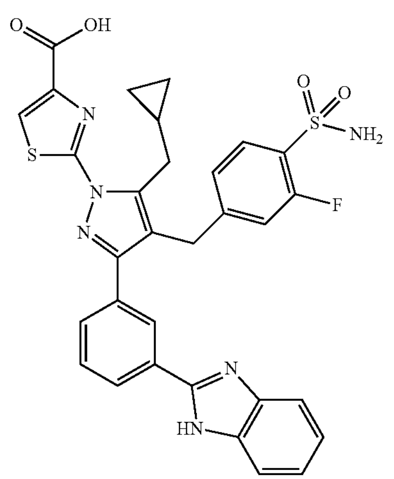 [SMILES: NS(=O)(=O)c1ccc(Cc2c(-c3cccc(-c4nc5ccccc5[nH]4)c3)nn(-c3nc(C(=O)O)cs3)c2CC2CC2)cc1F] | 2-(3-(3-(1H-benzo[d]imidazol-2-yl)phenyl)-5-(cyclopropylmethyl)-4-(3-fluoro-4-sulfamoylbenzyl)-1H-pyrazol-1-yl)thiazole-4-carboxylic acid: MS (ES) m/z 629.0 [M + H]$^+$; LCMS RT = 0.875 min. | +++ | 27 |

TABLE 7-continued

| Cmpd ID | Structure | Compound name and physical data | Inhibitory activity IC$_{50}$ (μM) | Example Method |
|---|---|---|---|---|
| 190 | 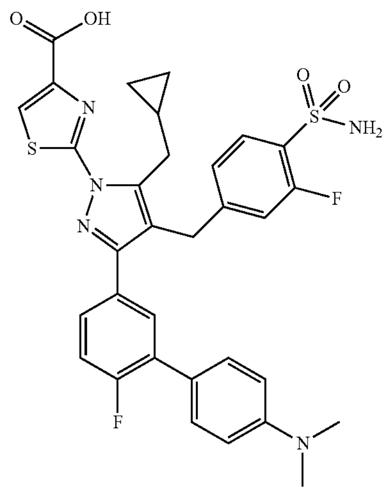 [SMILES: CN(C)c1ccc(-c2cc(-c3nn(-c4nc(C(=O)O)cs4)c(CC4CC4)c3Cc3ccc(S(N)(=O)=O)c(F)c3)ccc2F)cc1] | 2-(5-(cyclopropylmethyl)-3-(4'-(dimethylamino)-6-fluoro-[1,1'-biphenyl]-3-yl)-4-(3-fluoro-4-sulfamoylbenzyl)-1H-pyrazol-1-yl)thiazole-4-carboxylic acid: MS (ES) m/z 649.0 [M + H]$^+$; LCMS RT = 1.065 min. | +++ | 28 |
| 191 | 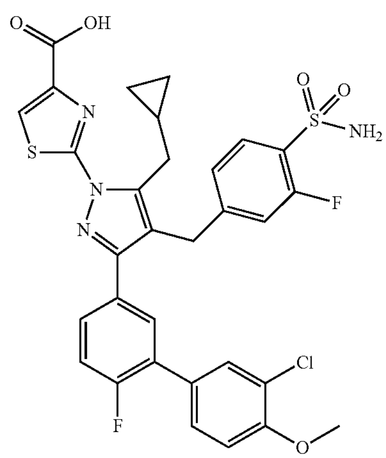 [SMILES: COc1ccc(-c2cc(-c3nn(-c4nc(C(=O)O)cs4)c(CC4CC4)c3Cc3ccc(S(N)(=O)=O)c(F)c3)ccc2F)cc1Cl] | 2-(3-(3'-chloro-6-fluoro-4'-methoxy-[1,1'-biphenyl]-3-yl)-5-(cyclopropylmethyl)-4-(3-fluoro-4-sulfamoylbenzyl)-1H-pyrazol-1-yl)thiazole-4-carboxylic acid: $^1$H NMR (400 MHz, CDCl3): δ 8.14 (s, 1H), 7.86 (t, J = 16 Hz, 1H), 7.42-7.53 (m, 3H), 7.24-7.27 (m, 1H), 7.18 (t, J = 16 Hz, 1H), 7.10 (d, J = 8 Hz, 1H), 6.99-7.05 (m, 2H), 5.02 (s, 2H), 4.10 (s, 2H), 4.00 (s, 3H), 3.185 (d, J = 4 Hz, 2H), 1.15-1.18 (m, 1H), 0.47-0.51 (m, 2H), 0.24-0.26 (m, 2H); MS (ES) m/z 671 [M + H]$^+$; LCMS RT = 1.38 min. | +++ | 28 |
| 192 | 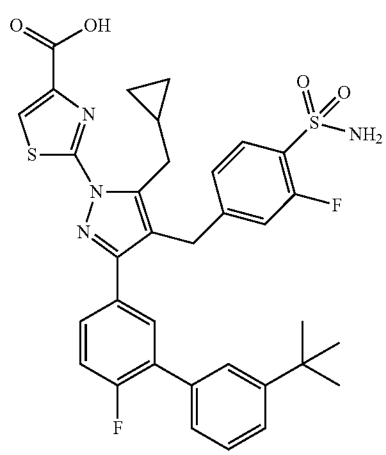 [SMILES: CC(C)(C)c1cccc(-c2cc(-c3nn(-c4nc(C(=O)O)cs4)c(CC4CC4)c3Cc3ccc(S(N)(=O)=O)c(F)c3)ccc2F)c1] | 2-(3-(3'-(tert-butyl)-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid: $^1$H NMR (MeOD) δ 8.20 (s, 1H), 7.77 (t, J = 7.90 Hz, 1H), 7.62-7.59 (m, 2H), 7.52 (d, J = 1.65 Hz, 1H), 7.45-7.42 (m, 1H), 7.37 (t, J = 7.90 Hz, 1H), 7.24-1.19 (m, 1H), 7.15 (dd, J = 1.32, 7.57 Hz, 1H), 7.12-7.08 (m, 2H), 4.20 (s, 2H), 3.26 (d, J = 6.90 Hz, 2H), 1.35 (s, 9H) 1.18-1.08 (m, 1H), 0.42-0.37 (m, 2H), 0.26-0.22 (m, 2H); MS (ES) m/z 663.0 [M + H]$^+$; LCMS RT = 0.890 min. | ++ | 28 |

TABLE 7-continued

| Cmpd ID | Structure | Compound name and physical data | Inhibitory activity IC$_{50}$ (μM) | Example Method |
|---|---|---|---|---|
| 193 | 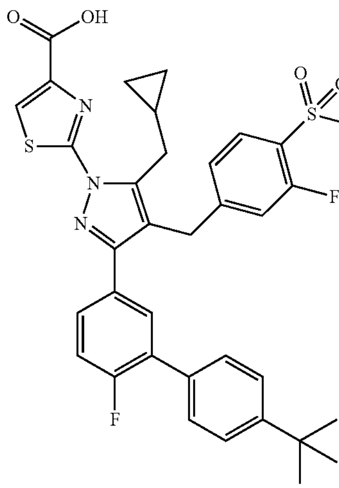 | 2-(3-(4'-(tert-butyl)-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid: $^1$H NMR (MeOD) δ 8.20 (s, 1H), 7.79 (t, J = 7.88 Hz, 1H), 7.63-7.59 (m, 1H), 7.53 (dd, J = 2.22, 7.50 Hz, 1H), 7.49-7.48 (m, 2H), 7.30 (dd, J = 1.58, 8.43 Hz, 2H), 7.23-7.18 (m, 1H), 7.12 (s, 1H), 7.10 (d, 2.11 Hz, 1H), 4.19 (s, 2H), 3.29 (d, 6.41 Hz, 2H), 1.38 (s, 9H), 1.19-1.11 (m, 1H), 0.44-0.40 (m, 2H), 0.29-0.25 (m, 2H); MS (ES) m/z 663.0 [M + H]$^+$; LCMS M/Z = 1.406 min. | ++ | 28 |
| 194 | 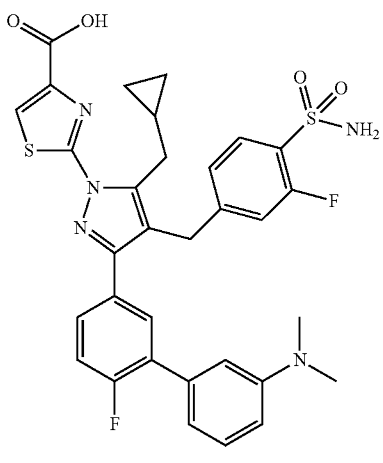 [SMILES: CN(C)c1cccc(-c2cc(-c3nn(-c4nc(C(=O)O)cs4)c(CC4CC4)c3Cc3ccc(S(N)(=O)=O)c(F)c3)ccc2F)c1] | 2-(5-(cyclopropylmethyl)-3-(3'-(dimethylamino)-6-fluoro-[1,1'-biphenyl]-3-yl)-4-(3-fluoro-4-sulfamoylbenzyl)-1H-pyrazol-1-yl)thiazole-4-carboxylic acid: $^1$H NMR (DMSO) δ: 8.30 (s, 1H), 7.68-7.58 (m, 5H), 7.35 (t, J = 8.6 Hz, 1H), 7.29 (t, J = 7.7 Hz, 1H), 7.18 (d, J = 11.3 Hz, 1H), 7.07 (d, J = 8.0 Hz, 1H), 6.84 (s, 2H), 6.71 (s, J = 7.3 Hz, 1H), 4.18 (s, 2H), 3.15 (s, 2H), 2.92 (2, 6H), 1.14-1.13 (m, 1H), 0.34-0.32 (m, 2H), 0.22-0.21 (m, 2H). MS (ES) m/z 650.0 [M + H]$^+$; LCMS RT = 1.022 min. | +++ | 28 |
| 195 | 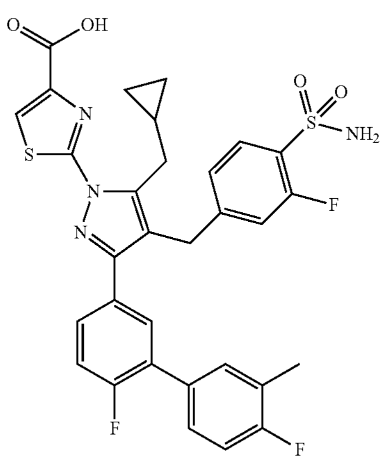 [SMILES: Cc1cc(-c2cc(-c3nn(-c4nc(C(=O)O)cs4)c(CC4CC4)c3Cc3ccc(S(N)(=O)=O)c(F)c3)ccc2F)ccc1F] | 2-(5-(cyclopropylmethyl)-3-(4',6-difluoro-3'-methyl-[1,1'-biphenyl]-3-yl)-4-(3-fluoro-4-sulfamoylbenzyl)-1H-pyrazol-1-yl)thiazole-4-carboxylic acid: $^1$H NMR (DMSO) δ: 8.31 (s, 1H), 7.69-7.60 (m, 4H), 7.51 (dd, J = 2.0, 7.5 Hz, 1H), 7.39-7.35 (m, 2H), 7.22-7.18 (m, 3H), 7.07 (d, J = 7.8 Hz, 2H), 4.18 (s, 2H), 3.18 (s, 3H), 2.28 (s, 3H), 0.16-0.12 (m, 1H), 0.37-0.32 (m, 2H), 0.23-0.22 (m, 2H). MS (ES) m/z 639.0 [M + H]$^+$; LCMS RT = 1.292 min. | +++ | 28 |

TABLE 7-continued

| Cmpd ID | Structure | Compound name and physical data | Inhibitory activity IC$_{50}$ (μM) | Example Method |
|---|---|---|---|---|
| 196 | 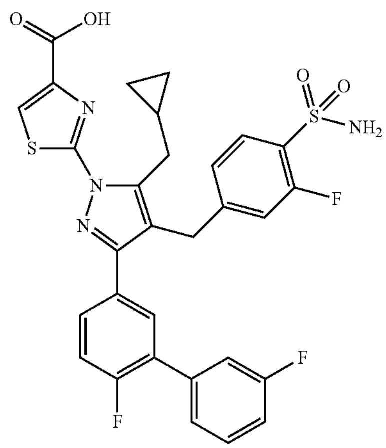 [SMILES: NS(=O)(=O)c1ccc(Cc2c(-c3ccc(F)c(-c4cccc(F)c4)c3)nn(-c3nc(C(=O)O)cs3)c2CC2CC2)cc1F] | 2-(5-(cyclopropylmethyl)-3-(3',6-difluoro-[1,1'-biphenyl]-3-yl)-4-(3-fluoro-4-sulfamoylbenzyl)-1H-pyrazol-1-yl)thiazole-4-carboxylic acid: $^1$H NMR (CDCl$_3$) δ 8.14 (s, 1H), 7.87 (d, J = 8 Hz, 2H), 7.51-7.55 (m, 1H), 7.47-7.49 (m, 1H), 7.36-7.42 (m, 1H), 7.28 (d, J = 8 Hz, 2H), 7.16-7.21 (m, 2H), 7.04-7.09 (m, 2H), 4.92 (s, 2H), 4.18 (s, 2H), 2.21-2.28 (m, 1H), 1.10-1.12 (m, 2H), 0.72-0.73 (m, 2H); MS (ES) 593 [M + H]$^+$; LCMS RT = 1.27 min. | +++ | 28 |
| 197 | 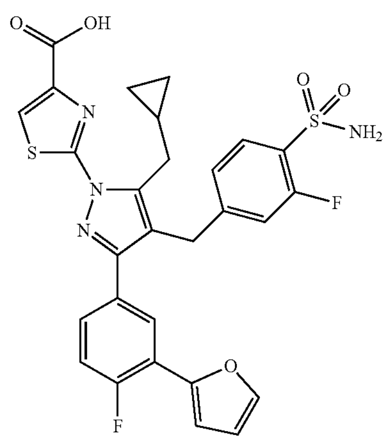 [SMILES: NS(=O)(=O)c1ccc(Cc2c(-c3ccc(F)c(-c4ccco4)c3)nn(-c3nc(C(=O)O)cs3)c2CC2CC2)cc1F] | 2-(5-(cyclopropylmethyl)-3-(3-(4,5-dihydrofuran-2-yl)-4-fluorophenyl)-4-(3-fluoro-4-sulfamoylbenzyl)-1H-pyrazol-1-yl)thiazole-4-carboxylic acid-MS (ES) m/z 599.0 [M + H]$^+$; LCMS RT = 1.06 min. | +++ | 28 |
| 198 | 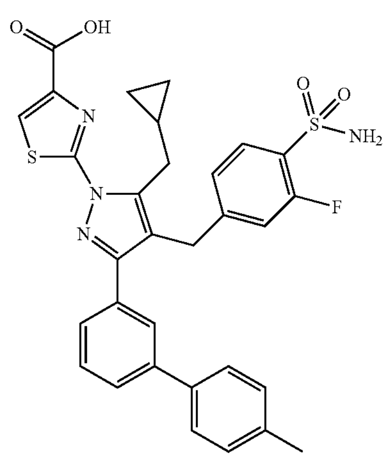 [SMILES: Cc1ccc(-c2cccc(-c3nn(-c4nc(C(=O)O)cs4)c(CC4CC4)c3Cc3ccc(S(N)(=O)=O)c(F)c3)c2)cc1] | 2-(5-(cyclopropylmethyl)-4-(3-fluoro-4-sulfamoylbenzyl)-3-(4'-methyl-[1,1'-biphenyl]-3-yl)-1H-pyrazol-1-yl)thiazole-4-carboxylic acid: $^1$H NMR (CDCl$_3$) δ: 8.13 (s, 1H), 7.82 (t, J = 7.6 Hz, 1H), 7.64 (s, 1H), 7.61 (dt, J = 2.0, 6.8 Hz, 1H), 7.49-7.44 (m, 2H), 7.38 (d, J = 8.4 Hz, 2H), 7.26 (d, J = 8.0 Hz, 2H), 7.10 (d, J = 8.4 Hz, 1H), 7.01 (d, J = 10.8 Hz, 1H), 4.12 (s, 2H), 3.20 (d, J = 6.6 Hz, 2H), 2.42 (s, 3H), 1.22-1.18 (m, 1H), 0.53-0.49 (m, 2H), 0.27-0.24 (m, 2H); MS (ES) m/z 603.0 [M + H]$^+$; LCMS RT = 1.298 min. | +++ | 28 |

TABLE 7-continued

| Cmpd ID | Structure | Compound name and physical data | Inhibitory activity IC$_{50}$ (μM) | Example Method |
|---|---|---|---|---|
| 199 | 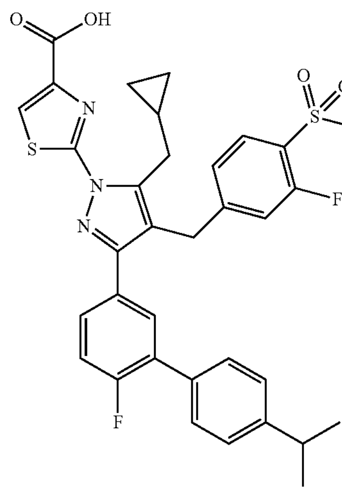 | 2-(5-(cyclopropylmethyl)-3-(6-fluoro-3'-isopropyl-[1,1'-biphenyl]-3-yl)-4-(3-fluoro-4-sulfamoylbenzyl)-1H-pyrazol-1-yl)thiazole-4-carboxylic acid: MS (ES) m/z 648.0 [M + H]$^+$; LCMS RT = 1.358 min. | +++ | 28 |
| 200 | 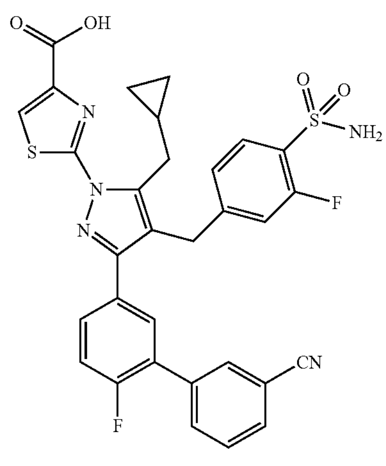 [SMILES: N#Cc1cccc(-c2cc(-c3nn(-c4nc(C(=O)O)cs4)c(CC4CC4)c3Cc3ccc(S(N)(=O)=O)c(F)c3)ccc2F)c1] | 2-(3-(3'-cyano-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid - $^1$H NMR (d$^6$-DMSO) δ: 8.31 (s, 1H), 8.03 (s, 1H), 7.89 (d, J = 7.4 Hz, 1H), 7.73-7.63 (m, 5H), 7.57 (s, 2H), 7.42 (d, J = 10.3 Hz, 1H), 7.16 (d, J = 11.2 Hz, 1H), 7.07 (d, J = 8.1 Hz, 1H), 4.21 (s, 2H), 3.18 (d, J = 6.8 Hz, 2H), 1.50 (bs, 1H), 0.36-0.34 (m, 2H), 0.24-0.23 (m, 2H); MS (ES) m/z 632.0 [M + H]$^+$; LCMS RT = 1.197 min. | +++ | 28 |
| 201 | 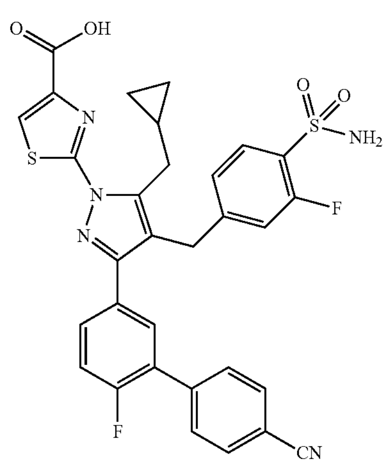 [SMILES: N#Cc1ccc(-c2cc(-c3nn(-c4nc(C(=O)O)cs4)c(CC4CC4)c3Cc3ccc(S(N)(=O)=O)c(F)c3)ccc2F)cc1] | 2-(3-(4'-cyano-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid: $^1$H NMR (400 MHz, CDCl3): δ 8.14 (s, 1H), 7.84 (t, J = 8 Hz, 1H), 7.75 (d, J = 8 Hz, 2H), 7.56-7.60 (m, 3H), 7.50-7.54 (m, 1H), 7.21 (t, J = 16 Hz, 1H), 7.08 (d, J = 8 Hz, 1H), 7.01 (d, J = 8 Hz, 1H), 5.12 (s, 2H), 4.11 (s, 2H), 3.20 (d, J = 8 Hz, 2H), 1.15-1.18 (m, 1H), 0.47-0.50 (m, 2H), 0.24-0.27 (m, 2H); MS (ES) m/z 632.0 [M + H]$^+$; LCMS RT = 1.22 min. | +++ | 28 |

TABLE 7-continued

| Cmpd ID | Structure | Compound name and physical data | Inhibitory activity IC$_{50}$ (μM) | Example Method |
|---|---|---|---|---|
| 202 | 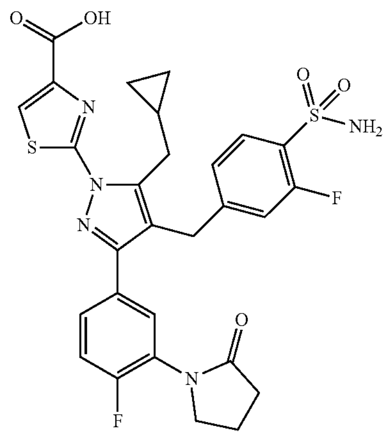 [SMILES: NS(=O)(=O)c1ccc(Cc2c(-c3ccc(F)c(N4CCCC4=O)c3)nn(-c3nc(C(=O)O)cs3)c2CC2CC2)cc1F] | 2-(5-(cyclopropylmethyl)-3-(4-fluoro-3-(2-oxopyrrolidin-1-yl)phenyl)-4-(3-fluoro-4-sulfamoylbenzyl)-1H-pyrazol-1-yl)thiazole-4-carboxylic acid: MS (ES) m/z 614.0 [M + H]$^+$; LCMS RT = 1.005 min. | +++ | 32 |
| 203 | 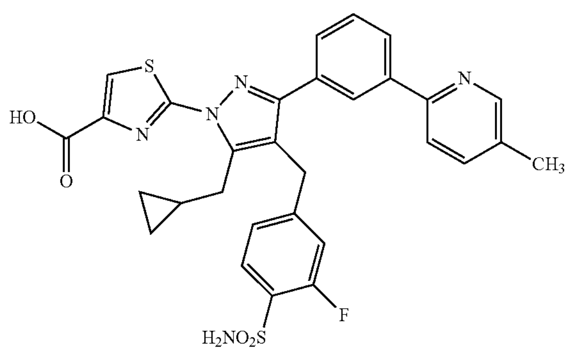 [SMILES: Cc1ccc(-c2cccc(-c3nn(-c4nc(C(=O)O)cs4)c(CC4CC4)c3Cc3ccc(S(N)(=O)=O)c(F)c3)c2)nc1] | 2-(5-(cyclopropylmethyl)-4-(3-fluoro-4-sulfamoylbenzyl)-3-(3-(5-methylpyridin-2-yl)phenyl)-1H-pyrazol-1-yl)thiazole-4-carboxylic acid: MS [M + H]$^+$ 604.0. | +++ | Example 28 |
| 204 | 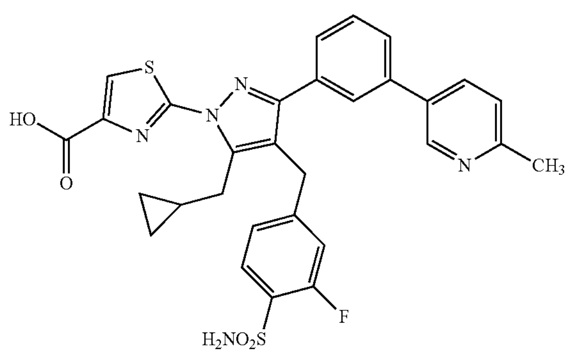 [SMILES: Cc1ccc(-c2cccc(-c3nn(-c4nc(C(=O)O)cs4)c(CC4CC4)c3Cc3ccc(S(N)(=O)=O)c(F)c3)c2)cn1] | 2-(5-(cyclopropylmethyl)-4-(3-fluoro-4-sulfamoylbenzyl)-3-(3-(6-methylpyridin-3-yl)phenyl)-1H-pyrazol-1-yl)thiazole-4-carboxylic acid: MS [M + H]$^+$ 604.0. | +++ | Example 28 |
| 205 | 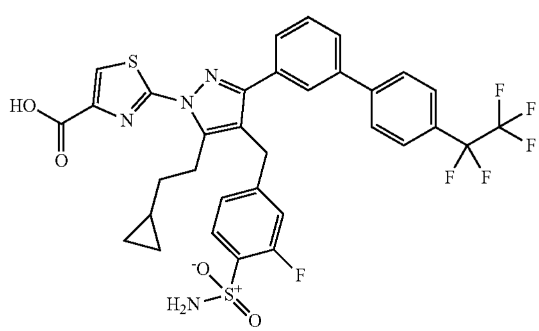 | 2-(5-(2-cyclopropylethyl)-4-(3-fluoro-4-sulfamoylbenzyl)-3-(4'-(perfluoroethyl)-[1,1'-biphenyl]-3-yl)-1H-pyrazol-1-yl)thiazole-4-carboxylic acid: $^1$H NMR (400 MHz, MeOD) δ 8.06 (s, 1H), 7.67-7.52 (m, 8H), 7.40 (dd, J = 7.3, 7.7 Hz, 1H), 6.99 (s, 1H), 6.97 (d, J = 3.82 Hz, 1H), 4.09 (s, 2H), 3.25 (dd, J = 7.5, 9.6 Hz, 2H), 1.44-1.39 (m, 2H), 0.68-0.60 (m, 1H), 0.27-0.22 (m, 2H), 0.01--0.02 (m, 2H); MS ([M + H]$^+$ 721.0. | ++ | Example 27 |

TABLE 7-continued

| Cmpd ID | Structure | Compound name and physical data | Inhibitory activity IC$_{50}$ (μM) | Example Method |
|---|---|---|---|---|
| 206 | 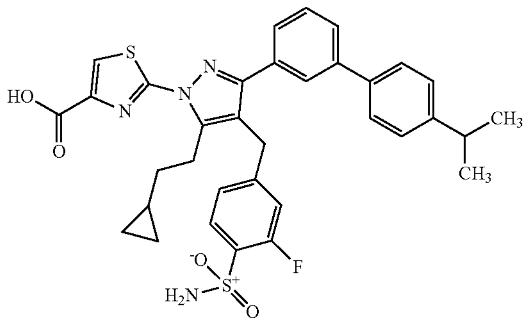 | 2-(5-(2-cyclopropylethyl)-4-(3-fluoro-4-sulfamoylbenzyl)-3-(4'-isopropyl-[1,1'-biphenyl]-3-yl)-1H-pyrazol-1-yl)thiazole-4-carboxylic acid: $^1$H NMR (400 MHz, MeOD) δ 8.03 (s, 1H), 7.66 (t, J = 7.6 Hz, 1H), 7.53 (s, 1H), 7.47 (d, J = 7.92 Hz, 1H), 7.42 (d, J = 7.92 Hz, 1H), 7.30 (t, J = 7.66 Hz, 1H), 7.23 (d, J = 8.2 Hz, 2H), 7.16 (d, J = 8.2 Hz, 2H), 6.96 (d, J = 9.5 Hz, 2H), 4.02 (s, 2H), 3.23-3.19 (m, 2H), 2.81 (septet, J = 6.87 Hz, 1H), 1.42-1.36 (m, 2H), 1.16 (d, J = 6.9 Hz, 6H), 0.67-0.59 (m, 1H), 0.26-0.22 (m, 2H), 0.01--0.02 (m, 2H); [M + H]$^+$ 645.0. | ++ | Example 27 |
| 207 | 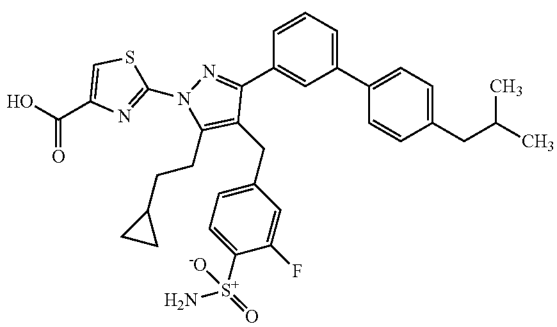 | 2-(5-(2-cyclopropylethyl)-4-(3-fluoro-4-sulfamoylbenzyl)-3-(4'-isobutyl-[1,1'-biphenyl]-3-yl)-1H-pyrazol-1-yl)thiazole-4-carboxylic acid: $^1$H NMR (400 MHz, MeOD) δ 8.04 (s, 1H), 7.66 (t, J = 8.03 Hz, 1H), 7.55 (s, 1H), 7.48 (d, J = 7.7 Hz, 1H), 7.42 (d, J = 7.7 Hz, 1H), 7.31 (t, J = 7.7 Hz, 1H), 7.23 (d, J = 8.2 Hz, 2H), 7.08 (d, J = 8.2 Hz, 1H), 6.98 (s, 1H), 6.96 (d, J = 2.4 Hz, 1H), 4.04 (s, 2H), 3.25-3.20 (m, 2H), 2.39 (d, J = 7.0 Hz, 2H), 1.78 (septet, J = 6.7 Hz, 1H), 1.43-1.37 (m, 2H), 0.81 (d, J = 6.7 Hz, 6H), 0.67-0.58 (m, 1H), 0.27-0.22 (m, 2H), 0.01-0.02 (m, 2H) ); MS [M + H]$^+$ 659.0. | ++ | Example 27 |
| 208 | 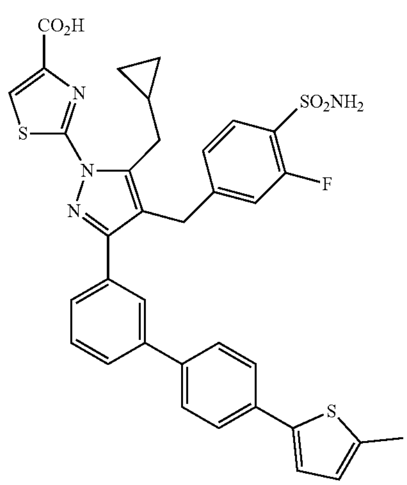 [SMILES: Cc1ccc(-c2ccc(-c3cccc(-c4nn(-c5nc(C(=O)O)cs5)c(CC5CC5)c4Cc4ccc(S(N)(=O)=O)c(F)c4)c3)cc2)s1] | 2-(5-(cyclopropylmethyl)-4-(3-fluoro-4-sulfamoylbenzyl)-3-(4'-(5-methylthiophen-2-yl)-[1,1'-biphenyl]-3-yl)-1H-pyrazol-1-yl)thiazole-4-carboxylic acid: $^1$H NMR (400 MHz, MeOD) δ 8.15 (s, 1H), 7.77 (t, J = 8.0 Hz, 1H), 7.70-7.67 (m, 1H), 7.62-7.53 (m, 1H), 7.58 (d, J = 8.4 Hz, 2H), 7.54 (d, J = 7.6 Hz, 1H), 7.43 (d, J = 7.6 Hz, 1H), 7.39 (d, J = 8.4 Hz, 2H), 7.18 (d, J = 3.6 Hz, 1H), 7.08 (dd, J = 10.4, 8.4 Hz, 2H), 6.74 (dd, J = 3.6, 1.2 Hz, 1H), 4.14 (s, 2H), 3.25 (d, J = 6.4 Hz, 2H), 2.49 (s, 3H), 1.14-1.09 (m, 1H), 0.44-0.38 (m, 2H), 0.27-0.22 (m, 2H); MS [M + H]$^+$ 685.3. | ++ | Example 28 |

TABLE 7-continued

| Cmpd ID | Structure | Compound name and physical data | Inhibitory activity IC$_{50}$ (μM) | Example Method |
|---|---|---|---|---|
| 209 | 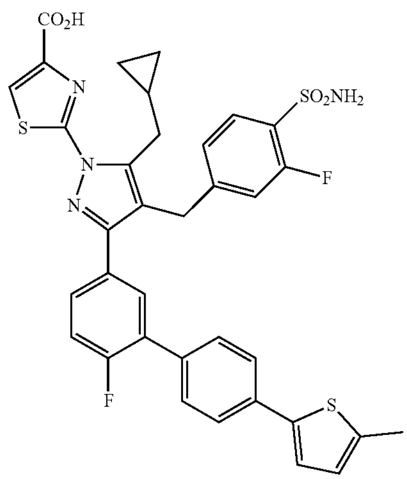 [SMILES: Cc1ccc(-c2ccc(-c3cc(-c4nn(-c5nc(C(=O)O)cs5)c(CC5CC5)c4Cc4ccc(S(N)(=O)=O)c(F)c4)ccc3F)cc2)s1] | 2-(5-(cyclopropylmethyl)-3-(6-fluoro-4'-(5-methylthiophen-2-yl)-[1,1'-biphenyl]-3-yl)-4-(3-fluoro-4-sulfamoylbenzyl)-1H-pyrazol-1-yl)thiazole-4-carboxylic acid: $^1$H NMR (400 MHz, MeOD) δ 8.17 (s, 1H), 7.79 (t, J = 8.0 Hz, 1H), 7.62 (d, J = 8.4 Hz, 2H), 7.59 (dd, J = 8.0, 6.0 Hz, 2H), 7.38 (dd, J = 8.4, 1.6 Hz, 2H), 7.24 (d, J = 3.6 Hz, 1H), 7.19 (d, J = 8.8 Hz, 1H), 7.12-7.07 (m, 2H), 6.77 (dd, J = 3.6, 1.2 Hz, 1H), 4.18 (s, 2H), 3.28 (d, J = 6.8 Hz, 2H), 2.52 (s, 3H), 1.16-1.09 (m, 1H), 0.44-0.39 (m, 2H), 0.28-0.23 (m, 2H); MS [M + H]$^+$ 703.1. | ++ | Example 28 |
| 210 | 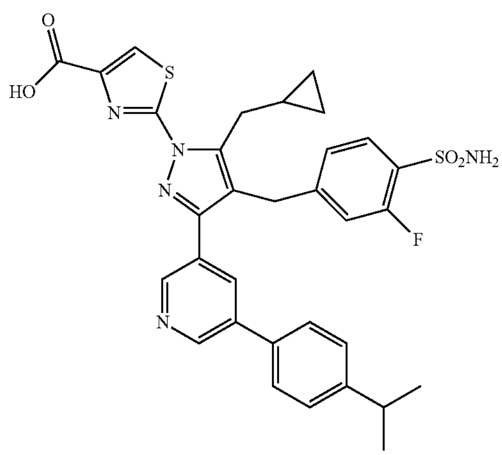 [SMILES: CC(C)c1ccc(-c2cncc(-c3nn(-c4nc(C(=O)O)cs4)c(CC4CC4)c3Cc3ccc(S(N)(=O)=O)c(F)c3)c2)cc1] | 2-[5-(cyclopropylmethyl)-4-[(3-fluoro-4-sulfamoylphenyl)methyl]-3-[5-(4-isopropylphenyl)pyridin-3-yl]pyrazol-1-yl]-1,3-thiazole-4-carboxylic acid, $^1$H NMR (400 MHz, MeOD-d$_3$) δ 8.85 (d, J = 21.0 Hz, 2H), 8.34 (bs, 1H), 8.25 (s, 1H), 7.78 (t, J = 7.8 Hz, 1H), 7.46 (d, J = 8.0 Hz, 2H), 7.04 (d, J = 7.6 Hz, 2H), 7.17-7.13 (m, 2H), 4.28 (2, 2H), 3.01-2.94 (m, 1H), 0.86 (s, 2H), 1.29 (d, J = 6.9 Hz, 2H), 1.20-1.14 (m, 1H), 0.44-0.41 (m, 2H), 0.30-0.28 (m, 2H). | +++ | Example 8 |
| 211 | 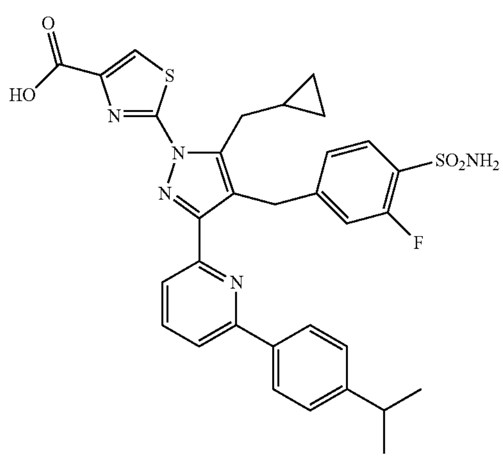 | 2-[5-(cyclopropylmethyl)-4-[(3-fluoro-4-sulfamoylphenyl)methyl]-3-[6-(4-isopropylphenyl)pyridin-2-yl]pyrazol-1-yl]-1,3-thiazole-4-carboxylic acid, $^1$H NMR (400 MHz, MeOD-d$_3$) δ 8.20 (s, 1H), 8.03 (d, J = 7.8 Hz, 1H), 7.87 (t, J = 8.1 Hz, 1H), 7.76 (d, J = 7.8 Hz, 1H), 7.70 (t, J = 8.0 Hz, 1H), 7.62 (d, J = 8.3 Hz, 2H), 7.22 (d, J = 14.1 Hz, 2H), 7.14-7.10 (M, 2H), 4.59 (s, 2H), 3.27 (d, J = 6.9 Hz, 2H), 2.92 (t, J = 6.8 Hz, 1H), 1.27 (d, J = 6.9 Hz, 2H), 1.11-1.07 (m, 1H), .037-.032 (m, 2H), 0.23-0.19 (m, 2H); MS [M + H]$^+$ = 660.0 | ++ | Example 8 |

TABLE 7-continued

| Cmpd ID | Structure | Compound name and physical data | Inhibitory activity IC$_{50}$ (μM) | Example Method |
|---|---|---|---|---|
| 212 | 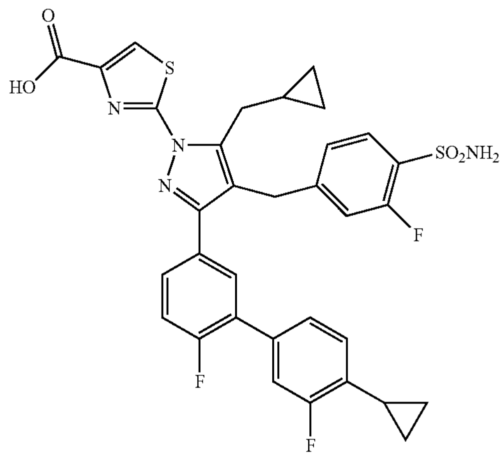 [SMILES: NS(=O)(=O)c1ccc(Cc2c(-c3ccc(F)c(-c4ccc(C5CC5)c(F)c4)c3)nn(-c3nc(C(=O)O)cs3)c2CC2CC2)cc1F] | 2-{3-[3-(4-cyclopropyl-3-fluorophenyl)-4-fluorophenyl]-5-(cyclopropylmethyl)-4-[(3-fluoro-4-sulfamoylphenyl)methyl]pyrazol-1-yl}-1,3-thiazole-4-carboxylic acid, $^1$H NMR (400 MHz, MeOD-d$_3$) δ 8.09 (1H, s), 7.76 (t, 1H, J = 8.0 Hz), 7.62-7.58 (m, 1H), 7.52 (dd, J = 7.5, 2.0 Hz, 1H), 7.22-7.17 (m, 2H), 7.02 (d, J = 12.0 Hz, 1H), 7.04 (d, J = 16.0 Hz, 2H), 7.02-6.95 (m, 2H), 4.17 (s, 2H), 3.28 (d, J = 6.5 Hz, 2H), 2.14-1.99 (m, 1H), 1.31-1.08 (m, 1H), 1.04-0.99 (m, 2H), 0.82-0.77 (m, 2H), 0.41-0.36 (m, 2H), 0.25-.021 (m, 2H); MS [M + H]$^+$ = 665.0 | ++ | Example 27 |
| 213 | 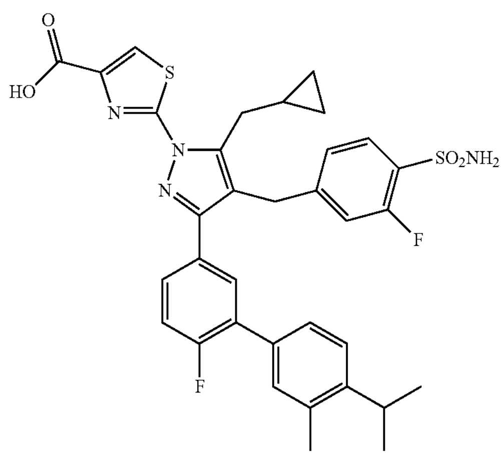 [SMILES: Cc1cc(-c2cc(-c3nn(-c4nc(C(=O)O)cs4)c(CC4CC4)c3Cc3ccc(S(N)(=O)=O)c(F)c3)ccc2F)ccc1C(C)C] | 2-[5-(cyclopropylmethyl)-3-[4-fluoro-3-(4-isopropyl-3-methylphenyl)phenyl]-4-[(3-fluoro-4-sulfamoylphenyl)methyl]pyrazol-1-yl]-1,3-thiazole-4-carboxylic acid, $^1$H NMR (400 MHz, MeOD-d$_3$) δ 8.17 (s, 1H), 7.73 (t, J = 7.8 Hz, 1H), 7.59-7.54 (m, 2H), 7.43-7.34 (m, 1H), 7.12-7.01 (m, 4H), 4.86 (s, 6H), 4.13 (s, 2H), 3.23 (d, J = 6.8 Hz, 2H), 2.01 (s, 2H), 1.20 (s, 3H), 1.13-1.06 (m, 1H), 0.39-0.35 (m, 2H), 0.28-0.21 (m, 2H). | +++ | Example 27 |
| 214 | 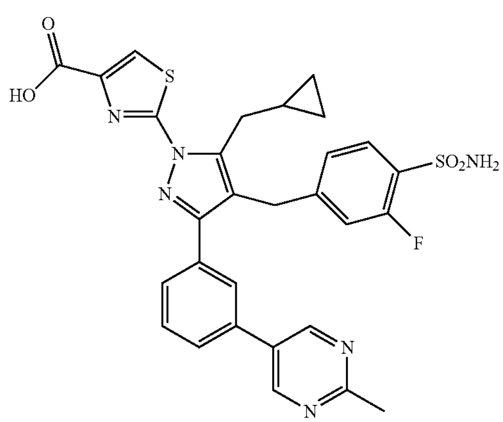 [SMILES: Cc1ncc(-c2cccc(-c3nn(-c4nc(C(=O)O)cs4)c(CC4CC4)c3Cc3ccc(S(N)(=O)=O)c(F)c3)c2)cn1] | 2-[5-(cyclopropylmethyl)-4-[(3-fluoro-4-sulfamoylphenyl)methyl]-3-[3-(2-methylpyrimidin-5-yl)phenyl]pyrazol-1-yl]-1,3-thiazole-4-carboxylic acid, $^1$H NMR (400 MHz, DMSO-d$_6$) δ 8.95 (s, 2H), 8.27 (s, 1H), 7.87 (s, 1H), 7.78 (d, J = 7.9 Hz, 1H), 7.65-7.61 (m, 2H), 7.58-7.54 (m, 2H), 7.14 (d, J = 11.6 Hz, 1H), 7.07 (d, J = 8.2 Hz, 1H), 4.22 (s, 2H), 3.19 (d, J = 6.7 Hz, 2H), 2.67 (s, 3H), 1.15 (bs, 1H), 0.38-0.33 (m, 2H), 0.24-0.23 (m, 2H); MS [M + H]$^+$ = 605.0 | +++ | Example 27 |

TABLE 7-continued

| Cmpd ID | Structure | Compound name and physical data | Inhibitory activity IC$_{50}$ (μM) | Example Method |
|---|---|---|---|---|
| 215 | 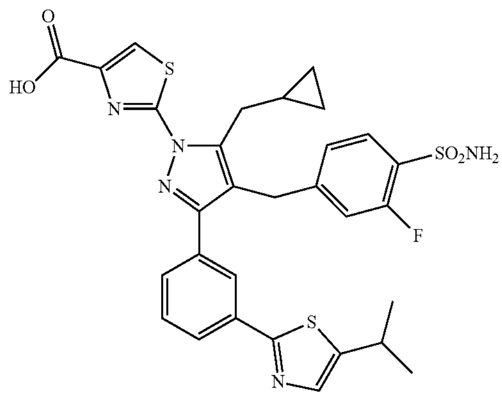 [SMILES: CC(C)c1cnc(-c2cccc(-c3nn(-c4nc(C(=O)O)cs4)c(CC4CC4)c3Cc3ccc(S(N)(=O)=O)c(F)c3)c2)s1] | 2-[5-(cyclopropylmethyl)-4-[(3-fluoro-4-sulfamoylphenyl)methyl]-3-[3-(5-isopropyl-1,3-thiazol-2-yl)phenyl]pyrazol-1-yl]-1,3-thiazole-4-carboxylic acid, $^1$H NMR (400 MHz, DMSO-d$_6$) δ 8.32 (s, 1H), 7.94 (s, 1H), 7.90 (d, J = 8.3 Hz, 1H), 7.69-7.66 (m, 2H), 7.65 (s, 1H), 7.57 (s, 1H), 7.53 (t, J = 11.4 Hz, 1H), 7.23 (d, J = 11.7 Hz, 1H), 7.09 (d, J = 7.8 Hz, 1H), 4.19 (s, 2H), 3.28-3.24 (m, 1H), 3.20 (d, J = 7.2 Hz, 2H), 1.32 (d, J = 6.8 Hz, 6H), 1.63-1.46 (m, 1H), 0.36-0.34 (m, 2H), 0.25-0.24 (m, 2H); MS [M + H]$^+$ = 638.0 | +++ | Example 27 |
| 216 | 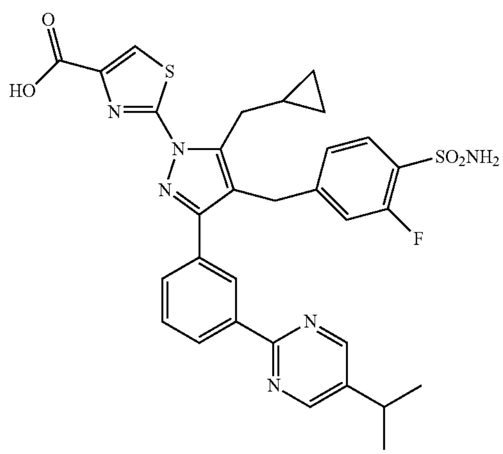 | 2-[5-(cyclopropylmethyl)-4-[(3-fluoro-4-sulfamoylphenyl)methyl]-3-[3-(5-isopropylpyrimidin-2-yl)phenyl]pyrazol-1-yl]-1,3-thiazole-4-carboxylic acid, $^1$H NMR (400 MHz, DMSO-d$_6$) δ 8.80 (s, 2H), 8.50 (s, 1H), 8.36 (d, J = 7.8 Hz, 1H), 8.30 (2, 1H), 7.73-7.65 (m, 2H), 7.60-7.54 (m, 4H), 7.21 (d, J = 10.8 Hz, 1H), 7.09 (d, J = 7.9 Hz, 1H), 4.18 (s, 2H), 3.21 (d, J = 7.0 Hz, 2H), 2.99 (m, 1H), 1.29 (d, J = 7.0 Hz, 6H), 1.18-1.41 (m 1H), 0.39-0.35 (m, 2H), 0.26-0.24 (m, 2H); MS [M + H]$^+$ = 661.0 | +++ | Example 27 |
| 217 | 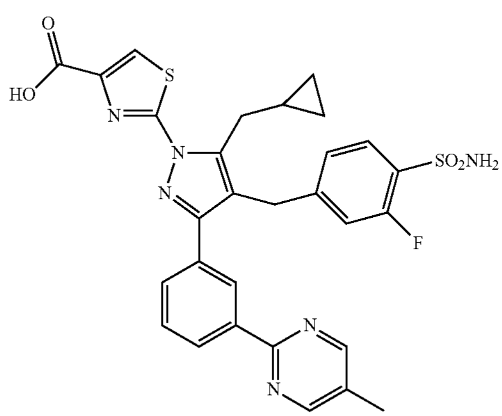 [SMILES: Cc1cnc(-c2cccc(-c3nn(-c4nc(C(=O)O)cs4)c(CC4CC4)c3Cc3ccc(S(N)(=O)=O)c(F)c3)c2)nc1] | 2-[5-(cyclopropylmethyl)-4-[3-fluoro-4-sulfamoylphenyl)methyl]-3-[3-(5-methylpyrimidin-2-yl)phenyl]pyrazol-1-yl]-1,3-thiazole-4-carboxylicacid, $^1$H NMR (400 MHz, CDCl3-d$_3$) δ 8.62 (s, 2H), 8..40 (s, 1H), 8.33 (d, J = 8.3Hz, 1H), 8.01 (s, 1H), 7.71-7.67 (m, 2H), 7.48 (t, J = 7.8 Hz, 1H), 7.05 (d, J = 8.5 Hz, 1H), 6.99 (d, J = 3.1 Hz, 1H), 4.11 (s, 2H), 3.41 (t, J = 1.6 Hz, 1H), 3.46 (d, J = 6.6 Hz, 2H), 2.35 (s, 3H), 1.24-1.14 (m, 1H), 0.45-0.42 (m, 2H), 0.26-0.24 (m, 2H); MS [M + H]$^+$ = 605.0c | +++ | Example 27 |

TABLE 7-continued

| Cmpd ID | Structure | Compound name and physical data | Inhibitory activity IC$_{50}$ (μM) | Example Method |
|---|---|---|---|---|
| 218 | 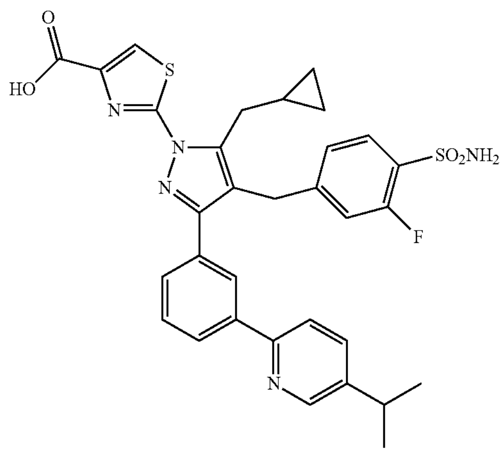 | 2-[5-(cyclopropylmethyl)-4-[(3-fluoro-4-sulfamoylphenyl)methyl]-3-[3-(5-isopropylpyridin-2-yl)phenyl]pyrazol-1-yl]-1,3-thiazole-4-carboxylicacid, $^1$H NMR (400 MHz, MeOD-d$_3$) δ 8.58 (d, J = 1.9 Hz, 1H), 8.25 (dd, J = 4.5, 8.4 Hz, 1H), 8.21 (s, 1H), 7.92 (bs, 1H), 7.89 (d, J = 7.8 Hz, 1H), 7.80 (t, J = 8.6 Hz, 2H), 7.72 (t, J = 8.1 Hz, 1H), 7.60 (t, J = 7.8 Hz, 1H), 710-7.07 (m, 2H), 4.20 (s, 2H), 3.19-3.12 (m, 1H), 1.38 (d, J = 7.0 Hz, 6H), 1.18-1.14 (m, 1H), 0.42-0.40 (m, 2H), 0.29-0.25 (m, 2H); MS [M + H]$^+$ = 660.0 | +++ | Example 27 |
| 219 | 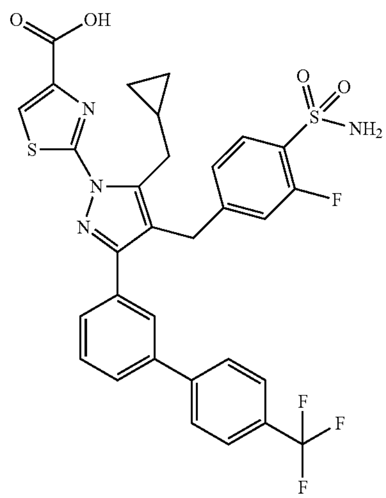 [SMILES: NS(=O)(=O)c1ccc(Cc2c(-c3cccc(-c4ccc(C(F)(F)F)cc4)c3)nn(-c3nc(C(=O)O)cs3)c2CC2CC2)cc1F] | 2-(5-(cyclopropylmethyl)-4-(3-fluoro-4-sulfamoylbenzyl)-3-(4'-(trifluoromethyl)-[1,1'-biphenyl]-3-yl)-1H-pyrazol-1-yl)thiazole-4-carboxylic acid, $^1$H NMR (400 MHz, MeOD-d$_3$) δ 8.20 (s, 1H), 7.79-7.76 (s, 1H), 7.75-7.70 (m, 2H), 7.69-7.65 (m, 2H), 7.64-7.60 (m, 3H), 7.49 (t, J = 7.8 Hz, 1H), 7.12-7.07 (m, 2H), 4.19 (s, 2H), 3.27 (d, J = 6.9 Hz, 2H), 1.20-1.09 (m, 1H), 0.43-0.37 (m, 2H), 0.28-0.23 (m, 2H); MS (ES) 657.0 [M + H]$^+$, LCMS RT = 1.273 min. | +++ | Example 28 |
| 220 | 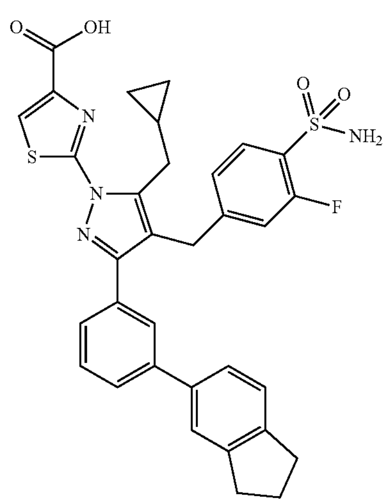 [SMILES: NS(=O)(=O)c1ccc(Cc2c(-c3cccc(-c4ccc5c(c4)CCC5)c3)nn(-c3nc(C(=O)O)cs3)c2CC2CC2)cc1F] | 2-(5-(cyclopropylmethyl)-3-(3-(2,3-dihydro-1H-inden-5-yl)phenyl)-4-(3-fluoro-4-sulfamoylbenzyl)-1H-pyrazol-1-yl)thiazole-4-carboxylic acid, $^1$H NMR (400 MHz, MeOD-d$_3$) δ 8.19 (s, 1H), 7.79-7.74 (M, 1H), 7.64-7.63 (m, 1H), 7.60-7.54 (m, 2H), 7.42 (t, J = 7.7 Hz, 1H), 7.29 (s, 1H), 7.23 (d, J = 7.7 Hz, 1H), 7.19-7.15 (m, 1H), 7.12-7.08 (m, 2H), 4.19 (s, 2H), 3.26 (d, J = 6.7 Hz, 2H), 2.96-2.89 (m, 4H), 2.09 (quintet, J = 7.4 Hz, 2H), 1.17-1.08 (m, 1H), 0.42-0.37 (m, 2H), 0.26-0.22 (m, 2H); MS (ES) 629.0 [M + H]$^+$, LCMS RT = 1.316 min. | +++ | Example 28 |

TABLE 7-continued

| Cmpd ID | Structure | Compound name and physical data | Inhibitory activity IC$_{50}$ (μM) | Example Method |
|---|---|---|---|---|
| 221 | 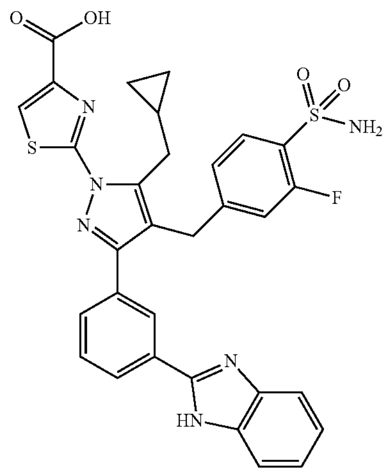 [SMILES: NS(=O)(=O)c1ccc(Cc2c(-c3cccc(-c4nc5ccccc5[nH]4)c3)nn(-c3nc(C(=O)O)cs3)c2CC2CC2)cc1F] | 2-(3-(3-(1H-benzo[d]imidazol-2-yl)phenyl)-5-(cyclopropylmethyl)-4-(3-fluoro-4-sulfamoylbenzyl)-1H-pyrazol-1-yl)thiazole-4-carboxylic acid, $^1$H NMR (400 MHz, MeOD-d$_3$) δ 8.41 (bs, 1H), 8.24 (s, 1H), 8.11-8.08 (m, 1H), 7.86-7.83 (m, 1H), 7.79 (q, J = 3.1 Hz, 2H), 7.72-7.66 (m, 2H), 7.58-7.55 (m, 2H), 7.09-7.02 (m, 2H), 4.27 (s, 2H), 1.21-1.12 (m, 1H), 0.45-0.41 (m, 2H), 0.30-0.26 (m, 2H); MS (ES) 629.0 [M + H]$^+$, LCMS RT = 0.873 min. | +++ | Example 27 |
| 222 | 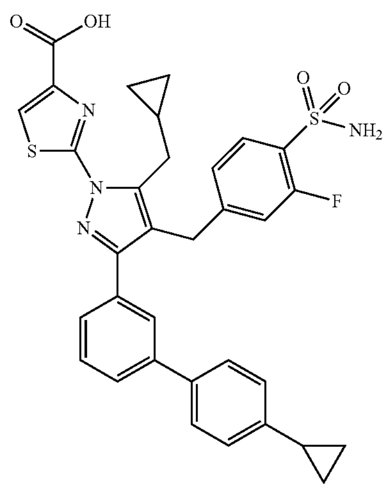 [SMILES: NS(=O)(=O)c1ccc(Cc2c(-c3cccc(-c4ccc(C5CC5)cc4)c3)nn(-c3nc(C(=O)O)cs3)c2CC2CC2)cc1F] | 2-(3-(4'-cyclopropyl-[1,1'-biphenyl]-3-yl)-5-(cyclopropylmethyl)-4-(3-fluoro-4-sulfamoylbenzyl)-1H-pyrazol-1-yl)thiazole-4-carboxylic acid, $^1$H NMR (400 MHz, MeOD-d$_3$) δ 8.19 (s, 1H), 7.79-7.75 (m, 1H), 7.62-7.60 (m, 1H), 7.60-7.53 (m, 2H), 7.42 (t, J = 7.7 Hz, 1H), 7.30-7.26 (m, 2H), 7.13-7.07 (m, 4H), 4.17 (s, 2H), 3.26 (d, J = 6.9 Hz, 2H), 1.96-1.87 (m, 1H), 1.18-1.11 (m, 1H), 1.00-0.95 (m, 2H), 0.74-0.69 (m, 2H), 0.43-0.37 (m, 2H), 0.27-0.22 (m, 2H); MS (ES) 629.0 [M + H]$^+$, LCMS RT = 1.301 min. | ++ | Example 28 |
| 223 | 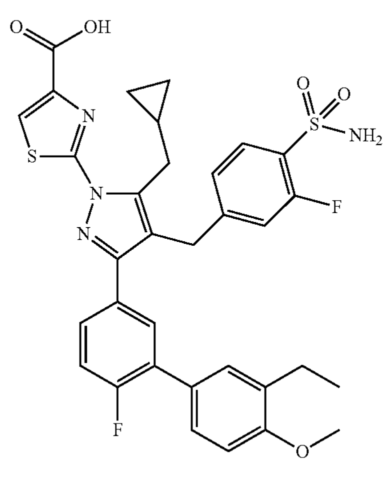 [SMILES: CCc1cc(-c2cc(-c3nn(-c4nc(C(=O)O)cs4)c(CC4CC4)c3Cc3ccc(S(N)(=O)=O)c(F)c3)ccc2F)ccc1OC] | 2-(5-(cyclopropylmethyl)-3-(3'-ethyl-6-fluoro-4'-methoxy-[1,1'-biphenyl]-3-yl)-4-(3-fluoro-4-sulfamoylbenzyl)-1H-pyrazol-1-yl)thiazole-4-carboxylic acid, $^1$H NMR (400 MHz, MeOD-d$_3$) δ 8.19 (s, 1H), 7.79-7.74 (m, 1H), 7.58-7.54 (m, 1H), 7.51-7.48 (m, 1H), 7.24 (s, 1H), 7.17 (dd, J = 8.5, 10.7 Hz, 1H), 7.11 (s, 1H), 7.10-7.05 (m, 2H), 6.96 (d, J = 8.5 Hz, 1H), 4.18 (s, 2H), 3.87 (s, 3H), 3.26 (d, J = 6.8 Hz, 2H), 2.64 (q, J = 7.5 Hz, 2H), 1.18 (t, J = 7.5 Hz, 3H), 1.15-1.10 (m, 1H), 0.42-0.37 (m, 2H), 0.26-0.22 (m, 2H); MS (ES) 665.0 [M + H]$^+$, LCMS RT = 1.307 min. | ++ | Example 27 |

TABLE 7-continued

| Cmpd ID | Structure | Compound name and physical data | Inhibitory activity IC$_{50}$ (μM) | Example Method |
|---|---|---|---|---|
| 224 | 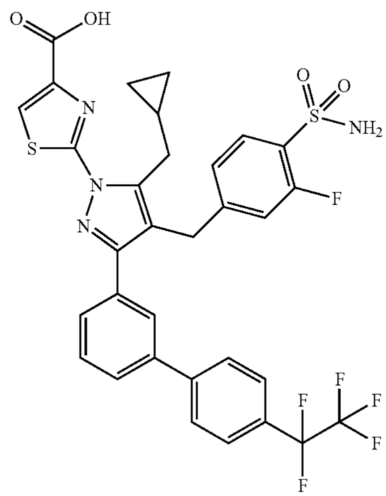 [SMILES: NS(=O)(=O)c1ccc(Cc2c(-c3cccc(-c4ccc(C(F)(F)C(F)(F)F)cc4)c3)nn(-c3nc(C(=O)O)cs3)c2CC2CC2)cc1F] | 2-(5-(cyclopropylmethyl)-4-(3-fluoro-4-sulfamoylbenzyl)-3-(4'-(perfluoroethyl)-[1,1'-biphenyl]-3-yl)-1H-pyrazol-1-yl)thiazole-4-carboxylic acid, $^1$H NMR (400 MHz, MeOD-d$_3$) δ 8.21 (s, 1H), 7.89-7.72 (m, 3H), 7.71 (s, 2H), 7.68 (s, 2H) 7.65 (bs, 1H), 7.51 (t, J = 7.8 Hz, 1H), 7.13-7.08 (m, 2H), 4.21 (s, 2H), 1.19-1.10 (m, 1H), 0.44-0.38 (m, 2H), 0.29-0.24 (m, 2H); MS (ES) 707.0 [M + H]$^+$, LCMS RT = 0.871 min. | ++ | Example 27 |
| 225 | 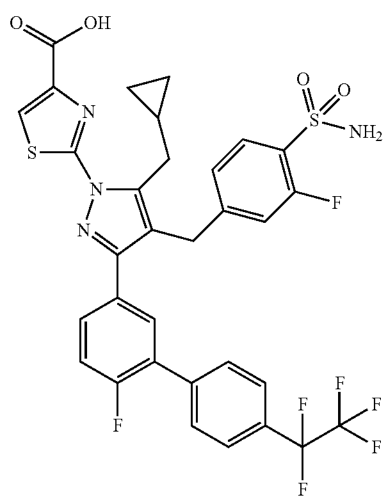 [SMILES: NS(=O)(=O)c1ccc(Cc2c(-c3ccc(F)c(-c4ccc(C(F)(F)C(F)(F)F)cc4)c3)nn(-c3nc(C(=O)O)cs3)c2CC2CC2)cc1F] | 2-(5-(cyclopropylmethyl)-3-(6-fluoro-4'-(perfluoroethyl)-[1,1'-biphenyl]-3-yl)-4-(3-fluoro-4-sulfamoylbenzyl)-1H-pyrazol-1-yl)thiazole-4-carboxylic acid, $^1$H NMR (400 MHz, MeOD-d$_3$) δ 8.20 (s, 1H), 7.77-7.71 (m, 3H), 7.70-7.66 (1H), 7.63-7.58 (m, 3H), 7.26 (dd, J = 8.7, 10.4 Hz, 1H), 7.09 (s, 1H), 7.08-7.06 (m, 1H), 4.19 (s, 2H), 3.28 (d, J = 6.80, 2H), 1.17-1.10 (m, 1H), 0.43-0.37 (m, 2H), 0.28-0.23 (m, 2H); MS (ES) 725.0 [M + H]$^+$, LCMS RT = 0.870 min. | ++ | Example 27 |
| 226 | 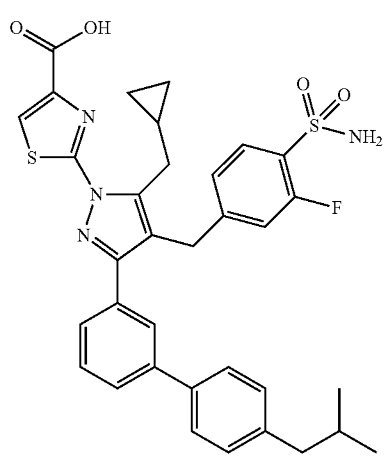 [SMILES: CC(C)Cc1ccc(-c2cccc(-c3nn(-c4nc(C(=O)O)cs4)c(CC4CC4)c3Cc3ccc(S(N)(=O)=O)c(F)c3)c2)cc1] | 2-(5-(cyclopropylmethyl)-4-(3-fluoro-4-sulfamoylbenzyl)-3-(4'-isobutyl-[1,1'-biphenyl]-3-yl)-1H-pyrazol-1-yl)thiazole-4-carboxylic acid, $^1$H NMR (400 MHz, MeOD-d$_3$) δ 8.19 (s, 1H), 7.79-7.74 (m, 1H), 7.67 (s, 1H), 7.58 (dd, J = 7.8, 21.1 Hz, 2H), 7.44 (t, J = 7.8 Hz, 1H), 7.35 (d, J = 8.1 Hz, 2H), 7.21 (d, J = 8.1 Hz, 2H), 7.14-7.08 (m, 2H), 4.20 (s, 2H), 3.28 (d, J = 6.8 Hz, 2H), 2.51 (d, J = 7.1 Hz, 2H), 1.95-1.86 (m, 1H), 1.19-1.10 (m, 1H), 0.93 (d, J = 6.6 Hz, 6H), 0.43-0.39 (m, 2H), 0.28-0.23 (m, 2H); MS (ES) 645.2 [M + H]$^+$, LCMS RT = 0.944 min. | ++ | Example 28 |

TABLE 7-continued

| Cmpd ID | Structure | Compound name and physical data | Inhibitory activity IC$_{50}$ (μM) | Example Method |
|---|---|---|---|---|
| 227 | 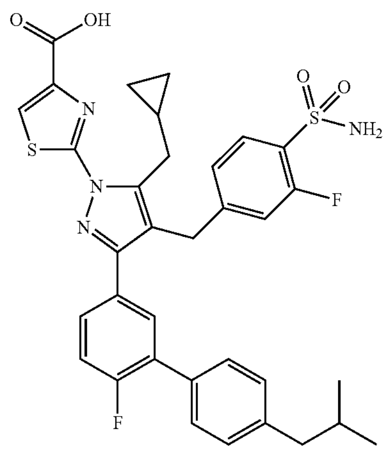 [SMILES: CC(C)Cc1ccc(-c2cc(-c3nn(-c4nc(C(=O)O)cs4)c(CC4CC4)c3Cc3ccc(S(N)(=O)=O)c(F)c3)ccc2F)cc1] | 2-(5-(cyclopropylmethyl)-3-(6-fluoro-4'-isobutyl-[1,1'-biphenyl]-3-yl)-4-(3-fluoro-4-sulfamoylbenzyl)-1H-pyrazol-1-yl)thiazole-4-carboxylic acid); MS (ES) 663.2 [M +H]$^+$, LCMS RT = 0.951 min. | ++ | Example 28 |
| 228 | 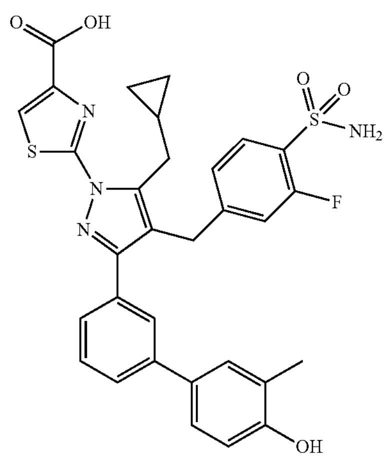 [SMILES: Cc1cc(-c2cccc(-c3nn(-c4nc(C(=O)O)cs4)c(CC4CC4)c3Cc3ccc(S(N)(=O)=O)c(F)c3)c2)ccc1O] | 2-(5-(cyclopropylmethyl)-4-(3-fluoro-4-sulfamoylbenzyl)-3-(4'-hydroxy-3'-methyl-[1,1'-biphenyl]-3-yl)-1H-pyrazol-1-yl)thiazole-4-carboxylic acid; MS (ES) 619.0 [M + H]$^+$, LCMS RT = 1.104 min. | +++ | Example 27 |
| 229 | 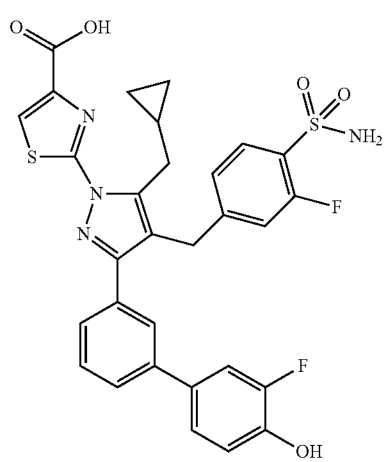 [SMILES: NS(=O)(=O)c1ccc(Cc2c(-c3cccc(-c4ccc(O)c(F)c4)c3)nn(-c3nc(C(=O)O)cs3)c2CC2CC2)cc1F] | 2-(5-(cyclopropylmethyl)-3-(3'-fluoro-4'-hydroxy-[1,1'-biphenyl]-3-yl)-4-(3-fluoro-4-sulfamoylbenzyl)-1H-pyrazol-1-yl)thiazole-4-carboxylic acid; MS (ES) 623.0 [M + H]$^+$, LCMS RT = 1.073 min. | +++ | Example 27 |

TABLE 7-continued

| Cmpd ID | Structure | Compound name and physical data | Inhibitory activity IC$_{50}$ (μM) | Example Method |
|---|---|---|---|---|
| 230 | 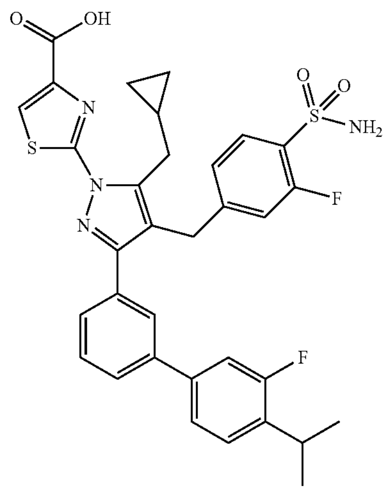 [SMILES: CC(C)c1ccc(-c2cccc(-c3nn(-c4nc(C(=O)O)cs4)c(CC4CC4)c3Cc3ccc(S(N)(=O)=O)c(F)c3)c2)cc1F] | 2-(5-(cyclopropylmethyl)-3-(3'-fluoro-4'-isopropyl-[1,1'-biphenyl]-3-yl)-4-(3-fluoro-4-sulfamoylbenzyl)-1H-pyrazol-1-yl)thiazole-4-carboxylic acid, $^1$H NMR (400 MHz, MeOD-d3) δ 8.15 (s, 1H), 7.80-7.74 (m, 1H), 7.68 (s, 1H), 7.63-7.56 (m, 2H), 7.48-7.43 (m, 1H), 7.38-7.33 (m, 1H), 7.21 (d, J = 11.7 Hz, 1H), 7.16-7.08 (m, 3H), 4.21 (s, 2H), 1.29 (d, J = 6.9 Hz, 6H), 1.20-1.11 (m, 1H), 0.43-0.37 (m, 2H), 0.27-0.22 (m, 2H); MS (ES) 649.0 [M +H]$^+$, LCMS RT = 1.346 min. | ++ | Example 27 |
| 231 | 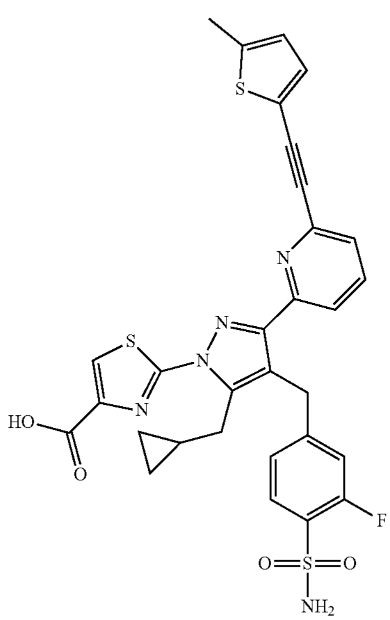 [SMILES: Cc1ccc(C#Cc2cccc(-c3nn(-c4nc(C(=O)O)cs4)c(CC4CC4)c3Cc3ccc(S(N)(=O)=O)c(F)c3)n2)s1] | 2-(5-(cyclopropylmethyl)-4-(3-fluoro-4-sulfamoylbenzyl)-3-(6-((5-methylthiophen-2-yl)ethynyl)pyridin-2-yl)-1H-pyrazol-1-yl)thiazole-4-carboxylic acid, $^1$H NMR (400 MHz, DMSO-d$_6$) δ 13.14 (s, 1H), 8.34 (s, 1H), 7.97 (dd, J = 8.0, 1.1 Hz, 1H), 7.90 (t, J = 7.8 Hz, 1H), 7.60 (t, J = 8.0 Hz, 1H), 7.56 (dd, J = 7.6, 1.1 Hz, 1H), 7.51 (s, 2H), 7.36 (d, J = 3.5 Hz, 1H), 7.26 (dd, J = 11.5, 1.5 Hz, 1H), 7.16 (dd, J = 8.2, 1.6 Hz, 1H), 6.89 (dt, J = 3.6, 1.2 Hz, 1H), 4.38 (s, 2H), 3.26 (d, J = 6.9 Hz, 2H), 1.26-1.15 (m, 1H), 0.43-0.30 (m, 2H), 0.34-0.20 (m, 2H); MS (ES) 634 [M + H]$^+$. | +++ | 7 |

| Cmpd ID | Structure | Compound name and physical data | Inhibitory activity IC$_{50}$ (μM) | Example Method |
|---|---|---|---|---|
| 232 | 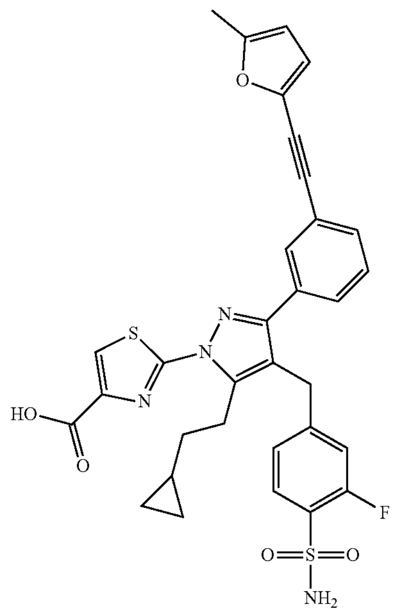 [SMILES: Cc1ccc(C#Cc2cccc(-c3nn(-c4nc(C(=O)O)cs4)c(CCC4CC4)c3Cc3ccc(S(N)(=O)=O)c(F)c3)c2)o1] | 2-(5-(2-cyclopropylethyl)-4-(3-fluoro-4-sulfamoylbenzyl)-3-(3-((5-methylfuran-2-yl)ethynyl)phenyl)-1H-pyrazol-1-yl)thiazole-4-carboxylic acid, $^1$H NMR (400 MHz, DMSO-d$_6$) δ 13.13 (s, 1H), 8.29 (s, 1H), 7.68 (d, J = 7.6 Hz, 2H), 7.58 (s, 3H), 7.58-7.43 (m, 2H), 7.18 (d, J = 11.2 Hz, 1H), 7.07 (d, J = 8.1 Hz, 1H), 6.81 (s, 1H), 6.22 (s, 1H), 4.17 (s, 2H), 3.25 (s, 2H), 2.31 (s, 3H), 1.48-1.38 (m, 2H), 0.74 (s, 1H), 0.31 (d, J = 8.0 Hz, 2H), 0.12 (s, 2H); MS (ES) 631 [M + H]$^+$. | +++ | 7 |
| 233 | 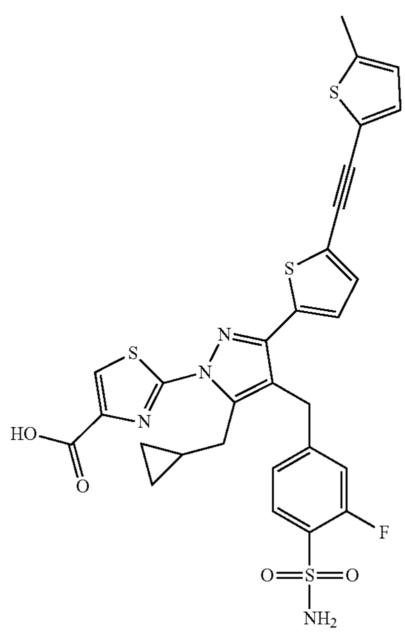 [SMILES: Cc1ccc(C#Cc2ccc(-c3nn(-c4nc(C(=O)O)cs4)c(CC4CC4)c3Cc3ccc(S(N)(=O)=O)c(F)c3)s2)s1] | 2-(5-(cyclopropylmethyl)-4-(3-fluoro-4-sulfamoylbenzyl)-3-(5-((5-methylthiophen-2-yl)ethynyl)thiophen-2-yl)-1H-pyrazol-1-yl)thiazole-4-carboxylic acid, $^1$H NMR (400 MHz, DMSO-d$_6$) δ 13.01 (s, 1H), 8.29 (s, 1H), 7.66 (t, J = 7.9 Hz, 1H), 7.55 (s, 2H), 7.31 (d, J = 3.9 Hz, 1H), 7.23 (dd, J = 3.6, 0.5 Hz, 1H), 7.18 (dd, J = 11.4, 1.6 Hz, 1H), 7.12 (d, J = 3.9 Hz, 1H), 7.07 (dd, J = 8.1, 1.6 Hz, 1H), 6.81 (dt, J = 3.6, 1.1 Hz, 1H), 4.21 (s, 2H), 3.14 (d, J = 6.9 Hz, 2H), 2.44 (d, J = 1.0 Hz, 3H), 1.18-1.02 (m, 0H), 0.36-0.24 (m, 2H), 0.24-0.13 (m, 2H); MS (ES) 639 [M + H]$^+$. | ++ | 7 |

TABLE 7-continued

| Cmpd ID | Structure | Compound name and physical data | Inhibitory activity IC$_{50}$ (μM) | Example Method |
|---|---|---|---|---|
| 234 | 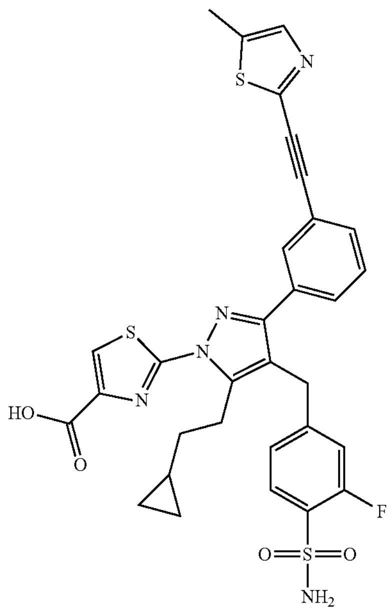 | 2-(5-(2-cyclopropylethyl)-4-(3-fluoro-4-sulfamoylbenzyl)-3-(3-((5-methylthiazol-2-yl)ethynyl)phenyl)-1H-pyrazol-1-yl)thiazole-4-carboxylic acid, $^1$H NMR (400 MHz, DMSO-d$_6$) δ 13.10 (s, 1H), 8.25 (s, 1H), 7.77 (td, J = 1.7, 0.6 Hz, 1H), 7.68-7.58 (m, 4H), 7.57-7.44 (m, 3H), 7.15 (dd, J = 11.4, 1.5 Hz, 1H), 7.04 (dd, J = 8.2, 1.6 Hz, 1H), 4.16 (s, 2H), 3.26-3.17 (m, 2H), 2.48 (s, 2H), 1.40 (q, J = 7.4 Hz, 2H), 0.75-0.65 (m, 1H), 0.33-0.24 (m, 2H), 0.13-0.04 (m, 2H); MS (ES) 648 M + H]$^+$. | +++ | 7 |
| 235 | 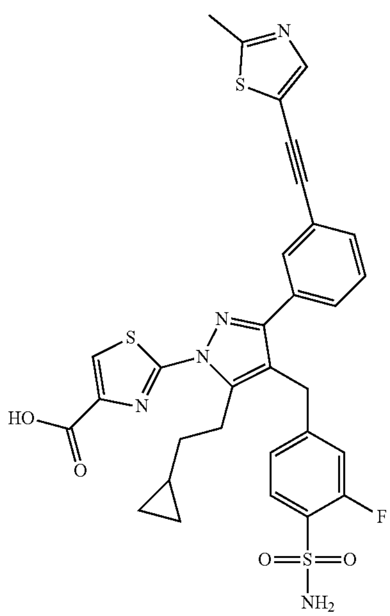 [SMILES: Cc1ncc(C#Cc2cccc(-c3nn(-c4nc(C(=O)O)cs4)c(CCC4CC4)c3Cc3ccc(S(N)(=O)=O)c(F)c3)c2)s1] | 2-(5-(2-cyclopropylethyl)-4-(3-fluoro-4-sulfamoylbenzyl)-3-(3-((2-methylthiazol-5-yl)ethynyl)phenyl)-1H-pyrazol-1-yl)thiazole-4-carboxylic acid, $^1$H NMR (400 MHz, DMSO-d$_6$) δ 13.13 (s, 1H), 8.28 (s, 1H), 7.96 (s, 1H), 7.74-7.62 (m, 2H), 7.65-7.53 (m, 4H), 7.48 (td, J = 7.7, 0.6 Hz, 1H), 7.19 (dd, J = 11.3, 1.5 Hz, 1H), 7.07 (dd, J = 8.1, 1.6 Hz, 1H), 4.18 (s, 2H), 3.24 (d, J = 8.3 Hz, 2H), 2.69 (s, 3H), 1.43 (q, J = 7.4 Hz, 2H), 0.74 (td, J = 7.5, 3.8 Hz, 0H), 0.36-0.27 (m, 2H), 0.16-0.08 (m, 2H); MS (ES) 648 [M + H]$^+$. | +++ | 7 |

TABLE 7-continued

| Cmpd ID | Structure | Compound name and physical data | Inhibitory activity IC$_{50}$ (μM) | Example Method |
|---|---|---|---|---|
| 236 | 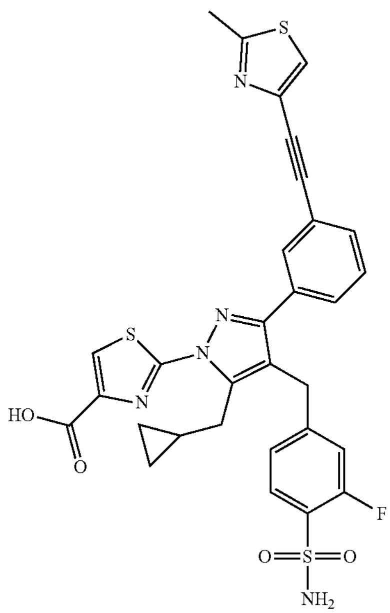 [SMILES: Cc1nc(C#Cc2cccc(-c3nn(-c4nc(C(=O)O)cs4)c(CC4CC4)c3Cc3ccc(S(N)(=O)=O)c(F)c3)c2)cs1] | 2-(5-(cyclopropylmethyl)-4-(3-fluoro-4-sulfamoylbenzyl)-3-(3-((2-methylthiazol-4-yl)ethynyl)phenyl)-1H-pyrazol-1-yl)thiazole-4-carboxylic acid, $^1$H NMR (400 MHz, DMSO-d$_6$) δ 13.16 (s, 1H), 8.32 (s, 1H), 7.91 (s, 1H), 7.79-7.52 (m, 7H), 7.47 (t, J = 7.8 Hz, 1H), 7.16 (dd, J = 11.3, 1.5 Hz, 1H), 7.07 (dd, J = 8.1, 1.6 Hz, 1H), 4.19 (s, 2H), 3.18 (d, J = 6.9 Hz, 2H), 2.68 (s, 3H), 1.21-1.08 (m, 1H), 0.40-0.26 (m, 2H), 0.30-0.19 (m, 2H); MS (ES) 634 [M + H]$^+$. | +++ | 7 |
| 237 | 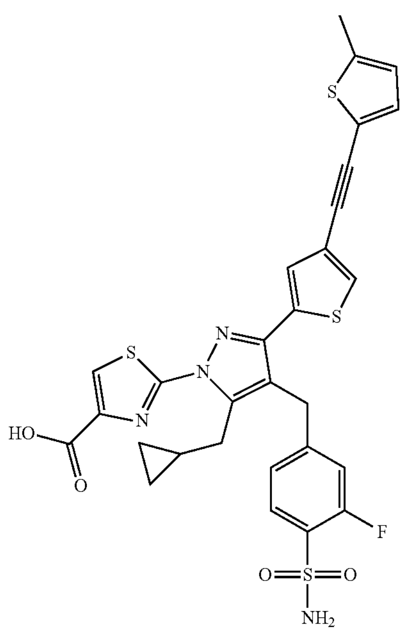 [SMILES: Cc1ccc(C#Cc2csc(-c3nn(-c4nc(C(=O)O)cs4)c(CC4CC4)c3Cc3ccc(S(N)(=O)=O)c(F)c3)c2)s1] | 2-(5-(cyclopropylmethyl)-4-(3-fluoro-4-sulfamoylbenzyl)-3-(4-((5-methylthiophen-2-yl)ethynyl)thiophen-2-yl)-1H-pyrazol-1-yl)thiazole-4-carboxylic acid, $^1$H NMR (400 MHz, DMSO-d$_6$) δ 13.15 (s, 1H), 8.30 (s, 1H), 7.91 (d, J = 1.3 Hz, 1H), 7.69 (t, J = 8.0 Hz, 1H), 7.58 (s, 2H), 7.33 (d, J = 1.3 Hz, 1H), 7.26-7.08 (m, 3H), 6.81 (dq, J = 3.4, 1.0 Hz, 1H), 4.25 (s, 2H), 3.16 (d, J = 6.9 Hz, 2H), 2.46 (d, J = 1.1 Hz, 3H), 1.22-1.04 (m, 1H), 0.36-0.28 (m, 2H), 0.23-0.15 (m, 2H); MS (ES) 639 [M + H]$^+$. | ++ | 7 |

TABLE 7-continued

| Cmpd ID | Structure | Compound name and physical data | Inhibitory activity IC$_{50}$ (μM) | Example Method |
|---|---|---|---|---|
| 238 | 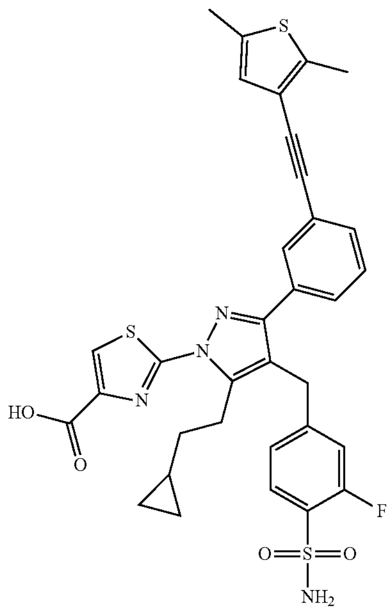 [SMILES: Cc1cc(C#Cc2cccc(-c3nn(-c4nc(C(=O)O)cs4)c(CCC4CC4)c3Cc3ccc(S(N)(=O)=O)c(F)c3)c2)c(C)s1] | 2-(5-(2-cyclopropylethyl)-3-(3-((2,5-dimethylthiophen-3-yl)ethynyl)phenyl)-4-(3-fluoro-4-sulfamoylbenzyl)-1H-pyrazol-1-yl)thiazole-4-carboxylic acid, $^1$H NMR (400 MHz, DMSO-d$_6$) δ 13.13 (s, 1H), 8.28 (s, 1H), 7.68 (t, J = 7.9 Hz, 1H), 7.63-7.56 (m, 4H), 7.52 (dt, J = 7.7, 1.5 Hz, 1H), 7.46 (td, J = 7.6, 0.7 Hz, 1H), 7.21 (dd, J = 11.4, 1.6 Hz, 1H), 7.09 (dd, J = 8.2, 1.6 Hz, 1H), 6.77 (q, J = 1.1 Hz, 1H), 4.17 (s, 2H), 3.29-3.20 (m, 2H), 2.44 (d, J = 0.7 Hz, 3H), 2.38 (t, J = 0.9 Hz, 3H), 1.44 (q, J = 7.2 Hz, 2H), 0.80-0.67 (m, 1H), 0.39-0.27 (m, 2H), 0.18-0.08 (m, 2H), MS (ES) 661 [M + H]$^+$. | ++ | 7 |
| 239 | 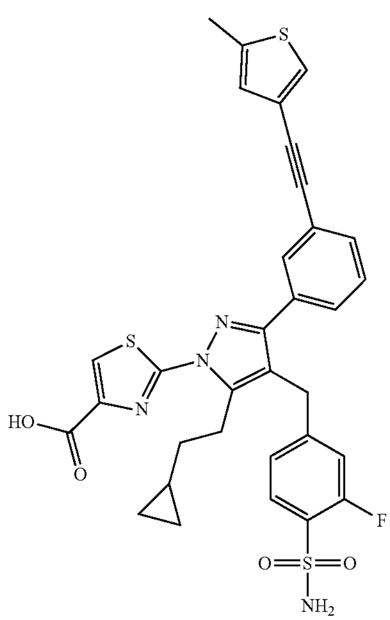 [SMILES: Cc1cc(C#Cc2cccc(-c3nn(-c4nc(C(=O)O)cs4)c(CCC4CC4)c3Cc3ccc(S(N)(=O)=O)c(F)c3)c2)cs1] | 2-(5-(2-cyclopropylethyl)-4-(3-fluoro-4-sulfamoylbenzyl)-3-(3-((5-methylthiophen-3-yl)ethynyl)phenyl)-1H-pyrazol-1-yl)thiazole-4-carboxylic acid, $^1$H NMR (400 MHz, DMSO-d$_6$) δ 13.13 (s, 1H), 8.29 (s, 1H), 7.73-7.41 (m, 7H), 7.20 (dd, J = 11.3, 1.6 Hz, 1H), 7.08 (dd, J = 8.1, 1.6 Hz, 1H), 6.95 (p, J = 1.1 Hz, 1H), 4.17 (s, 2H), 3.30-3.21 (m, 2H), 2.46 (d, J = 1.1 Hz, 3H), 1.44 (q, J = 7.2 Hz, 2H), 0.75 (tq, J = 8.0, 5.0, 3.9 Hz, 1H), 0.37-0.25 (m, 2H), 0.19-0.08 (m, 2H); MS (ES) 647 [M + H]$^+$. | ++ | 7 |

TABLE 7-continued

| Cmpd ID | Structure | Compound name and physical data | Inhibitory activity IC$_{50}$ (μM) | Example Method |
|---|---|---|---|---|
| 240 | 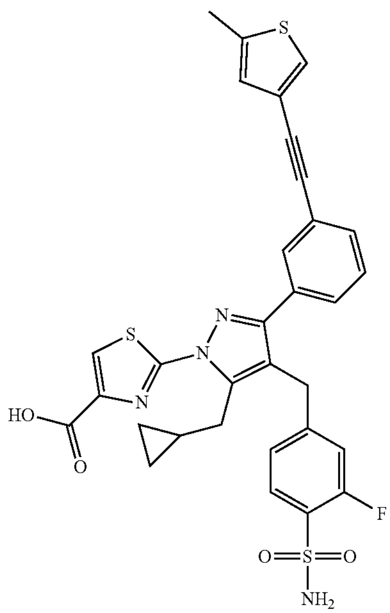 [SMILES: Cc1cc(C#Cc2cccc(-c3nn(-c4nc(C(=O)O)cs4)c(CC4CC4)c3Cc3ccc(S(N)(=O)=O)c(F)c3)c2)cs1] | 2-(5-(cyclopropylmethyl)-4-(3-fluoro-4-sulfamoylbenzyl)-3-(3-((5-methylthiophen-3-yl)ethynyl)phenyl)-1H-pyrazol-1-yl)thiazole-4-carboxylic acid, $^1$H NMR (400 MHz, DMSO-d$_6$) δ 13.16 (s, 1H), 8.31 (s, 1H), 7.71-7.40 (m, 7H), 7.18 (dd, J = 11.3, 1.6 Hz, 1H), 7.07 (dd, J = 8.2, 1.6 Hz, 1H), 6.95 (p, J = 1.1 Hz, 1H), 4.18 (s, 2H), 3.18 (d, J = 6.9 Hz, 2H), 2.46 (d, J = 1.1 Hz, 3H), 1.22-1.07 (m, 0H), 0.40-0.29 (m, 2H), 0.30-0.19 (m, 2H); MS (ES) 633 [M + H]$^+$. | +++ | 7 |
| 241 | 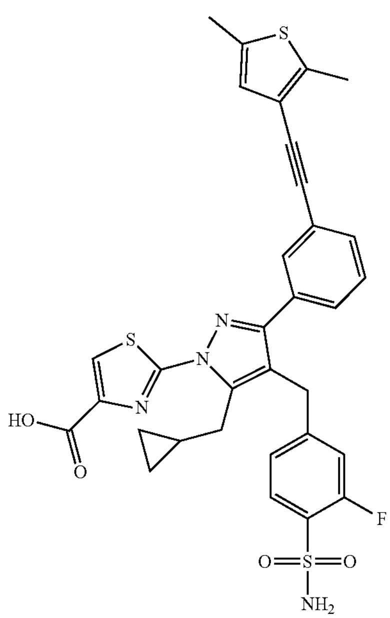 | 2-(5-(cyclopropylmethyl)-3-(3-((2,5-dimethylthiophen-3-yl)ethynyl)phenyl)-4-(3-fluoro-4-sulfamoylbenzyl)-1H-pyrazol-1-yl)thiazole-4-carboxylic acid, $^1$H NMR (400 MHz, DMSO-d$_6$) δ 13.16 (s, 1H), 8.31 (s, 1H), 7.67 (t, J = 8.0 Hz, 1H), 7.65-7.56 (m, 4H), 7.55-7.40 (m, 2H), 7.18 (dd, J = 11.3, 1.5 Hz, 1H), 7.08 (dd, J = 8.1, 1.6 Hz, 1H), 6.77 (q, J = 1.1 Hz, 1H), 4.18 (s, 2H), 3.17 (d, J = 6.9 Hz, 2H), 2.44 (d, J = 0.7 Hz, 3H), 2.38 (t, J = 0.9 Hz, 3H), 1.20-1.09 (m, 1H), 0.39-0.28 (m, 2H), 0.29-0.18 (m, 2H); MS (ES) 633 [M + H]$^+$. | ++ | 7 |

TABLE 7-continued

| Cmpd ID | Structure | Compound name and physical data | Inhibitory activity IC$_{50}$ (μM) | Example Method |
|---|---|---|---|---|
| 242 | 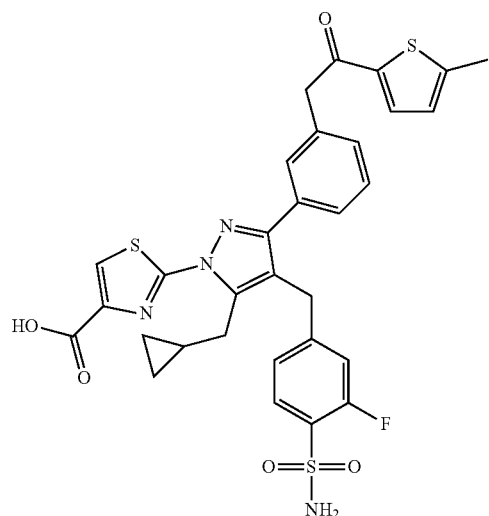 [SMILES: Cc1ccc(C(=O)Cc2cccc(-c3nn(-c4nc(C(=O)O)cs4)c(CC4CC4)c3Cc3ccc(S(N)(=O)=O)c(F)c3)c2)s1] | 2-(5-(cyclopropylmethyl)-4-(3-fluoro-4-sulfamoylbenzyl)-3-(3-(2-(5-methylthiophen-2-yl)-2-oxoethyl)phenyl)-1H-pyrazol-1-yl)thiazole-4-carboxylic acid, $^1$H NMR (400 MHz, DMSO-d$_6$) δ 13.14 (s, 1H), 8.29 (s, 1H), 7.91 (d, J = 3.7 Hz, 1H), 7.66-7.53 (m, 4H), 7.45-7.25 (m, 3H), 7.08 (dd, J = 11.4, 1.6 Hz, 1H), 7.08-6.94 (m, 2H), 4.26 (s, 2H), 4.13 (s, 2H), 3.16 (d, J = 6.9 Hz, 2H), 2.49 (s, 3H), 1.13 (ddtd, J = 13.0, 8.0, 6.9, 5.0 Hz, 1H), 0.39-0.27 (m, 2H), 0.30-0.17 (m, 2H); MS (ES) 651 [M + H]$^+$. | +++ | 7 |
| 243 | 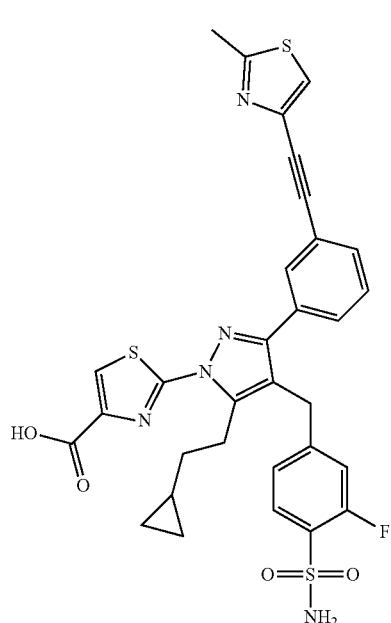 | 2-(5-(2-cyclopropylethyl)-4-(3-fluoro-4-sulfamoylbenzyl)-3-(3-((2-methylthiazol-4-yl)ethynyl)phenyl)-1H-pyrazol-1-yl)thiazole-4-carboxylic acid, $^1$H NMR (400 MHz, DMSO-d$_6$) δ 13.13 (s, 1H), 8.30 (s, 1H), 7.92 (s, 1H), 7.76-7.63 (m, 2H), 7.59 (s, 2H), 7.64-7.54 (m, 2H), 7.53-7.44 (m, 1H), 7.19 (dd, J = 11.3, 1.6 Hz, 1H), 7.08 (dd, J = 8.1, 1.6 Hz, 1H), 4.18 (s, 2H), 3.29-3.20 (m, 2H), 2.68 (s, 3H), 1.43 (q, J = 7.3 Hz, 2H), 0.82-0.67 (m, 1H), 0.38-0.25 (m, 2H), 0.19-0.08 (m, 2H); MS (ES) 648 [M + H]$^+$. | +++ | 7 |

TABLE 7-continued

| Cmpd ID | Structure | Compound name and physical data | Inhibitory activity IC$_{50}$ (μM) | Example Method |
|---|---|---|---|---|
| 244 | 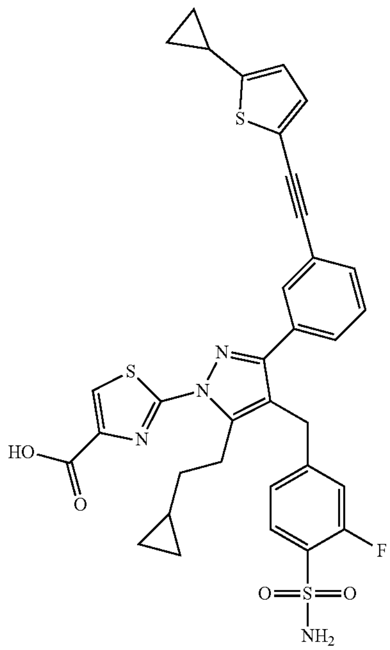 [SMILES: NS(=O)(=O)c1ccc(Cc2c(-c3cccc(C#Cc4ccc(C5CC5)s4)c3)nn(-c3nc(C(=O)O)cs3)c2CCC2CC2)cc1F] | 2-(5-(2-cyclopylethyl)-3-(3-((5-cyclopropylthiophen-2-yl)ethynyl)phenyl)-4-(3-fluoro-4-sulfamoylbenzyl)-1H-pyrazol-1-yl)thiazole-4-carboxylic acid, $^1$H NMR (400 MHz, DMSO-d$_6$) δ 13.13 (s, 1H), 8.28 (s, 1H), 7.72-7.63 (m, 2H), 7.66-7.48 (m, 4H), 7.46 (t, J = 7.7 Hz, 1H), 7.25-7.14 (m, 2H), 7.07 (dd, J = 8.2, 1.6 Hz, 1H), 6.82 (dd, J = 3.7, 0.7 Hz, 1H), 4.17 (s, 2H), 3.29-3.20 (m, 2H), 2.17 (tt, J = 8.3, 5.1 Hz, 1H), 1.43 (q, J = 7.4 Hz, 2H), 1.11-0.98 (m, 2H), 0.81-0.67 (m, 3H), 0.36-0.25 (m, 2H), 0.19-0.08 (m, 2H); MS (ES) 673 [M + H]$^+$. | ++ | 7 |
| 245 | 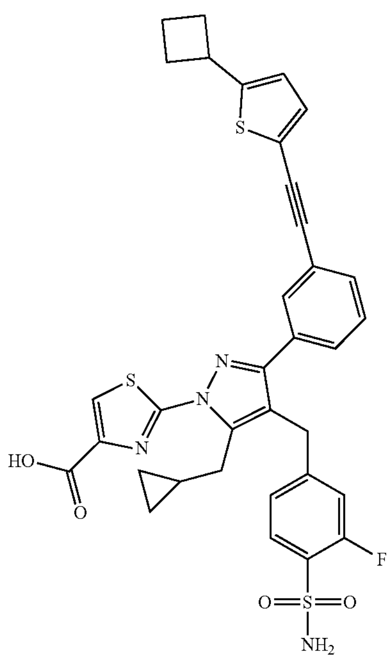 [SMILES: NS(=O)(=O)c1ccc(Cc2c(-c3cccc(C#Cc4ccc(C5CCC5)s4)c3)nn(-c3nc(C(=O)O)cs3)c2CC2CC2)cc1F] | 2-(3-(3-((5-cyclobutylthiophen-2-yl)ethynyl)phenyl)-5-(cyclopropylmethyl)-4-(3-fluoro-4-sulfamoylbenzyl)-1H-pyrazol-1-yl)thiazole-4-carboxylic acid, $^1$H NMR (400 MHz, DMSO-d$_6$) δ 13.16 (s, 1H), 8.31 (s, 1H), 7.71-7.62 (m, 2H), 7.66-7.54 (m, 3H), 7.52 (dt, J = 7.7, 1.4 Hz, 1H), 7.49-7.40 (m, 1H), 7.26 (d, J = 3.6 Hz, 1H), 7.16 (dd, J = 11.4, 1.6 Hz, 1H), 7.07 (dd, J = 8.1, 1.6 Hz, 1H), 6.88 (dd, J = 3.7, 0.9 Hz, 1H), 4.18 (s, 2H), 3.79-3.65 (m, 1H), 3.18 (d, J = 6.9 Hz, 2H), 2.45-2.32 (m, 2H), 2.19-2.04 (m, 2H), 2.05-1.88 (m, 1H), 1.91-1.78 (m, 1H), 1.21-1.08 (m, 1H), 0.41-0.27 (m, 2H), 0.31-0.16 (m, 2H), MS (ES) 673 [M + H]$^+$. | ++ | 7 |

TABLE 7-continued

| Cmpd ID | Structure | Compound name and physical data | Inhibitory activity IC$_{50}$ (μM) | Example Method |
|---|---|---|---|---|
| 246 | 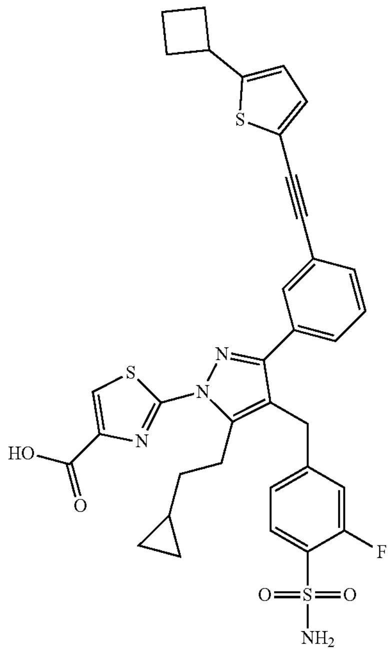 [SMILES: NS(=O)(=O)c1ccc(Cc2c(-c3cccc(C#Cc4ccc(C5CCC5)s4)c3)nn(-c3nc(C(=O)O)cs3)c2CCC2CC2)cc1F] | 2-(3-(3-((5-cyclobutylthiophen-2-yl)ethynyl)phenyl)-5-(2-cyclopropylethyl)-4-(3-fluoro-4-sulfamoylbenzyl)-1H-pyrazol-1-yl)thiazole-4-carboxylic acid, $^1$H NMR (400 MHz, DMSO-d$_6$) δ 13.13 (s, 1H), 8.28 (s, 1H), 7.72-7.61 (m, 2H), 7.62-7.49 (m, 4H), 7.46 (td, J = 7.7, 0.6 Hz, 1H), 7.26 (d, J = 3.7 Hz, 1H), 7.19 (dd, J = 11.4, 1.6 Hz, 1H), 7.08 (dd, J = 8.1, 1.6 Hz, 1H), 6.88 (dd, J = 3.7, 0.9 Hz, 1H), 4.17 (s, 2H), 3.79-3.65 (m, 1H), 3.29-3.21 (m, 2H), 2.47-2.36 (m, 1H), 2.40-2.32 (m, 1H), 2.19-2.04 (m, 2H), 2.09-1.88 (m, 1H), 1.91-1.78 (m, 1H), 1.43 (q, J = 7.4 Hz, 2H), 0.74 (td, J = 7.8, 4.8 Hz, 1H), 0.36-0.25 (m, 2H), 0.20-0.08 (m, 2H); MS (ES) 687 [M + H]$^+$. | ++ | 7 |
| 247 | 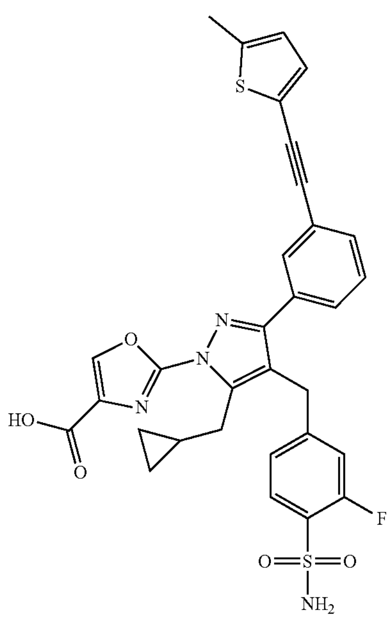 [SMILES: Cc1ccc(C#Cc2cccc(-c3nn(-c4nc(C(=O)O)co4)c(CC4CC4)c3Cc3ccc(S(N)(=O)=O)c(F)c3)c2)s1] | 2-(5-(cyclopropylmethyl)-4-(3-fluoro-4-sulfamoylbenzyl)-3-(3-((5-methylthiophen-2-yl)ethynyl)phenyl)-1H-pyrazol-1-yl)oxazole-4-carboxylic acid, MS (ES) 617 [M + H]$^+$. | +++ | 7 |

TABLE 7-continued

| Cmpd ID | Structure | Compound name and physical data | Inhibitory activity IC$_{50}$ (μM) | Example Method |
|---|---|---|---|---|
| 248 | 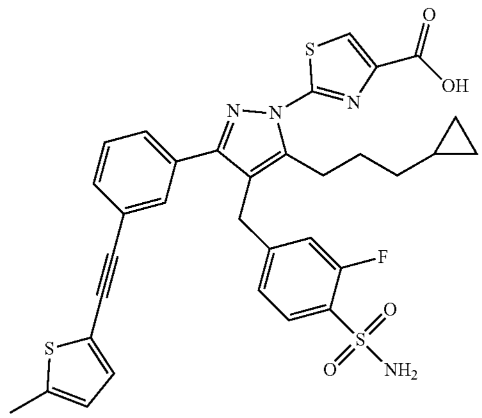 | 2-(5-(3-cyclopropylpropyl)-4-(3-fluoro-4-sulfamoylbenzyl)-3-(3-((5-methylthiophen-2-yl)ethynyl)phenyl)-1H-pyrazol-1-yl)thiazole-4-carboxylic acid, MS (ES) 617 [M + H]$^+$. | ++ | 7 |
| 249 | 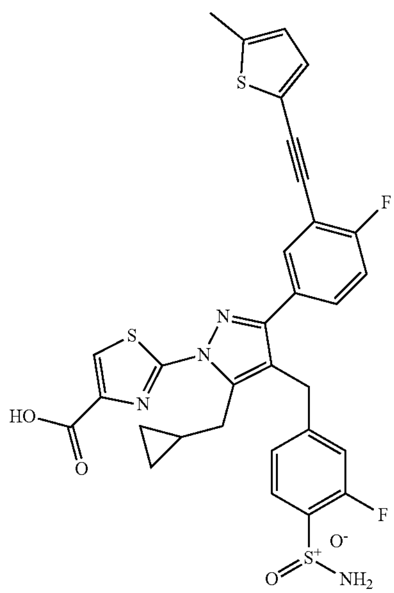 | 2-(5-(cyclopropylmethyl)-3-(4-fluoro-3-((5-methylthiophen-2-yl)ethynyl)phenyl)-4-(3-fluoro-4-sulfamoylbenzyl)-1H-pyrazol-1-yl)thiazole-4-carboxylic acid, 1H NMR (400 MHz, DMSO-d6) δ 13.18 (s, 1H), 8.32 (s, 1H), 7.74 (dd, J = 6.9, 2.3 Hz, 1H), 7.66 (t, J = 7.9 Hz, 1H), 7.61 (ddd, J = 8.6, 5.0, 2.3 Hz, 1H), 7.59 (s, 2H), 7.37 (dd, J = 9.4, 8.7 Hz, 1H), 7.29 (dd, J = 3.6, 0.5 Hz, 1H), 7.17 (dd, J = 11.3, 1.6 Hz, 1H), 7.06 (dd, J = 8.1, 1.6 Hz, 1H), 6.86 (dt, J = 3.6, 1.1 Hz, 1H), 4.17 (s, 2H), 3.18 (d, J = 6.9 Hz, 2H), 2.48 (d, J = 1.1 Hz, 3H), 1.21-1.08 (m, 1H), 0.40-0.28 (m, 2H), 0.30-0.19 (m, 2H); MS [M + H]+ = 651 | +++ | 7, 8 |

Example 35

This example describes the cellular inhibition of lactate production, as measured by the assay set forth in Example 6, of exemplary compounds of formula (I) in an embodiment of the invention. See Table 8. The lactate activity in Table 8 is represented by 0 to 3 pluses as follows: +++<1 μM; ++1-10 μM; +10-57 μM; and ->57 μM.

TABLE 8

| Cmpd ID | Lactate activity |
|---|---|
| 101 | +++ |
| 102 | +++ |
| 103 | +++ |
| 104 | +++ |
| 105 | +++ |
| 106 | +++ |
| 107 | +++ |
| 108 | +++ |
| 109 | +++ |
| 110 | +++ |
| 111 | +++ |
| 112 | +++ |
| 113 | +++ |
| 114 | +++ |
| 115 | +++ |
| 117 | +++ |
| 118 | +++ |
| 119 | +++ |
| 120 | +++ |
| 121 | +++ |
| 122 | +++ |
| 123 | +++ |
| 124 | +++ |
| 125 | +++ |
| 127 | +++ |
| 129 | +++ |
| 130 | +++ |

TABLE 8-continued

| Cmpd ID | Lactate activity |
|---|---|
| 131 | +++ |
| 132 | +++ |
| 133 | +++ |
| 137 | +++ |
| 138 | +++ |
| 139 | +++ |
| 141 | +++ |
| 142 | +++ |
| 143 | +++ |
| 144 | +++ |
| 146 | +++ |
| 149 | +++ |
| 150 | +++ |
| 151 | +++ |
| 153 | +++ |
| 155 | +++ |
| 156 | +++ |
| 157 | +++ |
| 162 | +++ |
| 164 | +++ |
| 165 | +++ |
| 166 | +++ |
| 167 | +++ |
| 168 | +++ |
| 169 | +++ |
| 173 | – |
| 174 | – |
| 175 | – |
| 176 | – |
| 177 | – |
| 178 | – |
| 179 | – |

What is claimed is:

1. A compound of formula (II):

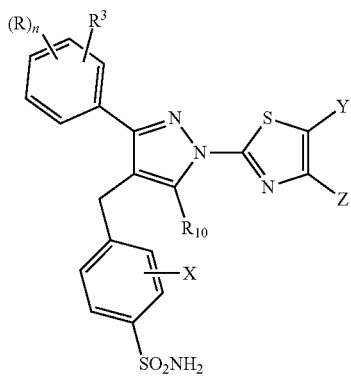

wherein
X is hydrogen or a halogen;
Y is hydrogen or $C_1$-$C_2$alkyl;
Z is —$CO_2H$, —$CONH_2$, —CONH(CN), —$CONHSO_2CH_3$, —CONH(OH), —$COCF_3$, $CH(OH)CF_3$, —$CH_2OH$, or —$B(OH)_2$;
n is 0, 1, 2, or 3;
R is independently chosen at each occurrence from halogen, hydroxyl, $C_1$-$C_4$alkyl, or $C_1$-$C_4$ alkoxy;
$R^3$ is a —$C(O)CH_3$, substituted or unsubstituted phenyl group, a substituted or unsubstituted indanyl group, a substituted or unsubstituted tetrahydronaphthyl group, a substituted or unsubstituted cyclohexenyl group, a substituted or unsubstituted indenyl group, substituted or unsubstituted 2,6-diazaspiro[3.3]heptanyl group, a substituted or unsubstituted imidazolyl group, a substituted or unsubstituted dihydrofuranyl group, a substituted or unsubstituted pyrrolidinyl group, a substituted or unsubstituted pyridyl group, a substituted or unsubstituted pyrimidinyl group, a substituted or unsubstituted thiazolyl group, a substituted or unsubstituted spiro[2.5]oct-5-enyl, a substituted or unsubstituted benzimidazolyl group, or -L-Q, wherein L is an $C_2$-$C_4$alkynylene group, an ethenylene group, a cyclopropylene group, or a cyclobutylene group, and wherein Q is hydrogen, $C_1$-$C_5$alkyl group, a substituted or unsubstituted five-membered heterocycle having 1 to 3 heteroatoms selected from N, O, and S, —$NR^5C(O)R^4$, —$C(O)NR^5R^6$, wherein $R^4$ is hydrogen, $C_1$-$C_5$alkyl, or substituted or unsubstituted phenyl, and $R^5$ and $R^6$ are each independently hydrogen or $C_1$-$C_5$alkyl, or $R^5$ and $R^6$ taken together form a ring, or $R^4$ and $R^5$ taken together form a ring;
$R^{10}$ is (cyclopropyl)$C_0$-$C_4$alkyl, which cyclopropyl is optionally substituted with methyl or cyclopropyl or fused to a cyclopropyl group in spiro orientation, or $R^{10}$ is (cyclopropyl)$C_1$-$C_4$alkyl in which the $C_1$-$C_4$alkyl is substituted with cyclopropyl;
or a pharmaceutically acceptable salt thereof.

2. The compound or salt of claim 1, wherein X is fluorine.

3. The compound or salt of claim 1, wherein $R^3$ is a substituted phenyl group, substituted with fluorine, chlorine, a $C_1$-$C_5$alkyl group, —$CF_3$, —$CHF_2$, $CH_3O$—, $CH_3CO$—, —CN, —$N(CH_3)_2$, or a combination thereof.

4. The compound or salt of claim 1, wherein $R^3$ is -L-Q and Q is a furanyl, thiophenyl, oxazolyl, thiazolyl, or 2,3-dihydrofuranyl group, each of which Q is unsubstituted or substituted with one or more substituents independently selected at each occurrence from halogen, $C_1$-$C_4$alkyl, $C_1$-$C_4$alkoxy, trifluoromethyl, difluoromethyl, cyclopropyl, and cyclobutyl.

5. The compound or salt of claim 1, wherein $R^3$ is a spiro[2.5]oct-5-enyl group, cis-ethenylene group, or a trans-ethenylene group.

6. The compound or salt of claim 1, wherein $R^3$ is a substituted imidazolyl group, a substituted dihydrofuranyl group, a substituted pyrrolidinyl group, or a substituted thiazolyl group each of which $R^3$ is substituted with fluorine, chlorine, $C_1$-$C_5$alkyl, —$CHF_2$, —$CF_3$, or a combination thereof.

7. The compound or salt of claim 1, wherein $R^3$ is -L-Q, where L is an ethynylene group and Q is a five-membered heteroaryl group, that is unsubstituted or substituted with one or more substituents independently chosen from halogen, $C_1$-$C_5$alkyl, $C_1$-$C_5$alkoxy, —$CHF_2$, —$CF_3$, cyclopropyl, and cyclobutyl.

8. The compound or salt of claim 7, where Q is a five-membered heteroaryl group chosen from thienyl, thiazolyl, oxazolyl, and furanyl, each of which is unsubstituted or substituted with one or more substituents independently chosen from halogen, $C_1$-$C_5$alkyl, $C_1$-$C_5$alkoxy, —$CHF_2$, —$CF_3$, cyclopropyl, and cyclobutyl.

9. The compound or salt of claim 1, wherein $R^{10}$ is (cyclopropyl)$CH_2$— or (cyclopropyl)$CH_2CH_2$—.

10. The compound or salt of claim 1, wherein Y is hydrogen.

11. The compound or salt of claim 1, wherein Z is —COOH, —$CH_2OH$, or —$CONH_2$.

12. The compound or salt of claim 1, wherein
n is 0;
X is fluorine in the meta position;
Y is hydrogen;
Z is —COOH, —$CH_2OH$, or —$CONH_2$;

R³ is -L-Q, where L is an ethynylene group and Q is a five-membered heteroaryl group, chosen from thienyl, thiazolyl, oxazolyl, and furanyl, each of which is unsubstituted or substituted with one or more substituents independently chosen from halogen, $C_1$-$C_5$alkyl, $C_1$-$C_5$alkoxy, —CHF₂, —CF₃, cyclopropyl, and cyclobutyl; and R¹⁰ is (cyclopropyl)$C_0$-$C_4$alkyl.

13. The compound of claim 1 or pharmaceutically acceptable salt thereof, wherein the compound is 2-(5-(cyclopropylmethyl)-3-(6-fluoro-4'-methyl-2',3',4',5'-tetrahydro-[1,1'-biphenyl]-3-yl)-4-(3-fluoro-4-sulfamoylbenzyl)-1H-pyrazol-1-yl)thiazole-4-carboxylic acid (101);

2-(5-(cyclopropylmethyl)-3-(6-fluoro-4'-(trifluoromethyl)-2',3',4',5'-tetrahydro-[1,1'-biphenyl]-3-yl)-4-(3-fluoro-4-sulfamoylbenzyl)-1H-pyrazol-1-yl)thiazole-4-carboxylic acid (102);

2-(5-(cyclopropylmethyl)-3-(6-fluoro-2'-methyl-2',3',4',5'-tetrahydro-[1,1'-biphenyl]-3-yl)-4-(3-fluoro-4-sulfamoylbenzyl)-1H-pyrazol-1-yl)thiazole-4-carboxylic acid (103);

2-(5-(cyclopropylmethyl)-3-(6-fluoro-4'-methoxy-2',3',4',5'-tetrahydro-[1,1'-biphenyl]-3-yl)-4-(3-fluoro-4-sulfamoylbenzyl)-1H-pyrazol-1-yl)thiazole-4-carboxylic acid (104);

2-(5-(cyclopropylmethyl)-3-(4-fluoro-3-(1H-inden-2-yl)phenyl)-4-(3-fluoro-4-sulfamoylbenzyl)-1H-pyrazol-1-yl)thiazole-4-carboxylic acid (105);

2-(5-(cyclopropylmethyl)-3-(6-fluoro-4',4'-dimethyl-2',3',4',5'-tetrahydro-[1,1'-biphenyl]-3-yl)-4-(3-fluoro-4-sulfamoylbenzyl)-1H-pyrazol-1-yl)thiazole-4-carboxylic acid (106);

2-(5-(cyclopropylmethyl)-4-(3-fluoro-4-sulfamoylbenzyl)-3-(4',4',6-trifluoro-2',3',4',5'-tetrahydro-[1,1'-biphenyl]-3-yl)-1H-pyrazol-1-yl)thiazole-4-carboxylic acid (107);

2-(5-(cyclopropylmethyl)-3-(4-fluoro-3-(spiro[2.5]oct-5-en-6-yl)phenyl)-4-(3-fluoro-4-sulfamoylbenzyl)-1H-pyrazol-1-yl)thiazole-4-carboxylic acid (108);

2-(3-(3-(but-1-yn-1-yl)-4-fluorophenyl)-5-(cyclopropylmethyl)-4-(3-fluoro-4-sulfamoylbenzyl)-1H-pyrazol-1-yl)thiazole-4-carboxylic acid (109);

2-(3-(3-((5-(tert-butyl)thiophen-2-yl)ethynyl)-4-fluorophenyl)-5-(cyclopropylmethyl)-4-(3-fluoro-4-sulfamoylbenzyl)-1H-pyrazol-1-yl)thiazole-4-carboxylic acid (110);

2-(5-(cyclopropylmethyl)-3-(4-fluoro-3-((2-methylthiazol-5-yl)ethynyl)phenyl)-4-(3-fluoro-4-sulfamoylbenzyl)-1H-pyrazol-1-yl)thiazole-4-carboxylic acid (111);

2-(5-(cyclopropylmethyl)-4-(3-fluoro-4-sulfamoylbenzyl)-3-(3-((5-methylthiophen-2-yl)ethynyl)phenyl)-1H-pyrazol-1-yl)thiazole-4-carboxylic acid (112);

2-(5-(2-cyclopropylethyl)-3-(4-fluoro-3-((5-methylthiophen-2-yl)ethynyl)phenyl)-4-(3-fluoro-4-sulfamoylbenzyl)-1H-pyrazol-1-yl)thiazole-4-carboxylic acid (113);

2-(5-(cyclopropylmethyl)-3-(4-fluoro-3-((5-methylthiazol-2-yl)ethynyl)phenyl)-4-(3-fluoro-4-sulfamoylbenzyl)-1H-pyrazol-1-yl)thiazole-4-carboxylic acid (114);

2-(5-(2-cyclopropylethyl)-4-(3-fluoro-4-sulfamoylbenzyl)-3-(3-((5-methylthiophen-2-yl)ethynyl)phenyl)-1H-pyrazol-1-yl)thiazole-4-carboxylic acid (115);

2-(5-(1-cyclopropylethyl)-4-(3-fluoro-4-sulfamoylbenzyl)-3-(3-((5-methylthiophen-2-yl)ethynyl)phenyl)-1H-pyrazol-1-yl)thiazole-4-carboxylic acid (116);

2-(5-(cyclopropylmethyl)-3-(3-((5-cyclopropylthiophen-2-yl)ethynyl)phenyl)-4-(3-fluoro-4-sulfamoylbenzyl)-1H-pyrazol-1-yl)thiazole-4-carboxylic acid (117);

2-(3-(3-((5-chlorothiophen-2-yl)ethynyl)phenyl)-5-(cyclopropylmethyl)-4-(3-fluoro-4-sulfamoylbenzyl)-1H-pyrazol-1-yl)thiazole-4-carboxylic acid (118);

(E)-2-(5-(cyclopropylmethyl)-4-(3-fluoro-4-sulfamoylbenzyl)-3-(3-(2-(5-methylthiophen-2-yl)vinyl)phenyl)-1H-pyrazol-1-yl)thiazole-4-carboxylic acid (119);

2-(5-(cyclopropylmethyl)-4-(3-fluoro-4-sulfamoylbenzyl)-3-(3-((3-methylthiophen-2-yl)ethynyl)phenyl)-1H-pyrazol-1-yl)thiazole-4-carboxylic acid (120);

2-(5-(cyclopropylmethyl)-3-(3-((5-(difluoromethyl)thiophen-2-yl)ethynyl)phenyl)-4-(3-fluoro-4-sulfamoylbenzyl)-1H-pyrazol-1-yl)thiazole-4-carboxylic acid (121);

2-(5-(cyclopropylmethyl)-4-(3-fluoro-4-sulfamoylbenzyl)-3-(3-((5-methyloxazol-2-yl)ethynyl)phenyl)-1H-pyrazol-1-yl)thiazole-4-carboxylic acid (122);

2-(4-(3-fluoro-4-sulfamoylbenzyl)-5-((1-methylcyclopropyl)methyl)-3-(3-((5-methylthiophen-2-yl)ethynyl)phenyl)-1H-pyrazol-1-yl)thiazole-4-carboxylic acid (123);

2-(5-(cyclopropylmethyl)-4-(3-fluoro-4-sulfamoylbenzyl)-3-(3-((5-(trifluoromethyl)thiophen-2-yl)ethynyl)phenyl)-1H-pyrazol-1-yl)thiazole-4-carboxylic acid (124);

2-(5-(cyclopropylmethyl)-3-(3-((3,5-dimethylthiophen-2-yl)ethynyl)phenyl)-4-(3-fluoro-4-sulfamoylbenzyl)-1H-pyrazol-1-yl)thiazole-4-carboxylic acid (125);

2-(5-(dicyclopropylmethyl)-4-(3-fluoro-4-sulfamoylbenzyl)-3-(3-((5-methylthiophen-2-yl)ethynyl)phenyl)-1H-pyrazol-1-yl)thiazole-4-carboxylic acid (126);

2-(5-(cyclopropylmethyl)-4-(3-fluoro-4-sulfamoylbenzyl)-3-(3-((5-isopropylthiophen-2-yl)ethynyl)phenyl)-1H-pyrazol-1-yl)thiazole-4-carboxylic acid (127);

2-(5-(2-cyclopropylpropan-2-yl)-4-(3-fluoro-4-sulfamoylbenzyl)-3-(3-((5-methylthiophen-2-yl)ethynyl)phenyl)-1H-pyrazol-1-yl)thiazole-4-carboxylic acid (128);

2-(5-(cyclopropylmethyl)-4-(3-fluoro-4-sulfamoylbenzyl)-3-(3-((5-methylfuran-2-yl)ethynyl)phenyl)-1H-pyrazol-1-yl)thiazole-4-carboxylic acid (129);

2-(5-(cyclopropylmethyl)-4-(3-fluoro-4-sulfamoylbenzyl)-3-(3-(2-(5-methylthiophen-2-yl)cyclopropyl)phenyl)-1H-pyrazol-1-yl)thiazole-4-carboxylic acid (130);

2-(4-(3-fluoro-4-sulfamoylbenzyl)-3-(3-((5-methylthiophen-2-yl)ethynyl)phenyl)-5-(spiro[2.2]pentan-1-yl)-1H-pyrazol-1-yl)thiazole-4-carboxylic acid (131);

2-(5-(cyclopropylmethyl)-4-(3-fluoro-4-sulfamoylbenzyl)-3-(3-((cis)-3-(5-methylthiophen-2-yl)cyclobutyl)phenyl)-1H-pyrazol-1-yl)thiazole-4-carboxylic acid (132);

2-(5-(cyclopropylmethyl)-4-(3-fluoro-4-sulfamoylbenzyl)-3-(3-3-(5-methylthiophen-2-yl)cyclobutyl)phenyl)-1H-pyrazol-1-yl)thiazole-4-carboxylic acid (133);

2-(5-([1,1'-bi(cyclopropan)]-2-yl)-4-(3-fluoro-4-sulfamoylbenzyl)-3-(3-((5-methylthiophen-2-yl)ethynyl)phenyl)-1H-pyrazol-1-yl)thiazole-4-carboxylic acid (134);

(2-(5-(cyclopropylmethyl)-4-(3-fluoro-4-sulfamoylbenzyl)-3-(3-((5-methylthiophen-2-yl)ethynyl)phenyl)-1H-pyrazol-1-yl)thiazol-4-yl)boronic acid (135);

2-(5-(cyclopropylmethyl)-4-(3-fluoro-4-sulfamoylbenzyl)-3-(3',4',6-trifluoro-[1,1'-biphenyl]-3-yl)-1H-pyrazol-1-yl)thiazole-4-carboxylic acid (136);

2-(5-(cyclopropylmethyl)-3-(3',6-difluoro-4'-methyl-[1,1'-biphenyl]-3-yl)-4-(3-fluoro-4-sulfamoylbenzyl)-1H-pyrazol-1-yl)thiazole-4-carboxylic acid (137);

2-(5-(cyclopropylmethyl)-3-(6-fluoro-4'-(trifluoromethyl)-[1,1'-biphenyl]-3-yl)-4-(3-fluoro-4-sulfamoylbenzyl)-1H-pyrazol-1-yl)thiazole-4-carboxylic acid (138);

2-(3-(4'-chloro-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid (139);

2-(3-(3-acetyl-4-fluorophenyl)-5-(cyclopropylmethyl)-4-(3-fluoro-4-sulfamoylbenzyl)-1H-pyrazol-1-yl)thiazole-4-carboxylic acid (140);

2-(5-(cyclopropylmethyl)-3-(6-fluoro-3'-methyl-[1,1'-biphenyl]-3-yl)-4-(3-fluoro-4-sulfamoylbenzyl)-1H-pyrazol-1-yl)thiazole-4-carboxylic acid (141);

2-(5-(cyclopropylmethyl)-3-(6-fluoro-4'-isopropyl-[1,1'-biphenyl]-3-yl)-4-(3-fluoro-4-sulfamoylbenzyl)-1H-pyrazol-1-yl)thiazole-4-carboxylic acid (142);

2-(5-(cyclopropylmethyl)-3-(4-fluoro-3-(5,6,7,8-tetrahydronaphthalen-2-yl)phenyl)-4-(3-fluoro-4-sulfamoylbenzyl)-1H-pyrazol-1-yl)thiazole-4-carboxylic acid (143);

2-(3-(4'-chloro-3',6-difluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid (144);

2-(5-(cyclopropylmethyl)-3-(3-(pyrrolidine-1-carbonyl)phenyl)-4-(4-sulfamoylbenzyl)-1H-pyrazol-1-yl)thiazole-4-carboxylic acid (145);

2-(5-(cyclopropylmethyl)-3-(6-fluoro-2',3',4',5'-tetrahydro-[1,1'-biphenyl]-3-yl)-4-(3-fluoro-4-sulfamoylbenzyl)-1H-pyrazol-1-yl)thiazole-4-carboxylic acid (146);

2-(3-(3-(tert-butylcarbamoyl)-4-fluorophenyl)-5-(cyclopropylmethyl)-4-(3-fluoro-4-sulfamoylbenzyl)-1H-pyrazol-1-yl) thiazole-4-carboxylic acid (147);

2-(5-(cyclopropylmethyl)-3-(3-(4,5-dihydrofuran-2-yl)-4-fluorophenyl)-4-(3-fluoro-4-sulfamoylbenzyl)-1H-pyrazol-1-yl)thiazole-4-carboxylic acid (148);

2-(3-(3'-chloro-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid (149);

2-(5-(cyclopropylmethyl)-3-(6-fluoro-4'-methoxy-3'-methyl-[1,1'-biphenyl]-3-yl)-4-(3-fluoro-4-sulfamoylbenzyl)-1H-pyrazol-1-yl)thiazole-4-carboxylic acid (150);

2-(5-(cyclopropylmethyl)-3-(6-fluoro-3',5'-dimethyl-[1,1'-biphenyl]-3-yl)-4-(3-fluoro-4-sulfamoylbenzyl)-1H-pyrazol-1-yl)thiazole-4-carboxylic acid (151);

2-(3-(3-benzamido-4-fluorophenyl)-5-(cyclopropylmethyl)-4-(3-fluoro-4-sulfamoylbenzyl)-1H-pyrazol-1-yl)thiazole-4-carboxylic acid (152);

2-(5-(cyclopropylmethyl)-3-(6-fluoro-3',5'-dimethoxy-[1,1'-biphenyl]-3-yl)-4-(3-fluoro-4-sulfamoylbenzyl)-1H-pyrazol-1-yl)thiazole-4-carboxylic acid (153);

2-(5-(cyclopropylmethyl)-3-(4-fluoro-3-(2-oxopyrrolidin-1-yl)phenyl)-4-(3-fluoro-4-sulfamoylbenzyl)-1H-pyrazol-1-yl)thiazole-4-carboxylic acid (154);

2-(5-(cyclopropylmethyl)-3-(3-(2,3-dihydro-1H-inden-5-yl)-4-fluorophenyl)-4-(3-fluoro-4-sulfamoylbenzyl)-1H-pyrazol-1-yl)thiazole-4-carboxylic acid (155);

2-(5-(cyclopropylmethyl)-4-(3-fluoro-4-sulfamoylbenzyl)-3-(3',5',6-trifluoro-[1,1'-biphenyl]-3-yl)-1H-pyrazol-1-yl)thiazole-4-carboxylic acid (156);

2-(5-(cyclopropylmethyl)-3-(3',5'-dichloro-6-fluoro-[1,1'-biphenyl]-3-yl)-4-(3-fluoro-4-sulfamoylbenzyl)-1H-pyrazol-1-yl)thiazole-4-carboxylic acid (157);

2-(5-(cyclopropylmethyl)-3-(4-fluoro-3-(6-isopropyl-2,6-diazaspiro[3.3]heptan-2-yl)phenyl)-4-(3-fluoro-4-sulfamoylbenzyl)-1H-pyrazol-1-yl)thiazole-4-carboxylic acid (158);

2-(5-(cyclopropylmethyl)-3-(4-fluoro-3-(1H-imidazol-2-yl)phenyl)-4-(3-fluoro-4-sulfamoylbenzyl)-1H-pyrazol-1-yl)thiazole-4-carboxylic acid (159);

2-(3-(3-(1H-benzo[d]imidazol-2-yl)-4-fluorophenyl)-5-(cyclopropylmethyl)-4-(3-fluoro-4-sulfamoylbenzyl)-1H-pyrazol-1-yl)thiazole-4-carboxylic acid (160);

2-(5-(cyclopropylmethyl)-3-(4-fluoro-3-(2-methyl-1H-imidazol-5-yl)phenyl)-4-(3-fluoro-4-sulfamoylbenzyl)-1H-pyrazol-1-yl)thiazole-4-carboxylic acid (161);

2-(5-(cyclopropylmethyl)-3-(4-fluoro-3-((5-methylthiophen-2-yl)ethynyl)phenyl)-4-(3-fluoro-4-sulfamoylbenzyl)-1H-pyrazol-1-yl)thiazole-4-carboxamide (162);

2-(5-(cyclopropylmethyl)-4-(3-fluoro-4-sulfamoylbenzyl)-3-(3-((5-methylthiophen-2-yl)ethynyl)phenyl)-1H-pyrazol-1-yl)thiazole-4-carboxamide (163);

2-(3-(4'-chloro-3'-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid (164);

2-(5-(cyclopropylmethyl)-4-(3-fluoro-4-sulfamoylbenzyl)-3-(4'-methoxy-3'-methyl-[1,1'-biphenyl]-3-yl)-1H-pyrazol-1-yl)thiazole-4-carboxylic acid (165);

2-(3-(4'-chloro-[1,1'-biphenyl]-3-yl)-5-(cyclopropylmethyl)-4-(3-fluoro-4-sulfamoylbenzyl)-1H-pyrazol-1-yl)thiazole-4-carboxylic acid (166);

2-(5-(cyclopropylmethyl)-3-(3'-fluoro-4'-methyl-[1,1'-biphenyl]-3-yl)-4-(3-fluoro-4-sulfamoylbenzyl)-1H-pyrazol-1-yl)thiazole-4-carboxylic acid (167);

2-(3-(4'-(tert-butyl)-[1,1'-biphenyl]-3-yl)-5-(cyclopropylmethyl)-4-(3-fluoro-4-sulfamoylbenzyl)-1H-pyrazol-1-yl)thiazole-4-carboxylic acid (168);

2-(5-(cyclopropylmethyl)-4-(3-fluoro-4-sulfamoylbenzyl)-3-(4'-isopropyl-[1,1'-biphenyl]-3-yl)-1H-pyrazol-1-yl)thiazole-4-carboxylic acid (169);

2-(3-(4'-chloro-3'-methyl-[1,1'-biphenyl]-3-yl)-5-(cyclopropylmethyl)-4-(3-fluoro-4-sulfamoylbenzyl)-1H-pyrazol-1-yl)thiazole-4-carboxylic acid (170);

2-(3-(4'-cyclopropyl-3'-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid (171);

2-(3-(3'-chloro-4'-methoxy-[1,1'-biphenyl]-3-yl)-5-(cyclopropylmethyl)-4-(3-fluoro-4-sulfamoylbenzyl)-1H-pyrazol-1-yl)thiazole-4-carboxylic acid (172);

2-(5-(cyclopropylmethyl)-4-(3-fluoro-4-sulfamoylbenzyl)-3-(3'-isopropyl-[1,1'-biphenyl]-3-yl)-1H-pyrazol-1-yl)thiazole-4-carboxylic acid (173);

2-(5-(cyclopropylmethyl)-4-(3-fluoro-4-sulfamoylbenzyl)-3-(5,6,7,8-tetrahydronaphthalen-2-yl)phenyl)-1H-pyrazol-1-yl)thiazole-4-carboxylic acid (174);

2-(3-(3'-chloro-[1,1'-biphenyl]-3-yl)-5-(cyclopropylmethyl)-4-(3-fluoro-4-sulfamoylbenzyl)-1H-pyrazol-1-yl)thiazole-4-carboxylic acid (175);

2-(3-(4'-cyano-[1,1'-biphenyl]-3-yl)-5-(cyclopropylmethyl)-4-(3-fluoro-4-sulfamoylbenzyl)-1H-pyrazol-1-yl)thiazole-4-carboxylic acid (176);

2-(5-(cyclopropylmethyl)-3-(3',5'-difluoro-[1,1'-biphenyl]-3-yl)-4-(3-fluoro-4-sulfamoylbenzyl)-1H-pyrazol-1-yl)thiazole-4-carboxylic acid (177);

2-(5-(cyclopropylmethyl)-3-(4'-(dimethylamino)-[1,1'-biphenyl]-3-yl)-4-(3-fluoro-4-sulfamoylbenzyl)-1H-pyrazol-1-yl)thiazole-4-carboxylic acid (178);

N-cyano-2-(5-(cyclopropylmethyl)-4-(3-fluoro-4-sulfamoylbenzyl)-3-(3-((5-methylthiophen-2-yl)ethynyl)phenyl)-1H-pyrazol-1-yl)thiazole-4-carboxamide (179);

2-(5-(cyclopropylmethyl)-4-(3-fluoro-4-sulfamoylbenzyl)-3-(3-((5-methylthiophen-2-yl)ethynyl)phenyl)-1H-pyrazol-1-yl)-N-(methylsulfonyl)thiazole-4-carboxamide (180);

4-((5-(cyclopropylmethyl)-1-(4-(hydroxymethyl)thiazol-2-yl)-3-(3-((5-methylthiophen-2-yl)ethynyl)phenyl)-1H-pyrazol-4-yl)methyl)-2-fluorobenzenesulfonamide (181);

2-(5-(cyclopropylmethyl)-3-(3'-ethyl-4'-methoxy-[1,1'-biphenyl]-3-yl)-4-(3-fluoro-4-sulfamoylbenzyl)-1H-pyrazol-1-yl)thiazole-4-carboxylic acid (182);

2-(3-(4'-cyclopropyl-[1,1'-biphenyl]-3-yl)-5-(cyclopropylmethyl)-4-(3-fluoro-4-sulfamoylbenzyl)-1H-pyrazol-1-yl)thiazole-4-carboxylic acid (183);

2-(3-(4'-cyclobutyl-[1,1'-biphenyl]-3-yl)-5-(cyclopropylmethyl)-4-(3-fluoro-4-sulfamoylbenzyl)-1H-pyrazol-1-yl)thiazole-4-carboxylic acid (184);

2-(3-(4'-chloro-6-fluoro-3'-methyl-[1,1'-biphenyl]-3-yl)-5-(cyclopropylmethyl)-4-(3-fluoro-4-sulfamoylbenzyl)-1H-pyrazol-1-yl)thiazole-4-carboxylic acid (185);

2-(5-(cyclopropylmethyl)-3-(3'-ethyl-6-fluoro-4'-methoxy-[1,1'-biphenyl]-3-yl)-4-(3-fluoro-4-sulfamoylbenzyl)-1H-pyrazol-1-yl)thiazole-4-carboxylic acid (186);

2-(5-(cyclopropylmethyl)-4-(3-fluoro-4-sulfamoylbenzyl)-3-(4'-(2,2,2-trifluoroethyl)-[1,1'-biphenyl]-3-yl)-1H-pyrazol-1-yl)thiazole-4-carboxylic acid (187);

2-(3-(3-(tert-butylcarbamoyl)phenyl)-5-(cyclopropylmethyl)-4-(4-sulfamoylbenzyl)-1H-pyrazol-1-yl)thiazole-4-carboxylic acid (188);

2-(3-(3-(1H-benzo[d]imidazol-2-yl)phenyl)-5-(cyclopropylmethyl)-4-(3-fluoro-4-sulfamoylbenzyl)-1H-pyrazol-1-yl)thiazole-4-carboxylic acid (189);

2-(5-(cyclopropylmethyl)-3-(4'-(dimethylamino)-6-fluoro-[1,1'-biphenyl]-3-yl)-4-(3-fluoro-4-sulfamoylbenzyl)-1H-pyrazol-1-yl)thiazole-4-carboxylic acid (190);

2-(3-(3'-chloro-6-fluoro-4'-methoxy-[1,1'-biphenyl]-3-yl)-5-(cyclopropylmethyl)-4-(3-fluoro-4-sulfamoylbenzyl)-1H-pyrazol-1-yl)thiazole-4-carboxylic acid (191);

2-(3-(3'-(tert-butyl)-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid (192);

2-(3-(4'-(tert-butyl)-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid (193);

2-(5-(cyclopropylmethyl)-3-(3'-(dimethylamino)-6-fluoro-[1,1'-biphenyl]-3-yl)-4-(3-fluoro-4-sulfamoylbenzyl)-1H-pyrazol-1-yl)thiazole-4-carboxylic acid (194);

2-(5-(cyclopropylmethyl)-3-(4',6-difluoro-3'-methyl-[1,1'-biphenyl]-3-yl)-4-(3-fluoro-4-sulfamoylbenzyl)-1H-pyrazol-1-yl)thiazole-4-carboxylic acid (195);

2-(5-(cyclopropylmethyl)-3-(3',6-difluoro-[1,1'-biphenyl]-3-yl)-4-(3-fluoro-4-sulfamoylbenzyl)-1H-pyrazol-1-yl)thiazole-4-carboxylic acid (196);

2-(5-(cyclopropylmethyl)-4-(3-fluoro-4-sulfamoylbenzyl)-3-(4'-methyl-[1,1'-biphenyl]-3-yl)-1H-pyrazol-1-yl)thiazole-4-carboxylic acid (198);

2-(5-(cyclopropylmethyl)-3-(6-fluoro-3'-isopropyl-[1,1'-biphenyl]-3-yl)-4-(3-fluoro-4-sulfamoylbenzyl)-1H-pyrazol-1-yl)thiazole-4-carboxylic acid (199);

2-(3-(3'-cyano-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid (200);

2-(3-(4'-cyano-6-fluoro-[1,1'-biphenyl]-3-yl)-5-(cyclopropylmethyl)-4-(3-fluoro-4-sulfamoylbenzyl)-1H-pyrazol-1-yl)thiazole-4-carboxylic acid (201);

2-(5-(cyclopropylmethyl)-3-(4-fluoro-3-(2-oxopyrrolidin-1-yl)phenyl)-4-(3-fluoro-4-sulfamoylbenzyl)-1H-pyrazol-1-yl)thiazole-4-carboxylic acid (202);

2-(5-(cyclopropylmethyl)-4-(3-fluoro-4-sulfamoylbenzyl)-3-(3-(5-methylpyridin-2-yl)phenyl)-1H-pyrazol-1-yl)thiazole-4-carboxylic acid (203);

2-(5-(cyclopropylmethyl)-4-(3-fluoro-4-sulfamoylbenzyl)-3-(3-(6-methylpyridin-3-yl)phenyl)-1H-pyrazol-1-yl)thiazole-4-carboxylic acid (204);

2-(5-(2-cyclopropyl ethyl)-4-(3-fluoro-4-sulfamoylbenzyl)-3-(4'-(perfluoroethyl)-[1,1'-biphenyl]-3-yl)-1H-pyrazol-1-yl)thiazole-4-carboxylic acid (205);

2-(5-(2-cyclopropyl ethyl)-4-(3-fluoro-4-sulfamoylbenzyl)-3-(4'-isopropyl-[1,1'-biphenyl]-3-yl)-1H-pyrazol-1-yl)thiazole-4-carboxylic acid (206);

2-(5-(2-cyclopropylethyl)-4-(3-fluoro-4-sulfamoylbenzyl)-3-(4'-isobutyl-[1,1'-biphenyl]-3-yl)-1H-pyrazol-1-yl)thiazole-4-carboxylic acid (207);

2-(5-(cyclopropylmethyl)-4-(3-fluoro-4-sulfamoylbenzyl)-3-methylthiophen-2-yl)-[1,1'-biphenyl]-3-yl)-1H-pyrazol-1-yl)thiazole-4-carboxylic acid (208);

2-(5-(cyclopropylmethyl)-3-(6-fluoro-4'-(5-methylthiophen-2-yl)-[1,1'-biphenyl]-3-yl)-4-(3-fluoro-4-sulfamoylbenzyl)-1H-pyrazol-1-yl)thiazole-4-carboxylic acid (209);

2-[5-(cyclopropylmethyl)-4-[(3-fluoro-4-sulfamoylphenyl)methyl]-3-[5-(4-isopropylphenyl)pyridin-3-yl]pyrazol-1-yl]-1,3-thiazole-4-carboxylic acid (210);

2-[5-(cyclopropylmethyl)-4-[(3-fluoro-4-sulfamoylphenyl)methyl]-3-[6-(4-isopropylphenyl)pyridin-2-yl]pyrazol-1-yl]-1,3-thiazole-4-carboxylic acid (211);

2-{3-[3-(4-cyclopropyl-3-fluorophenyl)-4-fluorophenyl]-5-(cyclopropylmethyl)-4-[(3-fluoro-4-sulfamoylphenyl)methyl]pyrazol-1-yl}-1,3-thiazole-4-carboxylic acid (212);

2-[5-(cyclopropylmethyl)-3-[4-fluoro-3-(4-isopropyl-3-methylphenyl)phenyl]-4-[(3-fluoro-4-sulfamoylphenyl)methyl]pyrazol-1-yl]-1,3-thiazole-4-carboxylic acid (213);

2-[5-(cyclopropylmethyl)-4-[(3-fluoro-4-sulfamoylphenyl)methyl]-3-[3-(2-methylpyrimidin-5-yl)phenyl]pyrazol-1-yl]-1,3-thiazole-4-carboxylic acid (214);

2-[5-(cyclopropylmethyl)-4-[(3-fluoro-4-sulfamoylphenyl)methyl]-3-[3-(5-isopropyl-1,3-thiazol-2-yl)phenyl]pyrazol-1-yl]-1,3-thiazole-4-carboxylic acid (215);

2-[5-(cyclopropylmethyl)-4-[(3-fluoro-4-sulfamoylphenyl)methyl]-3-[3-(5-isopropylpyrimidin-2-yl)phenyl]pyrazol-1-yl]-1,3-thiazole-4-carboxylic acid (216);

2-[5-(cyclopropylmethyl)-4-[(3-fluoro-4-sulfamoylphenyl)methyl]-3-[3-(5-methylpyrimidin-2-yl)phenyl]pyrazol-1-yl]-1,3-thiazole-4-carboxylicacid (217);

2-[5-(cyclopropylmethyl)-4-[(3-fluoro-4-sulfamoylphenyl)methyl]-3-[3-(5-isopropylpyridin-2-yl)phenyl]pyrazol-1-yl]-1,3-thiazole-4-carboxylicacid (218);

2-(5-(cyclopropylmethyl)-4-(3-fluoro-4-sulfamoylbenzyl)-3-(4'-(trifluoromethyl)-[1,1'-biphenyl]-3-yl)-1H-pyrazol-1-yl)thiazole-4-carboxylic acid (219);

2-(5-(cyclopropylmethyl)-3-(3-(2,3-dihydro-1H-inden-5-yl)phenyl)-4-(3-fluoro-4-sulfamoylbenzyl)-1H-pyrazol-1-yl)thiazole-4-carboxylic acid (220);

2-(3-(3-(1H-benzo[d]imidazol-2-yl)phenyl)-5-(cyclopropylmethyl)-4-(3-fluoro-4-sulfamoylbenzyl)-1H-pyrazol-1-yl)thiazole-4-carboxylic acid (221);

2-(3-(4'-cyclopropyl-[1,1'-biphenyl]-3-yl)-5-(cyclopropylmethyl)-4-(3-fluoro-4-sulfamoylbenzyl)-1H-pyrazol-1-yl)thiazole-4-carboxylic acid (222);

2-(5-(cyclopropylmethyl)-3-(3'-ethyl-6-fluoro-4'-methoxy-[1,1'-biphenyl]-3-yl)-4-(3-fluoro-4-sulfamoylbenzyl)-1H-pyrazol-1-yl)thiazole-4-carboxylic acid (223);

2-(5-(cyclopropylmethyl)-4-(3-fluoro-4-sulfamoylbenzyl)-3-(4'-(perfluoroethyl)-[1,1'-biphenyl]-3-yl)-1H-pyrazol-1-yl)thiazole-4-carboxylic acid (224);

2-(5-(cyclopropylmethyl)-3-(6-fluoro-4'-(perfluoroethyl)-[1,1'-biphenyl]-3-yl)-4-(3-fluoro-4-sulfamoylbenzyl)-1H-pyrazol-1-yl)thiazole-4-carboxylic acid (225);

2-(5-(cyclopropylmethyl)-4-(3-fluoro-4-sulfamoylbenzyl)-3-(4'-isobutyl-[1,1'-biphenyl]-3-yl)-1H-pyrazol-1-yl)thiazole-4-carboxylic acid (226);

2-(5-(cyclopropylmethyl)-3-(6-fluoro-4'-isobutyl-[1,1'-biphenyl]-3-yl)-4-(3-fluoro-4-sulfamoylbenzyl)-1H-pyrazol-1-yl)thiazole-4-carboxylic acid) (227);

2-(5-(cyclopropylmethyl)-4-(3-fluoro-4-sulfamoylbenzyl)-3-(4'-hydroxy-3'-methyl-[1,1'-biphenyl]-3-yl)-1H-pyrazol-1-yl)thiazole-4-carboxylic acid (228);

2-(5-(cyclopropylmethyl)-3-(3'-fluoro-4'-hydroxy-[1,1'-biphenyl]-3-yl)-4-(3-fluoro-4-sulfamoylbenzyl)-1H-pyrazol-1-yl)thiazole-4-carboxylic acid (229);

2-(5-(cyclopropylmethyl)-3-(3'-fluoro-4'-isopropyl-[1,1'-biphenyl]-3-yl)-4-(3-fluoro-4-sulfamoylbenzyl)-1H-pyrazol-1-yl)thiazole-4-carboxylic acid (230);

2-(5-(cyclopropylmethyl)-4-(3-fluoro-4-sulfamoylbenzyl)-3-(6-((5-methylthiophen-2-yl)ethynyl)pyridin-2-yl)-1H-pyrazol-1-yl)thiazole-4-carboxylic acid (231);

2-(5-(2-cyclopropylethyl)-4-(3-fluoro-4-sulfamoylbenzyl)-3-(3-((5-methylfuran-2-yl)ethynyl)phenyl)-1H-pyrazol-1-yl)thiazole-4-carboxylic acid (232);

2-(5-(cyclopropylmethyl)-4-(3-fluoro-4-sulfamoylbenzyl)-3-(5-((5-methylthiophen-2-yl)ethynyl)thiophen-2-yl)-1H-pyrazol-1-yl)thiazole-4-carboxylic acid (233);

2-(5-(2-cyclopropylethyl)-4-(3-fluoro-4-sulfamoylbenzyl)-3-(3-((5-methylthiazol-2-yl)ethynyl)phenyl)-1H-pyrazol-1-yl)thiazole-4-carboxylic acid (234);

2-(5-(2-cyclopropylethyl)-4-(3-fluoro-4-sulfamoylbenzyl)-3-(3-((2-methylthiazol-5-yl)ethynyl)phenyl)-1H-pyrazol-1-yl)thiazole-4-carboxylic acid (235);

2-(5-(cyclopropylmethyl)-4-(3-fluoro-4-sulfamoylbenzyl)-3-(3-((2-methylthiazol-4-yl)ethynyl)phenyl)-1H-pyrazol-1-yl)thiazole-4-carboxylic acid (236);

2-(5-(cyclopropylmethyl)-4-(3-fluoro-4-sulfamoylbenzyl)-3-(4-((5-methylthiophen-2-yl)ethynyl)thiophen-2-yl)-1H-pyrazol-1-yl)thiazole-4-carboxylic acid (237);

2-(5-(2-cyclopropylethyl)-3-(3-((2,5-dimethylthiophen-3-yl)ethynyl)phenyl)-4-(3-fluoro-4-sulfamoylbenzyl)-1H-pyrazol-1-yl)thiazole-4-carboxylic acid (238);

2-(5-(2-cyclopropylethyl)-4-(3-fluoro-4-sulfamoylbenzyl)-3-(3-((5-methylthiophen-3-yl)ethynyl)phenyl)-1H-pyrazol-1-yl)thiazole-4-carboxylic acid (239);

2-(5-(cyclopropylmethyl)-4-(3-fluoro-4-sulfamoylbenzyl)-3-(3-((5-methylthiophen-3-yl)ethynyl)phenyl)-1H-pyrazol-1-yl)thiazole-4-carboxylic acid (240);

2-(5-(cyclopropylmethyl)-3-(3-((2,5-dimethylthiophen-3-yl)ethynyl)phenyl)-4-(3-fluoro-4-sulfamoylbenzyl)-1H-pyrazol-1-yl)thiazole-4-carboxylic acid (241);

2-(5-(cyclopropylmethyl)-4-(3-fluoro-4-sulfamoylbenzyl)-3-(3-(2-(5-methylthiophen-2-yl)-2-oxoethyl)phenyl)-1H-pyrazol-1-yl)thiazole-4-carboxylic acid (242);

2-(5-(2-cyclopropylethyl)-4-(3-fluoro-4-sulfamoylbenzyl)-3-(3-((2-methylthiazol-4-yl)ethynyl)phenyl)-1H-pyrazol-1-yl)thiazole-4-carboxylic acid (243);

2-(5-(2-cyclopropylethyl)-3-(3-((5-cyclopropylthiophen-2-yl)ethynyl)phenyl)-4-(3-fluoro-4-sulfamoylbenzyl)-1H-pyrazol-1-yl)thiazole-4-carboxylic acid (244);

2-(3-(3-((5-cyclobutylthiophen-2-yl)ethynyl)phenyl)-5-(cyclopropylmethyl)-4-(3-fluoro-4-sulfamoylbenzyl)-1H-pyrazol-1-yl)thiazole-4-carboxylic acid (245);

2-(3-(3-((5-cyclobutylthiophen-2-yl)ethynyl)phenyl)-5-(2-cyclopropylethyl)-4-(3-fluoro-4-sulfamoylbenzyl)-1H-pyrazol-1-yl)thiazole-4-carboxylic acid (246);

2-(5-(cyclopropylmethyl)-4-(3-fluoro-4-sulfamoylbenzyl)-3-(3-((5-methylthiophen-2-yl)ethynyl)phenyl)-1H-pyrazol-1-yl)oxazole-4-carboxylic acid (247);

2-(5-(3-cyclopropylpropyl)-4-(3-fluoro-4-sulfamoylbenzyl)-3-(3-((5-methylthiophen-2-yl)ethynyl)phenyl)-1H-pyrazol-1-yl)thiazole-4-carboxylic acid (248); or 2-(5-(cyclopropylmethyl)-3-(4-fluoro-3-((5-methylthiophen-2-yl)ethynyl)phenyl)-4-(3-fluoro-4-sulfamoylbenzyl)-1H-pyrazol-1-yl)thiazole-4-carboxylic acid (249).

14. A pharmaceutical composition comprising at least one compound or pharmaceutically acceptable salt of claim 1 and a pharmaceutically acceptable carrier.

15. A method of inhibiting lactate dehydrogenase A (LDHA) activity or lactate dehydrogenase B (LDHB) in a cell comprising administering a compound of claim 1 or a pharmaceutically acceptable salt thereof to a cell, whereby activity of LDHA or LDHB is inhibited.

16. A method of treating fibrosis or cancer in a patient, comprising administering to the patient an effective amount of the compound of claim 1, or a pharmaceutically acceptable salt thereof.

17. The method of treating fibrosis of claim 16, wherein the fibrosis is idiopathic pulmonary fibrosis.

18. A method of treating a patient with cancer cells resistant to an anti-cancer agent, comprising administering to the patient an effective amount of the compound of claim 1, or a pharmaceutically acceptable salt thereof, and the anti-cancer agent, whereby the compound, or the pharmaceutically acceptable salt thereof re-sensitizes the cancer cells to the anti-cancer agent.

\* \* \* \* \*

UNITED STATES PATENT AND TRADEMARK OFFICE
CERTIFICATE OF CORRECTION

| | | |
|---|---|---|
| PATENT NO. | : 10,954,228 B2 | Page 1 of 1 |
| APPLICATION NO. | : 16/313727 | |
| DATED | : March 23, 2021 | |
| INVENTOR(S) | : David J. Maloney et al. | |

It is certified that error appears in the above-identified patent and that said Letters Patent is hereby corrected as shown below:

In the Specification

Column 1, Line 16, the following statement should be added:
FEDERAL RESEARCH STATEMENT
This invention was made with government support under HHSN261200800001E, and CA051497 awarded by the National Institutes of Health. The government has certain rights in the invention.

Signed and Sealed this
Twenty-first Day of October, 2025

John A. Squires
*Director of the United States Patent and Trademark Office*